US008822495B2

(12) United States Patent
Schwink et al.

(10) Patent No.: US 8,822,495 B2
(45) Date of Patent: Sep. 2, 2014

(54) AZACYCLYL-SUBSTITUTED ARYLDIHYDROISOQUINOLINONES, PROCESS FOR THEIR PREPARATION AND THEIR USE AS MEDICAMENTS

(75) Inventors: Lothar Schwink, Frankfurt am Main (DE); Siegfried Stengelin, Frankfurt am Main (DE); Matthias Gossel, Frankfurt am Main (DE); Gerhard Hessler, Frankfurt am Main (DE); Torsten Haack, Frankfurt am Main (DE); Petra Lennig, Frankfurt am Main (DE)

(73) Assignee: Sanofi, Paris (FR)

( * ) Notice: Subject to any disclaimer, the term of this patent is extended or adjusted under 35 U.S.C. 154(b) by 1225 days.

(21) Appl. No.: 12/191,662

(22) Filed: Aug. 14, 2008

(65) Prior Publication Data

US 2009/0264403 A1 Oct. 22, 2009

Related U.S. Application Data

(63) Continuation of application No. PCT/EP2007/001212, filed on Feb. 13, 2007.

(30) Foreign Application Priority Data

Feb. 15, 2006 (DE) .......................... 10 2006 007 045

(51) Int. Cl.

| | | |
|---|---|---|
| *A61K 31/551* | (2006.01) |
| *A61K 31/541* | (2006.01) |
| *A61K 31/5377* | (2006.01) |
| *A61K 31/496* | (2006.01) |
| *A61K 31/4725* | (2006.01) |
| *C07D 405/14* | (2006.01) |
| *C07D 401/14* | (2006.01) |
| *C07D 401/10* | (2006.01) |
| *C07D 487/04* | (2006.01) |
| *C07D 487/10* | (2006.01) |
| *C07D 417/14* | (2006.01) |
| *C07D 513/04* | (2006.01) |
| *C07D 413/14* | (2006.01) |
| *C07D 407/14* | (2006.01) |
| *C07D 413/04* | (2006.01) |

(52) U.S. Cl.
CPC .......... *A61K 31/4725* (2013.01); *A61K 31/496* (2013.01); *A61K 31/5377* (2013.01); *A61K 31/541* (2013.01); *A61K 31/551* (2013.01); *C07D 405/14* (2013.01); *C07D 401/14* (2013.01); *C07D 401/10* (2013.01); *C07D 487/04* (2013.01); *C07D 487/10* (2013.01); *C07D 417/14* (2013.01); *C07D 513/04* (2013.01); *C07D 413/04* (2013.01); *C07D 407/14* (2013.01)

USPC ..... 514/309; 514/218; 514/228.2; 514/235.2; 514/253.05; 514/278; 514/210.16; 544/62; 544/128; 544/363; 546/15; 546/141

(58) Field of Classification Search
CPC .. C07D 405/14; C07D 401/14; C07D 401/10; C07D 487/04; C07D 487/10; C07D 417/14; C07D 513/04; C07D 413/14; C07D 407/14; A61K 31/551; A61K 31/541; A61K 31/5377; A61K 31/496; A61K 31/4725
USPC .............. 514/278, 218, 228.2, 235.2, 253.05, 514/309, 210.16; 546/15, 141; 544/62, 128, 544/363

See application file for complete search history.

(56) References Cited

U.S. PATENT DOCUMENTS

| | | | |
|---|---|---|---|
| 4,329,353 A | * | 5/1982 | Stokbroekx et al. .......... 514/278 |
| 5,416,094 A | * | 5/1995 | Lal et al. ....................... 514/307 |
| 2005/0256124 A1 | | 11/2005 | Goodfellow et al. |

FOREIGN PATENT DOCUMENTS

| | | |
|---|---|---|
| WO | WO 03/033480 | 4/2003 |
| WO | WO 2005/042541 | 5/2005 |

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Supporting information for Staas et al. J. Org. Chem. 2002, 67, 8276-8279.*
Souza, E. P., et. al., A Short facile Route to 1-Hydrazinoisoquinoline: Ring Closure Reactions of Substituted 1-Hydrazinoisoquinoline derivatives and substituted 2-(4-Carbethoxy)Phenyl-1(2H)-Isoquinolinone Derivatives and Their Biological Activity, Indian J. Chemistry Section B, vol. 33, No. 12, (1994), pp. 1150-1158.

* cited by examiner

*Primary Examiner* — Joseph Kosack
*Assistant Examiner* — Matthew Coughlin
(74) *Attorney, Agent, or Firm* — Scully, Scott, Murphy & Presser, P.C.

(57) ABSTRACT

The invention relates to azacyclyl-substituted aryldihydroisoquinolinones and their derivatives, and their physiologically tolerated salts and physiologically functional derivatives, their preparation, medicaments comprising at least one azacyclyl-substituted aryldihydroisoquinolinone of the invention or its derivative, and the use of the azacyclyl-substituted aryldihydroisoquinolinones of the invention and their derivatives as MCH antagonists.

31 Claims, No Drawings

AZACYCLYL-SUBSTITUTED ARYLDIHYDROISOQUINOLINONES, PROCESS FOR THEIR PREPARATION AND THEIR USE AS MEDICAMENTS

This application is a Continuation of International Application No. PCT/EP2007/001212, filed Feb. 13, 2007, which is incorporated herein by reference in its entirety.

FIELD OF THE INVENTION

The invention relates to azacyclyl-substituted aryldihydroisoquinolinones and their derivatives, and their physiologically tolerated salts and physiologically functional derivatives, their preparation, medicaments comprising at least one azacyclyl-substituted aryldihydroisoquinolinone of the invention or its derivative, and the use of the azacyclyl-substituted aryldihydroisoquinolinones of the invention and their derivatives as medicaments.

BACKGROUND OF THE INVENTION

Compounds similar in their overall structure to the azacyclyl-substituted aryldihydroisoquinolinones and their derivatives described in the present application and having a pharmacological effect have been described in the prior art. Thus, for example, WO 01/72712 describes inhibitors of factor Xa which have a substituted isoquinolinone basic structure. WO 2005/103039 discloses 2-(3-aminopyrrolidin-1-yl)pyridines having an MCH-antagonistic effect for the treatment of obesity.

Compounds having an MCH-antagonistic effect for the treatment of obesity are described in the prior art (examples: WO2005047293, WO2004092181, WO2005103039, WO2004024702, WO2005042541, WO2003033476, WO2003033480, WO2001021577, WO2003035624, WO2002089729, WO2002006245, WO2002002744, WO2002057233, WO2003045313, WO2003097047, WO2002010146, WO 2003087044).

The invention was based on the object of providing compounds which bring about a weight reduction in mammals and which are suitable for the prevention and treatment of obesity and diabetes and of their diverse sequelae.

Surprisingly, a series of compounds which modulate the activity of MCH receptors has been found. In particular, the compounds are notable for an antagonism of the MCH1R.

SUMMARY OF THE INVENTION

The invention therefore relates to compounds of the formula I,

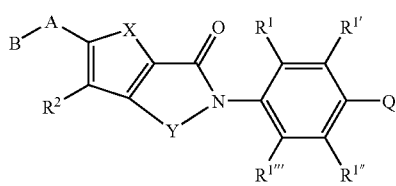

(I)

in which the meanings are

R1, R1', R1", R1'''
    independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R3)(R4), SO$_2$—CH$_3$, COOH, COO—(C$_1$-C$_6$)-alkyl, CON(R5)(R6), N(R7)CO(R8), N(R9)SO$_2$(R10), CO(R11), (C(R12)(R13))$_x$-O(R14);
    preferably independently of one another H, F, Cl, Br, OH, CF$_3$, NO$_2$, CN, OCF$_3$, O—(C$_1$-C$_6$)-alkyl, (C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_2$-C$_6$)-alkynyl, O—(C$_0$-C$_8$)-alkylene-aryl, CO(C$_1$-C$_6$)-alkyl;
    particularly preferably H, F, Cl, Br, CF$_3$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl;
    very particularly preferably H, F, Cl, O—(C$_1$-C$_6$)-alkyl, (C$_1$-C$_6$)-alkyl;
    where preferably at least two, particularly preferably at least three or all radicals R1, R1', R1" and R1''' are H;
R3, R4, R5, R6, R7, R9
    independently of one another H, (C$_1$-C$_8$)-alkyl;
    or
R3 and R4, R5 and R6
    form independently of one another optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur;
R8, R10, R11
    independently of one another H, (C$_1$-C$_8$)-alkyl, aryl; preferably independently of one another H, (C$_1$-C$_8$)-alkyl;
R12, R13
    independently of one another H, (C$_1$-C$_8$)-alkyl;
R14 H, (C$_1$-C$_6$)-alkyl, aryl; preferably H, (C$_1$-C$_6$)-alkyl;
x 0, 1, 2, 3, 4, 5, 6;
R2 H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$—CH$_3$, COOH, COO—(C$_1$-C$_6$)-alkyl, CON(R17)(R18), N(R19)CO(R20), N(R21)SO$_2$(R22), CO(R23), (C(R24)(R25))$_x$—O(R26);
    preferably H, F, Cl, Br, I, OH, CF$_3$, NO$_2$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl;
    particularly preferably H, F, Cl, Br, CF$_3$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl;
    very particularly preferably H, F, Cl, O—(C$_1$-C$_6$)-alkyl, (C$_1$-C$_6$)-alkyl;
    in particular very particularly preferably H;
R15, R16, R17, R18, R19, R21
    independently of one another H, (C$_1$-C$_8$)-alkyl;
    or
R15 and R16, R17 and R18
    form independently of one another and optionally together with the nitrogen atom to which they are bonded a 5-6 membered ring which, apart from the nitrogen atom, may also comprise 0-1 further heteroatoms from the group of NH, N—(C$_1$-C$_6$)-alkyl, oxygen and sulfur;
R20, R22, R23
    independently of one another H, (C$_1$-C$_8$)-alkyl, aryl; preferably independently of one another H, (C$_1$-C$_8$)-alkyl;

R24, R25
  independently of one another H, $(C_1-C_8)$-alkyl;
R26 H, $(C_1-C_6)$-alkyl, aryl; preferably H, $(C_1-C_6)$-alkyl;
x' 0, 1, 2, 3, 4, 5, 6;
Y $C(R27)(R27')C(R28)(R28')$, $C(R29)=C(R29')$; preferably $C(R27)(R27')C(R28)(R28')$;
R27, R27', R28, R28', R29, R29'
  independently of one another H, F, Cl, Br, CN, $(C_1-C_8)$-alkyl, $(C_2-C_6)$-alkenyl, $(C_2-C_6)$-alkynyl; preferably H, $(C_1-C_6)$-alkyl, particularly preferably H;
X S, O, $C(R30)=C(R30')$; preferably S, $C(R30)=C(R30')$; particularly preferably $C(R30)=C(R30')$;
R30, R30'
  independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, $N(R15)(R16)$, $SO_2$—$CH_3$, COOH, COO—$(C_1-C_6)$-alkyl, $CON(R17)(R18)$, $N(R19)CO(R20)$, $N(R21)SO_2(R22)$, $CO(R23)$, $(C(R24)(R25))_{x'}$-$O(R26)$;
  preferably H, F, Cl, Br, I, OH, $CF_3$, $NO_2$, $OCF_3$, O—$(C_1-C_6)$-alkyl, O—$(C_1-C_4)$-alkoxy-$(C_1-C_4)$-alkyl, $(C_1-C_6)$-alkyl, $(C_2-C_6)$-alkenyl, $(C_2-C_6)$-alkynyl;
  particularly preferably H, F, Cl, Br, $CF_3$, CN, $OCF_3$, O—$(C_1-C_6)$-alkyl, $(C_1-C_4)$-alkoxy-$(C_1-C_4)$-alkyl, $(C_1-C_6)$-alkyl;
  very particularly preferably H, F, Cl, O—$(C_1-C_6)$-alkyl, $(C_1-C_6)$-alkyl;
A a bond or a linker having 1 to 8 members, where the members are selected from the group consisting of O, S, $SO_2$, $N(R31)$, CO, $C(R32)(R33)$, $C(R34)=C(R34')$, cyclopropylene, C≡C, resulting in a chemically reasonable radical;
  preferably a bond or a linker having 1 to 6 members, where the members are selected from the group consisting of O, $N(R31)$, CO, $C(R32)(R33)$, $C(R34)=C(R34')$, C≡C, resulting in a chemically reasonable radical;
  particularly preferably a bond or a linker having 1 to 5 members, where the members are selected from the group consisting of O, $N(R31)$, CO, $C(R32)(R33)$, C≡C, resulting in a chemically reasonable radical;
  very particularly preferably a bond or a linker having 1 to 5 members, where the members are selected from the group consisting of O, $N(R31)$, CO, $C(R32)(R33)$, C≡C, resulting in a chemically reasonable radical, where the linker contains no O—CO groups;
R31, R34, R34'
  independently of one another H, $(C_1-C_8)$-alkyl;
R32, R33
  independently of one another H, $(C_1-C_6)$-alkyl, OH, O—$(C_1-C_6)$-alkyl;
B H, $N(R35)(R36)$, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi-, tri- or spirocyclic ring which may comprise 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, $CO(R37)$, $CON(R38)(R39)$, hydroxy, $COO(R40)$, $N(R41)CO(C_1-C_6)$-alkyl, $N(R42)(R43)$, $SO_2CH_3$, $SCF_3$ or S—$(C_1-C_6)$-alkyl;
  preferably H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, $CO(R37)$, $CON(R38)(R39)$, hydroxy, $COO(R40)$, $N(R41)CO(C_1-C_6)$-alkyl, $N(R42)(R43)$ or $SO_2CH_3$;
  particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, $CO(R37)$, $CON(R38)(R39)$, hydroxy, $COO(R40)$, $N(R41)CO(C_1-C_6)$-alkyl, $N(R42)(R43)$ or $SO_2CH_3$;
  very particularly preferably H, $(C_1-C_8)$-alkyl, $(C_1-C_4)$-alkoxy-$(C_1-C_4)$-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, $CO(R37)$, hydroxy, $N(R41)CO(C_1-C_6)$-alkyl, $N(R42)(R43)$ or $SO_2CH_3$;
R35, R36, R37, R38, R39, R40, R41, R42, R43
  independently of one another H, $(C_1-C_8)$-alkyl;
or
R38 and R39, R42 and R43
  form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;
Q mono-, bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, $CO(R44)$, $(C(R45)(R46))_o$-R47, $CO(C(R45)(R46))_p$-R48, where Q comprises in total at least two N atoms;
Q is preferably linked to the group

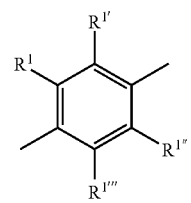

via a ring nitrogen atom of the group Q;
R44 H, $(C_1-C_8)$-alkyl;
R45, R46
  independently of one another H, $(C_1-C_8)$-alkyl, OH, $(C_3-C_8)$-cycloalkyl, $(C_1-C_4)$-alkoxy-$(C_1-C_4)$-alkyl; preferably H, $(C_1-C_6)$-alkyl; particularly preferably H;

o, p independently of one another 0, 1, 2, 3, 4, 5, 6; preferably 0, 1, 2, 3, 4;

R47, R48
    independently of one another OH, F, O—$(C_1$-$C_8)$-alkyl, CON(R49)(R50), N(R51)CO(R52), N(R53)(R54), $CO_2$(R55), $SO_2$Me, CN, a 3-10 membered ring system having 0 to 3 heteroatoms selected from the group of N, O and S, which may be substituted by one or more of the following substituents: F, Cl, Br, $CF_3$, $(C_1$-$C_8)$-alkyl, O—$(C_1$-$C_8)$-alkyl, $(C_1$-$C_4)$-alkoxy-$(C_1$-$C_4)$-alkyl, CO(R56), oxo, OH;

R49, R50, R51, R52, R55, R56
    independently of one another H, $(C_1$-$C_8)$-alkyl;

or

R49 and R50
    form optionally together with the nitrogen atom to which they are bonded a 5-6 membered ring which, apart from the nitrogen atom, may also comprise 0-1 further heteroatoms from the group of NH, N—$(C_1$-$C_6)$-alkyl, oxygen and sulfur;

R53, R54
    independently of one another H, $(C_1$-$C_8)$-alkyl, $(C_1$-$C_4)$-alkoxy-$(C_1$-$C_4)$-alkyl, $(C_3$-$C_8)$-alkenyl, $(C_3$-$C_8)$-alkynyl, CO(R57), $(C(R58)(R59))_q$-R60, CO(C(R61)(R62))$_r$-R63, CO—O$(C_1$-$C_8)$-alkyl; or R53 and R54 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1$-$C_8)$-alkyl, $(C_1$-$C_6)$-alkyl, CO(R64), oxo, OH, $(C_1$-$C_4)$-alkoxy-$(C_1$-$C_4)$-alkyl, hydroxy-$(C_1$-$C_4)$-alkyl, CON(R65)(R66), N(R67)CO(R68), N(R69)(R70), $CO_2$(R71), $SO_2(C_1$-$C_6)$-alkyl;

R53 is preferably:
    H, $(C_1$-$C_8)$-alkyl, $(C(R58)(R59))_q$-R60, $(C_1$-$C_4)$-alkoxy-$(C_1$-$C_4)$-alkyl, $(C_3$-$C_8)$-alkenyl, $(C_3$-$C_8)$-alkynyl, CO—$(C_1$-$C_8)$-alkyl, CO—O$(C_1$-$C_8)$-alkyl, CO(C(R61)(R62))$_r$N(R76)(R77);

R54 is preferably:
    $(C_1$-$C_8)$-alkyl, $(C(R58)(R59))_q$-R60, $(C_1$-$C_4)$-alkoxy-$(C_1$-$C_4)$-alkyl, $(C_3$-$C_8)$-alkenyl, $(C_3$-$C_8)$-alkynyl;

or

R53 and R54 form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, $CF_3$, $(C_1$-$C_6)$-alkyl, O—$(C_1$-$C_8)$-alkyl, $(C_1$-$C_4)$-alkoxy-$(C_1$-$C_4)$-alkyl, hydroxy-$(C_1$-$C_4)$-alkyl, oxo, CO(R64), CON(R65)(R66), hydroxy, COO(R71), N(R67)CO$(C_1$-$C_6)$-alkyl, N(R69)(R70) or $SO_2(C_1$-$C_6)$-alkyl;

R53, R54 are very particularly preferably:
    $(C_1$-$C_8)$-alkyl, $(C(R58)(R59))_q$-R60, $(C_1$-$C_4)$-alkoxy-$(C_1$-$C_4)$-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1$-$C_6)$-alkyl, O—$(C_1$-$C_8)$-alkyl, $(C_1$-$C_4)$-alkoxy-$(C_1$-$C_4)$-alkyl, hydroxy-$(C_1$-$C_4)$-alkyl, oxo, CO(R64), hydroxy, N(R67)CO$(C_1$-$C_6)$-alkyl, or $SO_2(C_1$-$C_6)$-alkyl;

R58, R59
    independently of one another H, $(C_1$-$C_6)$-alkyl, OH;

R57, R61, R62, R64, R65, R66, R67, R68, R69, R70, R71
    independently of one another H, $(C_1$-$C_6)$-alkyl;

or

R69 and R70
    form optionally together with the nitrogen atom to which they are bonded a 5-6 membered ring which, apart from the nitrogen atom, may also comprise 0-1 further heteroatoms from the group of NH, N—$(C_1$-$C_6)$-alkyl, oxygen and sulfur;

q, r independently of one another 0, 1, 2, 3, 4, 5, 6;

R60, R63
    independently of one another OH, F, O—$(C_1$-$C_6)$-alkyl, CN, COO(R78), N(R74)CO$(C_1$-$C_6)$-alkyl, N(R76)(R77), CON(R72)(R73), $SO_2(C_1$-$C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1$-$C_6)$-alkyl, $(C_1$-$C_4)$-alkoxy-$(C_1$-$C_4)$-alkyl, hydroxy-$(C_1$-$C_4)$-alkyl, S—$(C_1$-$C_6)$-alkyl, $(C_1$-$C_6)$-alkyl, $(C_2$-$C_6)$-alkenyl, $(C_3$-$C_8)$-cycloalkyl, O—$(C_3$-$C_8)$-cycloalkyl, $(C_3$-$C_8)$-cycloalkenyl, O—$(C_3$-$C_8)$-cycloalkenyl, $(C_2$-$C_6)$-alkynyl, N(R76)(R77), COO(R78), $SO_2(C_1$-$C_6)$-alkyl and COOH;

preferably OH, F, O—$(C_1$-$C_6)$-alkyl, N(R74)CO$(C_1$-$C_6)$-alkyl, $SO_2(C_1$-$C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1$-$C_6)$-alkyl, $(C_1$-$C_4)$-alkoxy-$(C_1$-$C_4)$-alkyl, $(C_1$-$C_6)$-alkyl, $(C_2$-$C_6)$-alkenyl, $(C_2$-$C_6)$-alkynyl, N(R76)(R77) and $SO_2(C_1$-$C_6)$-alkyl;

R72, R73, R74, R76, R77, R78
    independently of one another H, $(C_1$-$C_8)$-alkyl;

or

R72 and R73, R76 and R77
    form independently of one another optionally together with the nitrogen atom to which they are bonded a 5-6 membered ring which, apart from the nitrogen atom, may also comprise 0-1 further heteroatoms from the group of NH, N—$(C_1$-$C_6)$-alkyl, oxygen and sulfur.

The invention relates to compounds of the formula I in the form of their racemates, enantiomer-enriched mixtures and pure enantiomers, and to their diastereomers and mixtures thereof.

DETAILED DESCRIPTION OF THE INVENTION

The compounds of the formula I are notable for exhibiting an improved solubility compared with compounds of similar structure in an aqueous media and at the same time exhibiting high activity. Preferred compounds of the invention are notable in particular for low blockade of the hERG channel. Preferred compounds of the invention further exhibit an improved metabolic stability compared with compounds of the prior art.

The alkyl, alkenyl and alkynyl radicals in the substituents R1, R2, R3, R4, R5, R6, R7, R8, R9, R10, R11, R12, R13, R14, R15, R16, R17, R18, R19, R20, R21, R22, R23, R24, R25, R26, R27, R27', R28, R28' R29, R29' R30, R30' R31, R32, R33, R34, R34', R35, R36, R37, R38, R39, R40, R41, R42, R43, R44, R45, R46, R47, R51, R52, R53, R54, R55, R56, R57, R58, R59, R60, R61, R62, R63, R64, R65, R66, R67, R68, R69, R70, R71, R72, R73, R74, R76, R77 and R78 may be either straight-chain, branched and/or optionally substituted by substituents such as (C1-C4)-alkoxy or halogen. This also applies when the alkyl, alkenyl and alkynyl radicals are part of another group, e.g. part of an alkoxy group (such as (C1-C4)-alkoxy-(C1-C4)-alkyl)). Suitable halogens are fluorine, chlorine, bromine and iodine, preferably fluorine, chlorine and bromine, particularly preferably fluorine.

Examples of alkyl groups are: methyl, ethyl, propyl, butyl, pentyl, hexyl, heptyl and octyl. Included therein are both the n-isomers of these radicals and branched isomers such as isopropyl, isobutyl, isopentyl, sec-butyl, tert-butyl, neopentyl, 3,3-dimethylbutyl, etc. Unless described otherwise, the term alkyl additionally also includes alkyl radicals which are unsubstituted or optionally substituted by one or more further radicals, for example by 1, 2, 3 or 4 identical or different radicals such as (C1-C4)-alkoxy or halogen. Examples of alkyl groups substituted by halogen are fluorinated alkyl groups such as $CF_3$, $CHF_2$, $CH_2F$, 3-fluoroprop-1-yl, 2,2,1,1-tetrafluoroethyl. It is moreover possible for the additional substituents to appear in any desired position of the alkyl radical. Unless defined otherwise, the alkyl radicals are preferably unsubstituted.

Cycloalkyl means in the context of the present application cycloalkyl and cycloalkylalkyl (alkyl which is in turn substituted by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as listed by way of example above for the alkyl radicals. Unless defined otherwise, the cycloalkyl radicals are preferably unsubstituted.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl.

Cycloalkenyl means in the context of the present application cycloalkenyl radicals and cycloalkenylalkyl radicals (alkyl which is substituted by cycloalkenyl), which comprise at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or non-conjugated double bonds (i.e. also alk-dienyl and alk-trienyl radicals), preferably one double bond in a linear or branched chain. The same applies to the triple bonds for alkynyl radicals. The alkenyl and alkynyl radicals may be unsubstituted or optionally substituted by one or more further radicals as listed by way of example above for the alkyl radicals. Unless defined otherwise, the alkenyl and alkynyl radicals are preferably unsubstituted.

Aryl refers in the present invention to radicals which are derived from monocyclic or bicyclic aromatic compounds comprising no ring heteroatoms. Where aryl refers to systems which are not monocyclic, the saturated form (perhydro form) or the partly unsaturated form (for example the dihydro form or tetrahydro form) is also possible for the second ring when the respective forms are known and stable. The term aryl also includes in the present invention for example bicyclic radicals in which both rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl.

Unless defined otherwise, the aryl radicals are preferably unsubstituted. Aryl is particularly preferably phenyl or naphthyl.

Heteroaryl radicals mean radicals derived from monocyclic or bicyclic aromatic compounds which comprise ring heteroatoms, preferably N, O or S. Otherwise, the statements made about aryl radicals apply to heteroaryl radicals.

A "tricycle" means structures having 3 rings which are linked together by more than one bond. Examples of such systems are fused systems with 3 rings and spirocycles with fused-on ring system.

A polycyclic group (bi-, tri- or spirocyclic ring structure) means in the context of the present application a group which is derived from spiranes, fused ring systems or bridged ring systems. The spiranes are notable for two rings having only one carbon atom in common and the ring planes of the two rings being perpendicular to one another. In the fused ring systems, two rings are linked together in such a way that they have two atoms in common. This type of linkage involves an "ortho fusion". Bridged ring systems are ring systems having a bridge of carbon atoms and/or heteroatoms between two nonadjacent atoms of a ring.

A "chemically reasonable radical" means in the context of the present invention a radical which is stable at room temperature and atmospheric pressure. In the context of the present invention, a "chemically reasonable radical" in the definition of group A in compounds of the formula I preferably means groups which have no heteroatom-heteroatom bonds between the individual members of the groups.

A "nonaromatic" ring means in the context of the present application preferably a ring which is saturated or partly unsaturated. In this connection, a partly unsaturated ring according to the present application has one or, where appropriate, a plurality of double bonds, but the partly unsaturated ring is not aromatic. The term "nonaromatic" in the context of the present application also includes "nonheteroaromatic" rings.

The compounds of the formula I may have one or more centers of asymmetry. The compounds of the formula I may therefore exist in the form of their racemates, enantiomer-enriched mixtures, pure enantiomers, diastereomers and mixtures of diastereomers. The present invention encompasses all these isomeric forms of the compounds of the formula I. These isomeric forms may be obtained by known methods, even if not expressly described in some cases.

Pharmaceutically acceptable salts are, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts are ammonium salts, alkali metal salts (such as sodium and potassium salts), alkaline earth metal salts (such as magnesium and calcium salts) and salts of trometamol (2-amino-2-hydroxymethyl-1,3-propanediol), diethanolamine, lysine or ethylenediamine.

Salts with a pharmaceutically unacceptable anion, such as, for example, trifluoroacetate, likewise belong within the framework of the invention as useful intermediates for the preparation or purification of pharmaceutically acceptable salts and/or for use in nontherapeutic, for example in vitro, applications.

The term "physiologically functional derivative" used herein refers to any physiologically tolerated derivative of a compound of the formula I of the invention, for example an ester, which on administration to a mammal such as, for example, a human is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

If radicals or substituents may occur more than once in the compounds of the formula I, they may all have the stated meanings independently of one another and be identical or different.

The symbols in compound I preferably have independently of one another the following meanings:

R1, R1', R1", R1'''
  independently of one another H, F, Cl, Br, OH, $CF_3$, $NO_2$, CN, $OCF_3$, O—($C_1$-$C_6$)-alkyl, ($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_2$-$C_6$)-alkynyl, O—($C_0$-$C_8$)-alkylene-aryl, CO($C_1$-$C_6$)-alkyl;
  particularly preferably H, F, Cl, Br, $CF_3$, CN, $OCF_3$, O—($C_1$-$C_6$)-alkyl, ($C_1$-$C_4$)-alkoxy-($C_1$-$C_4$)-alkyl, ($C_1$-$C_6$)-alkyl, CO($C_1$-$C_6$)-alkyl;
  very particularly preferably H, F, Cl, O—($C_1$-$C_6$)-alkyl, ($C_1$-$C_6$)-alkyl, CO($C_1$-$C_6$)-alkyl;
  a particularly preferably H, F, methyl, O-methyl, CO-methyl;
  where preferably at least two, particularly preferably at least three or all radicals R1, R1', R1" and R1''' are H.
R2 H, F, Cl, Br, I, OH, $CF_3$, $NO_2$, CN, $OCF_3$, O—($C_1$-$C_6$)-alkyl, ($C_1$-$C_4$)-alkoxy-($C_1$-$C_4$)-alkyl, ($C_1$-$C_6$)-alkyl, ($C_2$-$C_6$)-alkenyl, ($C_2$-$C_6$)-alkynyl;
  particularly preferably H, F, Cl, Br, $CF_3$, CN, $OCF_3$, O—($C_1$-$C_6$)-alkyl, ($C_1$-$C_4$)-alkoxy-($C_1$-$C_4$)-alkyl, ($C_1$-$C_6$)-alkyl;
  very particularly preferably H, F, Cl, O—($C_1$-$C_6$)-alkyl, ($C_1$-$C_6$)-alkyl;
  in particular very particularly preferably H.
Y C(R27)(R27')C(R28)(R28'); where
  R27, R27', R28, R28'
    are independently of one another H, ($C_1$-$C_8$)-alkyl, ($C_2$-$C_6$)-alkenyl, ($C_2$-$C_6$)-alkynyl; preferably H, ($C_1$-$C_6$)-alkyl, particularly preferably H.
X S, C(R30)=C(R30'); preferably C(R30)=C(R30'); where
  R30, R30'
    are independently of one another H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R15)(R16), $SO_2$—$CH_3$, COOH, COO—($C_1$-$C_6$)-alkyl, CON(R17)(R18), N(R19)CO(R20), N(R21)$SO_2$(R22), CO(R23), (C(R24)(R25))$_x$-O(R26);
  preferably H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, ($C_1$-$C_6$)-alkyl, ($C_2$-$C_6$)-alkenyl, ($C_2$-$C_6$)-alkynyl;
  particularly preferably H, F, Cl, Br, $CF_3$, CN, $OCF_3$, O—($C_1$-$C_6$)-alkyl, O—($C_1$-$C_4$)-alkoxy-($C_1$-$C_4$)-alkyl, ($C_1$-$C_6$)-alkyl;
  very particularly preferably H, F, Cl, O—($C_1$-$C_6$)-alkyl, ($C_1$-$C_6$)-alkyl;
  in particular very particularly preferably H.
A a bond or a linker having 1 to 6 members, where the members are selected from the group consisting of O, N(R31), CO, C(R32)(R33), C(R34)=C(R34'), C≡C, resulting in a chemically reasonable radical;
  particularly preferably a bond or a linker having 1 to 5 members, where the members are selected from the group consisting of O, N(R31), CO, C(R32)(R33), C≡C, resulting in a chemically reasonable radical;
  very particularly preferably a bond or a linker having 1 to 5 members, where the members are selected from the group consisting of O, N(R31), CO, C(R32)(R33), C≡C, resulting in a chemically reasonable radical, where the linker comprises no O—CO groups;
  in particular preferably a bond, O, NH, CH(OH), $CH_2$, CO, C≡C, HC=CH, $CH_2$—O, CH($CH_3$)—O, CO—CH($CH_3$)—O, CO—NH, NH—CO, N($CH_3$)—CO, COCH$_2$O, CH(OH)CH$_2$O, O—CO—NH, C(OH)($CH_3$)—C≡C, COCH$_2$CH$_2$O;
  in particular very preferably O, NH, CH(OH), $CH_2$, CO, C≡C, HC=CH, $CH_2$—O, CH($CH_3$)—O, CO—CH($CH_3$)—O, CO—NH, NH—CO, N($CH_3$)—CO, COCH$_2$O, CH(OH)CH$_2$O, O—CO—NH, C(OH)($CH_3$)—C≡C, COCH$_2$CH$_2$O; where
R31, R34, R34'
  are independently of one another H, ($C_1$-$C_8$)-alkyl;
R32, R33
  are independently of one another H, ($C_1$-$C_6$)-alkyl, OH, O—($C_1$-$C_6$)-alkyl.
B H, hydroxy-($C_1$-$C_4$)-alkyl, ($C_1$-$C_8$)-alkyl, ($C_1$-$C_4$)-alkoxy-($C_1$-$C_4$)-alkyl, ($C_2$-$C_8$)-alkenyl, ($C_2$-$C_8$)-alkynyl, a 3 to 10-membered mono-, bi- or spirocyclic ring which may comprise 0 to 4 heteroatoms selected from the group of oxygen, nitrogen and sulfur, where the ring system may additionally be substituted by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO(R37), CON(R38)(R39), hydroxy, COO(R40), N(R41)CO($C_1$-$C_6$)-alkyl, N(R42)(R43) or $SO_2CH_3$;
  particularly preferably H, hydroxy-($C_1$-$C_4$)-alkyl, ($C_1$-$C_8$)-alkyl, ($C_1$-$C_4$)-alkoxy-($C_1$-$C_4$)-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_4$)-alkyl, oxo, CO(R37), CON(R38)(R39), hydroxy, COO(R40), N(R41)CO($C_1$-$C_6$)-alkyl, N(R42)(R43) or $SO_2CH_3$;
  very particularly preferably H, ($C_1$-$C_8$)-alkyl, ($C_1$-$C_4$)-alkoxy-($C_1$-$C_4$)-alkyl, a 3 to 10-membered mono-, bi- or spirocyclic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl, N(R42)(R43) or $SO_2CH_3$;

R35, R36, R37, R38, R39, R40, R41, R42, R43
independently of one another H, $(C_1-C_8)$-alkyl;
or
R38 and R39, R42 and R43
form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur.

In a preferred embodiment, B is:
B  H, N(R35)(R36), hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi-, tri- or spirocyclic nonaromatic ring which may comprise 0 to 4 heteroatoms selected from the group of oxygen, nitrogen and sulfur, where the ring system may additionally be substituted by one or more of the following substituents: F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43), $SO_2CH_3$, $SCF_3$ or S—$(C_1-C_6)$-alkyl;

preferably H, hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, a 3 to 10-membered mono-, bi- or spirocyclic nonaromatic ring which may comprise 0 to 4 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;

particularly preferably H, $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43) or $SO_2CH_3$;

very particularly preferably $(C_1-C_8)$-alkyl, $(C_1-C_4)$-alkoxy-$(C_1-C_4)$-alkyl, a 3 to 10-membered mono-, bi- or spirocyclic nonaromatic ring which may comprise 0 to 3 heteroatoms selected from the group of oxygen, nitrogen and sulfur, where the ring system may additionally be substituted by F, Cl, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), hydroxy, N(R41)CO$(C_1-C_6)$-alkyl, or $SO_2CH_3$;

in particular preferably hydroxy-$(C_1-C_4)$-alkyl, $(C_1-C_8)$-alkyl, $(C_1-C_4)$-alkoxy-$(C_1-C_4)$-alkyl, a monocyclic ring, selected from the group:

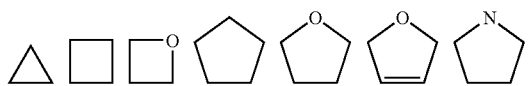

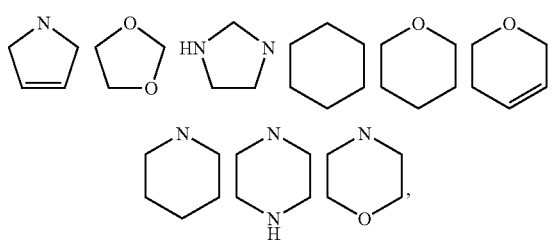

where the ring system may be substituted one- or two times by F, $CF_3$, CN, methyl, ethyl, methoxy, oxo, hydroxy, $SO_2$-methyl;

in particularly very preferably hydroxy-$(C_1-C_4)$-alkyl, $(C_1-C_8)$-alkyl, $(C_1-C_4)$-alkoxy-$(C_1-C_4)$-alkyl, a monocyclic ring, selected from the group:

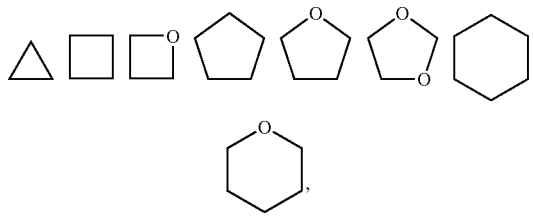

where the ring system may be substituted one- or two times by F, methyl, ethyl, methoxy, hydroxy; where
R35, R36, R37, R38, R39, R40, R41, R42, R43 have the meanings mentioned above.

A particularly preferable embodiment is the compound in which B-A has the meanings:

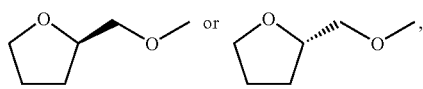

wherein the ring may be substituted one time by methyl or OH.

A further particularly preferable embodiment is the compound in which B-A has the meanings:

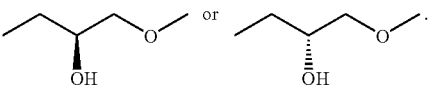

Q mono-, bi-, tri- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by one or more of the following substituents: F, OH, $CF_3$, CN, $OCF_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R44), $(C(R45)(R46))_o$-R47, $CO(C(R45)(R46))_p$-R48, where Q comprises a total of at least two N atoms;

Q is preferably linked to the group

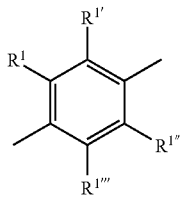

via a ring nitrogen atom of the group Q; where
R44 is H, $(C_1-C_8)$-alkyl;
R45, R46
are independently of one another H, $(C_1-C_6)$-alkyl; particularly preferably H;
o, p are independently of one another 0, 1, 2, 3, 4;
R47, R48
are independently of one another OH, F, O—$(C_1-C_8)$-alkyl, CON(R49)(R50), N(R51)CO(R52), N(R53)(R54), $CO_2$(R55), $SO_2$Me, CN, a 3-10 membered ring system having 0 to 3 heteroatoms selected from the group of N, O and S, which may be substituted by one or more of the following substituents: F, Cl, Br, $CF_3$, $(C_1-C_8)$-alkyl, O—$(C_1-C_8)$-alkyl, $(C_1-C_4)$-alkoxy-$(C_1-C_4)$-alkyl, CO(R56), oxo, OH;
R49, R50, R51, R52, R55, R56
are independently of one another H, $(C_1-C_8)$-alkyl;
or
R49 and R50
form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;
R53 is H, $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl, CO—$(C_1-C_8)$-alkyl, CO—$O(C_1-C_8)$-alkyl, CO(C(R61)(R62))$_r$N(R76)(R77);
R54 is $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl;
or
R53 and R54 form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), CON(R65)(R66), hydroxy, COO(R71), N(R67)CO$(C_1-C_6)$-alkyl, N(R69)(R70) or $SO_2(C_1-C_6)$-alkyl;
R53, R54 are very particularly preferably:
$(C_1-C_8)$-alkyl, $(C(R58)(R59))_q$-R60, $(C_1-C_4)$-alkoxy-$(C_1-C_4)$-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), hydroxy, N(R67)CO$(C_1-C_6)$-alkyl, or $SO_2(C_1-C_6)$-alkyl;
R58, R59
are independently of one another H, $(C_1-C_6)$-alkyl, OH;
R57, R61, R62, R64, R65, R66, R67, R69, R70, R71
are independently of one another H, $(C_1-C_6)$-alkyl;
or
R69 and R70
form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;
q, r are independently of one another 0, 1, 2, 3, 4, 5, 6; preferably 0, 1, 2, 3, 4; particularly preferably 0, 1, 2; very particularly preferably 0, 1;
R60 is OH, F, O—$(C_1-C_6)$-alkyl, N(R74)CO$(C_1-C_6)$-alkyl, $SO_2(C_1-C_6)$-alkyl, 3-12 membered mono-, bi- or spirocyclic ring which may comprise one or more heteroatoms from the group of N, O and S, and the 3-12 membered ring further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, N(R76)(R77) and $SO_2(C_1-C_6)$-alkyl;
R72, R73, R74, R76, R77, R78
are independently of one another H, $(C_1-C_8)$-alkyl;
or
R72 and R73, R76 and R77
form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur.
In a preferred embodiment Q is:
mono-, bi- or spirocyclic saturated or partly unsaturated ring structure having one nitrogen atom and 0-3 further heteroatoms selected from the group of N, O and S, where the rings of the structure may be spiro-linked, fused or bridged, and where the ring system may be substituted by $(C(R45)(R46))_o$-R47, where Q comprises a total of at least two N atoms, and Q is linked to the group

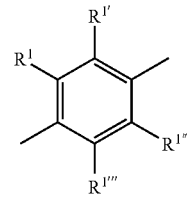

via a ring nitrogen atom of the group Q, where
R45, R46
are independently of one another H, $(C_1-C_6)$-alkyl; preferably H;
o, p are 0, 1; preferably 0;
R47 is N(R53)(R54);
R53, R54 are
$(C_1-C_8)$-alkyl, $(C(R58)(R59))_q$-R60, $(C_1-C_4)$-alkoxy-$(C_1-C_4)$-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_6)$-alkyl, $(C_1-C_4)$-alkoxy-$(C_1-C_4)$-alkyl, hydroxy-$(C_1-C_4)$-alkyl, oxo, CO(R64), hydroxy, N(R67)CO$(C_1-C_6)$-alkyl, or $SO_2(C_1-C_6)$-alkyl;

R58, R59, R64, R67 are

H, $(C_1-C_6)$-alkyl, OH;

R60 is OH, F, O—$(C_1-C_6)$-alkyl, N(R74)CO$(C_1-C_6)$-alkyl, SO$_2$$(C_1-C_6)$-alkyl, 3-12 membered mono-, bi- or spirocyclic ring which may comprise one or more heteroatoms from the group of N, O and S, and the 3-12 membered ring further substituents such as F, Cl, Br, OH, CF$_3$, NO$_2$, CN, OCF$_3$, oxo, O—$(C_1-C_6)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, N(R76)(R77) and SO$_2$$(C_1-C_6)$-alkyl;

R74, R76, R77 are independently of one another H, $(C_1-C_8)$-alkyl;

or

R76 and R77 form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur.

In a particularly preferred embodiment, Q is:

Q a group of the general formula:

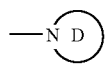

in which the ring D has the following meanings:

saturated monocyclic 5-7-membered azacycle which comprises an element N(R53) or C(R45)((CH$_2$)$_o$—N(R53)(R54)); saturated 6-11 membered azabicycle or spirocycle which comprises an element N(R53) or C(R45)((CH$_2$)$_o$—N(R53)(R54));

Q is preferably:

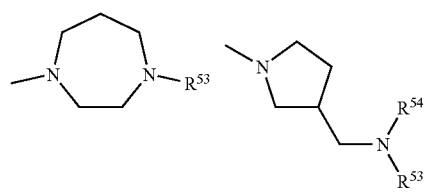

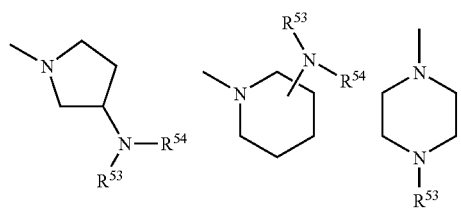

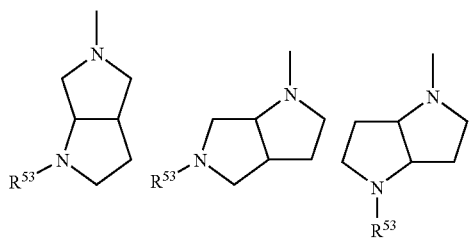

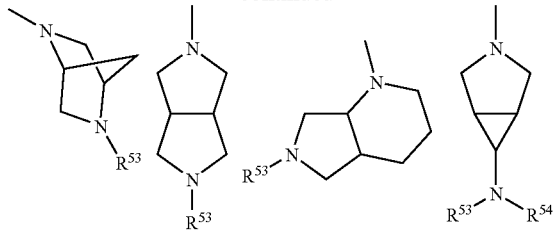

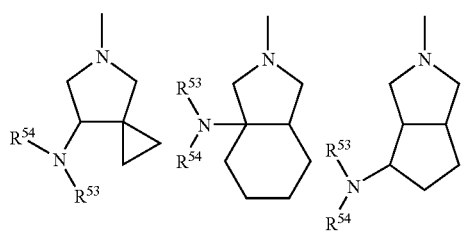

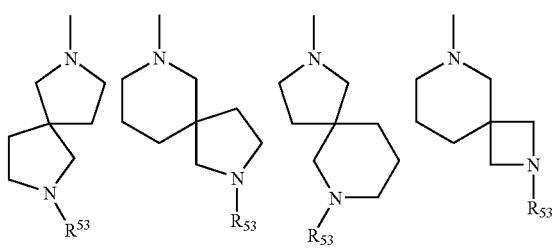

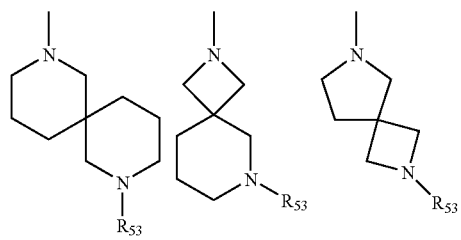

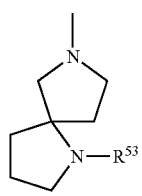

where the groups may, apart from R53, R54, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

Q is particularly preferably:

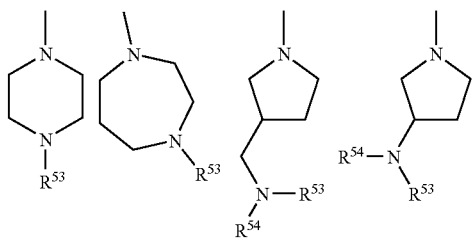

-continued

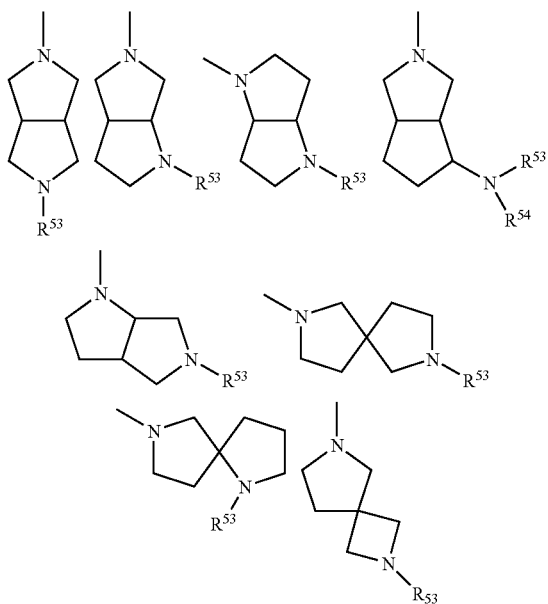

where the groups may optionally be substituted by one or more substituents selected from F, OH, oxo, $(C_1-C_6)$-alkyl, $O-(C_1-C_6)$-alkyl, $(C_1-C_4)$-alkoxy-$(C_1-C_4)$-alkyl; the aforementioned groups Q preferably have no further substituents;

Q is very particularly preferably:

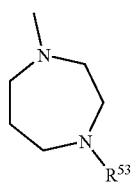

where the group may, apart from R53, optionally be substituted by one or more substituents selected from F, OH, oxo, $(C_1-C_6)$-alkyl, $O-(C_1-C_6)$-alkyl, $(C_1-C_4)$-alkoxy-$(C_1-C_4)$-alkyl, hydroxy-$(C_1-C_4)$-alkyl; the aforementioned groups Q preferably have no further substituents;

Further Q is very particularly preferably:

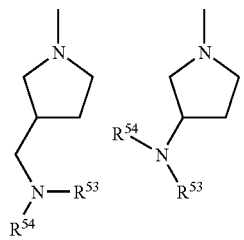

where the groups may, apart from R53, R54, optionally be substituted by one or more substituents selected from F, OH, oxo, $(C_1-C_6)$-alkyl, $O-(C_1-C_6)$-alkyl, $(C_1-C_4)$-alkoxy-$(C_1-C_4)$-alkyl, hydroxy-$(C_1-C_4)$-alkyl; the aforementioned groups Q preferably have no further substituents;

Further Q is very particularly preferably:

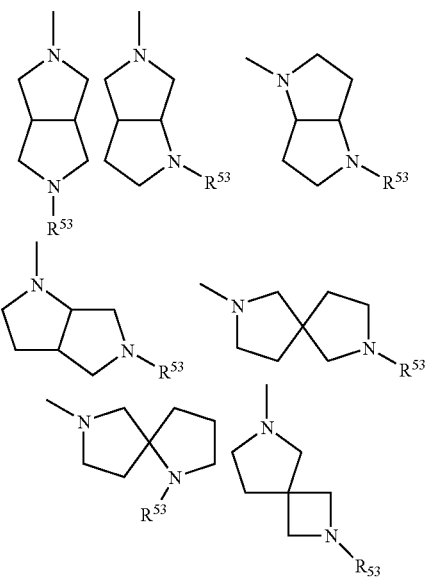

where the groups may optionally be substituted by one or more substituents selected from F, OH, oxo, $(C_1-C_6)$-alkyl, $O-(C_1-C_6)$-alkyl, $(C_1-C_4)$-alkoxy-$(C_1-C_4)$-alkyl; the aforementioned groups Q preferably have no further substituents;

Q is in particular preferably:

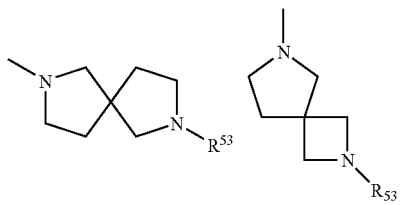

where the groups may optionally be substituted by one or more substituents selected from F, OH, oxo, $(C_1-C_6)$-alkyl, $O-(C_1-C_6)$-alkyl, $(C_1-C_4)$-alkoxy-$(C_1-C_4)$-alkyl; the aforementioned groups Q preferably have no further substituents; where the radicals R45, R53 and R54 and the index o have the aforementioned meanings.

In a further preferred embodiment the meanings are:

R53 H, $(C_1-C_8)$-alkyl, $(C(R58)(R59))_q$-R60, $(C_1-C_4)$-alkoxy-$(C_1-C_4)$-alkyl, $CO(C(R61)(R62))_r$-R63, $(C_3-C_8)$-alkenyl, $(C_3-C_8)$-alkynyl, $CO-(C_1-C_8)$-alkyl, $CO-O(C_1-C_8)$-alkyl;

R54 $(C_1-C_8)$-alkyl, $(C(R58)(R59))_q$-R60, $(C_1-C_4)$-alkoxy-$(C_1-C_4)$-alkyl, $CO(C(R61)(R62))_r$-R63, $(C_3-C_8)$-alkenyl, $(C_3-C_8)$-alkynyl;

or

R53 and R54 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, $O-(C_1-C_8)$-alkyl, $(C_1-C_6)$-alkyl, CO(R64), oxo, OH, $(C_1-C_4)$-alkoxy-$(C_1-C_4)$-alkyl, hydroxy-$(C_1-C_4)$-alkyl, CON(R65)(R66), N(R67)CO(R68), N(R69)(R70), $CO_2$(R71), $SO_2(C_1-C_6)$-alkyl;

R45 H, (C$_1$-C$_6$)-alkyl;
q, r 0, 1, 2, 3, 4;
R60, R63
  independently of one another OH, F, O—(C$_1$-C$_6$)-alkyl, N(R74)CO(C$_1$-C$_6$)-alkyl, SO$_2$(C$_1$-C$_6$)-alkyl, 3-12 membered mono-, bi- or spirocyclic ring which may comprise one or more heteroatoms from the group of N, O and S, and the 3-12 membered ring may comprise further substituents such as F, Cl, Br, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, hydroxy-(C$_1$-C$_4$)-alkyl, (C$_1$-C$_6$)-alkyl, (C$_2$-C$_6$)-alkenyl, (C$_2$-C$_6$)-alkynyl, N(R76)(R77) and SO$_2$(C$_1$-C$_6$)-alkyl.

In a further preferred embodiment the meanings are:
R53, R54 independently of one another (C$_1$-C$_8$)-alkyl, (C(R58)(R59))$_q$-R60, (C$_1$-C$_4$)-alkoxy-(C$_1$-C$_4$)-alkyl;
or
R53 and R54 form together with the nitrogen atom to which they are bonded a 4 to 10-membered mono-, bi- or spirocyclic ring which, apart from the nitrogen atom, comprises 0 to 2 additional heteroatoms selected from the group of N, O and S and may additionally be substituted by one or more of the following substituents: F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, CO(R64), oxo, OH, N(R67)CO (C$_1$-C$_6$)-alkyl or SO$_2$(C$_1$-C$_6$)-alkyl.

In a further preferred embodiment the meanings are:
R53 and R54 form together with the nitrogen atom to which they are bonded a 6 to 10-membered bi- or spirocyclic ring which, apart from the nitrogen atom, comprises 0 to 2 additional heteroatoms selected from the group of N, O and S and may additionally be substituted by one or more of the following substituents: F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, CO(R64), oxo, OH, N(R67)CO (C$_1$-C$_6$)-alkyl or SO$_2$(C$_1$-C$_6$)-alkyl.

In a further preferred embodiment, the present invention relates to compounds of the general formula I, in which Y and X have the following meanings:
Y C(R27)(R27')C(R28)(R28'); where
R27, R27', R28, R28'
  are independently of one another independently of one another H, (C$_1$-C$_8$)-alkyl, (C$_3$-C$_6$)-alkenyl, (C$_3$-C$_6$)-alkynyl; preferably H, (C$_1$-C$_6$)-alkyl, particularly preferably H; and
X is C(R30)=C(R30'); where
R30, R30'
  are independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$—CH$_3$, COOH, COO—(C$_1$-C$_6$)-alkyl, CON(R17)(R18), N(R19)CO(R20), N(R21)SO$_2$(R22), CO(R23), (C(R24)(R25))$_x$-O(R26);
  preferably H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl;
  particularly preferably H, F, Cl, Br, CF$_3$, CN, OCF$_3$, O—(C$_1$-C$_6$)-alkyl, O—(C$_1$-C$_4$)-alkoxy-(C$_1$-C$_4$)-alkyl, (C$_1$-C$_6$)-alkyl;
  very particularly preferably H, F, Cl, O—(C$_1$-C$_6$)-alkyl, (C$_1$-C$_6$)-alkyl;
  in particular very particularly preferably H;
and the further radicals and groups of the compound of the formula I have the aforementioned meanings.

In a further preferred embodiment, the present invention relates to compounds of the general formula I, in which Y and X have the following meanings:
Y C(R27)(R27')C(R28)(R28'), C(R29)=C(R29'); preferably C(R27)(R27')C(R28)(R28'); and
R27, R27', R28, R28', R29, R29'
  independently of one another H, (C$_1$-C$_8$)-alkyl; preferably H;
and
X S, O; preferably S.

In a further preferred embodiment, the present invention relates to compounds of the general formula I, in which Y and X have the following meanings:
Y C(R29)=C(R29');
R29, R29'
  independently of one another independently of one another H, (C$_1$-C$_8$)-alkyl; preferably H;
and
X S, O, C(R30)=C(R30'); preferably S, C(R30)=C(R30');
R30, R30'
  independently of one another H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, (C$_2$-C$_6$)-alkynyl, (C$_0$-C$_8$)-alkylene-aryl, O—(C$_0$-C$_8$)-alkylene-aryl, S-aryl, N(R15)(R16), SO$_2$—CH$_3$, COOH, COO—(C$_1$-C$_6$)-alkyl, CON(R17)(R18), N(R19)CO(R20), N(R21)SO$_2$(R22), CO(R23), (CR24R25)$_x$-O(R26);
  preferably H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl;
  particularly preferably H, F, Cl, Br, CF$_3$, CN, OCF$_3$, O—(C$_1$-C$_6$)-alkyl, O—(C$_1$-C$_4$)-alkoxy-(C$_1$-C$_4$)-alkyl, (C$_1$-C$_6$)-alkyl;
  very particularly preferably H, F, Cl, O—(C$_1$-C$_6$)-alkyl, (C$_1$-C$_6$)-alkyl;
  in particular very particularly preferably H.

In a further particularly preferred embodiment, the present invention relates to compounds of the formula Ia

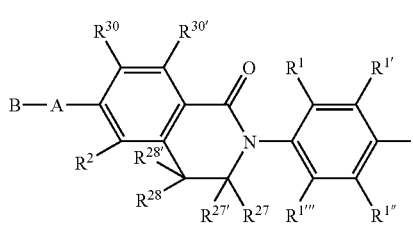

Ia in which Q is a group

, and the ring D in the group

has the following meanings:
  saturated monocyclic 5-7-membered azacycle which comprises an element N(R53) or C(R45)((CH$_2$)$_o$—N(R53)

(R54)); a saturated 6-11 membered azabicycle or spirocycle which comprises an element N(R53) or C(R45) ((CH$_2$)$_o$—N(R53)(R54));

Q is preferably:

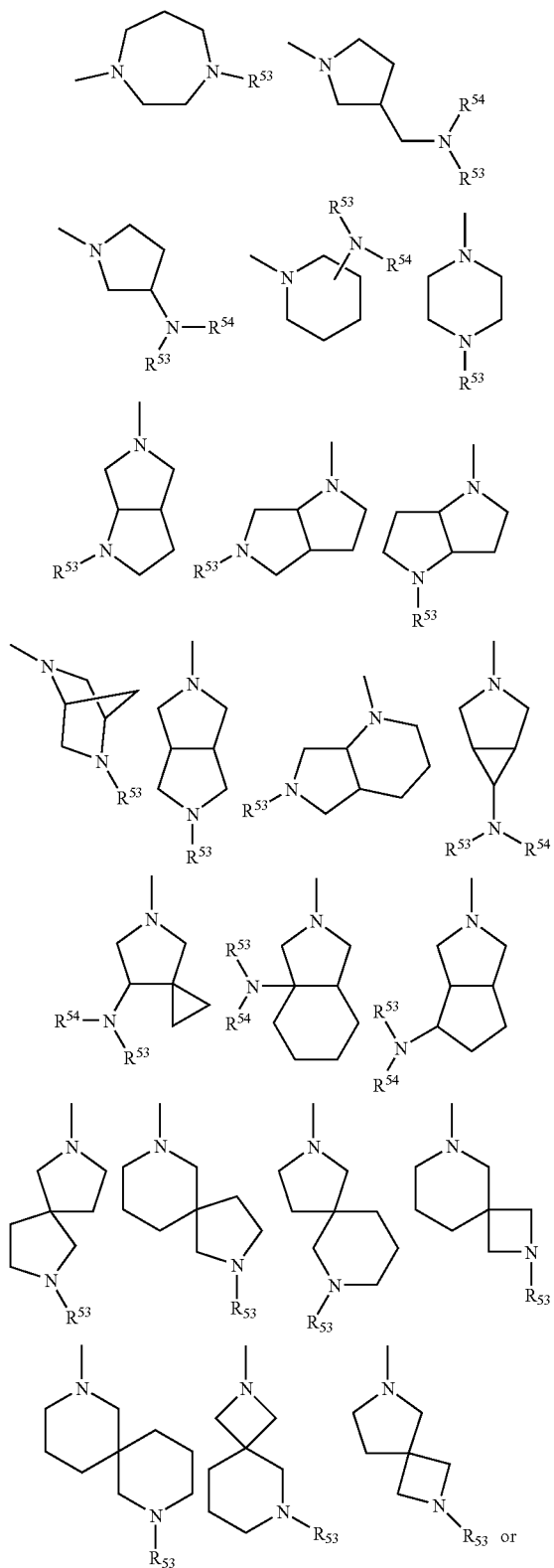

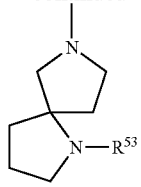

where the groups may, apart from R53, R54, optionally be substituted by one or more substituents selected from F, OH, oxo, (C$_1$-C$_6$)-alkyl, O—(C$_1$-C$_6$)-alkyl, (C$_1$-C$_4$)-alkoxy-(C$_1$-C$_4$)-alkyl; the aforementioned groups Q preferably have no further substituents;

Q is particularly preferably:

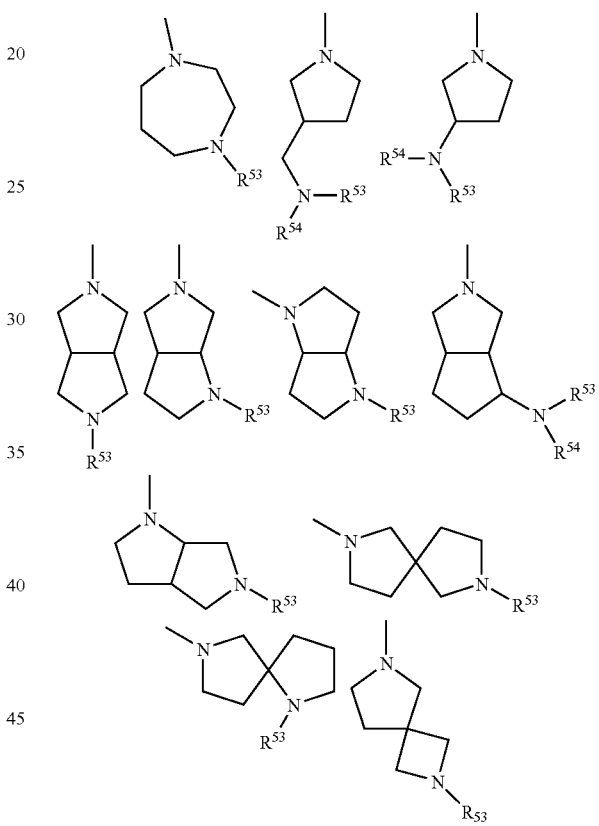

where the groups may, apart from R53, R54, optionally be substituted by one or more substituents selected from F, OH, oxo, (C$_1$-C$_6$)-alkyl, O—(C$_1$-C$_6$)-alkyl, (C$_1$-C$_4$)-alkoxy-(C$_1$-C$_4$)-alkyl; the aforementioned groups Q preferably have no further substituents;

Q is particularly preferably:

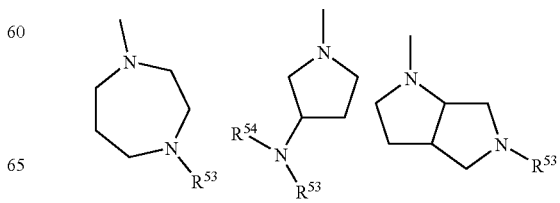

-continued

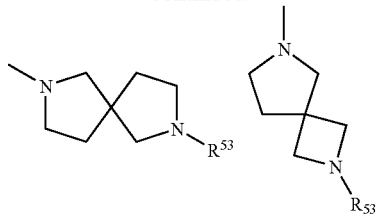

where the groups may, apart from R53, R54, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

Q is very particularly preferably:

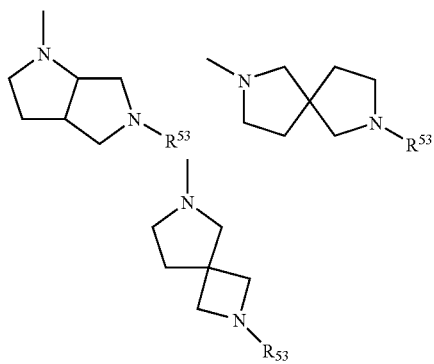

where the groups may, apart from R53, optionally be substituted by one or more substituents selected from F, OH, oxo, $(C_1-C_6)$-alkyl, O—$(C_1-C_6)$-alkyl, $(C_1-C_4)$-alkoxy-$(C_1-C_4)$-alkyl; the aforementioned groups Q preferably have no further substituents;

R45 H, $(C_1-C_6)$-alkyl; preferably H;

o 0, 1, 2, 3, 4, 5, 6; preferably 0, 1, 2; particularly preferably 0, 1; very particularly preferably 0;

R53, R54
independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R57), $(C(R58)(R59))_q$-R60, CO(C(R61)(R62))_rR63, CO—O$(C_1-C_8)$-alkyl; or R53 and R54 form together with the nitrogen atom to which they are bonded a 4 to 10-membered mono-, bi- or spirocyclic ring which, apart from the nitrogen atom, comprises 0 to 3 additional heteroatoms selected from the group of N, O and S, and may additionally be substituted by one or more of the following substituents: F, Cl, Br, $CF_3$, O—$(C_1-C_8)$-alkyl, $(C_1-C_6)$-alkyl, CO(R64), oxo, OH, $(C_1-C_4)$-alkoxy-$(C_1-C_4)$-alkyl, hydroxy-$(C_1-C_4)$-alkyl, CON(R65)(R66), N(R67)CO(R68), N(R69)(R70), $CO_2$(R71), $SO_2(C_1-C_6)$-alkyl;

R53 is preferably:
H, $(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl, CO—$(C_1-C_8)$-alkyl, CO—O$(C_1-C_8)$-alkyl, CO(C(R61)(R62))_rN(R76)(R77);

R54 is preferably:
$(C_1-C_8)$-alkyl, $(C(R58)(R59))_q$-R60, $(C_1-C_4)$-alkoxy-$(C_1-C_4)$-alkyl, $(C_3-C_8)$-alkenyl, $(C_3-C_8)$-alkynyl;
or
R53 and R54 form preferably together with the nitrogen atom to which they are bonded a 4 to 10-membered mono-, bi- or spirocyclic ring which, apart from the nitrogen atom, may comprise 0 to 3 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), CON(R65)(R66), hydroxy, COO(R71), N(R67)CO$(C_1-C_6)$-alkyl, N(R69)(R70) or $SO_2(C_1-C_6)$-alkyl;

R53, R54 are very particularly preferably:
$(C_1-C_8)$-alkyl, $(C(R58)(R59))_q$-R60, $(C_1-C_4)$-alkoxy-$(C_1-C_4)$-alkyl; or R53 and R54 form together with the nitrogen atom to which they are bonded a 4 to 10-membered mono-, bi- or spirocyclic ring which, apart from the nitrogen atom, may comprise 0 to 2 additional heteroatoms selected from the group of oxygen, nitrogen and sulfur, where the heterocyclic ring system may additionally be substituted by F, Cl, Br, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R64), hydroxy, N(R67)CO$(C_1-C_6)$-alkyl or $SO_2(C_1-C_6)$-alkyl;

R58, R59
independently of one another H, $(C_1-C_6)$-alkyl, OH;

R57, R61, R62, R64, R65, R66, R67, R68, R69, R70, R71
independently of one another H, $(C_1-C_6)$-alkyl;
or
R69 and R70
form optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

q, r independently of one another 0, 1, 2, 3, 4, 5, 6;

R60, R63
independently of one another OH, F, O—$(C_1-C_6)$-alkyl, CN, COO(R78), N(R74)CO$(C_1-C_6)$-alkyl, N(R76)(R77), CON(R72)(R73), $SO_2(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, N(R76)(R77), COO(R78), $SO_2(C_1-C_6)$-alkyl and COOH;
preferably OH, F, O—$(C_1-C_6)$-alkyl, N(R74)CO$(C_1-C_6)$-alkyl, $SO_2(C_1-C_6)$-alkyl, 3-12 membered mono-, bi- or spirocyclic ring which may comprise one or more heteroatoms from the group of N, O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, hydroxy-$(C_1-C_4)$-alkyl, $(C_1-C_6)$-alkyl, $(C_2-C_6)$-alkenyl, $(C_2-C_6)$-alkynyl, N(R76)(R77) and $SO_2(C_1-C_6)$-alkyl;

R72, R73, R74, R76, R77, R78
independently of one another H, $(C_1-C_8)$-alkyl;
or
R72 and R73, R76 and R77
form independently of one another optionally together with the nitrogen atom to which they are bonded a 5-6 membered ring which, apart from the nitrogen atom, may also comprise 0-1 further heteroatoms from the group of NH, N—$(C_1-C_6)$-alkyl, oxygen and sulfur;

and the further radicals and groups in the compound of the formula Ia have the aforementioned meanings.

In a further embodiment, the present invention relates to compounds of the formula I, in which Q and X have the following meanings:

Q a group

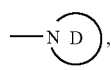

where the group

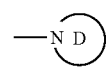

has the aforementioned meanings; and
X S or O; preferably S.

A further aspect of the present invention is thus compounds of the formula Ib

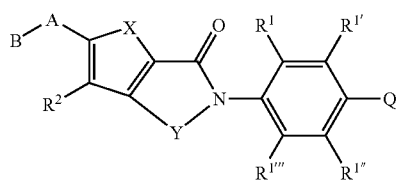

in which
X is S or O; preferably S;
Q is

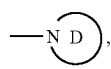

where

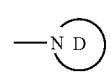

has the aforementioned meanings;
and the further radicals and groups in the compound of the formula Ib have the aforementioned meanings.

In a further embodiment, the present invention relates to compounds of the formula I, in which Y, X and Q have the following meanings:
Y C(R29)=C(R29'); where
R29, R29'
  are independently of one another H, $(C_1-C_8)$-alkyl, $(C_3-C_6)$-alkenyl, $(C_3-C_6)$-alkynyl; preferably H, $(C_1-C_6)$-alkyl, particularly preferably H;
X C(R30)=C(R30'); where
R30, R30'
  are independently of one another H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, $(C_2-C_6)$-alkynyl, $(C_0-C_8)$-alkylene-aryl, O—$(C_0-C_8)$-alkylene-aryl, S-aryl, N(R15)(R16), $SO_2$—$CH_3$, COOH, COO—$(C_1-C_6)$-alkyl, CON(R17)(R18), N(R19)CO(R20), N(R21)$SO_2$(R22), CO(R23), $(C(R24)(R25))_x$-O(R26);
  preferably H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, $(C_1-C_6)$-alkyl, $(C_2-C_6)$-alkenyl, $(C_2-C_6)$-alkynyl;
  particularly preferably H, F, Cl, Br, $CF_3$, CN, $OCF_3$, O—$(C_1-C_6)$-alkyl, O—$(C_1-C_4)$-alkoxy-$(C_1-C_4)$-alkyl, $(C_1-C_6)$-alkyl;
  very particularly preferably H, F, Cl, O—$(C_1-C_6)$-alkyl, $(C_1-C_6)$-alkyl;
  in particular very particularly preferably H; and
Q a group

where the group

has the aforementioned meanings.

A further aspect of the present invention is thus compounds of the formula Ic

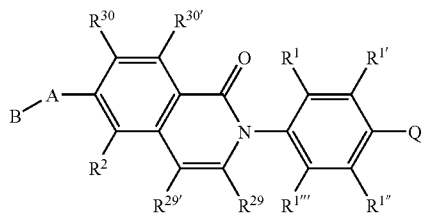

in which the radicals and groups in the compound of the formula Ic have the aforementioned meanings, where Q is a group of the formula

with the aforementioned meanings.

A very particularly preferred embodiment of the present invention are compounds in which the meanings are:
Y C(R29)=C(R29');
X C(R30)=C(R30');
Q

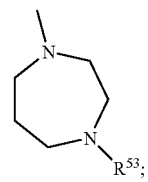

R53 H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, $(C(R58)(R59))_q$-R60.

A further very particularly preferred embodiment of the present invention are compounds in which the meanings are:
Y C(R29)=C(R29');
X C(R30)=C(R30');
Q saturated 6-11 membered azaspirocycle which comprises an element N(R53);
R53 H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, $(C(R58)(R59))_q$-R60.

A further very particularly preferred embodiment of the present invention are compounds in which the meanings are:
Y C(R29)=C(R29');
X C(R30)=C(R30');
Q saturated monocyclic 5-7-membered azacycle which comprises an element $C(R45)((CH_2)_o-N(R53)(R54))$;
R53, R54
  independently of one another H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, $(C(R58)(R59))_q$-R60; or R53 and R54 form together with the nitrogen atom to which they are bonded a 4 to 10-membered mono-, bi- or spirocyclic ring which, apart from the nitrogen atom, comprises 0 to 3 additional heteroatoms selected from the group of N, O and S and may additionally be substituted by one or more of the following substituents: F, Cl, Br, $CF_3$, O—$(C_1-C_8)$-alkyl, $(C_1-C_6)$-alkyl, CO(R64), oxo, OH, $(C_1-C_4)$-alkoxy-$(C_1-C_4)$-alkyl, hydroxy-$(C_1-C_4)$-alkyl, N(R67)CO(R68), $SO_2(C_1-C_6)$-alkyl.

A further very particularly preferred embodiment of the present invention are compounds in which the meanings are:
Y C(R27)(R27')C(R28)(R28');
X C(R30)=C(R30');
Q

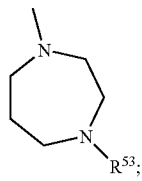

R53 $(C_1-C_4)$-alkoxy-$(C_1-C_4)$-alkyl, $(C(R58)(R59))_q$-R60;
R58, 59
  independently of one another H, OH;
q, r independently of one another 1, 2, 3, 4;
R60, R63
  independently of one another F, O—$(C_1-C_6)$-alkyl, N(R74)CO$(C_1-C_6)$-alkyl, $SO_2(C_1-C_6)$-alkyl, 3-12 membered mono-, bi- or spirocyclic ring which comprises 0 to 3 additional heteroatoms from the group of O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, hydroxy-$(C_1-C_4)$-alkyl, $(C_1-C_6)$-alkyl, $(C_2-C_6)$-alkenyl, $(C_2-C_6)$-alkynyl and $SO_2(C_1-C_6)$-alkyl.

A further very particularly preferred embodiment of the present invention are compounds in which the meanings are:
Y C(R27)(R27')C(R28)(R28');
X C(R30)=C(R30');
Q saturated 6-11 membered spirocycle which comprises an element N(R53);
R53 $(C_1-C_4)$-alkoxy-$(C_1-C_4)$-alkyl, $(C(R58)(R59))_q$-R60;
R58, 59
  independently of one another H, OH;
q 1, 2, 3, 4;
R60, R63
  independently of one another F, O—$(C_1-C_6)$-alkyl, N(R74)CO$(C_1-C_6)$-alkyl, $SO_2(C_1-C_6)$-alkyl, 3-12 membered mono-, bi- or spirocyclic ring which comprises 0 to 3 additional heteroatoms from the group of O and S, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, hydroxy-$(C_1-C_4)$-alkyl, $(C_1-C_6)$-alkyl, $(C_2-C_6)$-alkenyl, $(C_2-C_6)$-alkynyl and $SO_2(C_1-C_6)$-alkyl.

A further very particularly preferred embodiment of the present invention are compounds in which the meanings are:
Y C(R27)(R27')C(R28)(R28');
X C(R30)=C(R30');
Q saturated monocyclic 5-7-membered azacycle which comprises an element $C(R45)((CH_2)_o-N(R53)(R54))$;
R45 H;
o 0, 1, 2;
R53 H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, $(C(R58)(R59))_q$-R60;
R54 $(C(R58)(R59))_q$-R60, $(C_1-C_4)$-alkoxy-$(C_1-C_4)$-alkyl, CO(R57), CO(C(R61)(R62))$_r$-R63;
R58, 59 independently of one another H, OH;
q 1, 2, 3, 4;
R60, R63
  independently of one another F, O—$(C_1-C_6)$-alkyl, N(R74)CO$(C_1-C_6)$-alkyl, $SO_2(C_1-C_6)$-alkyl, 3-12 membered mono-, bi- or spirocyclic ring which comprises no heteroatoms, and the 3-12 membered ring may comprise further substituents such as F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, hydroxy-$(C_1-C_4)$-alkyl, $(C_1-C_6)$-alkyl, $(C_2-C_6)$-alkenyl, $(C_2-C_6)$-alkynyl and $SO_2(C_1-C_6)$-alkyl.

A further very particularly preferred embodiment of the present invention are compounds in which the meanings are:
Y C(R27)(R27')C(R28)(R28');
X C(R30)=C(R30');
Q saturated monocyclic 5-7-membered azacycle which comprises an element $C(R45)((CH_2)_o-N(R53)(R54))$;
R45 H;
o 0, 1, 2;
R53 H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, $(C(R58)(R59))_q$-R60;
R54 $(C(R58)(R59))_{q*}$-R60';
q* 0;
R60' $SO_2(C_1-C_6)$-alkyl, 3-12 membered mono-, bi- or spirocyclic ring which comprises no heteroatoms, and the 3-12 membered ring is substituted by one or more of the following substituents F, Cl, Br, OH, $CF_3$, $NO_2$, CN, $OCF_3$, oxo, O—$(C_1-C_6)$-alkyl, $(C_1-C_4)$-alkoxy-$(C_1-C_4)$-alkyl, hydroxy-$(C_1-C_4)$-alkyl, $(C_1-C_6)$-alkyl, $(C_2-C_6)$-alkenyl, $(C_2-C_6)$-alkynyl and $SO_2(C_1-C_6)$-alkyl.

A further very particularly preferred embodiment of the present invention are compounds in which the meanings are:
Y C(R27)(R27')C(R28)(R28');
X C(R30)=C(R30');
Q saturated monocyclic 5-7-membered azacycle which comprises an element $C(R45)((CH_2)_o-N(R53)(R54))$;
R45 H;
o 0, 1, 2;
R53 and R54 form together with the nitrogen atom to which they are bonded a 5 to 6-membered monocyclic ring which, apart from the nitrogen atom, comprises 0 to 3 additional heteroatoms selected from the group of N, O and S and is substituted by one or more of the following substituents: F, Cl, Br, $CF_3$, O—$(C_1$-$C_8)$-alkyl, $(C_1$-$C_6)$-alkyl, CO(R64), oxo, OH, $(C_1$-$C_4)$-alkoxy-$(C_1$-$C_4)$-alkyl, hydroxy-$(C_1$-$C_4)$-alkyl, N(R67)CO(R68), $SO_2$ $(C_1$-$C_6)$-alkyl.

A further very particularly preferred embodiment of the present invention are compounds in which the meanings are:
Y C(R27)(R27')C(R28)(R28');
X C(R30)=C(R30');
Q saturated monocyclic 5-7-membered azacycle which comprises an element C(R45)(($CH_2)_o$—N(R53)(R54));
o 0, 1, 2;
R53 and R54 form together with the nitrogen atom to which they are bonded a 4 or a 7-membered monocyclic ring which, apart from the nitrogen atom, comprises 0 to 3 additional heteroatoms selected from the group of N, O and S and may additional be substituted by one or more of the following substituents: F, Cl, Br, $CF_3$, O—$(C_1$-$C_8)$-alkyl, $(C_1$-$C_6)$-alkyl, CO(R64), oxo, OH, $(C_1$-$C_4)$-alkoxy-$(C_1$-$C_4)$-alkyl, hydroxy-$(C_1$-$C_4)$-alkyl, N(R67) CO(R68), $SO_2(C_1$-$C_6)$-alkyl.

A further very particularly preferred embodiment of the present invention are compounds in which the meanings are:
Y C(R27)(R27')C(R28)(R28');
X C(R30)=C(R30');
Q saturated monocyclic 5-7-membered azacycle which comprises an element C(R45)(($CH_2)_o$—N(R53)(R54));
R53 and R54 form together with the nitrogen atom to which they are bonded a 6 to 10-membered bi- or spirocyclic ring which, apart from the nitrogen atom, comprises 0 to 3 additional heteroatoms selected from the group of N, O and S and may additional be substituted by one or more of the following substituents: F, Cl, Br, $CF_3$, O—$(C_1$-$C_8)$-alkyl, $(C_1$-$C_6)$-alkyl, CO(R64), oxo, OH, $(C_1$-$C_4)$-alkoxy-$(C_1$-$C_4)$-alkyl, hydroxy-$(C_1$-$C_4)$-alkyl, N(R67)CO(R68), $SO_2(C_1$-$C_6)$-alkyl.

The compounds of the invention of the general formula I can be prepared in analogy to processes known to the skilled worker. Suitable processes for preparing the compounds of the invention of the general formula I are mentioned by way of example below (see in particular methods A, B, C, D, E, F, G, H, I, J, K, L, M, N, O, P, Q, R, S, T, U, V, W, X, Y, Z, AA, AB, AC, AD, AE, AF, AH, AI, AJ, AK, AL and schemes 1 to 5).

A novel reaction sequence for preparing the compounds of the invention of the general formula I includes the following steps:
i) dimetallation of aromatic carboxylic acids alkylated, preferably methylated, in the ortho position, to form a dianion, and trapping of the formed dianion with aldehydes or reagents which liberate aldehydes, such as paraformaldehyde, resulting in corresponding substituted aromatic carboxylic acids which have a hydroxyalkyl substituent in the position ortho to the carboxylic acid group, and where appropriate preparation of the corresponding bicyclic lactones from the substituted aromatic carboxylic acids which have a hydroxyalkyl substituent in the position ortho to the carboxylic acid group, by elimination of water;
ii) subsequent reaction of the substituted aromatic carboxylic acids which have a hydroxyalkyl substituent in the position ortho to the carboxylic acid group, or where appropriate of the corresponding bicyclic lactones, with a halogenating agent, resulting in the corresponding haloalkyl-substituted aroyl halides;
iii) subsequent reaction of the haloalkyl-substituted aroyl halides with primary aromatic amines, and subsequent cyclization of the resulting reaction products by addition of base to give pyridone-fused aromatic compounds; and
iv) where appropriate further reaction of the pyridone-fused aromatic compounds;
resulting in the compounds of the formula I.

Depending on the substitution pattern of the compounds of the general formula I, the desired compounds are obtained directly after the reaction in step iii), or a further reaction (step iv)) is necessary where appropriate in order to obtain the desired compounds of the general formula I. Suitable reaction conditions for carrying out the individual steps of the aforementioned process are known to the skilled worker.

Preferred embodiments of said steps, as well as the preparation of the starting substances employed in the steps, are known to the skilled worker below and mentioned by way of example in said schemes and methods, and examples.

This invention further relates to the use of compounds of the formula I and their pharmaceutical compositions as MCH receptor ligands. The MCH receptor ligands of the invention are particularly suitable as modulators of the activity of the MCH1R.

The role of MCH in regulating the energy balance has now been well documented (Qu, D. et al. Nature 1996, 380, 243-7; Shimada, M. et al. Nature 1998, 396, 670-4; Chen, Y et al. Endocrinology 2002, 143, 2469-77; Endocrinology 2003, 144, 4831-40; Review: G. Hervieu, Expert Opin. Ther. Targets 2003, 7, 495-511; Shi, Y., Peptides 2004, 25, 1605-11).

There are also indications that MCH antagonists can have a beneficial influence on centrally related disorders such as, for example, anxiety states, depressions (Borowsky, B. et al. Nature Medicine 2002, 8, 825-30; Review: G. Hervieu, Expert Opin. Ther. Targets 2003, 7, 495-511; Chaki, S. et al., Drug Dev. Res. 2005, 65, 278-290; Dyck, B., Drug Dev. Res. 2005, 65, 291-300).

Compounds of this type are particularly suitable for the treatment and/or prevention of
1. Obesity
2. Diabetes mellitus, especially type 2 diabetes, including the prevention of the sequelae associated therewith.
   Particular aspects in this connection are
   hyperglycemia,
   improvement in insulin resistance,
   improvement in glucose tolerance,
   protection of the pancreatic β cells
   prevention of macro- and microvascular disorders
3. Dyslipidemias and the sequelae thereof such as, for example, atherosclerosis, coronary heart disease, cerebrovascular disorders etc, especially those (but not restricted thereto) which are characterized by one or more of the following factors:
   high plasma triglyceride concentrations, high postprandial plasma triglyceride concentrations
   low HDL cholesterol concentration
4. Various other conditions which may be associated with the metabolic syndrome, such as:
   thromboses, hypercoagulable and prothrombotic stages (arterial and venous)
   high blood pressure
   heart failure such as, for example (but not restricted thereto), following myocardial infarction, hypertensive heart disease or cardiomyopathy
5. Psychiatric indications such as
   depressions
   anxiety states
   disturbances of the circadian rhythm
   affection disorders
   schizophrenia
   addictive disorders Formulations The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of body weight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contains a defined amount of at least one compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain at least one compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of at least one compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories. These can be produced by mixing at least one compound of the formula I with one or more conventional solid carriers, for example cocoa buffer, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished as selective MCH1R antagonists by their low toxicity, the small effect on metabolizing enzymes and their few side effects. In particular, preferred compounds of the invention are notable for low blockade of the hERG channel. In addition, preferred compounds of the formula I are noticeably soluble in aqueous systems and thus particularly suitable for pharmaceutical development. The pharmacological effect is moreover achieved in in vivo test models after oral administration from well-tolerated vehicles.

The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure.

Combinations with Other Medicaments

The compounds of the invention can be administered alone or in combination with one or more further pharmacologically active substances which have, for example, beneficial effects on metabolic disturbances or disorders frequently associated therewith. Examples of such medicaments are
1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients
8. active ingredients for the treatment of high blood pressure
9. active ingredients for the treatment of heart failure and
10. active ingredients for the treatment and/or prevention of complications caused by diabetes or associated with diabetes
11. active ingredients for the treatment of neurodegenerative conditions
12. active ingredients for the treatment of diseases of the central nervous system
13. active ingredients for the treatment of medicament-, nicotine- or alcohol addiction
14. pain killers They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Examples of active ingredients suitable for combination products are listed below:

All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or Apidra® (HMR 1964) or those described in WO2005005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1-derivatives such as, for example, exenatide, liraglutide or those which have been disclosed in WO98/08871 or WO2005027978 of Novo Nordisk A/S, in WO01/04156 of Zealand or in WO00/34331 of Beaufour-lpsen, Pramlintide Acetate (Symlin; Amylin Pharmaceuticals), and orally effective hypoglycemic active ingredients. The active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase
modulators of glucose transporter 4 (GLUT4),
inhibitors of glutamine-fructose-6-phosphate amidotransferase (GFAT),
GLP-1 agonists, potassium channel openers such as, for example, those which have been disclosed in WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption,
inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, at least one compound of the formula I is administered in combination with an HMGCoA reductase inhibitor such as simvastatin, fluvastatin, pravastatin, lovastatin, atorvastatin, cerivastatin, rosuvastatin or L-659699

In one embodiment of the invention, at least one compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO2005042692), MD-0727 (Microbia Inc., WO2005021497) or with compounds as described in WO2002066464 (Kotobuki Pharmaceutical Co. Ltd.), WO2005062824 (Merck & Co.) or WO2005061451 and WO2005061452 (AstraZeneca AB).

In one embodiment of the invention, at least one compound of the formula I is administered in combination with a PPAR gamma agonist such as, for example, rosiglitazone, pioglitazone, JTT-501, GI 262570, R-483 or CS-011 (rivoglitazone).

In one embodiment of the invention, at least one compound of the formula I is administered in combination with a PPAR alpha agonist such as, for example, GW9578, GW-590735, K-111, LY-674, KRP-101 or DRF-10945.

In one embodiment of the invention, at least one compound of the formula I is administered in combination with a mixed PPAR alpha/gamma agonist such as, for example, muraglitazar, tesaglitazar, naveglitazar, LY-510929, ONO-5129, E-3030 or as described in WO00/64888, WO00/64876, WO03/020269, WO20040758911 WO2004076402, WO2004075815, WO2004076447, WO2004076428, WO2004076401, WO2004076426, WO2004076427, WO2006018118, WO2006018115, und WO2006018116 or in J. P. Berger et al., TRENDS in Pharmacological Sciences 28(5), 244-251, 2005.

In one embodiment of the invention, at least one compound of the formula I is administered in combination with a PPAR delta agonist such as, for example, GW-501516 or as described in WO2005097762, WO2005097786, WO2005097763, und WO2006029699.

In one embodiment, at least one compound of the formula I is administered in combination with metaglidasen or with MBX-2044 or other partial PPAR gamma agonists/antagonists.

In one embodiment of the invention, at least one compound of the formula I is administered in combination with a fibrate such as, for example, fenofibrate, clofibrate or bezafibrate.

In one embodiment of the invention, at least one compound of the formula I is administered in combination with an MTP inhibitor such as, for example, implitapide, BMS-201038, R-103757 or those described in WO2005085226.

In one embodiment of the invention, at least one compound of the formula I is administered in combination with a CETP inhibitor such as, for example, torcetrapib or JTT-705.

In one embodiment of the invention, at least one compound of the formula I is administered in combination with a bile acid absorption inhibitor (see, for example, U.S. Pat. No. 6,245,744, U.S. Pat. No. 6,221,897 or WO0/61568), such as, for example, HMR 1741 or those as described in DE 10 2005 033099.1 and DE 10 2005 033100.9.

In one embodiment of the invention, at least one compound of the formula I is administered in combination with a polymeric bile acid adsorbent such as, for example, cholestyramine or colesevelam.

In one embodiment of the invention, at least one compound of the formula I is administered in combination with an LDL receptor inducer (see U.S. Pat. No. 6,342,512), such as, for example, HMR1171, HMR1586 or those as described in WO2005097738.

In one embodiment, at least one compound of the formula I is administered in combination with Omacor® (omega-3 fatty acids; highly concentrated ethyl esters of eicosapentaenoic acid and of docosahexaenoic acid).

In one embodiment of the invention, at least one compound of the formula I is administered in combination with an ACAT inhibitor such as, for example, avasimibe.

In one embodiment of the invention, at least one compound of the formula I is administered in combination with an antioxidant such as, for example, OPC-14117, probucol, tocopherol, ascorbic acid, β-carotene or selenium.

In one embodiment of the invention, at least one compound of the formula I is administered in combination with a vitamin such as, for example, vitamin B6 or vitamin B12.

In one embodiment of the invention, at least one compound of the formula I is administered in combination with a lipoprotein lipase modulator such as, for example, ibrolipim (NO-1886).

In one embodiment of the invention, at least one compound of the formula I is administered in combination with an ATP citrate lyase inhibitor such as, for example, SB-204990.

In one embodiment of the invention, at least one compound of the formula I is administered in combination with a squalene synthetase inhibitor such as, for example, BMS-188494 or as described in WO2005077907.

In one embodiment of the invention, at least one compound of the formula I is administered in combination with a lipoprotein (a) antagonist such as, for example, gemcabene (CI-027).

In one embodiment of the invention, at least one compound of the formula I is administered in combination with an HM74A receptor agonist such as, for example, nicotinic acid.

In one embodiment of the invention, at least one compound of the formula I is administered in combination with a lipase inhibitor such as, for example, orlistat or cetilistat (ATL-962).

In one embodiment, at least one compound of the formula I is administered in combination with insulin.

In one embodiment, at least one compound of the formula I is administered in combination with a sulfonylurea such as, for example, tolbutamide, glibenclamide, glipizide or glimepiride.

In one embodiment, at least one compound of the formula I is administered in combination with a biguanide such as, for example, metformin.

In another embodiment, at least one compound of the formula I is administered in combination with a meglitinide such as, for example, repaglinide or nateglinide.

In one embodiment, at least one compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, at least one compound of the formula I is administered in combination with an α-glucosidase inhibitor such as, for example, miglitol or acarbose. In one embodiment, at least one compound of the formula I is administered in combination with an active ingredient which acts on the ATP-dependent potassium channel of the beta cells, such as, for example, tolbutamide, glibenclamide, glipizide, glimepiride or repaglinide.

In one embodiment, at least one compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, at least one compound of the formula I is administered in combination with substances which influence hepatic glucose production, such as, for example an inhibitor of glycogen phosphorylase, such as, for example, PSN-357 or FR-258900 or those as described in WO2003084922, WO2004007455, WO2005073229-31 or WO2005067932.

In one embodiment, at least one compound of the formula I is administered in combination with glucagon receptor antagonists such as, for example, A-770077, NNC-25-2504 or as described in WO2004100875 or WO2005065680.

In one embodiment, at least one compound of the formula I is administered in combination with activators of glucokinase, such as, for example, RO-4389620, LY-2121260 (WO2004063179), PSN-105, PSN-110, GKA-50 or such as described in WO2004072031, WO2004072066, WO 05103021, WO 06016178, WO 00058293, WO 00183465, WO 00183478, WO 00185706, WO 00185707, WO 01044216, GB 02385328, WO 02008209, WO 02014312, WO 0246173, WO 0248106, DE 10259786, WO 03095438, U.S. Pat. No. 4,067,939, WO 04052869, EP 1532980, WO 03055482, WO 04002481, WO 05049019, WO 05066145, WO 05123132, WO 03080585, WO03097824, WO 04081001, WO 05063738, WO 05090332, WO 04063194, WO 01020327, WO 03000262, WO 03000267, WO 03015774, WO 04045614, WO 04046139, WO 05044801, WO 05054200, WO 05054233, WO 05056530, WO 05080359, WO 05080360 or WO 05121110.

In one embodiment, at least one compound of the formula I is administered in combination with an inhibitor of gluconeogenesis, such as, for example, FR-225654. In one embodiment, at least one compound of the formula I is administered in combination with inhibitors of fructose-1,6-bisphosphatase (FBPase), such as, for example, CS-917.

In one embodiment, at least one compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment, at least one compound of the formula I is administered in combination with inhibitors of glutamine-fructose-6-phosphate amidotransferase (GFAT), as are described for example in WO2004101528.

In one embodiment, at least one compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964X or as are described in WO2003074500, WO2003106456, WO200450658, WO2005058901, WO2005012312, WO2005012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment, at least one compound of the formula I is administered in combination with inhibitors of 11-beta-hydroxysteroid dehydrogenase 1 (11β-HSD1), such as, for example, BVT-2733 or those as are described for example in WO200190090-94, WO200343999, WO2004112782, WO200344000, WO200344009, WO2004112779, WO2004113310, WO2004103980, WO2004112784, WO 2003065983, WO2003104207, WO2003104208, WO2004106294, WO2004011410, WO2004033427, WO2004041264, WO2004037251, WO2004056744, WO2004065351, WO2004089367, WO2004089380, WO2004089470-71, WO2004089896, WO2005016877 or WO2005097759.

In one embodiment, at least one compound of the formula I is administered in combination with inhibitors of protein tyrosine phosphatase 1B (PTP1B), as are described for example in WO200119830-31, WO200117516, WO2004506446, WO2005012295, PCT/EP2005/005311, PCT/EP2005/005321, PCT/EP2005/007151, PCT/EP2005/ or DE 10 2004 060542.4.

In one embodiment, at least one compound of the formula I is administered in combination with modulators of the sodium-dependent glucose transporter 1 or 2 (SGLT1, SGLT2), such as, for example, KGA-2727, T-1095, SGL-0010, AVE 2268 and SAR 7226 or as are described for example in WO2004007517, WO200452903, WO200452902, WO2005121161, PCT/EP2005/005959, WO2005085237, JP2004359630 or by A. L. Handlon in Expert Opin. Ther. Patents (2005) 15(11), 1531-1540.

In one embodiment, at least one compound of the formula I is administered in combination with modulators of GPR40.

In one embodiment, at least one compound of the formula I is administered in combination with inhibitors of hormone-sensitive lipase (HSL) as described for example in WO1/17981, WO01/66531, WO2004035550, WO2005073199 or WO03/051842.

In one embodiment, at least one compound of the formula I is administered in combination with inhibitors of acetyl-CoA carboxylase (ACC), such as, for example, those as described in WO199946262, WO200372197, WO2003072197 or WO2005044814.

In one embodiment, at least one compound of the formula I is administered in combination with an inhibitor of phosphoenolpyruvate carboxykinase (PEPCK), such as, for example, those as described in WO2004074288.

In one embodiment, at least one compound of the formula I is administered in combination with an inhibitor of glycogen synthase kinase 3 beta (GSK-3 beta), as described for example in US2005222220, WO2005085230, WO2005111018, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727 or WO2004046117.

In one embodiment, at least one compound of the formula I is administered in combination with an inhibitor of protein kinase C beta (PKC beta), such as, for example, ruboxistaurin.

In one embodiment, at least one compound of the formula I is administered in combination with an endothelin A receptor antagonist such as, for example, avosentan (SPP-301).

In one embodiment, at least one compound of the formula I is administered in combination with inhibitors of "I-kappaB kinase" (IKK inhibitors), as are described for example in WO2001000610, WO2001030774, WO2004022553 or WO2005097129.

In one embodiment, at least one compound of the formula I is administered in combination with modulators of the glucocorticoid receptor, like those described for example in WO2005090336.

In a further embodiment, at least one compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists such as, for example, naphthalene-1-sulfonic acid {4-[(4-amino-quinazolin-2-ylamino)methyl]cyclohexylmethyl}amide hydrochloride (CGP 71683A); peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO2005080424;

cannabinoid receptor 1 antagonists (such as, for example, rimonabant, SR147778 or those as are described for example in EP 0656354, WO 00/15609, WO02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509 or WO2005077897);

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chloro-phenyl)-2-oxoethyl]amide; (WO 01/91752)) or LB53280, LB53279, LB53278 or THIQ, MB243, RY764, CHIR-785, PT-141 or those that are described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, EP1538159, WO2004072076 or WO2004072077;

orexin receptor antagonists (e.g. 1-(2-methylbenzoxazol-6-yl)-3-[1,5]naphthyridin-4-ylurea hydrochloride (SB-334867-A) or those as are described for example in WO200196302, WO200185693, WO2004085403 or WO2005075458);

histamine H3 receptor agonists (e.g. ABT-834, ABT-239, 3-cyclohexyl-1-(4,4-dimethyl-1,4,6,7-tetrahydroimidazo[4,5-c]pyridin-5-yl)propan-1-one oxalic acid salt (WO 00/63208) or those as are described in WO200064884, WO2005082893, FR2870846 WO2005037810, Celanire, S., et al. Drug Discovery Today 2005, 10, 1613-1627);

CRF antagonists (e.g. [2-methyl-9-(2,4,6-trimethylphenyl)-9H-1,3,9-triazafluoren-4-yl]dipropylamine (WO 00/66585));

CRF BP antagonists (e.g. urocortin);
urocortin agonists;
β3 agonists (such as, for example, 1-(4-chloro-3-methanesulfonylmethylphenyl)-2-[2-(2,3-dimethyl-1H-indol-6-yloxy)ethylamino]ethanol hydrochloride (WO 01/83451));
MSH (melanocyte-stimulating hormone) agonists;
MCH (melanin-concentrating hormone) receptor antagonists (such as, for example, NGD-4715, AMG-076, NBI-845, A-761, A-665798, A-798, ATC-0175, T-226296, T-71, GW-803430 or compounds such as are described in WO2003/15769, WO2005085200, WO2005019240, WO2004011438, WO2004012648, WO2003015769, WO2004072025, WO2005070898, WO2005070925, WO2004039780, WO2003033476, WO2002006245, WO2002002744, WO2003004027 or FR2868780);
CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180); serotonin reuptake inhibitors (e.g. dexfenfluramine);
mixed serotoninergic and noradrenergic compounds (e.g. WO 00/71549);
5-HT receptor agonists, e.g. 1-(3-ethylbenzofuran-7-yl)piperazine oxalic acid salt (WO 01/09111);
5-HT2C receptor agonists (such as, for example, APD-356, BVT-933 or those as are described in WO200077010, WO20077001-02, WO2005019180, WO2003064423, WO200242304 or WO2005082859);
5-HT6 receptor antagonists as are described for example in WO2005058858;
bombesin receptor agonists (BRS-3 agonists);
galanin receptor antagonists;
growth hormone (e.g. human growth hormone or AOD-9604);

growth hormone-releasing compounds (tertiary butyl 6-benzyloxy-1-(2-diisopropyl-aminoethylcarbamoyl)-3,4-dihydro-1H-isoquinoline-2-carboxylate (WO 01/85695));
growth hormone secretagogue receptor antagonists (ghrelin antagonists) such as, for example, A-778193 or those as are described in WO2005030734;
TRH agonists (see, for example, EP 0 462 884);
uncoupling protein 2 or 3 modulators;
leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);
DA agonists (bromocriptine or Doprexin);
lipase/amylase inhibitors (like those described for example in WO 00/40569);
inhibitors of diacylglycerol O-acyltransferases (DGATs) as described for example in US2004/0224997, WO2004094618, WO200058491, WO2005044250, WO2005072740, JP2005206492 or WO2005013907;
inhibitors of fatty acid synthase (FAS) such as, for example, C75 or those as described in WO2004005277;
oxyntomodulin;
oleoyl-estrone;
or thyroid hormone receptor agonists such as, for example: KB-2115 or those as described in WO20058279, WO200172692, WO200194293, WO2003084915, WO2004018421 or WO2005092316.

In one embodiment, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindole or phentermine.

In one embodiment, at least one compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main. Combination with Caromax® is possible in one preparation or by separate administration of compounds of the formula I and Caromax®. Caromax® can in this connection also be administered in the form of food products such as, for example, in bakery products or muesli bars.

In one embodiment, at least one compound of the formula I is administered in combination with PDE (Phosphodiesterase) inhibitors such as, for example, described in WO2003/077949 or WO2005012485.

In one embodiment, at least one compound of the formula I is administered in combination with NAR-1 (Nicotinic acid receptor) agonists such as for example described in WO2004094429.

In one embodiment, at least one compound of the formula I is administered in combination with CB2 (Cannabinoid receptor 2) agonists such as for example described in US2005/143448.

In one embodiment, at least one compound of the formula I is administered in combination with H1 (Histamine receptor 1) agonists such as for example described in WO2005101979.

In one embodiment, at least one compound of the formula I is administered in combination with Bupropion, such as for example described in WO2006017504.

In one embodiment, at least one compound of the formula I is administered in combination with Opiate receptor-antagonists such as for example described in WO2005107806 or WO2004094429.

In one embodiment, at least one compound of the formula I is administered in combination with inhibitors of the neutral Endopeptidase such as for example described in WO200202513, WO2002/06492, WO 2002040008, WO2002040022 or WO2002047670.

In one embodiment, at least one compound of the formula I is administered in combination with NPY (Neuropeptide Y) modulators such as for example described in WO2002047670.

In one embodiment, at least one compound of the formula I is administered in combination with a inhibitor of the sodium/hydrogen replacement protein such as described for example in WO2003092694.

In one embodiment, at least one compound of the formula I is administered in combination with modulators of the glucocorticoid receptor such as for example described in WO2005090336.

In one embodiment, at least one compound of the formula I is administered in combination with nicotine receptor-agonists such as for example described in WO2004094429.

In one embodiment, at least one compound of the formula I is administered in combination with NRIs (Norepinephrine reuptake inhibitor) such as for example described in WO2002053140.

In one embodiment, at least one compound of the formula I is administered in combination with MOA (E-beta-Methoxyacrylate), such as for example segeline, or such as for example described in WO2002053140.

In one embodiment, at least one compound of the formula I is administered in combination with an antithrombotic active ingredient such as for example Clopidogrel.

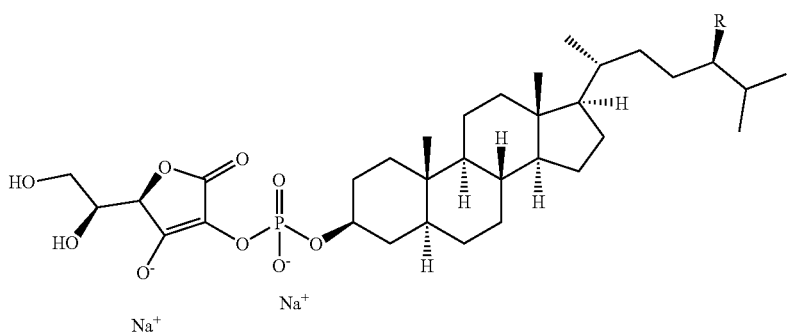

FM-VP4

R = CH$_3$⁻, CH$_2$—CH$_3$

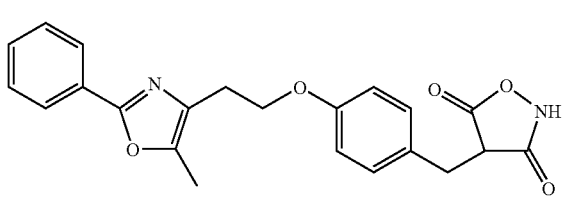

JTT-501

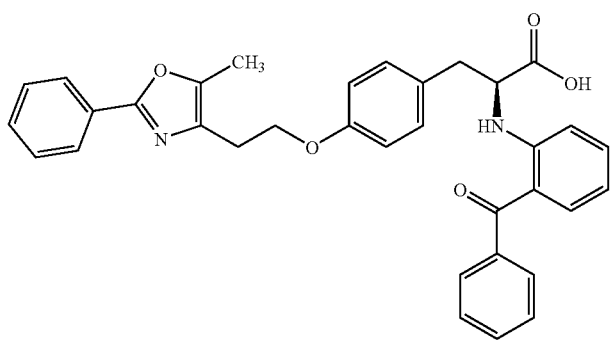

GI 262570

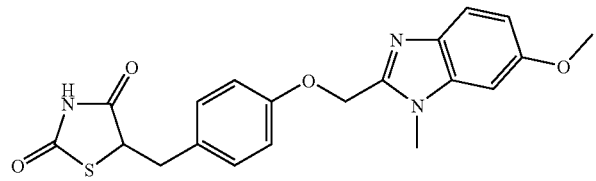
CS-011
rivoglitazone
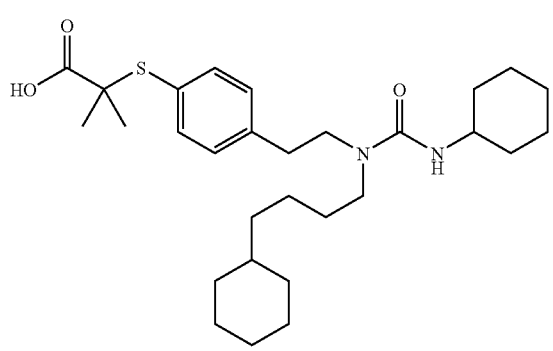
GW-9578
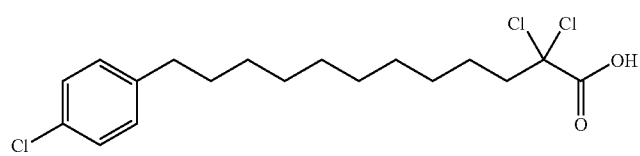
K-111
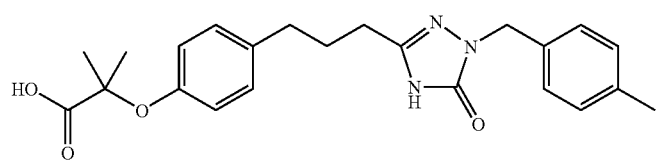
LY-674
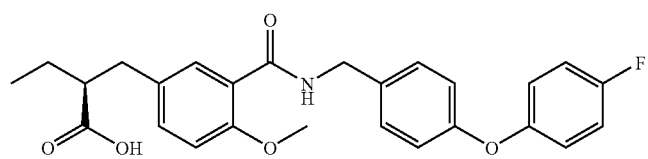
KRP-101
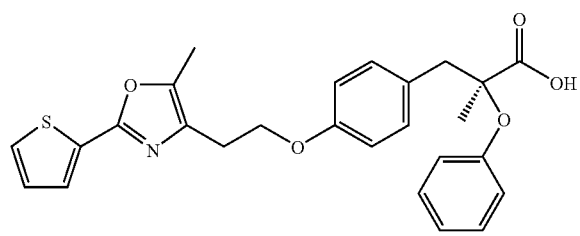
LY-510929
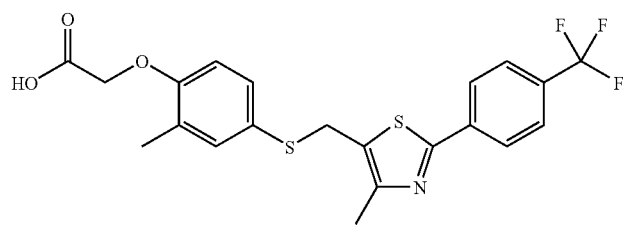
GW-501516

-continued
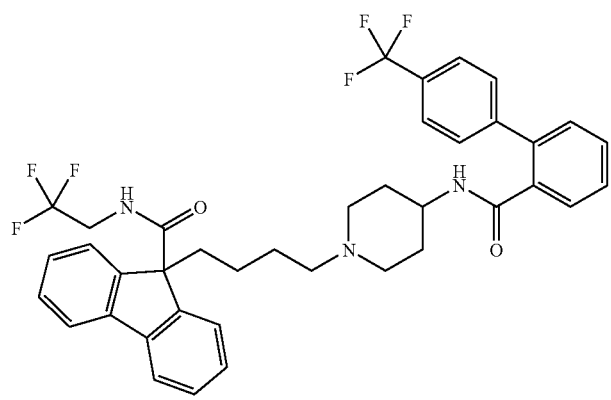
BMS-201038
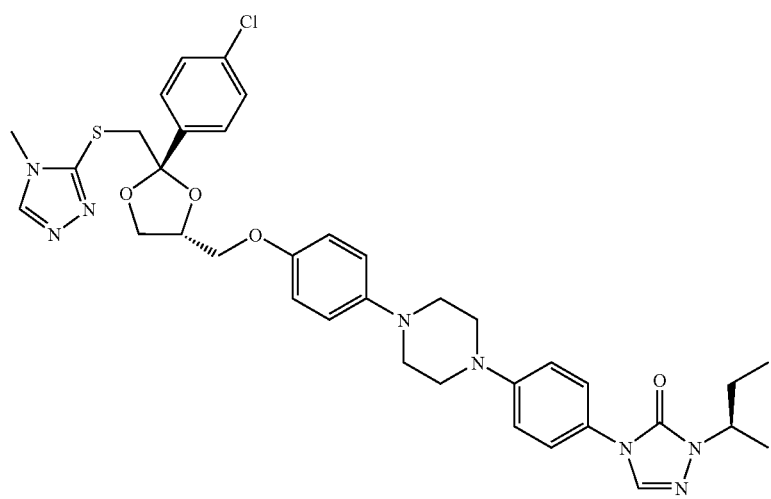
R-103757
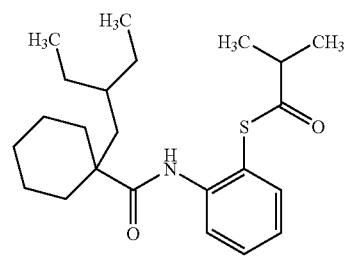
JTT-705
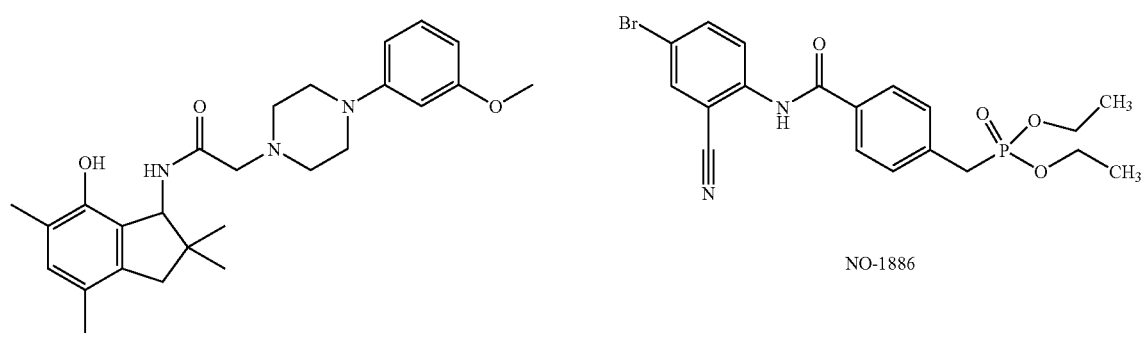
OPC-14117
NO-1886
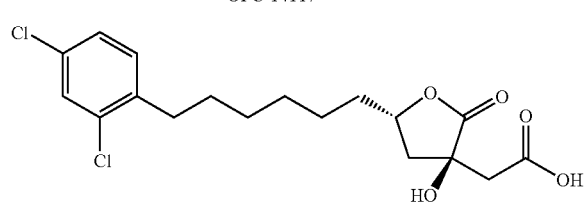
SB-204990

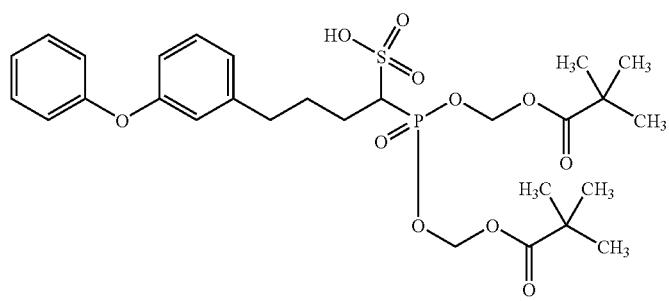
BMS-188494
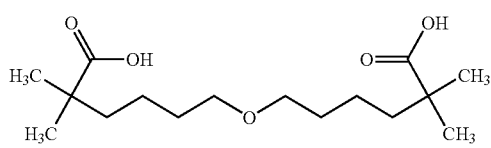
CI-1027
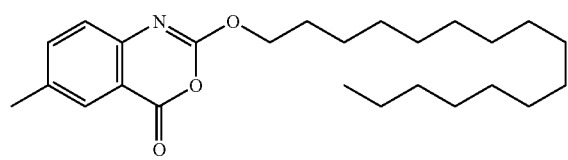
ATL-962
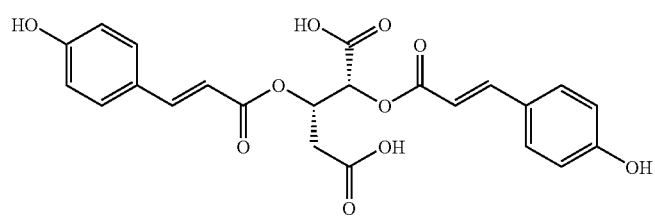
FR-258900
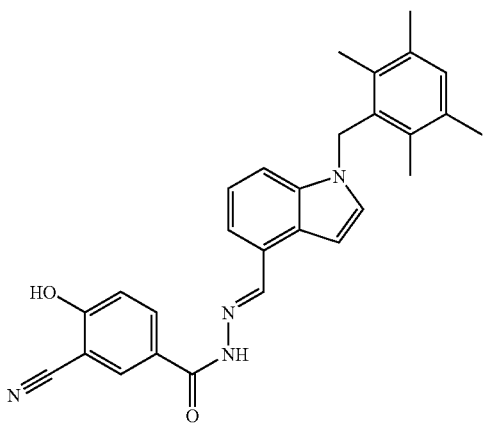
NNC-25-2504
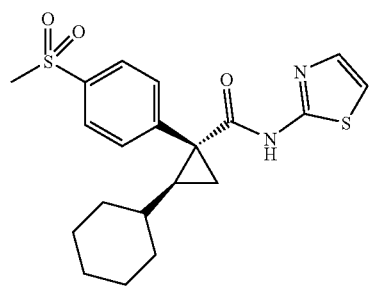
LY-2121260
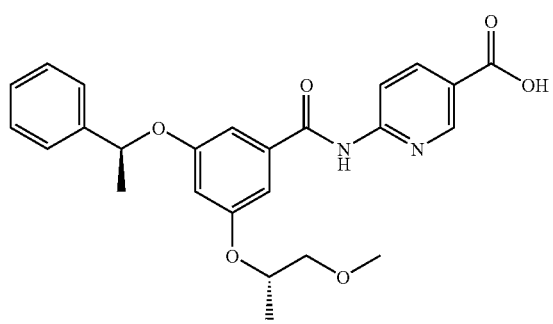
GKA-50

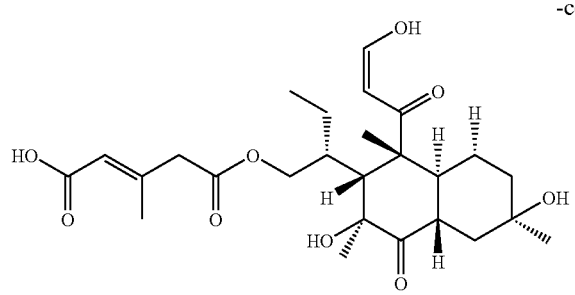
FR-225654
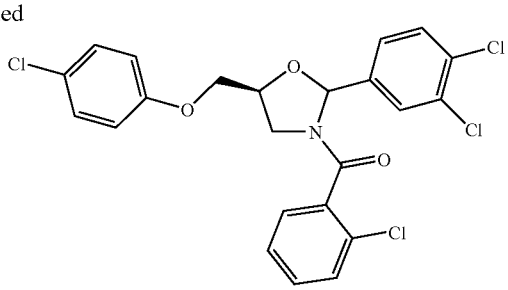
KST-48
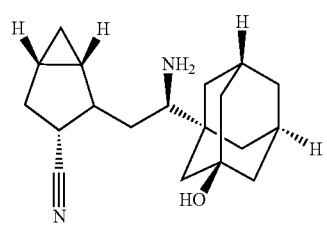
BMS-477118
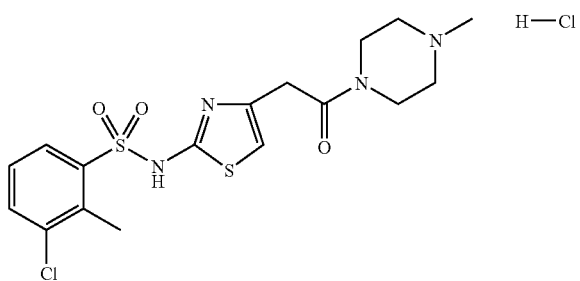
BVT-2733
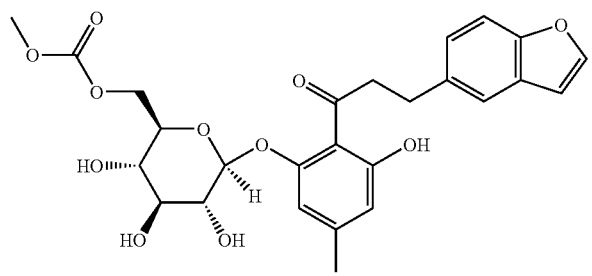
T-1095
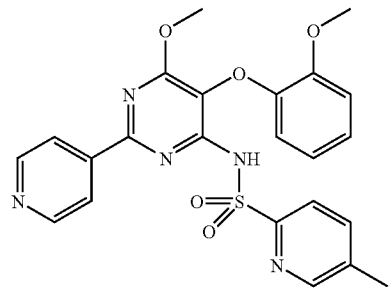
SPP-301
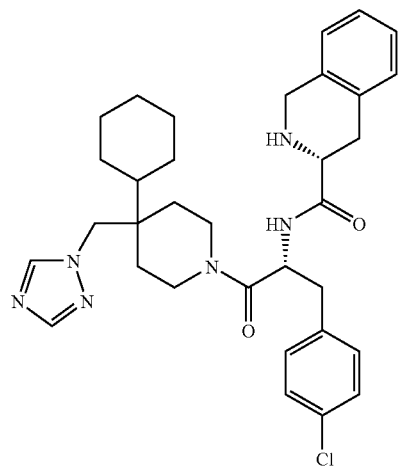
THIQ
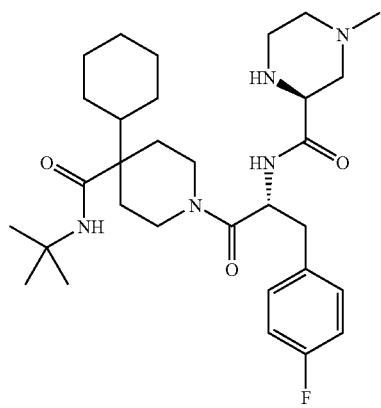
MB243

-continued
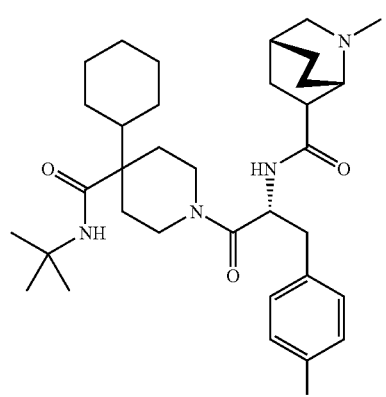
RY764
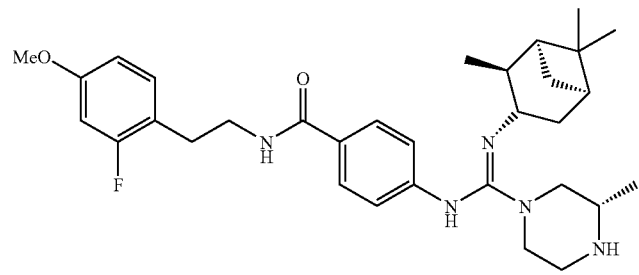
CHIR-785
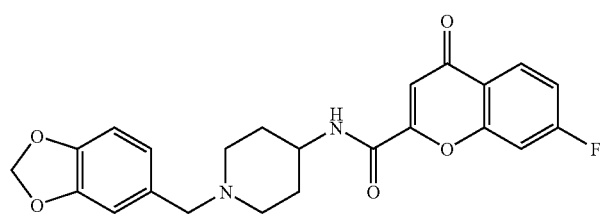
A-761
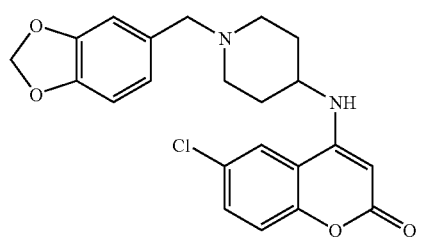
A-665798
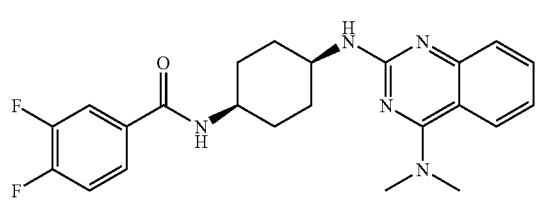
ATC-0175
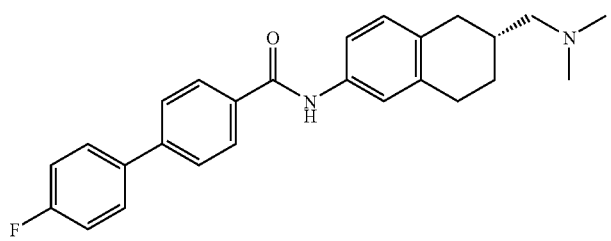
T-226296
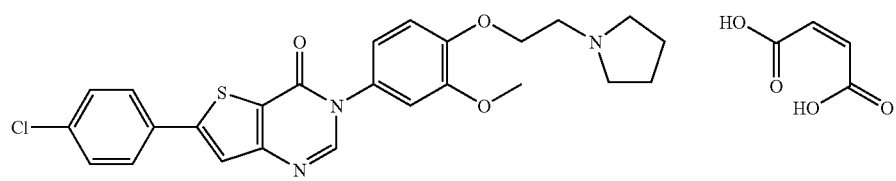
GW-803430

-continued
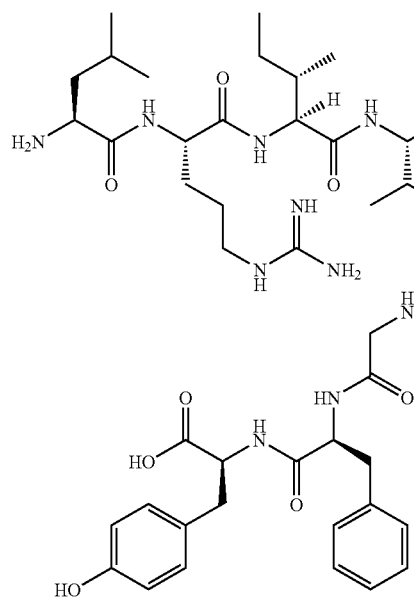
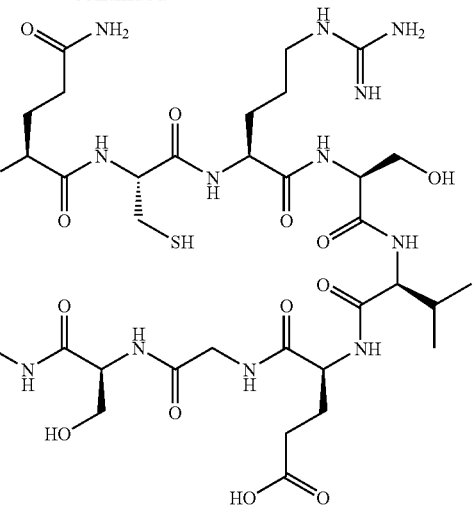
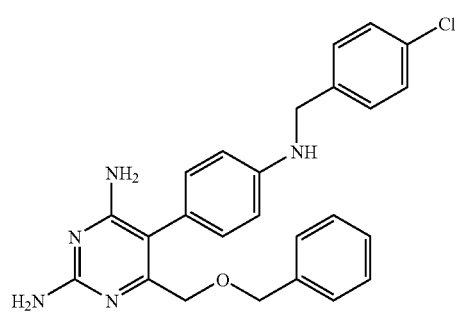
AOD-9604
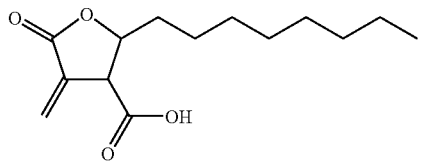
A-778193
C75
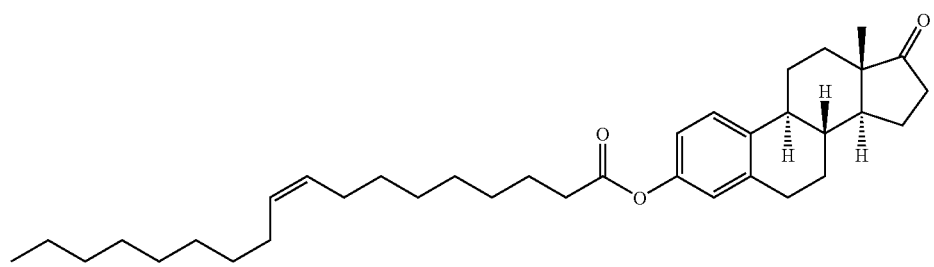
Oleoyl-estrone
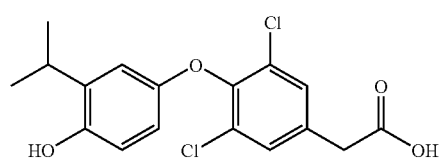
KB-2115

In one embodiment, the compounds of the formula I are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula I are administered in combination with medicaments having an antiinflammatory effect.

In one embodiment, the compounds of the formula I are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

Pharmacological Testing

Test Models

Suitability of the compounds of the invention as active pharmaceutical ingredient can be tested by means of various test models. Descriptions are given of such test models by way of example below.

Influence on the MCH receptor in vitro; determination of functional IC50 values of MCH1R antagonists Cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 276, 13554-13562, 2001). A difference from the reference was, however, the use of the plasmid pEAK8 from EDGE Biosystems (USA) for the construction of the expression vector. The host used for the transfection was a transformed HEK cell line named "PEAK Stable Cells" (likewise from EDGE Biosystems). Functional measurements of the cellular calcium flux after addition of agonist (MCH) in the presence of ligand of the invention took place with the aid of the FLIPR apparatus from Molecular Devices (USA), using protocols of the apparatus manufacturer. The compounds of the invention show a significant inhibition (>30%) of the signal induced by the agonist at a concentration of 100 µM, preferably at 10 µM, particularly preferably at 1 µM, very particularly preferably at 100 nM and even more particularly preferably at 10 nM.

Besides the functional activity it is also possible to determine the affinity for the MCH1R according to Audinot et al. (Br. J. Pharmacol. 2001, 133, 371-378). Preferred compounds of the invention show an IC50 of less than 1 µM, particularly preferably of less than 100 nM, very particularly preferably of less than 10 nM and even more particularly preferably of less than 1 nM.

Milk Intake by Female NMRI Mice

The anorectic effect is tested on female NMRI mice. After withdrawal of feed for 24 hours, the test substance is administered intraperitoneally or preferably orally by gavage. The animals are housed singly with free access to drinking water and, 30 minutes after administration of product, are offered condensed milk. The condensed milk consumption is determined every half hour for 7 hours, and the general condition of the animals is observed. The measured milk consumption is compared with the vehicle-treated control animals.

The vehicle itself has no influence on feed intake. Preferred tolerated vehicles for the administration are, for example, hydroxyethylcellulose (0.5% in water) or Solutol HS15 (5% in hydroxyethylcellulose (0.5% in water)).

Feed and Water Intake of Female Wistar Rats

As alternative to testing the anorectic effect on NMRI mice, it is also possible analogously to use female Wistar rats weighing about 220-250 g. The animals are accustomed to the experimental environment before the start of the study. In one embodiment, the animals have free access to feed and water up to the start of the experiment. In another embodiment, access of the animals to feed is withdrawn 24 hours before the administration. For the investigation of the test substance, the animals are housed singly with free access to feed and water. Feed intake and water intake are measured continuously every 30 minutes over a period of 22 hours using a computer-assisted system (TSE Drinking & Feeding Monitor). The measured feed and water consumption is compared with the vehicle-treated control animals.

Body Weight Gain of Diet-Induced Obese and Standard-Fed Mice

For these investigations, male C57BL6J mice 5 weeks old (weaning age) are accustomed either to a standard maintenance diet or to a high-fat and thus high-energy diet. After 12 weeks, the normally fed, slim mice have typically reached a body weight of about 25 g, and the fat-fed mice have reached one of about 35 g. The animals are housed singly, and the feed intake and water intake are determined individually. There is free access to feed and water during the experiment.

The test substances are administered orally in a vehicle and always tested by comparison with the vehicle control which is included in parallel. The vehicle itself has no influence on the feed intake, and is normally hydroxyethylcellulose (0.5% in water) or Solutol HS15 (5% in hydroxyethylcellulose (0.5% in water)). A corresponding group of slim mice is kept for each group of diet-induced obese mice.

Feed consumption and water consumption are determined each day in the first week and then once per week by reweighing the offered feed and water, respectively. The body weight is measured each day.

Blood samples are taken before and at the end of the treatment in order to determine serum parameters which provide information about changes in intermediary metabolism. It is additionally possible to determine the body fat content on the living animal by means of an impedance measurement (TO-BEC method).

Micronucleus Test (In Vitro)

The aim of the micronucleus test (in vitro) is to examine whether a test compound has the potential to elicit the formation of micronuclei (small membrane-bound DNA fragments) in various cell lines or primary cultures, with or without metabolic activation by S9 liver homogenate. The test system allows differentiation between the clastogenic and aneugenic potential of a test compound by an immunochemical labeling of the kinetochores or by staining the DNA fragments by the FISH (fluorescence in situ hybridization) method.

Brief description: The cells are treated in a 96-well microtiter plate with the test compound. The treatment time is typically 3 hours with metabolic activation or 24 hours without metabolic activation. Twenty four hours after the end of the treatment, the cells are isolated, fixed and stained. The cytotoxicity of the test compound is assessed according to the relative cell growth expressed as percentage growth or taking account of the doubling time as population doubling compared with the negative control. The highest test concentration should show not less than 30% surviving cells, or should be the concentration at which a precipitate of the test compound is observed. Duplicate determinations should be carried out with each test concentration. An accurate detailed description of the experiment is to be found in Kirsch-Volders et al. (Mutation Res. 2003, 540, 153-163).

Evaluation: The structural or numerical chromosomal damage is reported as the increase in the number of cells with micronuclei in an ensemble of 1000 cells at three analyzable test concentrations. The test is regarded as positive in the following cases:
 a) the increase in the number of cells with micronuclei is significant by comparison with the negative control (solvent or untreated), or
 b) the number of micronuclei is increased to a biologically relevant extent, concentration-dependently by comparison with the negative control.

A positive control must show a clear statistically significant effect by comparison with the negative control.

Preferred compounds of the invention are negative in the micronucleus test.

AMES II Test

The aim of the AMES II test is to examine whether a test compound has mutagenic potential.

Brief description: A mixed bacterial strain (mixed strains, 6 different *Salmonella typhimurium* strains with in each case a missence point mutation in the histidine operon) and the *Salmonella typhimurium* strain TA98 for detecting frame shift mutations is treated in a 384-well microtiter plate with various concentrations of the test substance with or without metabolic activation through addition of S9 liver homogenate (accurate descriptions of the experiment are to be found in the literature: P. Gee, D. M. Maron, B. N. Ames; Proc. Natl. Acad. Sci. USA 1994, 91, 11606 and Flückiger-Isler et al.; Mutation Res. 2004, 558, 181 and cit. lit.).

Mutagenic test compounds cause back-mutations and thus restore the functionality of endogenous histidine biosynthesis. Mutated bacteria are thus able to divide and expand to bacterial colonies.

Evaluation: If there is enhanced bacterial growth owing to mutations of the bacteria, then enzymes are digested in the growth medium. As a result, the pH in the medium falls and the color of the added indicator (bromocresol purple) changes from pale violet to yellow. The test is regarded as positive if the number of wells in which a color change is observed per concentration increases significantly by comparison with the control.

Preferred compounds of the invention are negative in the AMES II test.

Cytotoxicity Tests a) LDH Release

The aim of the test for LDH (lactate dehydrogenase) release is to examine whether a compound damages the integrity of the cell wall and may thus cause cell death.

Brief description: The LDH activity which enters the cell supernatant from the cytosol due to cell damage is measured by colorimetry. The cells are treated with the test compound. Fifty microliters of the culture supernatant are removed and mixed with the reaction solution (LDH kit, Roche, Mannheim) in accordance with the manufacturer's information. LDH catalyzes the conversion of lactate into pyruvate. During this, NAD+ is reduced to NADH/H+. The latter in turn reduces, under the influence of the added diaphorase, a likewise added yellow tetrazolium salt to the red formazan.

Evaluation: The formazan is quantified by measuring the absorption at 492 nM (e.g. with TECAN SPECTRAFluor Plus).

Preferred compounds of the invention show no significant increase in LDH activity at concentrations below 10 µM. Particularly preferred compounds show no increase below a concentration of 50 µM. Even further preferred compounds show no increase below a concentration of 250 µM.

b) Intracellular ATP Content

The aim of the test is to determine the total intracellular ATP content, which is a measure of the energy level and thus the vitality of a cell.

Brief description: 100 µL of cell culture medium are mixed in a well of a microtiter plate with 100 µL of the CellTiter-Glo reagent (following the manufacturer's instructions: Promega Technical Bulletin No. 228, CellTiter-Glo Luminescent Cell Viability Assay). The cultures are shaken at room temperature for 2 minutes and then incubated for 10 minutes until the luminescence signal has stabilized.

Evaluation: The luminescence is recorded, integrating over one second (e.g. with TECAN SPECTRAFluor Plus).

Preferred compounds of the invention show no significant reduction in the ATP levels at concentrations below 10 µM. Particularly preferred compounds show no reduction below a concentration of 50 µM. Even further preferred compounds show no reduction below a concentration of 250 µM.

c) Neutral Red Uptake

The aim of the test is to measure the uptake of neutral red (NR) into the lysosomes/endosomes and vacuoles of living cells, which is a quantitative measure of the number and vitality of the cells.

Brief description: The cells are washed with 150 µL of a preheated phosphate buffer solution (PBS) and incubated with 100 µL of the NR medium at 37° C. in a humidified atmosphere with 7.5% carbon dioxide for 3 hours. After the incubation, the NR medium is removed and the cells are washed with 150 µL of PBS. Removal of the PBS is followed by addition of exactly 150 µL of an ethanol/glacial acetic acid solution. After shaking for 10 minutes, the dye is extracted from the cells to give a homogeneous dye solution. An exact description of the test is to be found in the literature (E. Borenfreund, J. A. Puerner, Toxicol. Lett. 1985, 24(2-3), 119-124).

Evaluation: The absorption of the dye solution is determined at 540 nM using a microtiter plate reader as difference from the absorption of the ethanol/glacial acetic acid solution.

HERG Channel Blockade

The aim of the test is to determine the concentration range in which the test compound blocks the cardiac hERG channel. Blockade of the hERG channel, which is responsible for the Ikr current in the human heart, is associated with potentially fatal arrhythmias. For expression of the cDNA encoding the hERG channel it was cloned into the pcDNA3 vector (Invitrogen). Chinese hamster oocytes (CHO, American Type Culture Collection, Rockville, Md.) were transfected using lipofectamine (GIBCO/BRL, Grand Island, N.Y.) with the hERG cDNA and selected using G418 (GIBCO/BRL, Grand Island, N.Y.; 500 µg/mL). CHO cells with stable expression of the hERG channel were cultured on a HAM F-12 medium which was supplemented with 10% native bovine serum, 1× penicillin/streptomycin and 500 µg/mL G418 in an atmosphere of 95% air/5% carbon dioxide.

The cells selected for the patch clamp experiment are seeded on a plastic support 18-24 hours before the experiment. HERG channel currents are recorded at room temperature by the whole-cell variant of the patch clamp technique using an Axopatch 200B amplifier (Axon Instruments, Foster City, Calif.). The electrodes (3-6 megaohms resistance) are prepared from TW150F glass capillaries (World Precision Instruments, Sarasota, Fla.) and filled with the pipette solution (120 mM potassium aspartate, 20 mM KCl, 4 mM $Na_2ATP$, 5 mM HEPES, 1 mM $MgCl_2$; adjusted to pH 7.2 with KOH). The hERG channel currents are induced by a positive voltage pulse (20 mV) followed by a negative pulse (−40 mV) and are recorded for later analysis. As soon as the hERG channel current of the cell flushed with the control solution (130 mM NaCl, 5 mM KCl, 2.8 mM NaOAc, 1 mM MgCl2, mM HEPES; 10 mM glucose, 1 mM CaCl2; adjusted to pH 7.4 with NaOH) is stable, the cell is perfused with the test compound dissolved in the above control solution (by dilution of a 10 or 100 mM DMSO solution of the test compound so that the DMSO content is no more than 0.1%). The current is followed continuously until no further changes occur. The same procedure is repeated with increasing concentrations of the test compound. The maximum amplitude of the hERG current is measured in picoAmperes (pA) for each concentration and for each cell. The maximum amplitude in pA for each concentration of the test compound is compared with that of the pure control solution in the same cell and calculated as % of the control value.

Evaluation: The test compound is tested at various concentrations in 3-5 CHO cells which express hERG channel. The IC50 is obtained by use of nonlinear least squares regression (GraphPAD Software, San Diego, Calif.).

General Selectivity

In order to minimize the risk of unwanted side effects, it is desirable to keep the nonselective effect on biologically important functional units (e.g. receptors, ion channels and enzymes; for lists, see, for example, Whitebread, S. et al.; Drug Discovery Today 2005, 10, 1421-33 and Rolland, C. et al.; J. Med. Chem. 2005, 48, 6563-6574) by an active pharmaceutical ingredient as small as possible. General selectivity tests in a large number of in vitro test systems can be carried out by various specialized services (e.g. Cerep, Panlabs).

The compounds of the invention of the formula I exhibit, as selective MCH1R antagonists, selectivity factors of at least 30, preferably of 100, more preferably of 300 and even more preferably of 1000 vis à vis the affinity to other proteins. Examples of such proteins are serotonin receptor subtypes (e.g. the 5-HT2a receptor), muscarine receptor subtypes (e.g. the M1 receptor), adrenergic receptor subtypes (e.g. AR alpha1a), sodium and calcium channels (e.g. the L-type calcium channel).

Solubility in Aqueous Systems

Adequate solubility of a substance in aqueous solvent systems is an important prerequisite for a (reproducible) pharmacological effect. Solubilities in aqueous systems can be determined by various methods. Suitable examples of solution precipitation methods ("kinetic solubility") and methods which investigate the dissolution of a solid sample until an equilibrium is set up ("thermodynamic solubility").

a) Kinetic Solubility

A DMSO solution of the test compound (2.5 mM; 0.5 μL) is pipetted into 200 μL of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 μM using a nephelometer (e.g. Nephelostar Galaxy, BMG Labtech). The concentration of the test compound in the aqueous test solution is then raised to a theoretical 12.5 μM by adding further DMSO solution (2.5 mM; 0.5 μL), and the turbidity measurement is repeated. Further additions of DMSO solutions (1 μL, 2.5 mM; 0.5 μL, 10 mM; then 9×1 μL, 10 mM resulting in theoretical concentrations of 25 μM, 50 μM, 100 μM, 150 μM, 200 μM, 250 μM, 300 μM, 350 μM, 400 μM, 450 μM and 500 μM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values <6.25 μM, 6.25-500 μM and >500 μM.

Preferred compounds of the invention show a kinetic solubility in phosphate buffer (pH 7.4) of at least 12.5 μM; more preferably of at least 50 μM and even more preferably of at least 250 μM.

b) Thermodynamic Solubility

The integrated UV absorption from HPLC UV measurement of serial dilutions of the test compound in DMSO (500 μM, 100 μM, 50 μM, 10 μM and 1 μM) shows a linear correlation with the concentration in a calibration line. The test compound (500 μg) is shaken together with the aqueous test solution (250 μL) in a closed vessel (capacity: 1.5 mL) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration lines and stated as solubility of the test compound in the respective aqueous test solution.

Examples of aqueous test solutions are deionized water or aqueous phosphate buffer with various pH values (e.g. pH 1.2; pH 4.0; pH 6.8; pH 7.4; pH 9.0) which can be prepared from the commercial solution (phosphate buffered saline, 10×, Sigma) by dilution and adjustment with phosphoric acid or sodium hydroxide solution by standard methods. Preferred compounds of the invention show a solubility in phosphate buffer (pH 7.4) of at least 12.5 μM; more preferably of at least 50 μM and even more preferably of at least 250 μM.

Permeability

The test for permeability is carried out in CACO-2/TC7 cells which have been cultured (DMEM/Glutamax I/Gibco with high glucose content, HEPES 25 mM, 1% NEAA, 10% FBS, 40 μg/mL gentamycin; 37° C. surrounding temperature; 95% humidity- and 10% CO2 content) on Becton Dickinson filters (24-well, uncoated) for 21 days. The permeability is tested at a concentration of 20 μM for the test compound (1% DMSO in HBSS) with a pH gradient (apical: pH 6.5 and 0.5% BSA; basolateral: pH 7.4 and 5% BSA). Analysis takes place by means of LCMS/MS. Further descriptions of the test system and references for the experimental procedure are to be found in Balimane, P. V.; Drug Discovery Today 2005, 10(5), 335-343.

Inhibition of CYP Enzymes

The inhibition of CYP enzymes is determined on recombinant enzymes (obtained from Becton Dickinson) and fluorescent substrates (BD/Gentest) as recommended by the manufacturer (see Website http://www.bdbiosciences.com). Further descriptions of the test system and references for the experimental procedure are to be found in Zlokarnik, G.; Drug Discovery Today 2005, 10(21), 1443-1450.

Metabolic Stability

The metabolic stability is determined by incubating the test compound (5 µM) with microsomal liver fractions (1 mg/mL protein with 0.1% w/v BSA; 1 mM NADPH, 0.5% DMSO) at 37° C. Analysis at an incubation time of 0 and 20 minutes takes place by means of LCMS/MS. Further descriptions of the test system and references for the experimental procedure are to be found in Plant, N.; Drug Discovery Today 2004, 9(7), 328-336 and Lau, Y. Y. et al.; Pharmaceutical Res. 2002, 19(11), 1606-1610.

EXAMPLES

The examples and methods of production given below are for the purpose of explaining the invention, but without limiting it. The symbol R in following schemes represents the variables B-A and R' the variables R1, R1', R1'', R1''' und Q.

The compounds according to the invention of Formula I can be produced using reactions that are known in principle. Thus, isoquinolones for example can be produced according to the method described by Alvarez, M. et al., Science of Synthesis 2005, 15, 839-906. A novel reaction sequence (Scheme 1) for the production of isoquinolones comprises first submitting substituted derivatives of benzoic acid to an ortho-metallation and capturing the dianion that forms with e.g. methyl iodide (Method C2). The 2-methyl-benzoic acids thus obtained can be metallated twice more and this time the dianion is captured with e.g. paraformaldehyde (Method C1). Reaction of the 2-(2-hydroxyethyl)-benzoic acids, or of the bicyclic lactones resulting from them by acid-catalyzed intramolecular dehydration, with thionyl chloride yields 2-(2-chloroethyl)-benzoyl chlorides as main intermediate (Method B). These are cyclized to the desired isoquinolones by reaction with primary (aromatic) amines and then addition of strong bases (e.g. sodium hydride or potassium tert.-butylate) to the reaction mixture (Method A).

Scheme 1

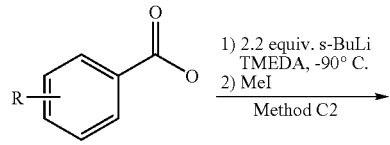

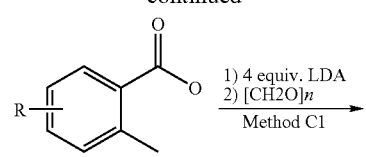

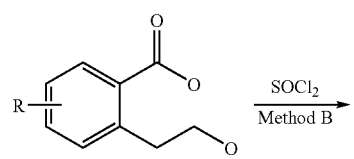

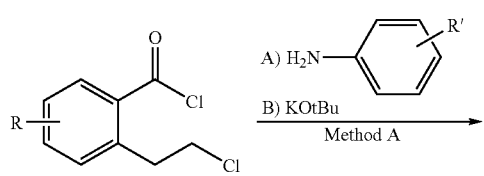

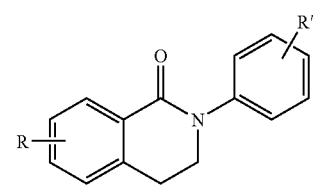

Alternatively isoquinolones can be obtained from 2-(2-hydroxyethyl)-benzoic acids by the routes shown in Scheme 1a. Treating the 2-(2-hydroxyethyl)-benzoic acids with acid produces the corresponding isochromanones, which can be treated for example with N-bromosuccinimide (NBS) to effect benzylic bromination, and can then be reacted to the corresponding isochromenone by treatment for example with triethylamine. Trimethylaluminum-catalyzed opening of the isochromanones with aromatic amines leads to 2-(2-hydroxyethyl)benzanilides (Method AG), which on the one hand can be converted to dihydroisoquinolones by transfer of the alcohol function to a leaving group (e.g. mesylate) and then treatment with a base. Furthermore, the 2-(2-hydroxyethyl)benzanilides can first be oxidized with oxidizing agents such as the Dess-Martin reagent and then reacted to isoquinolones by treatment with acid (Method AF). Isochromenones can also be converted directly to isoquinolones by means of trimethylaluminum after treatment with acid (Method AJ). Furthermore isoquinolinones can be converted to dihydroisoquinolinones by hydrogenation.

Schema 1a

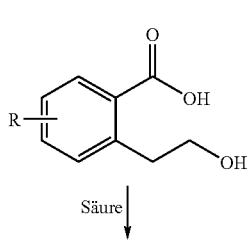

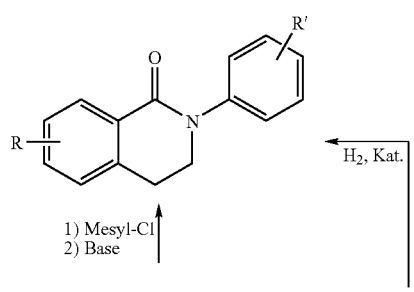

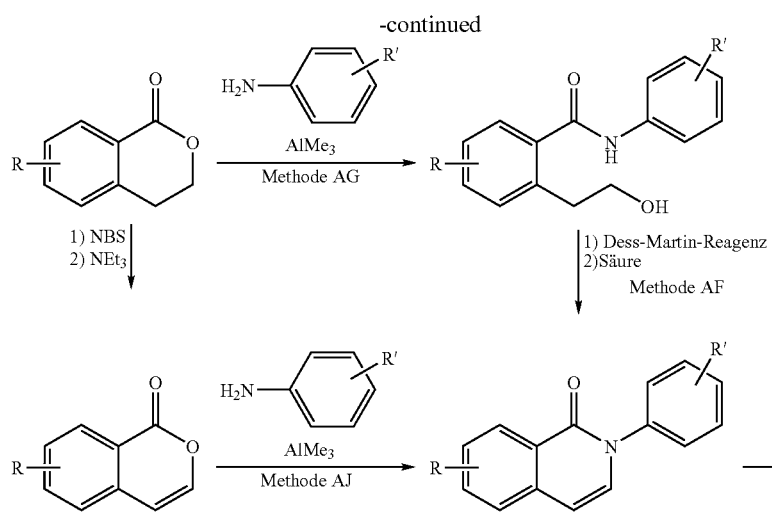

In a further variant for the synthesis of isoquinolones (Scheme 1b), 2-methyl-benzoic acids can be reacted with aromatic amines first to 2-methyl-benzanilides according to one of the many methods of amide linkage (for example via the acid chloride or TOTU-mediated; Method P). These can then be doubly deprotonated with a strong base (for example lithium 2,2,6,6-tetramethyl piperidide (LTMP)) and reacted with acylating reagents (for example N-formylmorpholine or N-methoxy-N-methyl-acetamides). Then treatment with acid produces the desired isoquinolones (Method Q).

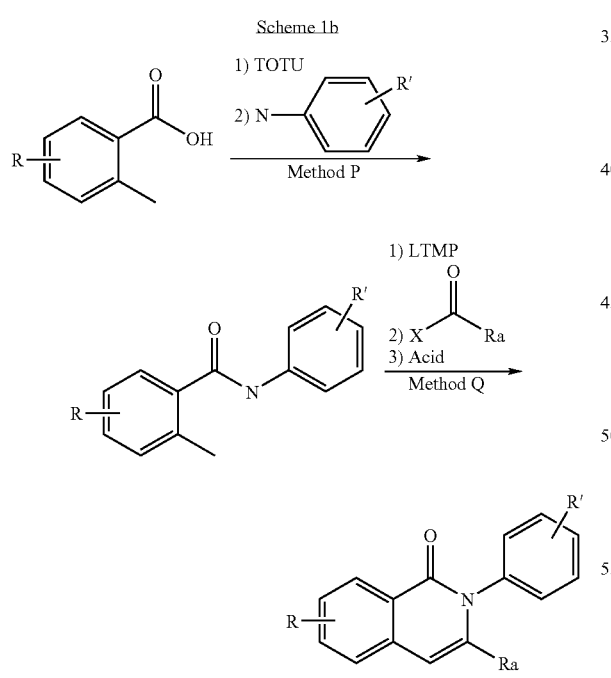

In another novel variant for the synthesis of isoquinolones, 3-hydroxy-isochroman-1-one, which can also be in the form of 2-(2-oxo-ethyl)-benzoic acids, can be reacted at elevated temperature with aromatic amines (Scheme 1c; Method AK). 3-Hydroxy-isochroman-1-one can be obtained for example by oxidation of corresponding precursors, which contain the indane skeleton.

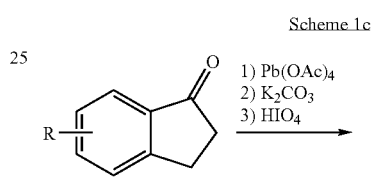
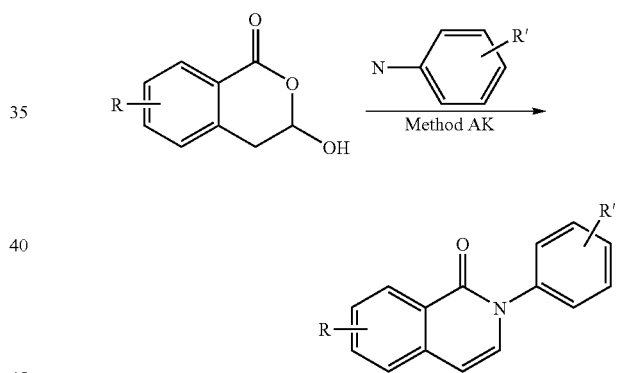

The necessary substituted aromatic amines can be obtained by nucleophilic substitution with aza cycles (Method E) on suitable fluoro-nitrobenzenes and then reduction of the nitro group (Methods D or F) (Scheme 2). In this case PG is (also a cleavable group) a group that is generally unreactive with respect to the conditions of methods E, F or D. Examples include alkyl groups and carbamates.

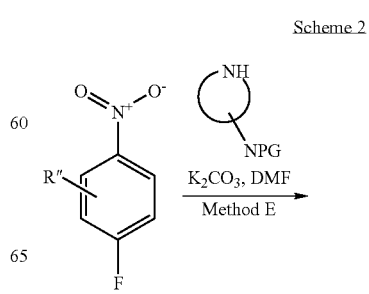

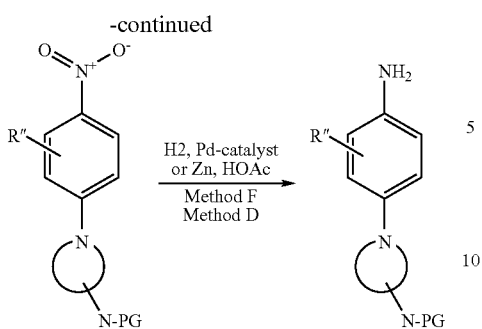

As a variant of the aza cycles, it is also possible to carry out transition metal-mediated aminations on the corresponding halogen-substituted isoquinolinones (Scheme 2a, Method R or R1).

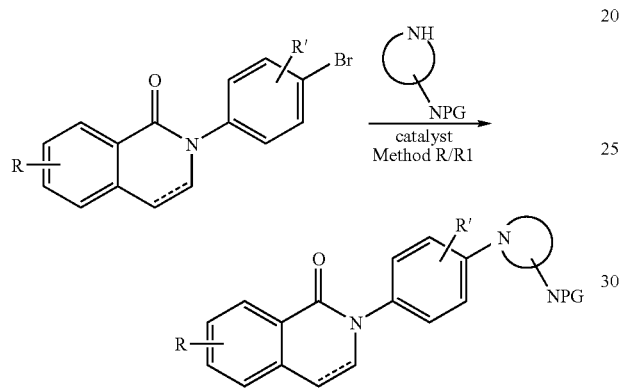

The N-PG group can be modified in various ways by known methods (see e.g. Scheme 3). Carbamate alkylation (Method I) followed by carbamate cleavage (Method H) may be mentioned as an example. Compounds obtained by carbamate cleavage with a basic N—H group react with a great many electrophiles (e.g. vinyl sulfone; Method G) or in the sense of a reductive alkylation (Method J).

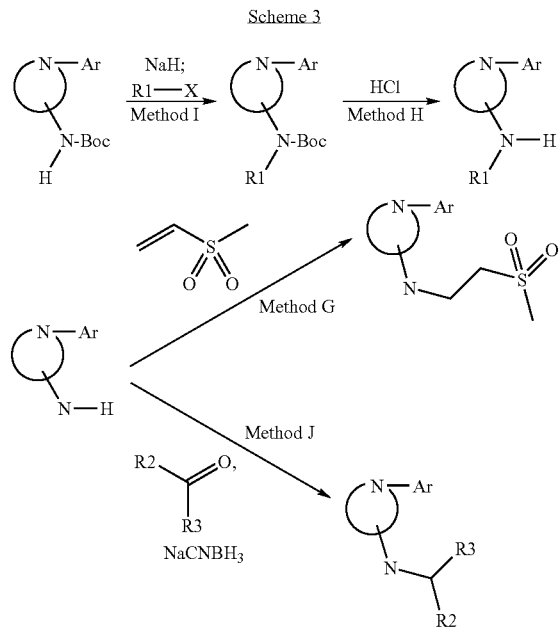

Other options for attachment of N-substituents by simple alkylation (Method X) or by alkylation with epoxides (Method U) are shown in Scheme 3a.

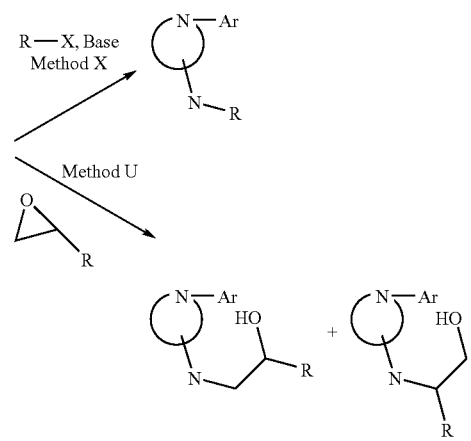

Yet another novel possibility is reductive amination of an azacyclyl-carbonyl compound with various amines (Scheme 3b; method J1). Enantiomeric mixtures that form can if necessary be separated by chiral-phase chromatography.

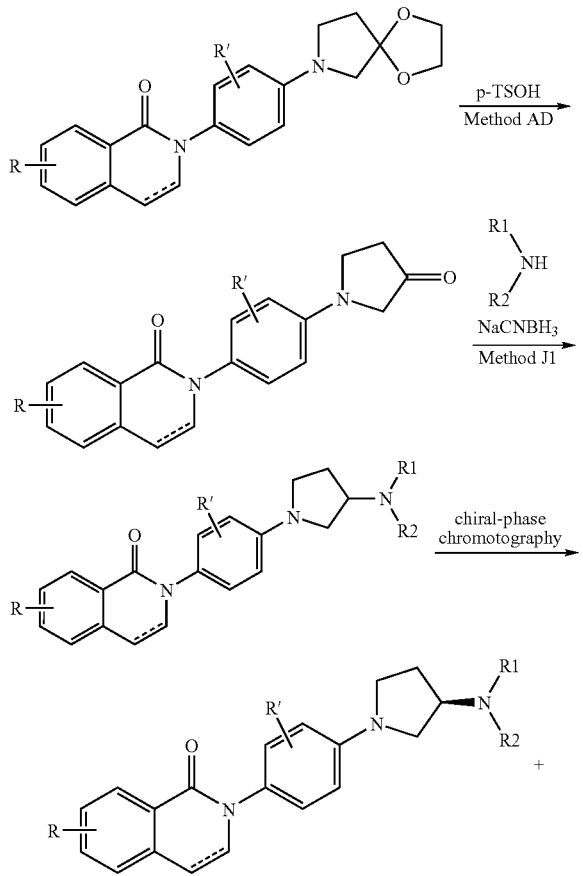

-continued

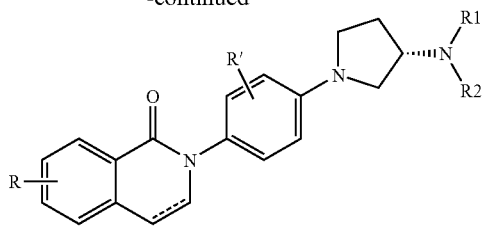

Another possible variant of substitution on the dihydroisoquinolinone skeleton is, among others, modification of functional groups (Scheme 4). For example, ether can be cleaved (Method L) and the OH group obtained can be reacted with various alkylating agents (Method K). After converting the OH group to a trifluoromethane sulfonate, ordinary substitution reactions can be carried out by nucleophiles without (e.g. Method N) or with transition-metal catalysts (Methods M and O).

Alternatively, according to Scheme 4a, hydroxy-isoquinolinones can be functionalized by reaction with electrophiles Ar—X, which are accessible for nucleophilic aromatic substitution (Method AB). Electrophiles such as epoxides (Method T) and alcohols, which were activated under Mitsunobu conditions (Method Y), are equally suitable. Trifluoromethane sulfonates also offer further possible variants. For example, after palladium-catalyzed alkoxylation and saponification of the ester thus obtained, a carboxylic acid is formed, which can be converted for example by Method P to the corresponding amides. The trifluoromethane sulfonate group can also be exchanged for amines and amides under transition-metal catalysis (Method R).

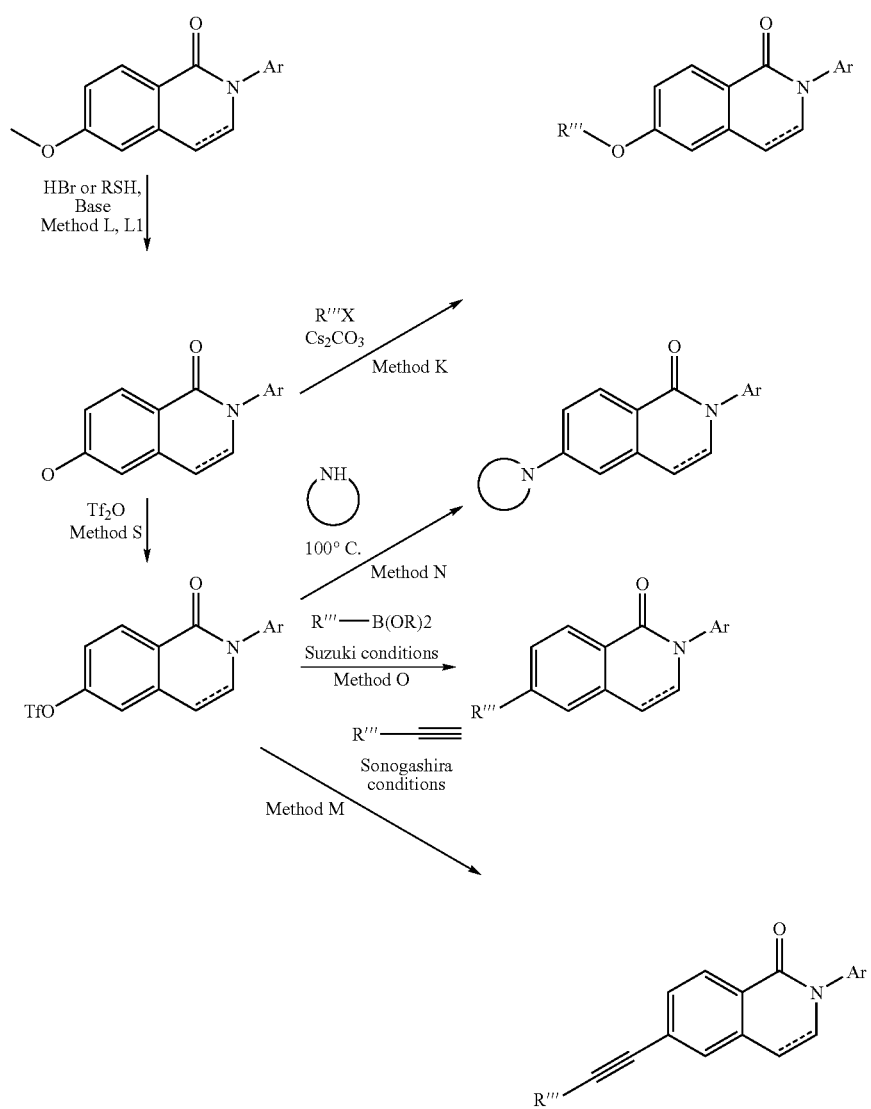

Scheme 4

Scheme 4a

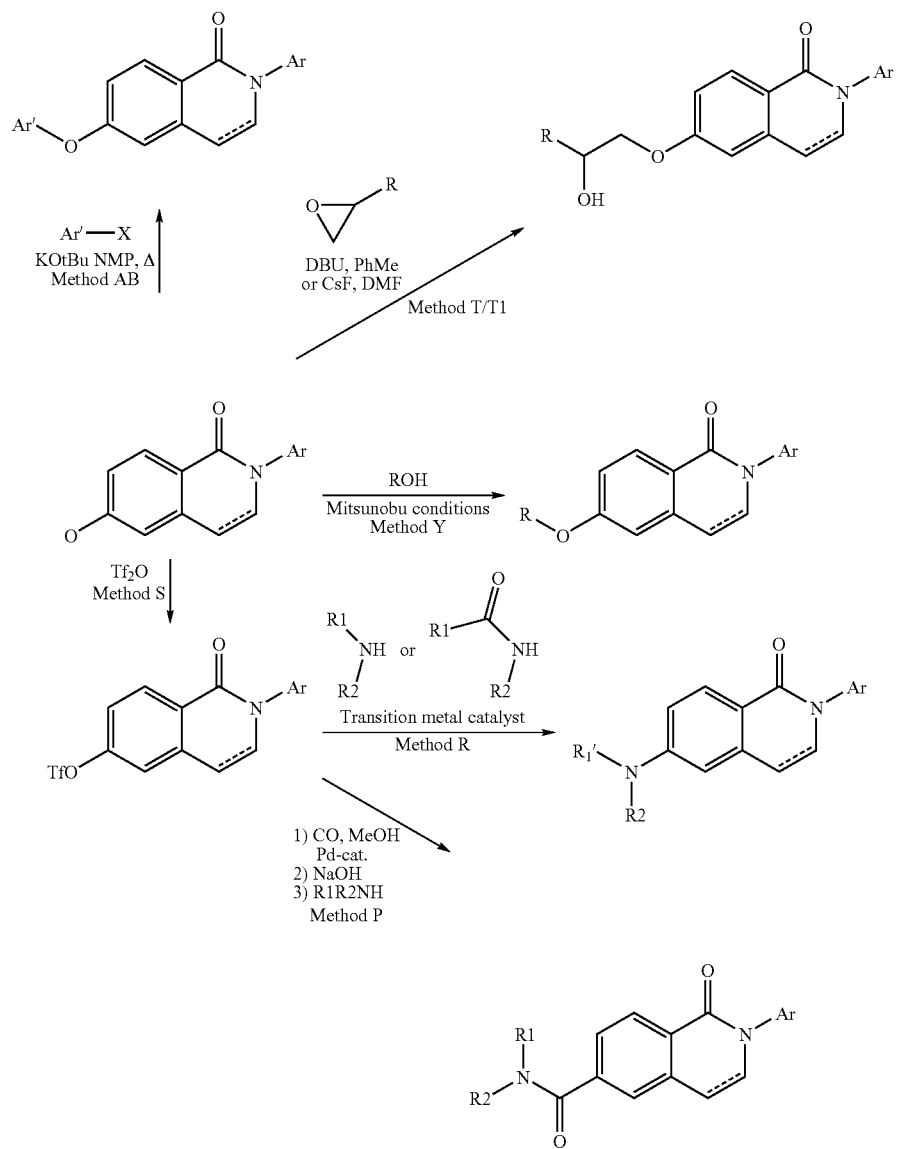

Descriptions of the general methods used can be found for example in the following places:
Method A, B, C1, C2, D, E in Example 1;
Method F, G and H according to Table 1;
Method I in Example 13;
Method J/J1 in Example 15/253;
Method K/K1 in Example 17/253;
Method L/L1 in Example 17/270;
Method N in Example 24;
Method M in Example 27;
Method O in Example 37;
Method P in Example 46;
Method Q in Example 66;
Method R/R1 in Example 90/340;
Method S in Example 24;
Method T/T1 in Example 141/274;
Method U, V, W and X according to Table 11;
Method Y according to Example 212;
Method Z according to Example 230;
Method AA according to Example 235;
Method AB according to Example 237;
Method AC, AD and AE in Example 253;
Method AF and AG in Example 288;
Method AH/AH1 according to Table 15/in Example 338;
Method AI according to Table 19;
Method AJ in Example 322;
Method AK in Example 357.
Method AL in Example 358.

General Explanations a) Mode of Drawing the Structural Formulae

Only non-hydrogen atoms are depicted for clarity in the structural formulae of the given examples.

b) Salt Forms

Many of the compounds of the invention are bases and can form salts with appropriately strong acids. The compounds can in particular be in the form of hydrotrifluoroacetates after purification by HPLC chromatography using a mobile phase containing trifluoroacetic acid. These can be converted into the free bases shown by simple treatment of a solution of the salts for example with sodium carbonate solution.

c) Units of the Characterizing Data

The unit of the indicated molecular weights is "g/mol". Peaks observed in the mass spectrum are stated as integral quotient of the molar molecular ion mass and the charge of the molecular ion (m/z).

Example 1

6-Butoxy-2-[3-chloro-4-(3-dimethylaminopyrrolidin-1-yl)phenyl]-3,4-dihydro-2H-isoquinolin-1-one

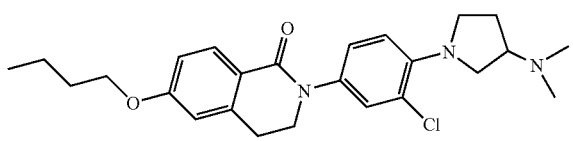 [SMILES: CCCCOc1ccc2c(c1)CCN(c1ccc(N3CCC(N(C)C)C3)c(Cl)c1)C2=O]

Method A

A solution of [1-(4-amino-2-chlorophenyl)pyrrolidin-3-yl]dimethylamine (98 mg) in THF (3 mL) was added dropwise to a solution of 4-butoxy-2-(2-chloroethyl)benzoyl chloride (100 mg) in THF (4 mL). Sodium hydride (55% in oil; 40 mg) was added to the resulting suspension and heated at 60° C. for 3 hours. An alternative possibility is also to employ potassium tert-butoxide as base at room temperature. After cooling, the precipitate was removed by filtration and the filtrate was concentrated. The residue was purified by preparative HPLC. The product with the molecular weight of 442.01 (C25H32ClN3O2) was obtained in this way; MS (ESI): 442 (M+H+).

Method B

4-Butoxy-2-(2-chloroethyl)benzoyl chloride

Thionyl chloride (5 g) was cooled to −10° C., and 4-butoxy-2-(2-hydroxyethyl)benzoic acid (1.0 g) was added in portions so that the internal temperature did not rise above −3° C. After 20 minutes at 0° C., the mixture was heated to reflux for 4 hours. Volatiles were removed in a rotary evaporator, and the residue was mixed twice with toluene (20 mL) and reevaporated. The resulting oil was reacted further without further purification.

Method C1

4-Butoxy-2-(2-hydroxyethyl)benzoic acid

A solution of 4-butoxy-2-methylbenzoic acid (2.5 g) in THF (15 mL) was added dropwise to a solution of LDA (freshly prepared from diisopropylamine (4.86 g) and n-butyllithium (32 mL; 1.5 M in hexane)) in THF (50 mL) at −78° C. After 10 minutes, paraformaldehyde (1.44 g) was added, and the mixture was allowed slowly to warm to room temperature. After 4 hours, water (10 mL) was added, and the volatile organic constituents were removed in a rotary evaporator. The residue was partitioned between water and diethyl ether. The aqueous phase was mixed with dichloromethane and cautiously acidified with hydrochloric acid at 0° C. Concentration of the organic phase afforded the desired product with the molecular weight of 238.29 (C13H18O4); MS (ESI): 239 (M+H+).

Method C2

4-Butoxy-2-methylbenzoic acid

A mixture of 4-butoxybenzoic acid (10 g), N,N,N',N'-tetramethylethylenediamine (13.2 g) and THF (75 mL) was cooled to −90° C., and sec-butyllithium (81 mL; 1.4 M in hexane) was added over the course of 30 minutes. After a further 30 minutes, the mixture was warmed to −78° C., and a solution of methyl iodide (12.8 mL) in THF (10 mL) was added dropwise. The reaction solution was allowed to warm to room temperature and the mixture was hydrolyzed with water and extracted with ethyl acetate. The organic phase was dried over magnesium sulfate and concentrated. The residue was purified by chromatography on silica gel. The product with the molecular weight of 208.26 (C12H16O3) was obtained in this way; MS (ESI): 209 (M+H+).

Method D

[1-(4-Amino-2-chlorophenyl)pyrrolidin-3-yl]dimethylamine

Zinc powder (3.0 g) was added in portions to a solution of [1-(2-chloro-4-nitrophenyl)-pyrrolidin-3-yl]dimethylamine (1.9 g) in glacial acetic acid (50 mL) cooled to 0° C. After the addition was complete, the mixture was stirred at room temperature for 30 minutes and then insolubles were filtered off with suction. The filtrate was concentrated in a rotary evaporator, and the residue was partitioned between sodium hydroxide solution and ethyl acetate. The organic phase was dried over magnesium sulfate and concentrated. The product with the molecular weight of 239.75 (C12H18ClN3) was obtained in this way; MS (ESI): 240 (M+H+).

Method E

[1-(2-Chloro-4-nitrophenyl)pyrrolidin-3-yl]dimethylamine

A mixture of 2-chloro-1-fluoro-4-nitrobenzene (4.79 g), dimethylpyrrolidin-3-ylamine (2.60 g), potassium carbonate (3.82 g) and DMF (35 mL) was stirred at room temperature for 4 hours. The reaction mixture was partitioned between water and ethyl acetate. The organic phase was extracted with hydrochloric acid (2 M), and the extract was basified with sodium hydroxide solution (2M). Extraction with ethyl acetate afforded an organic phase which was dried and concentrated. The product with the molecular weight of 269.73 (C12H16ClN3O2) was obtained in this way; MS (ESI): 270 (M+H+).

The exemplary compounds in table 1 were obtained by method A from the appropriate 2-(2-chloroethyl)benzoyl chlorides and the appropriate anilines.

TABLE 1

| Ex. No. | Structure | Molecular formula | Molecular weight | ESI-MS [M + H]+ |
|---------|-----------|-------------------|------------------|------------------|
| 2 | 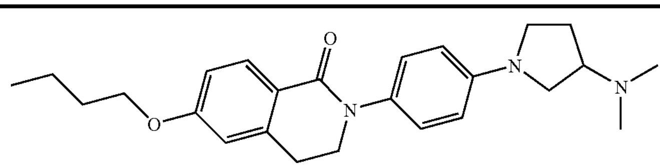 | C25H33N3O2 | 407.56 | 408 |

TABLE 1-continued

| Ex. No. | Structure | Molecular formula | Molecular weight | ESI-MS [M + H]+ |
|---|---|---|---|---|
| 3 | 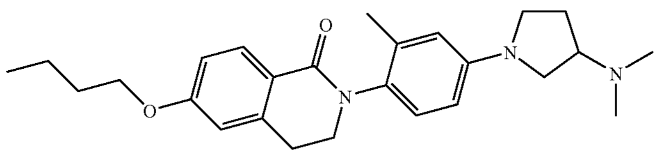 [SMILES: CCCCOc1ccc2c(c1)CCN(c1ccc(N3CCC(N(C)C)C3)cc1C)C2=O] | C26H35N3O2 | 421.59 | 422 |
| 4 | 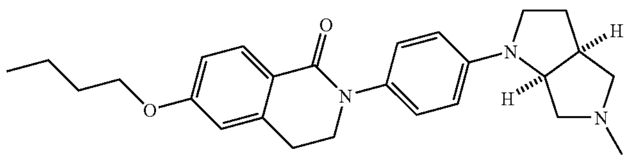 [SMILES: CCCCOc1ccc2c(c1)CCN(c1ccc(N3CC[C@H]4CN(C)C[C@H]43)cc1)C2=O] | C26H33N3O2 | 419.57 | 420 |
| 5 | 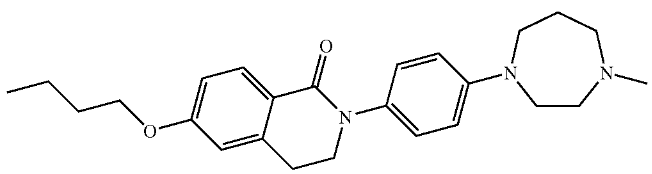 [SMILES: CCCCOc1ccc2c(c1)CCN(c1ccc(N3CCCN(C)CC3)cc1)C2=O] | C25H33N3O2 | 407.56 | 408 |
| 6 | 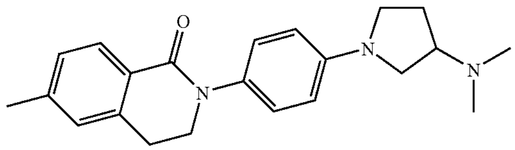 | C22H27N3O | 349.48 | 350 |
| 7 | 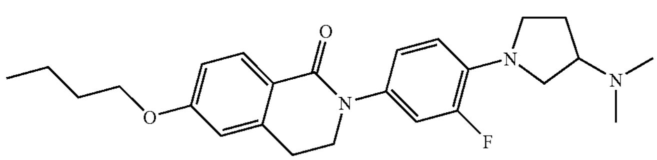 [SMILES: CCCCOc1ccc2c(c1)CCN(c1ccc(N3CCC(N(C)C)C3)c(F)c1)C2=O] | C25H32FN3O2 | 425.55 | 426 |
| 8 | 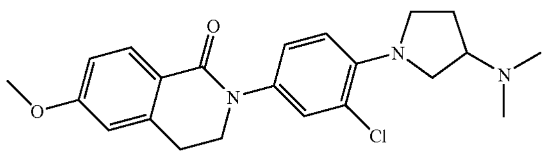 | C22H26ClN3O2 | 399.92 | 400 |
| 9 | 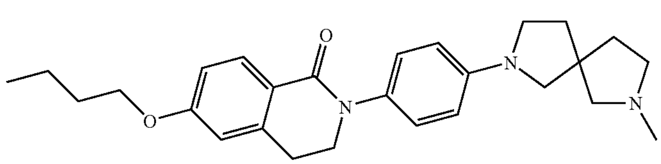 [SMILES: CCCCOc1ccc2c(c1)CCN(c1ccc(N3CCC4(CCN(C)C4)C3)cc1)C2=O] | C27H35N3O2 | 433.60 | 434 |
| 10 | 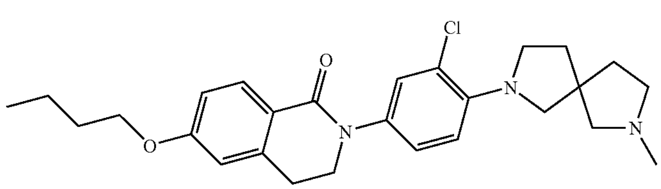 [SMILES: CCCCOc1ccc2c(c1)CCN(c1ccc(N3CCC4(CCN(C)C4)C3)c(Cl)c1)C2=O] | C27H34ClN3O2 | 468.04 | 468 |
| 11 | 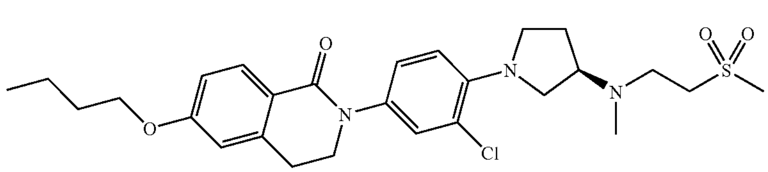 [SMILES: CCCCOc1ccc2c(c1)CCN(c1ccc(N3CC[C@@H](N(C)CCS(C)(=O)=O)C3)c(Cl)c1)C2=O] | C27H36ClN3O4 | 534.12 | 534 |

TABLE 1-continued

| Ex. No. | Structure | Molecular formula | Molecular weight | ESI-MS [M + H]+ |
|---|---|---|---|---|
| 12 | 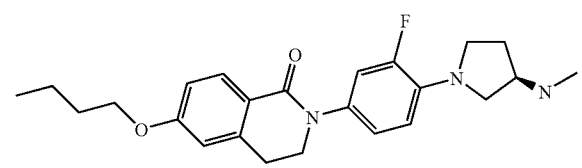 [SMILES: CCCCOc1ccc2c(c1)CCN(c1ccc(N3CC[C@@H](NC)C3)c(F)c1)C2=O] | C27H37N3O4S | 499.68 | 500 |

4-Methoxy-2-(2-chloroethyl)benzoyl chloride

4-Methoxy-2-methylbenzoic acid was firstly reacted with paraformaldehyde by method C, and the product was then reacted with thionyl chloride by method B.

4-Methyl-2-(2-chloroethyl)benzoyl chloride was obtained analogously.

Method F

[1-(4-Aminophenyl)pyrrolidin-3-yl]dimethylamine

A suspension of dimethyl[1-(4-nitrophenyl)pyrrolidin-3-yl]amine (5.0 g) and palladium(II) hydroxide (20% on carbon; 0.9 g) in ethanol (150 mL) was vigorously stirred under a hydrogen atmosphere (atmospheric pressure) for 3 hours. The catalyst was then removed by filtration and the filtrate was concentrated. The product with the molecular weight of 205.31 (C12H19N3) was obtained in this way; MS (ESI): 206 (M+H+). Dimethyl[1-(4-nitrophenyl)pyrrolidin-3-yl]amine was obtained by method E from 1-fluoro-4-nitrobenzene and dimethylpyrrolidin-3-ylamine.

The following anilines were prepared analogously by method F:
[1-(4-amino-3-methylphenyl)pyrrolidin-3-yl]dimethylamine;
4-((3aS*,6aS*)-5-methylhexahydropyrrolo[3,4-b]pyrrol-1-yl)phenylamine;
4-(4-methyl[1,4]diazepan-1-yl)phenylamine;
[1-(4-amino-2-fluorophenyl)pyrrolidin-3-yl]dimethylamine;
4-(7-methyl-2,7-diazaspiro[4.4]non-2-yl)phenylamine;
3-chloro-4-(7-methyl-2,7-diazaspiro[4.4]non-2-yl)phenylamine (the reduction by method F with palladium (10% on carbon) took place in ethyl acetate with addition of zinc bromide (10 mol %).

[(R)-1-(4-Aminophenyl)pyrrolidin-3-yl]-(2-methanesulfonylethyl)methylamine

[(R)-1-(2-Chloro-4-nitrophenyl)pyrrolidin-3-yl]-(2-methanesulfonylethyl)methylamine was dechlorinated and the nitro group was reduced to the amine under the conditions of method F. The crude product was purified by preparative HPLC. The product with the molecular weight of 297.42 (C14H23N3O2S) was obtained in this way; MS (ESI): 298 (M+H+). Since the dehalogenation reaction was incomplete, [(R)-1-(4-amino-2-chloro-phenyl)pyrrolidin-3-yl]-(2-methanesulfonylethyl)methylamine was also isolated. The product with the molecular weight of 331.87 (C14H22ClN3O2S) was obtained in this way; MS (ESI): 332 (M+H+).

Method G

[(R)-1-(2-Chloro-4-nitrophenyl)pyrrolidin-3-yl]-(2-methanesulfonylethyl)methylamine A mixture of [(R)-1-(2-chloro-4-nitrophenyl)pyrrolidin-3-yl]methylamine (384 mg), methanesulfonylethene (318 mg)

and methanol (5 mL) was stirred at room temperature for 12 hours. Volatiles were evaporated off and the residue was purified by preparative HPLC. The product with the molecular weight of 361.85 (C14H20ClN3O4S) was obtained in this way; MS (ESI): 362 (M+H+).

Method H

[(R)-1-(2-Chloro-4-nitrophenyl)pyrrolidin-3-yl]methylamine

A solution of [(R)-1-(2-chloro-4-nitrophenyl)pyrrolidin-3-yl]methylcarbamic acid tert-butyl ester (560 mg) in dichloromethane (2 mL) was mixed with trifluoroacetic acid (2 mL; alternatively a solution of HCl in dioxane or propanole-2 can be used) and stirred at room temperature for 5 hours. The reaction mixture was partitioned between dichloromethane and sodium carbonate solution. The organic phase was dried and concentrated. The product with the molecular weight of 255.71 (C11H14ClN3O2) was obtained in this way; MS (ESI): 256 (M+H+).

[(R)-1-(2-Chloro-4-nitrophenyl)pyrrolidin-3-yl]methylcarbamic acid tert-butyl ester was obtained from 2-chloro-1-fluoro-4-nitrobenzene and methyl-(R)-pyrrolidin-3-ylcarbamic acid tert-butyl ester by method E.

Example 13

6-Butoxy-2-[3-fluoro-4-((R)-3-methylaminopyrrolidin-1-yl)phenyl]-3,4-dihydro-2H-isoquinolin-1-one The carbamate was cleaved using hydrogen chloride (6N in isopropanol) to give {(R)-1-[4-(6-butoxy-1-oxo-3,4-dihydro-1H-isoquinolin-2-yl)-2-fluorophenyl]pyrrolidin-3-yl}methyl-carbamic acid tert-butyl ester. The product with the molecular weight of 411.52 (C24H30FN3O2) was obtained in this way; MS (ESI): 412 (M+H+).

{(R)-1-[4-(6-Butoxy-1-oxo-3,4-dihydro-1H-isoquinolin-2-yl)-2-fluorophenyl]pyrrolidin-3-yl}methylcarbamic acid tert-butyl ester 4-Butoxy-2-(2-chloroethyl)benzoyl chloride was reacted by method A with [(R)-1-(4-amino-2-fluorophenyl)pyrrolidin-3-yl]methylcarbamic acid tert-butyl ester. The product with the molecular weight of 511.64 (C29H38FN3O4) was obtained in this way; MS (ESI): 512 (M+H+).

[(R)-1-(4-Amino-2-fluorophenyl)pyrrolidin-3-yl] methylcarbamic acid tert-butyl ester

[(R)-1-(2-Fluoro-4-nitrophenyl)pyrrolidin-3-yl]methylcarbamic acid tert-butyl ester was hydrogenated under the conditions of method F. The product with the molecular weight of 309.39 (C16H24FN3O2) was obtained in this way; MS (ESI): 310 (M+H+).

Method I

[(R)-1-(2-Fluoro-4-nitrophenyl)pyrrolidin-3-yl]methylcarbamic acid tert-butyl ester Sodium hydride (0.6 g) was added in portions to a solution of [(R)-1-(2-fluoro-4-nitrophenyl)pyrrolidin-3-yl]carbamic acid tert-butyl ester (4.09 g) in DMF (10 mL). After gas evolution ceased, iodomethane (2.37 mL) was added dropwise. After 12 hours, the mixture is partitioned between water and ethyl acetate/hexane (1:1), and the organic phase is dried and concentrated. The product with the molecular weight of 339.37 (C16H22FN3O4) was obtained in this way; MS (ESI): 340 (M+H+).

[(R)-1-(2-Fluoro-4-nitrophenyl)pyrrolidin-3-yl]carbamic acid tert-butyl ester was obtained by method E from 1,2-difluoro-4-nitrobenzene and (R)-pyrrolidin-3-ylcarbamic acid tert-butyl ester.

Example 14

6-Butoxy-2-(3-fluoro-4-{(R)-3-[(2-methanesulfonylethyl)methylamino]pyrrolidin-1-yl}phenyl)-3,4-dihydro-2H-isoquinolin-1-one

6-Butoxy-2-[3-fluoro-4-((R)-3-methylaminopyrrolidin-1-yl)phenyl]-3,4-dihydro-2H-isoquinolin-1-one was reacted with methanesulfonylethene by method G. The product with the molecular weight of 517.67 (C27H36FN3O4S) was obtained in this way; MS (ESI): 518 (M+H+).

Example 15

6-Butoxy-2-[4-((R)-3-dimethylaminopyrrolidin-1-yl)-3-fluorophenyl]-3,4-dihydro-2H-isoquinolin-1-one

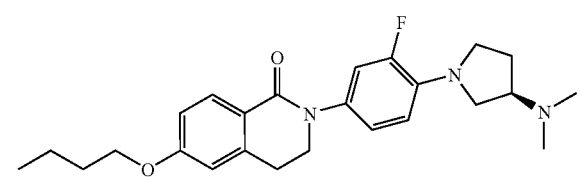 [SMILES: CCCCOc1ccc2c(c1)CCN(c1ccc(N3CC[C@@H](N(C)C)C3)c(F)c1)C2=O]

Method J

N,N-Diisopropylethylamine (11.5 mg), acetic acid (5.3 mg), formaldehyde (37% in water; 7.2 mg) and sodium cyanoborohydride (5.6 mg; polymer-bound material can also be employed as an alternative) were successively added to a solution of a 6-butoxy-2-[3-fluoro-4-((R)-3-methylaminopyrrolidin-1-yl)phenyl]-3,4-dihydro-2H-isoquinolin-1-one (hydrochloride; 40 mg) in THF (2 mL). After 12 hours, volatiles were removed and the residue was purified by preparative HPLC. The product with the molecular weight of 425.55 (C25H32FN3O2) was obtained in this way; MS (ESI): 426 (M+H+).

Example 16

6-Butoxy-2-{3-fluoro-4-[(R)-3-(isopropylmethylamino)pyrrolidin-1-yl]phenyl}-3,4-dihydro-2H-isoquinolin-1-one

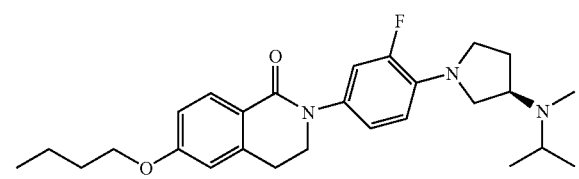 [SMILES: CCCCOc1ccc2c(c1)CCN(c1ccc(N3CC[C@@H](N(C)C(C)C)C3)c(F)c1)C2=O]

6-Butoxy-2-[3-fluoro-4-((R)-3-methylaminopyrrolidin-1-yl)phenyl]-3,4-dihydro-2H-isoquinolin-1-one (hydrochloride) was reductively alkylated with acetone by method J. The product with the molecular weight of 453.61 (C27H36FN3O2) was obtained in this way; MS (ESI): 454 (M+H+).

Example 17

6-Cyclopropylmethoxy-2-[4-((R)-3-dimethylaminopyrrolidin-1-yl)-3-fluorophenyl]-3,4-dihydro-2H-isoquinolin-1-one

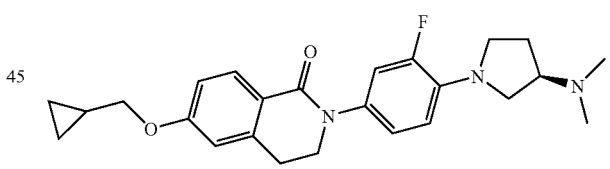

Method K

A solution of 2-[4-((R)-3-dimethylaminopyrrolidin-1-yl)-3-fluorophenyl]-6-hydroxy-3,4-dihydro-2H-isoquinolin-1-one (50 mg) in NMP (1.5 mL) was mixed with cesium carbonate (44 mg) and cyclopropylmethyl bromide (18.3 mg) and heated at 60° C. for 5 hours. The reaction mixture was filtered and concentrated. The residue was purified by preparative HPLC. The product with the molecular weight of 42.3.54 (C25H30FN3O2) was obtained in this way; MS (ESI): 424 (M+H+).

Method L

2-[4-((R)-3-Dimethylaminopyrrolidin-1-yl)-3-fluorophenyl]-6-hydroxy-3,4-dihydro-2H-isoquinolin-1-one A mixture of 2-[4-((R)-3-dimethylaminopyrrolidin-1-yl)-3-fluorophenyl]-6-methoxy-3,4-dihydro-2H-isoquinolin-1- one (9.3 g) and hydrogen bromide (48% strength in water; 140 mL) was heated at 100° C. for 12 hours. The cooled reaction solution was adjusted to pH 10 with sodium hydroxide solution (4N). The precipitate was filtered off with suction, washed with water until neutral and dried. The product with the molecular weight of 369.44 (C21H24FN3O2) was obtained in this way; MS (ESI): 370 (M+H+).

2-[4-((R)-3-Dimethylaminopyrrolidin-1-yl)-3-fluorophenyl]-6-methoxy-3,4-dihydro-2H-isoquinolin-1-one 2-(2-Chloroethyl)-4-methoxybenzoyl chloride was reacted with [(R)-1-(4-amino-2-fluorophenyl)pyrrolidin-3-yl]dimethylamine by method A. The product with the molecular weight of 383.47 (C22H26FN3O2) was obtained in this way; MS (ESI): 384 (M+H+).

[(R)-1-(4-Amino-2-fluorophenyl)pyrrolidin-3-yl]dimethylamine

[(R)-1-(2-Fluoro-4-nitrophenyl)pyrrolidin-3-yl]dimethylamine was hydrogenated by method F. The product with the molecular weight of 223.30 (C12H18FN3) was obtained in this way; MS (ESI): 224 (M+H+).

[(R)-1-(2-Fluoro-4-nitrophenyl)pyrrolidin-3-yl]dimethylamine

2-Difluoro-4-nitrobenzene was reacted with dimethyl-(R)-pyrrolidin-3-ylamine by method E. The product with the molecular weight of 253.28 (C12H16FN3O2) was obtained in this way; MS (ESI): 254 (M+H+).

1,2-[4-((R)-3-Dimethylaminopyrrolidin-1-yl)-3-fluorophenyl]-6-hydroxy-3,4-dihydro-2H-isoquinolin-1-one was reacted with the appropriate alkyl halides by method K, and the exemplary compounds in table 2 were obtained.

TABLE 2

| Ex. No. | Structure | Molecular formula | Molecular weight | ESI-MS [M + H]+ |
|---|---|---|---|---|
| 18 | 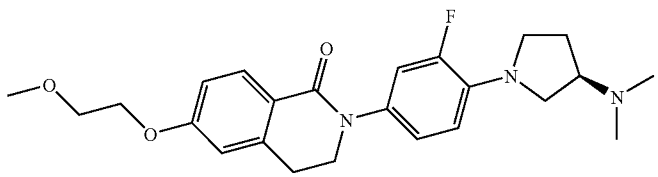 | C24H30FN3O3 | 427.52 | 428 |
| 19 | 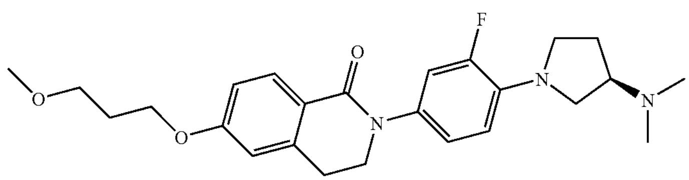 | C25H32FN3O3 | 441.55 | 442 |
| 20 | 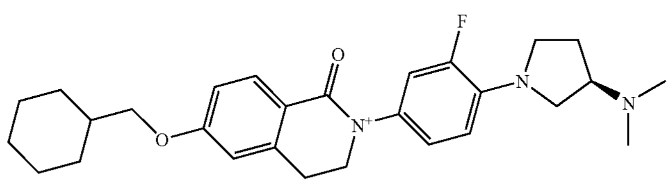 [SMILES: CN(C)[C@@H]1CCN(c2ccc([NH+]3CCc4cc(OCC5CCCCC5)ccc4C3=O)cc2F)C1] | C28H36FN3O2 | 465.62 | 466 |
| 21 | 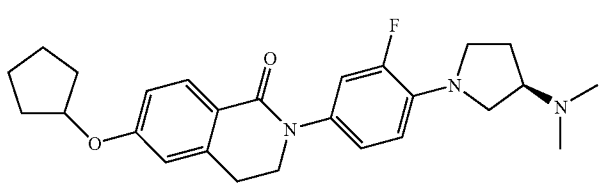 [SMILES: CN(C)[C@@H]1CCN(c2ccc(N3CCc4cc(OC5CCCC5)ccc4C3=O)cc2F)C1] | C26H32FN3O2 | 437.56 | 438 |
| 22 | 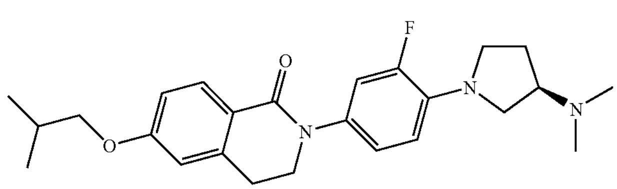 [SMILES: CC(C)COc1ccc2c(c1)CCN(c1ccc(N3CC[C@@H](N(C)C)C3)c(F)c1)C2=O] | C25H32FN3O2 | 425.55 | 426 |

| Ex. No. | Structure | Molecular formula | Molecular weight | ESI-MS [M + H]+ |
|---|---|---|---|---|
| 23 | 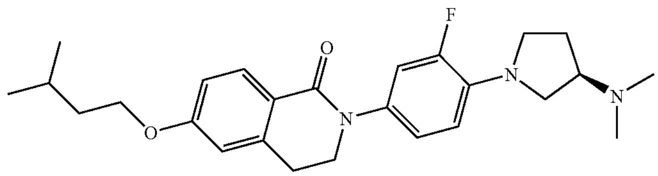 [SMILES: CC(C)CCOc1ccc2c(c1)CCN(c1ccc(N3CC[C@@H](N(C)C)C3)c(F)c1)C2=O] | C26H34FN3O2 | 439.58 | 440 |

Example 24

2-[4-((R)-3-Dimethylaminopyrrolidin-1-yl)-3-fluorophenyl]-6-(4-methylpiperidin-1-yl)-3,4-dihydro-2H-isoquinolin-1-one

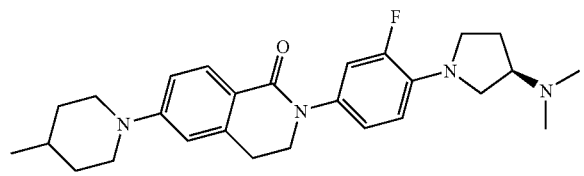

Method N

A mixture of trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester (75 mg) and 4-methylpiperidine (0.7 mL) was heated at 100° C. for 4 hours. Volatiles were evaporated off. The residue was purified by preparative HPLC. The product with the molecular weight of 450.60 (C27H35FN4O) was obtained in this way; MS (ESI): 451 (M+H+).

Method S

Trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester Trifluoromethanesulfonic anhydride (2.06 g) was added to a solution of 2-[4-((R)-3-dimethylaminopyrrolidin-1-yl)-3-fluorophenyl]-6-hydroxy-3,4-dihydro-2H-isoquinolin-1-one (1.5 g) and pyridine (0.64 g) in dichloromethane (40 mL) at 0° C. After 30 minutes, the mixture was partitioned between water and dichloromethane, and the organic phase was dried over magnesium sulfate and concentrated. The product with the molecular weight of 501.50 (C22H23F4N3O4S) was obtained in this way; MS (ESI): 502 (M+H+).

Example 25

2-[4-((R)-3-Dimethylaminopyrrolidin-1-yl)-3-fluorophenyl]-6-(4-methoxypiperidin-1-yl)-3,4-dihydro-2H-isoquinolin-1-one

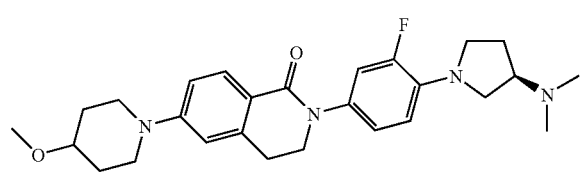

Trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester was reacted with 4-methoxypiperidine by method N. The product with the molecular weight of 466.60 (C27H35FN4O2) was obtained in this way; MS (ESI): 467 (M+H+).

Example 26

2-[4-((R)-3-Dimethylaminopyrrolidin-1-yl)-3-fluorophenyl]-6-piperidin-1-yl-3,4-dihydro-2H-isoquinolin-1-one

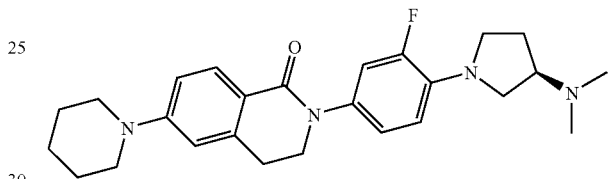

Trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester was reacted with piperidine by method N. The product with the molecular weight of 436.58 (C26H33FN4O) was obtained in this way; MS (ESI): 437 (M+H+).

Example 27

6-Cyclopropylethynyl-2-[4-((R)-3-dimethylaminopyrrolidin-1-yl)-3-fluorophenyl]-3,4-dihydro-2H-isoquinolin-1-one

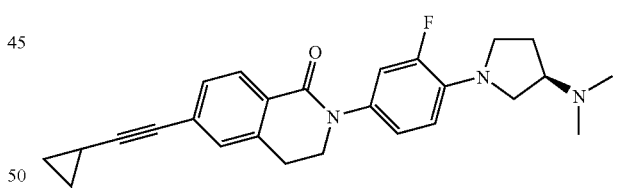

Method M

Ethynylcyclopropane (10.5 mg), triphenylphosphine (8.4 mg), cesium carbonate (104 mg), bis(triphenylphosphine) palladium(II) chloride (5.6 mg) and copper(I) iodide (6.1 mg) were successively added to a solution of trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester (80 mg) in NMP (2 mL). The mixture was heated at 85° C. for 4 hours. The reaction solution was concentrated. The residue was purified by preparative HPLC. The product with the molecular weight of 417.53 (C26H28FN3O) was obtained in this way; MS (ESI): 418 (M+H+).

Reaction of trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester with the appropriate alkynes by method M resulted in the exemplary compounds in table 3.

TABLE 3

| Ex. No. | Structure | Molecular formula | Molecular weight | ESI-MS [M + H]+ |
|---|---|---|---|---|
| 28 | 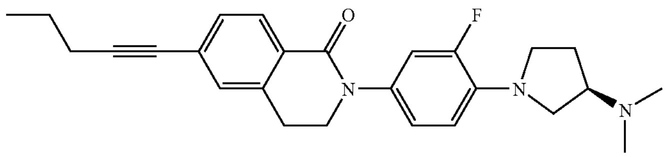 [SMILES: CCCC#Cc1ccc2c(c1)CCN(c1ccc(N3CC[C@@H](N(C)C)C3)c(F)c1)C2=O] | C26H30FN3O | 419.55 | 420 |
| 29 | 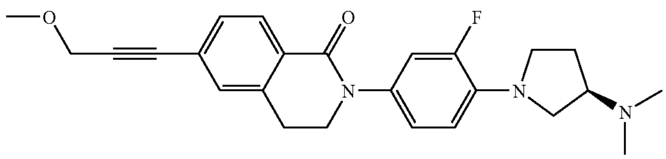 | C25H28FN3O2 | 421.52 | 422 |
| 30 | 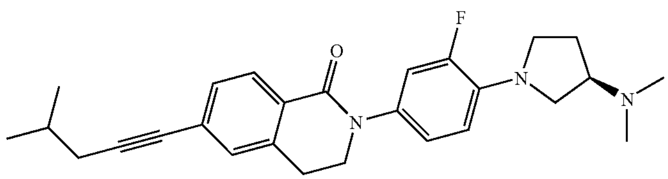 [SMILES: CC(C)CC#Cc1ccc2c(c1)CCN(c1ccc(N3CC[C@@H](N(C)C)C3)c(F)c1)C2=O] | C27H32FN3O | 433.57 | 434 |
| 31 | 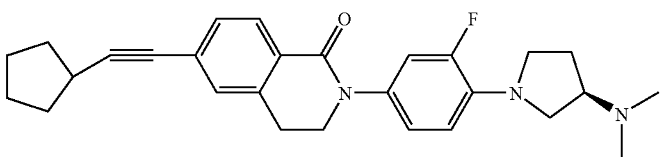 [SMILES: CN(C)[C@@H]1CCN(c2ccc(N3CCc4cc(C#CC5CCCC5)ccc4C3=O)cc2F)C1] | C28H32FN3O | 445.59 | 446 |
| 32 | 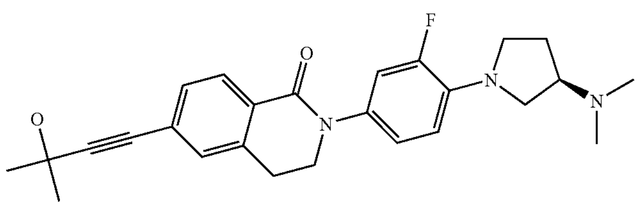 [SMILES: CN(C)[C@@H]1CCN(c2ccc(N3CCc4cc(C#CC(C)(C)O)ccc4C3=O)cc2F)C1] | C26H30FN3O2 | 435.55 | 436 |
| 33 | 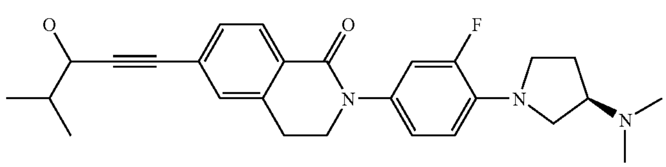 [SMILES: CC(C)C(O)C#Cc1ccc2c(c1)CCN(c1ccc(N3CC[C@@H](N(C)C)C3)c(F)c1)C2=O] | C27H32FN3O2 | 449.57 | 450 |
| 34 | 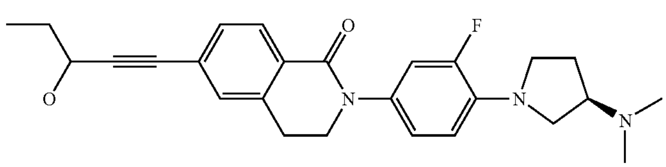 [SMILES: CCC(O)C#Cc1ccc2c(c1)CCN(c1ccc(N3CC[C@@H](N(C)C)C3)c(F)c1)C2=O] | C26H30FN3O2 | 435.55 | 436 |
| 35 | 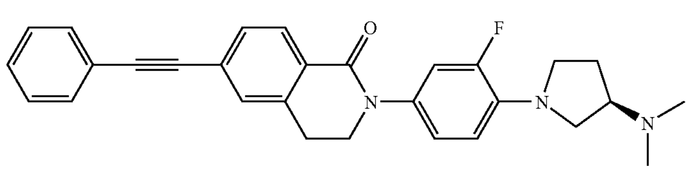 [SMILES: CN(C)[C@@H]1CCN(c2ccc(N3CCc4cc(C#Cc5ccccc5)ccc4C3=O)cc2F)C1] | C29H28FN3O | 453.56 | 454 |
| 36 | 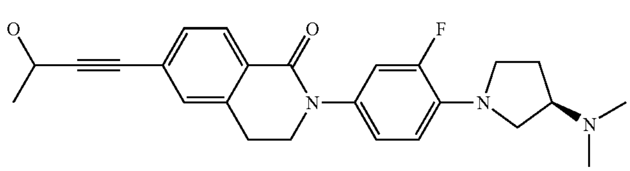 [SMILES: CC(O)C#Cc1ccc2c(c1)CCN(c1ccc(N3CC[C@@H](N(C)C)C3)c(F)c1)C2=O] | C25H28FN3O2 | 421.52 | 422 |

Example 37

6-(4-Chlorophenyl)-2-[4-((R)-3-dimethylamino-pyrrolidin-1-yl)-3-fluorophenyl]-3,4-dihydro-2H-isoquinolin-1-one

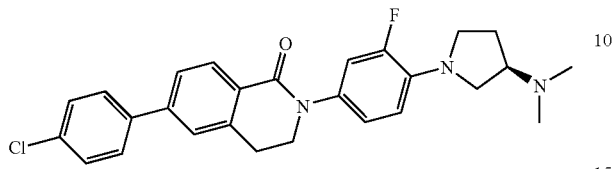

Method O

4-Chlorophenylboronic acid (18.7 mg), cesium carbonate (39 mg) in water/ethanol (0.5 mL/0.5 mL) and tetrakis(triphenylphosphine)palladium (13.8 mg) were successively added to a solution of trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester (60 mg) in toluene (2 mL). The mixture was heated to reflux for 2 hours. After cooling, the organic phase was separated off and concentrated. The residue was purified by preparative HPLC. The product with the molecular weight of 463.99 (C27H27ClFN3O) was obtained in this way; MS (ESI): 464 (M+H+).

Example 38

2-[4-((R)-3-Dimethylaminopyrrolidin-1-yl)-3-fluorophenyl]-6-(4-fluorophenyl)-3,4-dihydro-2H-isoquinolin-1-one

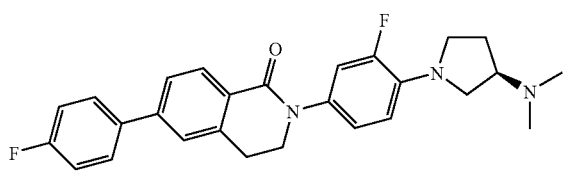 [SMILES: CN(C)[C@@H]1CCN(c2ccc(N3CCc4cc(-c5ccc(F)cc5)ccc4C3=O)cc2F)C1]

Trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester was reacted with 4-fluorophenylboronic acid by method O. The product with the molecular weight of 447.53 (C27H27F2N3O) was obtained in this way; MS (ESI): 448 (M+H+).

Example 39

2-{4-[3-(4-Acetylpiperazin-1-yl)pyrrolidin-1-yl]phenyl}-6-butoxy-3,4-dihydro-2H-isoquinolin-1-one

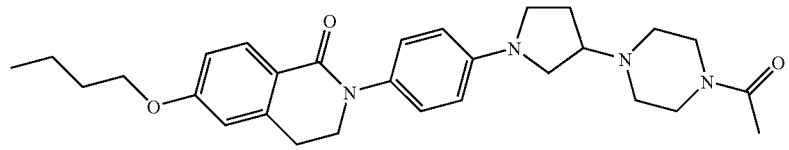 [SMILES: CCCCOc1ccc2c(c1)CCN(c1ccc(N3CCC(N4CCN(C(C)=O)CC4)C3)cc1)C2=O]

6-Butoxy-2-[4-(3-oxopyrrolidin-1-yl)phenyl]-3,4-dihydro-2H-isoquinolin-1-one was reacted with 1-piperazin-1-ylethanone by method J. The product with the molecular weight of 490.65 (C29H38N4O3) was obtained in this way; MS (ESI): 491 (M+H+).

6-Butoxy-2-[4-(3-oxopyrrolidin-1-yl)phenyl]-3,4-dihydro-2H-isoquinolin-1-one

A mixture of 6-butoxy-2-[4-(1,4-dioxa-7-azaspiro[4.4]non-7-yl)phenyl]-3,4-dihydro-2H-isoquinolin-1-one (1.40 g), p-toluenesulfonic acid (57 mg) and acetone (40 mL) was boiled under reflux for 12 hours and then concentrated. The residue was partitioned between sodium carbonate solution and ethyl acetate. The organic phase was dried and concentrated. The product with the molecular weight of 378.48 (C23H26N2O3) was obtained in this way; MS (ESI): 379 (M+H+).

6-Butoxy-2-[4-(1,4-dioxa-7-azaspiro[4.4]non-7-yl)phenyl]-3,4-dihydro-2H-isoquinolin-1-one 4-(1,4-Dioxa-7-azaspiro[4.4]non-7-yl)phenylamine was reacted with 4-butoxy-2-(2-chloroethyl)benzoyl chloride by method A. The product with the molecular weight of 438.57 (C26H34N2O4) was obtained in this way; MS (ESI): 439 (M+H+).

4-(1,4-Dioxa-7-azaspiro[4.4]non-7-yl)phenylamine

Trimethylchlorosilane (9.3 g) was slowly added to a solution of 1-benzyl-3-pyrrolidinone (5.0 g) in dichloromethane (30 mL) and ethylene glycol (2.67 g). After 18 hours, the mixture was poured into sodium hydroxide solution (1N). The organic phase was separated off, dried over magnesium sulfate and concentrated. The residue was dissolved in methanol (30 mL), and ammonium formate (5.2 g) and palladium hydroxide (10% on carbon, 300 mg) were added. The mixture was boiled under reflux for 8 hours, filtered and concentrated. The residue was reacted with 4-fluoronitrobenzene by method E. Hydrogenation was finally carried out by method F. The product with the molecular weight of 220.27 (C12H16N2O2) was obtained in this way; MS (ESI): 221 (M+H+).

The examples in table 4 were obtained analogously from 6-butoxy-2-[4-(3-oxopyrrolidin-1-yl)phenyl]-3,4-dihydro-2H-isoquinolin-1-one and the appropriate amines by method J.

TABLE 4

| Ex. No. | Structure | Molecular formula | Molecular weight | ESI-MS [M + H]+ |
|---|---|---|---|---|
| 40 | 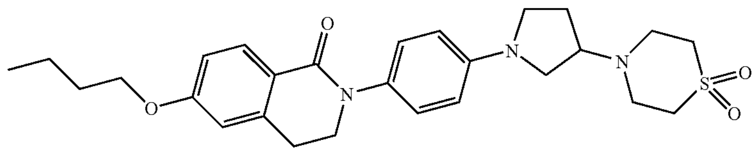 [SMILES: CCCCOc1ccc2c(c1)CCN(c1ccc(N3CCC(N4CCS(=O)(=O)CC4)C3)cc1)C2=O] | C27H35N3O4S | 497.66 | 498 |
| 41 | 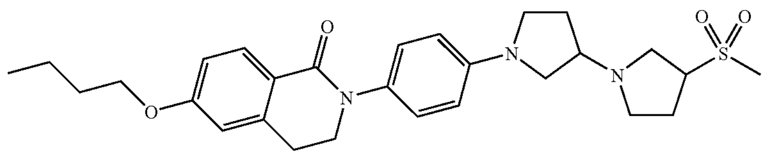 [SMILES: CCCCOc1ccc2c(c1)CCN(c1ccc(N3CCC(N4CCC(S(C)(=O)=O)C4)C3)cc1)C2=O] | C28H37N3O4S | 511.69 | 512 |
| 42 | 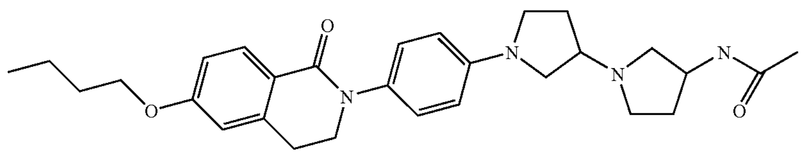 [SMILES: CCCCOc1ccc2c(c1)CCN(c1ccc(N3CCC(N4CCC(NC(C)=O)C4)C3)cc1)C2=O] | C29H38N4O3 | 490.65 | 491 |
| 43 | 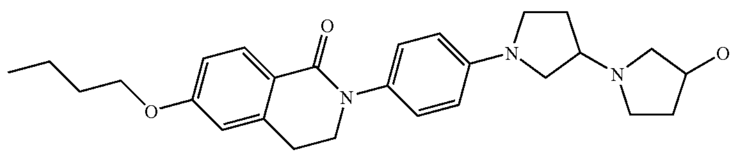 [SMILES: CCCCOc1ccc2c(c1)CCN(c1ccc(N3CCC(N4CCC(O)C4)C3)cc1)C2=O] | C27H35N3O3 | 449.60 | 450 |
| 44 | 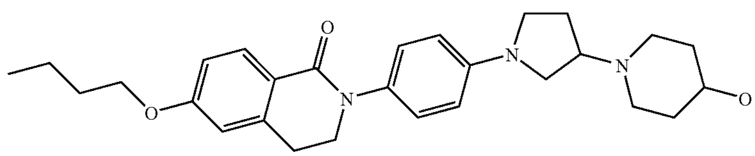 [SMILES: CCCCOc1ccc2c(c1)CCN(c1ccc(N3CCC(N4CCC(O)CC4)C3)cc1)C2=O] | C28H37N3O3 | 463.63 | 464 |
| 45 | 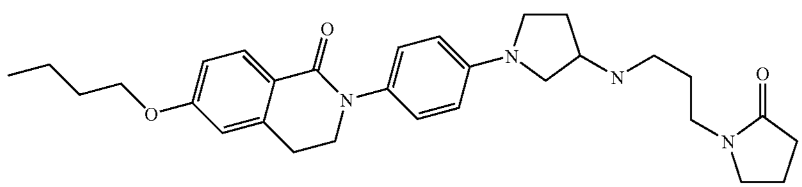 [SMILES: CCCCOc1ccc2c(c1)CCN(c1ccc(N3CCC(NCCCN4CCCC4=O)C3)cc1)C2=O] | C30H40N4O3 | 504.68 | 505 |

Example 46

2-[4-((R)-3-Dimethylaminopyrrolidin-1-yl)-3-fluorophenyl]-1-oxo-1,2,3,4-tetrahydroisoquinoline-6-carboxylic acid cyclopentylmethylamide

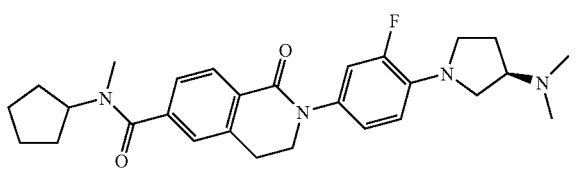 [SMILES: CN(C(=O)c1ccc2c(c1)CCN(c1ccc(N3CC[C@@H](N(C)C)C3)c(F)c1)C2=O)C1CCCC1]

Method P

TOTU (49.5 mg) was added to a mixture of 2-[4-((R)-3-dimethylaminopyrrolidin-1-yl)-3-fluorophenyl]-1-oxo-1,2,3,4-tetrahydroisoquinoline-6-carboxylic acid (60 mg), in N,N-diisopropylethylamine (26 µL) and NMP (1 mL) at 0° C. After 10 minutes, cyclopentylmethylamine (15 mg) was added, and the mixture was stirred for 4 hours. The reaction mixture was then partitioned between sodium bicarbonate solution and ethyl acetate. The organic phase was dried over sodium sulfate and concentrated. The residue was purified by preparative HPLC. The product with the molecular weight of 478.62 (C28H35FN4O2) was obtained in this way; MS (ESI): 479 (M+H+).

2-[4-((R)-3-Dimethylaminopyrrolidin-1-yl)-3-fluorophenyl]-1-oxo-1,2,3,4-tetrahydroisoquinoline-6-carboxylic acid A mixture of 2-[4-((R)-3-dimethylaminopyrrolidin-1-yl)-3-fluorophenyl]-1-oxo-1,2,3,4-tetrahydroisoquinoline-6-carboxylic acid methyl ester (0.80 g), sodium hydroxide (78 mg), methanol (20 mL) and water (10 mL) was boiled under reflux for 2 hours and then concentrated. The product with the molecular weight of 397.45 (C22H24FN3O3) was obtained in this way; MS (ESI): 398 (M+H+).

2-[4-((R)-3-Dimethylaminopyrrolidin-1-yl)-3-fluorophenyl]-1-oxo-1,2,3,4-tetrahydroisoquinoline-6-carboxylic acid methyl ester Triethylamine (1.0 g) and then Pd(dppf)Cl2 (365 mg) were added to a mixture of trifluoromethanesulfonic acid 2-[4-((R)-3-dimethylaminopyrrolidin-1-yl)-3-fluorophenyl]-1-oxo-1,2,3,4-tetrahydroisoquinolin-6-yl ester (2.5 g), DMF (50 mL) and methanol (25 mL). The mixture was heated at 50° C. in an autoclave under a CO atmosphere (5 bar) for 6 hours. The cooled and decompressed reaction mixture was partitioned between water and ethyl acetate. The organic phase was dried over sodium sulfate and concentrated. The residue was purified by preparative HPLC. The product with the molecular weight of 411.48 (C23H26FN3O3) was obtained in this way; MS (ESI): 412 (M+H+).

Example 47

6-Butoxy-2-[4-(3-dimethylaminopyrrolidin-1-yl)-3-fluorophenyl]-2H-isoquinolin-1-one

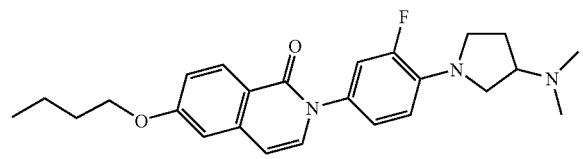 [SMILES: CCCCOc1ccc2c(=O)n(-c3ccc(N4CCC(N(C)C)C4)c(F)c3)ccc2c1]

n-Butyllithium (2.6M in toluene; 0.70 mL) was added to a solution of N,N-diisopropylamine (184 mg) in THF (30 mL) at −78° C. After 10 minutes, 4-butoxy-N-[4-(3-dimethylaminopyrrolidin-1-yl)-3-fluorophenyl]-2-methylbenzamide (0.30 g) was added, and the mixture was stirred at −78° C. for 30 minutes and then warmed to −20° C. DMF (53 mg) was added, and the reaction mixture was hydrolyzed after a further 30 minutes with hydrochloric acid. The reaction mixture was partitioned between sodium carbonate solution and ethyl acetate. The organic phase was dried over sodium sulfate and concentrated. The residue was purified by preparative HPLC. The product with the molecular weight of 423.54 (C25H30FN3O2) was obtained in this way; MS (ESI): 424 (M+H+).

4-Butoxy-N-[4-(3-dimethylaminopyrrolidin-1-yl)-3-fluorophenyl]-2-methylbenzamide 4-Butoxy-2-methylbenzoic acid was reacted with [1-(4-amino-2-fluorophenyl)pyrrolidin-3-yl]dimethylamine by method P. The product with the molecular weight of 413.54 (C24H32FN3O2) was obtained in this way; MS (ESI): 414 (M+H+).

Example 48

6-[4-((R)-3-Dimethylaminopyrrolidin-1-yl)phenyl]-2-p-tolyl-5,6-dihydro-4H-thieno[2,3-c]pyridin-7-one

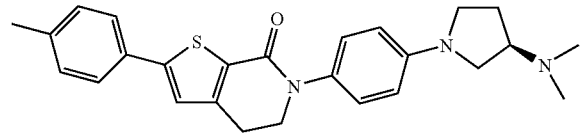

Firstly 3-methyl-5-p-tolylthiophene-2-carboxylic acid was reacted with paraformaldehyde by method C1, and then the product was treated with thionyl chloride by method B. The resulting 3-(2-chloroethyl)-5-p-tolylthiophene-2-carbonyl chloride was finally reacted with [(R)-1-(4-aminophenyl)pyrrolidin-3-yl]dimethylamine by method A. The product with the molecular weight of 431.60 (C26H29N3OS) was obtained in this way; MS (ESI): 432 (M+H+).

3-Methyl-5-p-tolylthiophene-2-carboxylic acid

A solution of 3-methyl-5-p-tolylthiophene-2-carbaldehyde (2.6 g) in 1,4-dioxane (30 mL) was mixed with a solution of sodium dihydrogenphosphate (5.77 g) in water, and sulfamic acid (1.87 g) was added. At 10° C., a solution of sodium chlorite (1.52 g) in water (20 mL) was added dropwise in such a way that the temperature did not rise above 10° C. Twenty minutes after the addition was complete, sodium sulfite (1.98 g) was added and the mixture was stirred for 15 minutes. The reaction mixture was acidified with hydrochloric acid and extracted with ethyl acetate. The organic phase was dried and concentrated. The product with the molecular weight of 232.30 (C13H12O2S) was obtained in this way; MS (ESI): 233 (M+H+).

3-Methyl-5-p-tolylthiophene-2-carbaldehyde

5-Bromo-3-methylthiophene-2-carbaldehyde (Spinelli, D. et al., J. Chem. Soc. Perkin Trans. 2, 1972, (12), 1866-9) was reacted with 4-methylphenylboronic acid by method J. The product with the molecular weight of 216.30 (C13H12OS) was obtained in this way; MS (ESI): 217 (M+H+).

Example 49

6-[4-(4-Methyl-[1,4]diazepan-1-yl)phenyl]-2-p-tolyl-5,6-dihydro-4H-thieno[2,3-c]pyridin-7-one

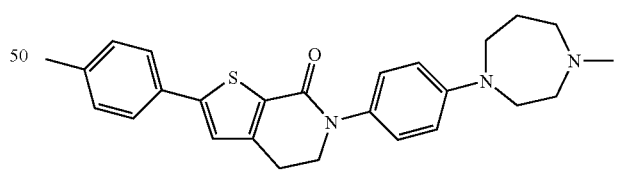

3-(2-Chloroethyl)-5-p-tolylthiophene-2-carbonyl chloride was reacted with 4-(4-methyl-[1,4]diazepan-1-yl)phenylamine by method A. The product with the molecular weight of 431.60 (C26H29N3OS) was obtained in this way; MS (ESI): 432 (M+H+).

According to Method N, trifluoro-methanesulfonic acid 2-[4-((R)-3-dimethylamino-pyrrolidin-1-yl)-3-fluorophenyl]-1-oxo-1,2,3,4-tetrahydro-isoquinolin-6-yl ester was reacted with various amines. The compounds presented in Table 5 were obtained.

TABLE 5

| Ex. No. | Structure | Empirical formula | Molecular weight | ESI-MS [M + H]+ |
|---|---|---|---|---|
| 50 | 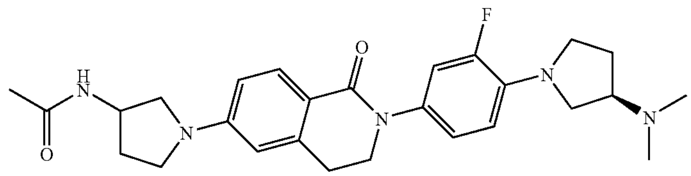 [SMILES: CC(=O)NC1CCN(c2ccc3c(c2)CCN(c2ccc(N4CC[C@@H](N(C)C)C4)c(F)c2)C3=O)C1] | C27H34FN5O2 | 479, 60 | 480 |
| 51 | 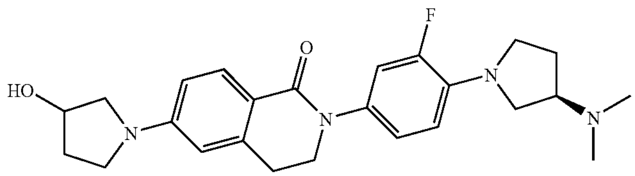 [SMILES: CN(C)[C@@H]1CCN(c2ccc(N3CCc4cc(N5CCC(O)C5)ccc4C3=O)cc2F)C1] | C25H31FN4O2 | 438, 55 | 439 |
| 52 | 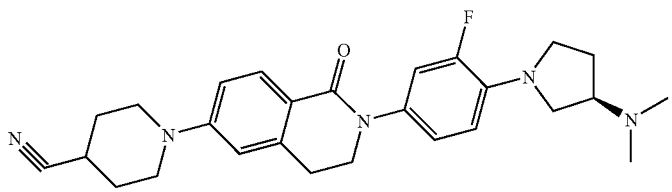 [SMILES: CN(C)[C@@H]1CCN(c2ccc(N3CCc4cc(N5CCC(C#N)CC5)ccc4C3=O)cc2F)C1] | C27H32FN5O | 461, 59 | 462 |
| 53 | 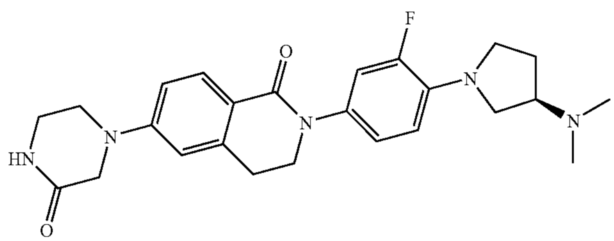 [SMILES: CN(C)[C@@H]1CCN(c2ccc(N3CCc4cc(N5CCNC(=O)C5)ccc4C3=O)cc2F)C1] | C25H30FN5O2 | 451, 55 | 452 |
| 54 | 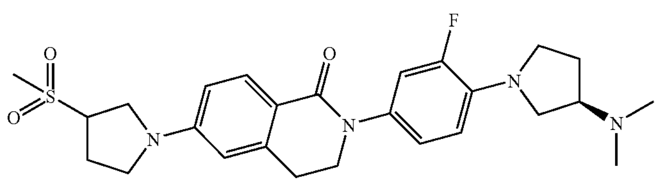 [SMILES: CN(C)[C@@H]1CCN(c2ccc(N3CCc4cc(N5CCC(S(C)(=O)=O)C5)ccc4C3=O)cc2F)C1] | C26H33FN4O3S | 500, 64 | 501 |
| 55 | 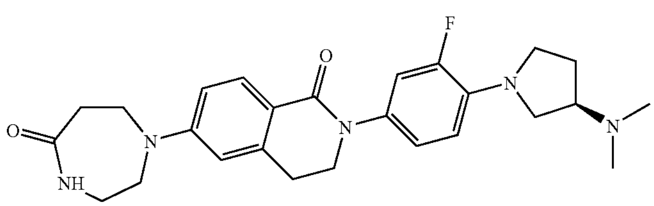 [SMILES: CN(C)[C@@H]1CCN(c2ccc(N3CCc4cc(N5CCNC(=O)CC5)ccc4C3=O)cc2F)C1] | C26H32FN5O2 | 465, 58 | 466 |
| 56 | 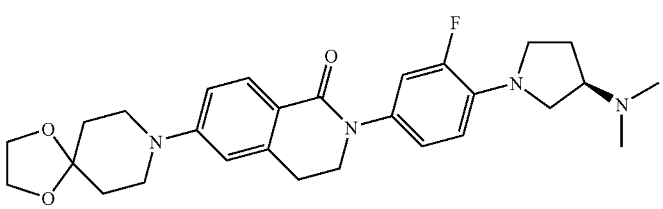 [SMILES: CN(C)[C@@H]1CCN(c2ccc(N3CCc4cc(N5CCC6(CC5)OCCO6)ccc4C3=O)cc2F)C1] | C28H35FN4O3 | 494, 62 | 495 |

TABLE 5-continued

| Ex. No. | Structure | Empirical formula | Molecular weight | ESI-MS [M + H]+ |
|---|---|---|---|---|
| 57 | 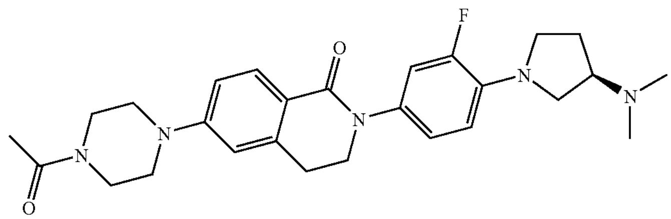 [SMILES: CC(=O)N1CCN(c2ccc3c(c2)CCN(c2ccc(N4CC[C@@H](N(C)C)C4)c(F)c2)C3=O)CC1] | C27H34FN5O2 | 479, 60 | 480 |
| 58 | 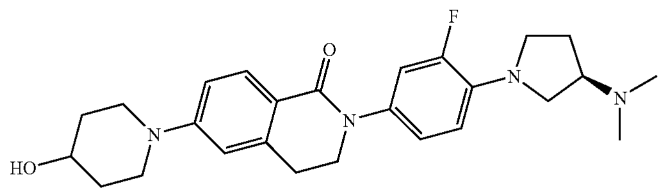 [SMILES: CN(C)[C@@H]1CCN(c2ccc(N3CCc4cc(N5CCC(O)CC5)ccc4C3=O)cc2F)C1] | C26H33FN4O2 | 452, 58 | 453 |

The example compounds in Table 6 were obtained by Method A from the corresponding 2-(2-chloroethyl)-benzoyl chlorides and the corresponding anilines.

TABLE 6

| Ex. No. | Structure | Empirical formula | Molecular weight | ESI-MS [M + H]+ |
|---|---|---|---|---|
| 59 | 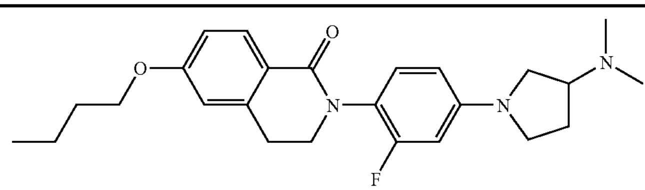 | C25H32FN3O2 | 425, 55 | 426 |
| 60 | 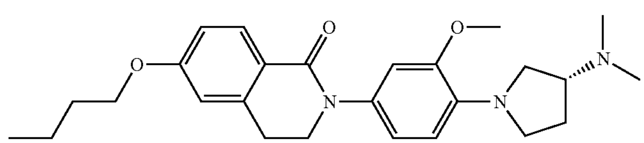 [SMILES: CCCCOc1ccc2c(c1)CCN(c1ccc(N3CC[C@@H](N(C)C)C3)c(OC)c1)C2=O] | C26H35N3O3 | 437, 59 | 438 |
| 61 | 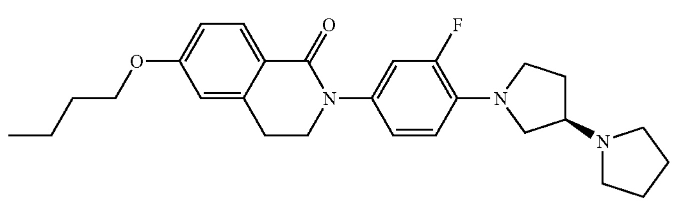 [SMILES: CCCCOc1ccc2c(c1)CCN(c1ccc(N3CC[C@@H](N4CCCC4)C3)c(F)c1)C2=O] | C27H34FN3O2 | 451, 59 | 452 |
| 62 | 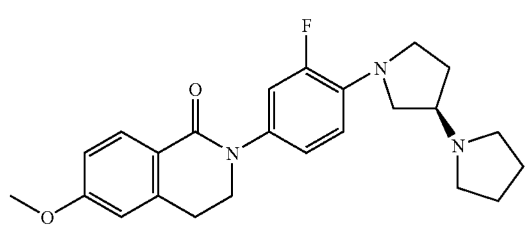 [SMILES: COc1ccc2c(c1)CCN(c1ccc(N3CC[C@@H](N4CCCC4)C3)c(F)c1)C2=O] | C24H28FN3O2 | 409, 51 | 410 |
| 63 | 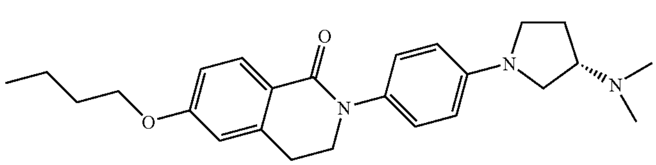 [SMILES: CCCCOc1ccc2c(c1)CCN(c1ccc(N3CC[C@H](N(C)C)C3)cc1)C2=O] | C25H33N3O2 | 407, 56 | 408 |

TABLE 6-continued

| Ex. No. | Structure | Empirical formula | Molecular weight | ESI-MS [M + H]+ |
|---|---|---|---|---|
| 64 | 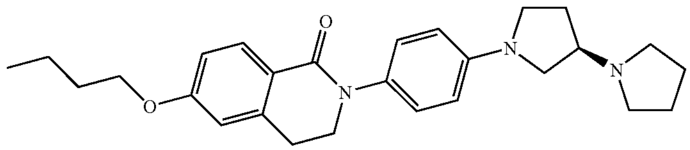 [SMILES: CCCCOc1ccc2c(c1)CCN(c1ccc(N3CC[C@@H](N4CCCC4)C3)cc1)C2=O] | C27H35N3O2 | 433, 60 | 434 |
| 65 | 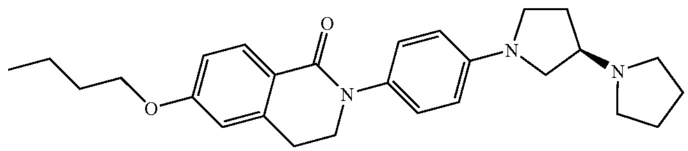 [SMILES: CCCCOc1ccc2c(c1)CCN(c1ccc(N3CC[C@@H](N4CCCC4)C3)cc1)C2=O] | C27H35FN3O2 | 433, 60 | 434 |

The anilines required were prepared according to Methods E and F by substitution on suitable 4-fluoro-nitrobenzenes with the corresponding amines followed by catalytic hydrogenation of the nitro function.

Preparation of (R)-[1,3']bipyrrolidinyl

Methansulfonic acid chloride (24.5 g) was added dropwise to a solution of (S)-3-hydroxypyrrolidine-1-carboxylic acid tert-butyl ester (40 g) and pyridine (17 g) in dichloromethane (200 mL) cooled on an ice bath, and the ice bath was removed after 15 minutes. After a further 2 hours at room temperature, the mixture was distributed between ethyl acetate and water. The organic phase was washed with dilute hydrochloric acid, dried over magnesium sulfate and concentrated. Pyrrolidine (20 mL) was added to the raw mesylate ((S)-3-methanesulfonyloxy-pyrrolidine-1-carboxylic acid tert-butyl ester) and heated at 100° C. oil-bath temperature. After cooling, the mixture was distributed between ethyl acetate and water. The organic phase was concentrated. The residue was dissolved in dichloromethane (150 mL) and an excess of hydrochloric acid (5 N in 2-propanol) was added. After 12 hours, volatile components were removed in the rotary evaporator. In this way the product was obtained with molecular weight 140.23 (C8H16N2); MS (ESI): 141 (M+H+) as dihydrochloride.

(S)-[1,3']Bipyrrolidinyl was obtained similarly (as dihydrochloride) from (R)-3-hydroxy-pyrrolidine-1-carboxylic acid tert-butyl ester.

By use of (S)-2-methyl-pyrrolidine in the substitution reaction step (2S,3'S)-2-methyl-[1,3']bipyrroldinyl is obtained.

Example 66

2-((R)-4-[1,3']Bipyrrolidinyl-1'-yl-3-fluorophenyl)-6-butoxy-2H-isoquinolin-1-one

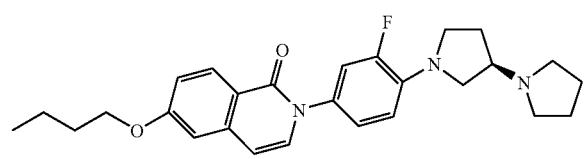 [SMILES: CCCCOc1ccc2c(=O)n(-c3ccc(N4CC[C@@H](N5CCCC5)C4)c(F)c3)ccc2c1]

Method Q n-Butyllithium (2.6 M in toluene; 5.0 mL) was added, at −78° C., to a solution of 2,2,6,6-tetramethyl piperidine (2.2 mL) in THF (30 mL). After 10 minutes, 4-N—((R)-4-[1,3'] bipyrrolidinyl-1'-yl-3-fluorophenyl)-4-butoxy-2-methyl-benzamide (1.8 g) in THF (10 mL) was added and the mixture was stirred for 40 minutes at −78° C. N-Formylmorpholine (1.2 g) was added to the deep-red solution, and after a further 30 minutes the reaction mixture was heated to room temperature and hydrochloric acid (6 N in water, 10 mL) was added. After 4 hours, the THF was removed by distillation in the rotary evaporator and the residue was distributed between sodium carbonate solution and ethyl acetate. The organic phase was dried over sodium sulfate and concentrated. The residue was purified by chromatography on silica gel. In this way the product was obtained with molecular weight 449.57 (C27H32FN3O2); MS (ESI): 450 (M+H+).

N—((R)-4-[1,3']Bipyrrolidinyl-1'-yl-3-fluorophenyl)-4-butoxy-2-methyl-benzamide

4-Butoxy-2-methyl-benzoic acid was reacted with (R)-4-[1,3']bipyrrolidinyl-1'-yl-3-fluorophenylamine according to Method P. In this way the product was obtained with molecular weight 439.58 (C26H34FN3O2); MS (ESI): 440 (M+H+).

Example 67

2-((R)-4-[1,3']Bipyrrolidinyl-1'-yl-phenyl)-6-butoxy-2H-isoquinolin-1-one

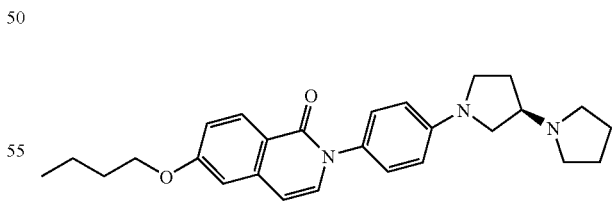

Firstly, 4-butoxy-2-methyl-benzoic acid was reacted with (R)-4-[1,3']bipyrrolidinyl-1'-yl-3-phenylamine according to Method P. The amide obtained was reacted with N-formylmorpholine according to Method Q. In this way the product was obtained with molecular weight 431.58 (C27H33N3O2); MS (ESI): 432 (M+H+).

Similarly, 4-methoxy-2-methyl-benzoic acid was reacted to 2-((R)-4-[1,3']bipyrrolidinyl-1'-yl-phenyl)-6-methoxy- 2H-isoquinolin-1-one. In this way the product was obtained with molecular weight 389.50 (C24H27N3O2); MS (ESI): 390 (M+H+).

Example 68

2-[4-((R)-3-Dimethylamino-pyrrolidin-1-yl)-3-fluorophenyl]-6-methoxy-2H-isoquinolin-1-one

Firstly, 4-methoxy-2-methyl-benzoic acid was reacted with [(R)-1-(4-amino-2-fluorophenyl)-pyrrolidin-3-yl]-dimethylamine according to Method P. The amide obtained was reacted with N-formylmorpholine according to Method Q. In this way the product was obtained with molecular weight 381.45 (C22H24FN3O2); MS (ESI): 382 (M+H+). Similarly, using (R)-4-[1,3']bipyrrolidinyl-1'-yl-3-fluorophenylamine, the product 2-((R)-4-[1,3']bipyrrolidinyl-1'-yl-3-fluorophenyl)-6-methoxy-2H-isoquinolin-1-one was obtained (molecular weight 407.49 (C24H26FN3O2); MS (ESI): 408 (M+H+)).

Example 69

2-((R)-4-[,3']Bipyrrolidinyl-1'-yl-phenyl)-6-butoxy-3-methyl-2H-isoquinolin-1-one

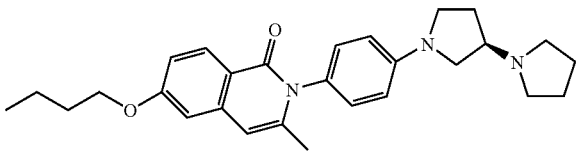 [SMILES: CCCCOc1ccc2c(=O)n(-c3ccc(N4CC[C@@H](N5CCCC5)C4)cc3)c(C)cc2c1]

n-Butyllithium (2.6 m in toluene; 1.2 mL) was added at −78° C. to a solution of 2,2,6,6-tetramethyl piperidine (0.51 mL) in THF (30 mL). After 10 minutes, 4-N—((R)-4-[1,3']bipyrrolidinyl-1'-yl-phenyl)-4-butoxy-2-methyl-benzamide (0.4 g) in THF (5 mL) was added and the mixture was stirred for 20 minutes at −78° C. N-Methoxy-N-methylacetamide (207 mg) was added to the deep-red solution and after a further 30 minutes the reaction mixture was heated to room temperature. After 2 hours the THF was removed by distillation in the rotary evaporator and the residue was distributed between water and ethyl acetate. The organic phase was dried over sodium sulfate and concentrated. The residue was purified by chromatography on silica gel and by preparative HPLC. In this way the product was obtained with molecular weight 445.61 (C28H35N3O2); MS (ESI): 446 (M+H+).

2-[4-((R)-3-Dimethylamino-pyrrolidin-1-yl)-3-fluorophenyl]-1-oxo-1,2,3,4-tetrahydroisoquinoline-6-carboxylic acid was reacted with various amines according to Method P. The products are summarized in Table 7.

TABLE 7

| Ex. No. | Structure | Empirical formula | Molecular weight | ESI-MS [M + H]+ |
|---|---|---|---|---|
| 070 | 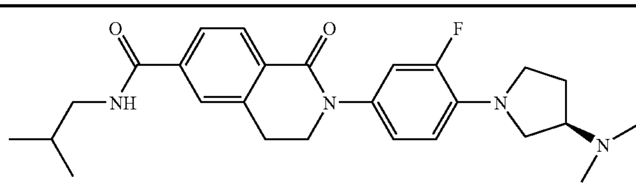 | C26H33FN4O2 | 452, 58 | 453 |
| 071 | 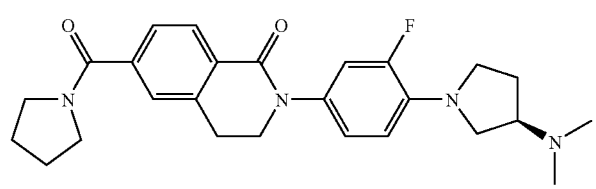 [SMILES: CN(C)[C@@H]1CCN(c2ccc(N3CCc4cc(C(=O)N5CCCC5)ccc4C3=O)cc2F)C1] | C26H31FN4O2 | 450, 56 | 451 |
| 072 | 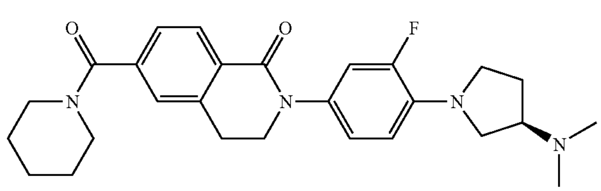 [SMILES: CN(C)[C@@H]1CCN(c2ccc(N3CCc4cc(C(=O)N5CCCCC5)ccc4C3=O)cc2F)C1] | C27H33FN4O2 | 464, 59 | 465 |
| 073 | 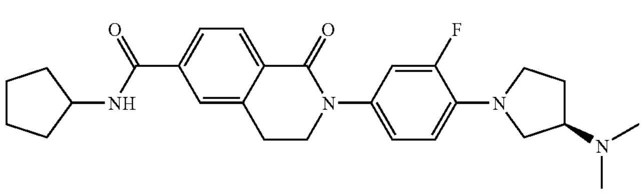 [SMILES: CN(C)[C@@H]1CCN(c2ccc(N3CCc4cc(C(=O)NC5CCCC5)ccc4C3=O)cc2F)C1] | C27H33FN4O2 | 464, 59 | 465 |

TABLE 7-continued

| Ex. No. | Structure | Empirical formula | Molecular weight | ESI-MS [M + H]+ |
|---|---|---|---|---|
| 074 | 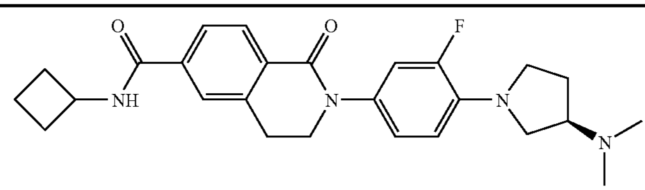 | C26H31FN4O2 | 450, 56 | 451 |
| 075 | 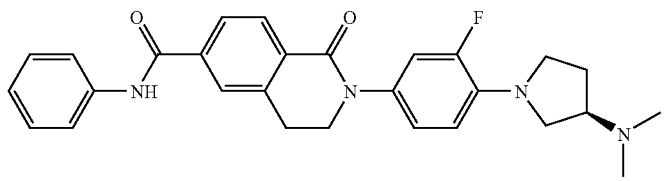 [SMILES: CN(C)[C@@H]1CCN(c2ccc(N3CCc4cc(C(=O)Nc5ccccc5)ccc4C3=O)cc2F)C1] | C28H29FN4O2 | 472, 57 | 473 |

Example 76

2-{2-[3-Fluoro-4-((R)-3-methylamino-pyrrolidin-1-yl)-phenyl]-1-oxo-1,2,3,4-tetrahydro-isoquinolin-6-yloxy}-N-methyl-acetamide

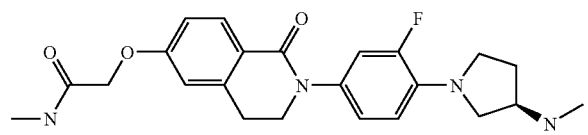

According to Method K, {(R)-1-[2-fluoro-4-(6-hydroxy-1-oxo-3,4-dihydro-1H-isoquinolin-2-yl)-phenyl]-pyrrolidin-3-yl}-methyl-carbamic acid tert-butyl ester was alkylated with 2-chloro-N-methyl-acetamide and the product was treated with hydrogen chloride (5 N in 2-propanol), releasing the amine. In this way the product was obtained with molecular weight 426.50 (C23H27FN4O3); MS (ESI): 427 (M+H+).

{(R)-1-[2-Fluoro-4-(6-hydroxy-1-oxo-3,4-dihydro-1H-isoquinolin-2-yl)-phenyl]-pyrrolidin-3-yl}-methyl-carbamic acid tert-butyl ester According to Method L, {(R)-1-[2-fluoro-4-(6-methoxy-1-oxo-3,4-dihydro-1H-isoquinolin-2-yl)-phenyl]-pyrrolidin-3-yl}-methyl-carbamic acid tert-butyl ester was treated with hydrogen bromide. The raw product (5.5 g) was dissolved in 1,4-dioxan (50 mL) and water (50 mL), sodium hydrogencarbonate (2.6 g) and lastly Boc2O (3.38 g) were added. After 3 hours the 1,4-dioxan was removed in the rotary evaporator and the residue was distributed between water and ethyl acetate. The organic phase was dried over sodium sulfate and concentrated. In this way the product was obtained with molecular weight 455.53 (C25H30FN3O4); MS (ESI): 456 (M+H+).

{(R)-1-[2-Fluoro-4-(6-methoxy-1-oxo-3,4-dihydro-1H-isoquinolin-2-yl)-phenyl]-pyrrolidin-3-yl}-methyl-carbamic acid tert-butyl ester According to Method B, 2-(2-chloroethyl)-4-methoxy-benzoyl chloride was reacted with [(R)-1-(4-amino-2-fluorophenyl)-pyrrolidin-3-yl]-methyl-carbamic acid tert-butyl ester. In this way the product was obtained with molecular weight 469.56 (C26H32FN3O4); MS (ESI): 470 (M+H+).

The products presented in Table 8 were obtained similarly, by reaction of {(R)-1-[2-fluoro-4-(6-hydroxy-1-oxo-3,4-dihydro-1H-isoquinolin-2-yl)-phenyl]-pyrrolidin-3-yl}-methyl-carbamic acid tert-butyl ester or {(R)-1-[2-fluoro-4-(6-hydroxy-1-oxo-1H-isoquinolin-2-yl)-phenyl]-pyrrolidin-3-yl}-methyl-carbamic acid tert-butyl ester with the corresponding alkylating agents (chloride, bromide or mesylate) and then cleavage of the intermediate carbamates.

| Ex. No. | Structure | Empirical formula | Molecular weight | ESI-MS [M + H]+ |
|---|---|---|---|---|
| 77 | 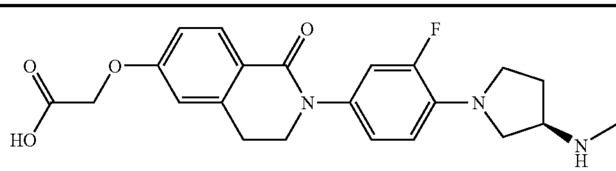 | C22H24FN3O4 | 413, 45 | 414 |
| 78 | 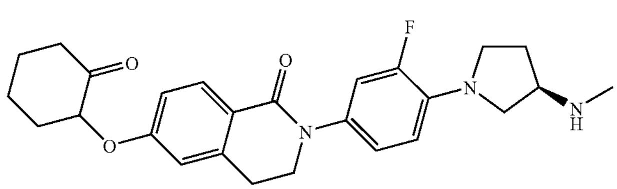 [SMILES: CN[C@@H]1CCN(c2ccc(N3CCc4cc(OC5CCCCC5=O)ccc4C3=O)cc2F)C1] | C26H30FN3O3 | 451, 55 | 452 |

-continued

| Ex. No. | Structure | Empirical formula | Molecular weight | ESI-MS [M + H]+ |
|---|---|---|---|---|
| 79 | 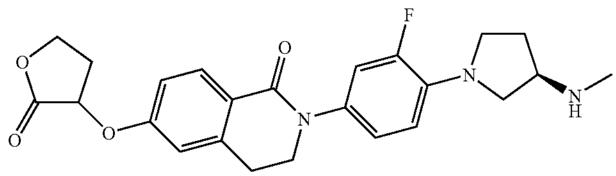 [SMILES: CN[C@@H]1CCN(c2ccc(N3CCc4cc(OC5CCOC5=O)ccc4C3=O)cc2F)C1] | C24H26FN3O4 | 439, 49 | 440 |
| 80 | 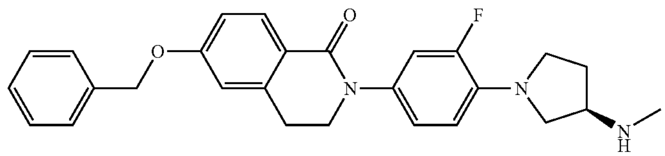 [SMILES: CN[C@@H]1CCN(c2ccc(N3CCc4cc(OCc5ccccc5)ccc4C3=O)cc2F)C1] | C27H28FN3O2 | 445, 54 | 446 |
| 81 | 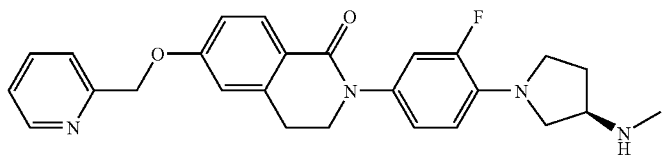 [SMILES: CN[C@@H]1CCN(c2ccc(N3CCc4cc(OCc5ccccn5)ccc4C3=O)cc2F)C1] | C26H27FN4O2 | 446, 53 | 447 |
| 82 | 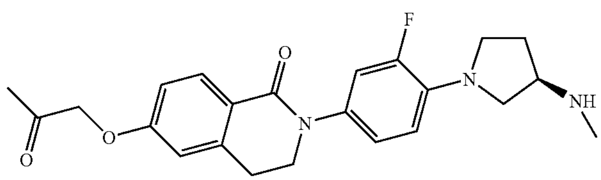 [SMILES: CN[C@@H]1CCN(c2ccc(N3CCc4cc(OCC(C)=O)ccc4C3=O)cc2F)C1] | C23H26FN3O3 | 411, 48 | 412 |
| 83 | 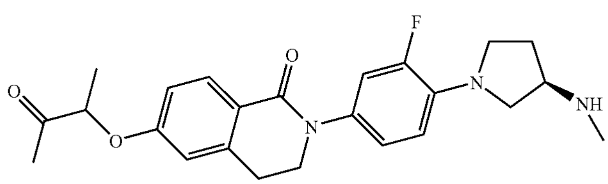 [SMILES: CN[C@@H]1CCN(c2ccc(N3CCc4cc(OC(C)C(C)=O)ccc4C3=O)cc2F)C1] | C24H28FN3O3 | 425, 51 | 426 |
| 84 | 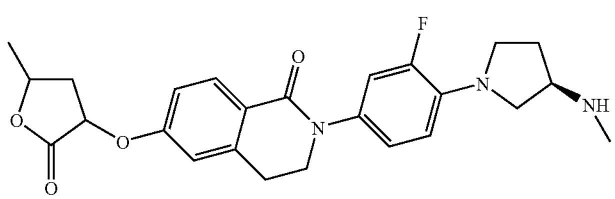 | C25H28FN3O4 | 453, 52 | 454 |
| 85 | 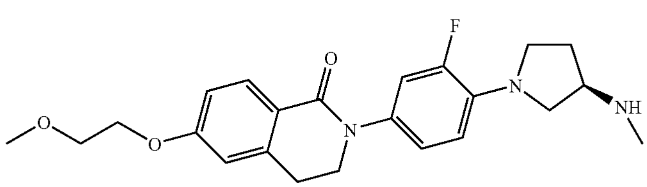 | C23H28FN3O3 | 413, 50 | 414 |
| 86 | 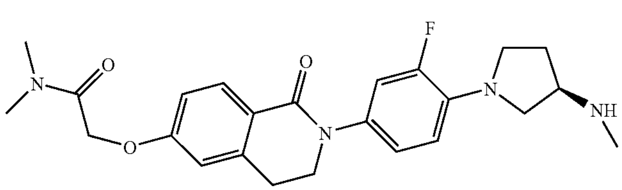 | C24H29FN4O3 | 440, 52 | 441 |

-continued

| Ex. No. | Structure | Empirical formula | Molecular weight | ESI-MS [M + H]+ |
|---|---|---|---|---|
| 87 | 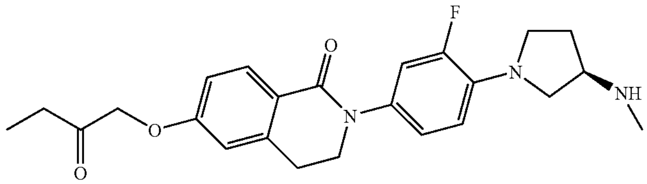 [SMILES: CCC(=O)COc1ccc2c(c1)CCN(c1ccc(N3CC[C@@H](NC)C3)c(F)c1)C2=O] | C24H28FN3O3 | 425, 51 | 426 |
| 88 | 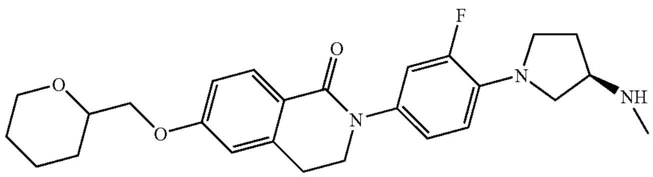 [SMILES: CN[C@@H]1CCN(c2ccc(N3CCc4cc(OCC5CCCCO5)ccc4C3=O)cc2F)C1] | C26H32FN3O3 | 453, 56 | 454 |
| 89 | 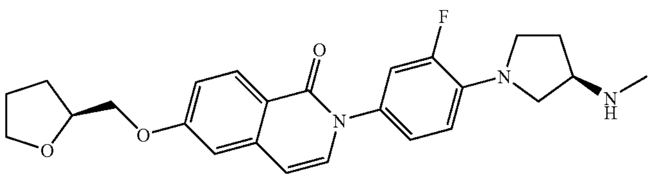 [SMILES: CN[C@@H]1CCN(c2ccc(-n3ccc4cc(OC[C@@H]5CCCO5)ccc4c3=O)cc2F)C1] | C25H28FN3O3 | 437, 52 | 438 |

The alkylating agent in Example 77 was bromo-acetic acid methyl ester. The methyl ester was also cleaved in the carbamate cleavage step.

{(R)-1-[2-Fluoro-4-(6-hydroxy-1-oxo-1H-isoquinolin-2-yl)-phenyl]-pyrrolidin-3-yl}-methyl-carbamic acid tert-butyl ester According to Method P, [(R)-1-(4-amino-2-fluorophenyl)-pyrrolidin-3-yl]-methyl-carbamic acid tert-butyl ester was reacted with 4-methoxy-2-methylbenzoic acid and the isoquinolinone skeleton was constructed according to Method Q. Then the methyl ether was cleaved according to Method L. Finally, the aminophenol thus obtained was reacted with Boc2O (aqueous sodium hydrogencarbonate solution/1,4-dioxan). In this way the product was obtained with molecular weight 453.52 (C25H28FN3O4); MS (ESI): 454 (M+H+).

Methanesulfonic acid (S)-1-(tetrahydro-furan-2-yl)methyl ester

Mesylchloride (12.1 g) was added to a mixture of (S)-1-(Tetrahydro-furan-2-yl)-methanol (10.0 g) and pyridine (55 mL) at −15° C. and stirred for 1.5 hours at room temperature. The mixture was poured into ice water and extracted with ethyl acetate. The organic phase was washed with a solution of potassium hydrogensulfate (20%) and with a solution of saturated sodium hydrogencarbonate, dried over magnesium sulfate and concentrated.

In a similar way Methanesulfonic acid (R)-1-(tetrahydro-furan-2-yl)methyl ester was obtained. In this way the product was obtained with molecular weight 180.05 (C6H12O4S); MS (ESI): 181 (M+H+).

Example 90

2-[4-((R)-3-Dimethylamino-pyrrolidin-1-yl)-3-fluorophenyl]-6-(2-oxo-pyrrolidin-1-yl)-3,4-dihydro-2H-isoquinolin-1-one

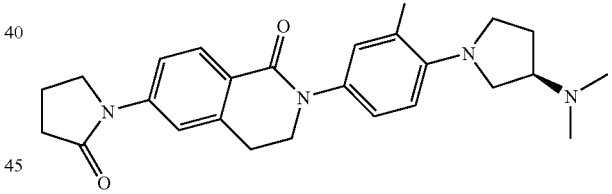

Method R

Palladium-II acetate (0.22 mg), 9,9-dimethyl-4,5-bis(diphenylphosphino)xanthene (5.8 mg) and cesium carbonate (49 mg) were added, under argon, to a mixture of trifluoromethanesulfonic acid 2-[4-((R)-3-dimethylamino-pyrrolidin-1-yl)-3-fluorophenyl]-1-oxo-1,2,3,4-tetrahydro-isoquinolin-6-yl ester (50 mg), 2-pyrrolidone (10.2 mg) and 1,4-dioxan (3 mL), heating for 5 hours at 100° C. The cooled reaction mixture was concentrated and purified by preparative HPLC. In this way the product was obtained with molecular weight 436.53 (C25H29FN4O2); MS (ESI): 437 (M+H+).

The products presented in Table 9 were obtained similarly, from trifluoro-methanesulfonic acid 2-[4-((R)-3-dimethylamino-pyrrolidin-1-yl)-3-fluorophenyl]-1-oxo-1,2,3,4-tetrahydro-isoquinolin-6-yl ester and the corresponding amides or amines.

TABLE 9
| Ex. No. | Structure | Empirical formula | Molecular weight | ESI-MS [M + H]+ |
|---|---|---|---|---|
| 91 | 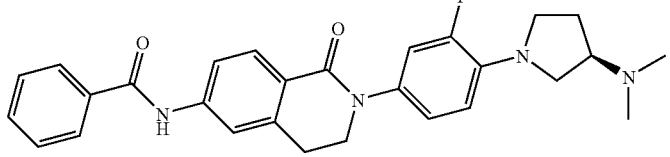 | C28H29FN4O2 | 472, 57 | 473 |
| 92 | 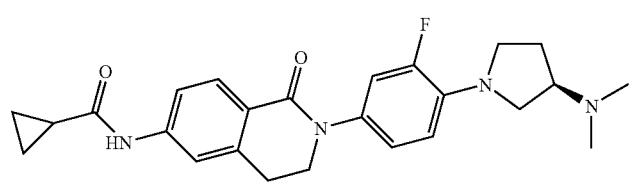 [SMILES: CN(C)[C@@H]1CCN(c2ccc(N3CCc4cc(NC(=O)C5CC5)ccc4C3=O)cc2F)C1] | C25H29FN4O2 | 436, 53 | 437 |
| 93 | 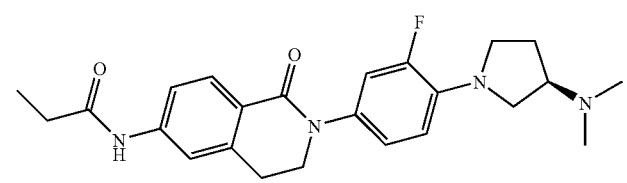 [SMILES: CCC(=O)Nc1ccc2c(c1)CCN(c1ccc(N3CC[C@@H](N(C)C)C3)c(F)c1)C2=O] | C24H29FN4O2 | 424, 52 | 425 |
| 94 | 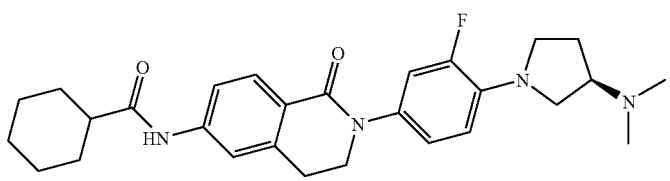 [SMILES: CN(C)[C@@H]1CCN(c2ccc(N3CCc4cc(NC(=O)C5CCCCC5)ccc4C3=O)cc2F)C1] | C28H35FN4O2 | 478, 62 | 479 |
| 95 | 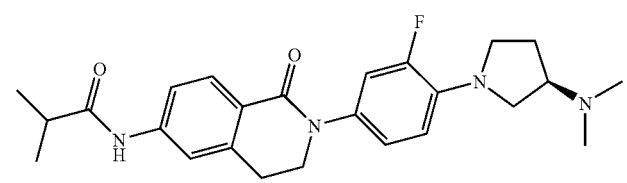 [SMILES: CC(C)C(=O)Nc1ccc2c(c1)CCN(c1ccc(N3CC[C@@H](N(C)C)C3)c(F)c1)C2=O] | C25H31FN4O2 | 438, 55 | 439 |
| 96 | 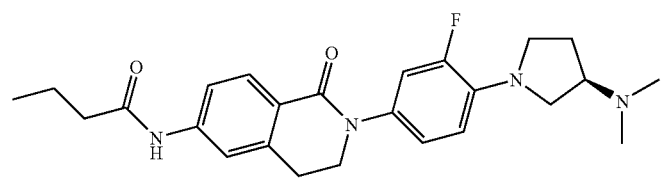 [SMILES: CCCC(=O)Nc1ccc2c(c1)CCN(c1ccc(N3CC[C@@H](N(C)C)C3)c(F)c1)C2=O] | C25H31FN4O2 | 438, 55 | 439 |
| 97 | 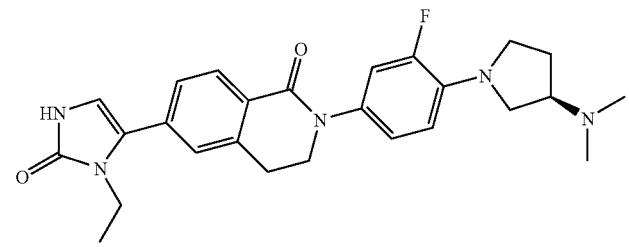 [SMILES: CCn1c(-c2ccc3c(c2)CCN(c2ccc(N4CC[C@@H](N(C)C)C4)c(F)c2)C3=O)c[nH]c1=O] | C26H30FN5O2 | 463, 56 | 464 |
| 98 | 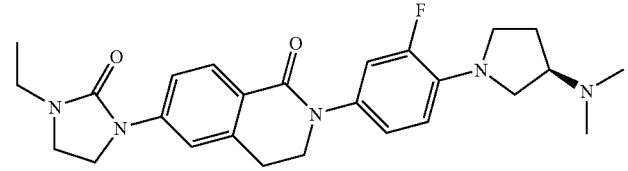 [SMILES: CCN1CCN(c2ccc3c(c2)CCN(c2ccc(N4CC[C@@H](N(C)C)C4)c(F)c2)C3=O)C1=O] | C26H32FN5O2 | 465, 58 | 466 |

TABLE 9-continued

| Ex. No. | Structure | Empirical formula | Molecular weight | ESI-MS [M + H]+ |
|---|---|---|---|---|
| 99 | 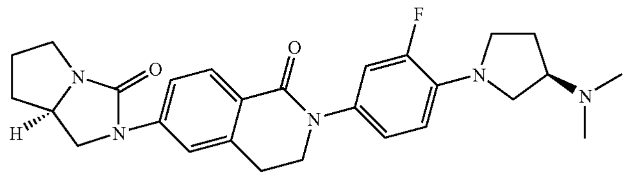 [SMILES: CN(C)[C@@H]1CCN(c2ccc(N3CCc4cc(N5C[C@H]6CCCN6C5=O)ccc4C3=O)cc2F)C1] | C27H32FN5O2 | 477,59 | 478 |
| 100 | 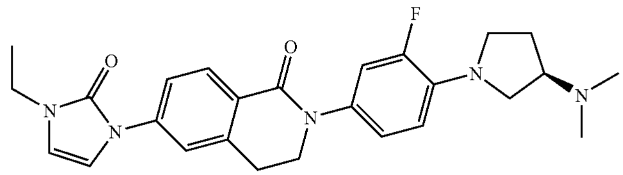 [SMILES: CCn1ccn(-c2ccc3c(c2)CCN(c2ccc(N4CC[C@@H](N(C)C)C4)c(F)c2)C3=O)c1=O] | C26H30FN5O2 | 463,56 | 464 |
| 101 | 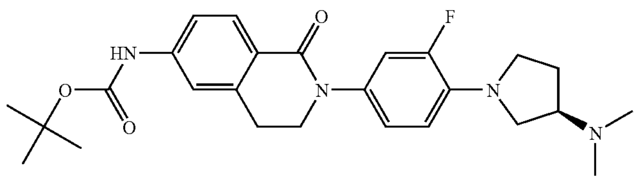 [SMILES: CN(C)[C@@H]1CCN(c2ccc(N3CCc4cc(NC(=O)OC(C)(C)C)ccc4C3=O)cc2F)C1] | C26H33FN4O3 | 468,58 | 469 |
| 102 | 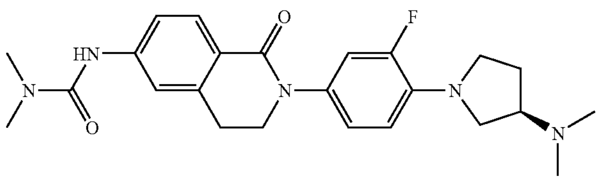 | C24H30FN5O2 | 439,54 | 440 |
| 103 | 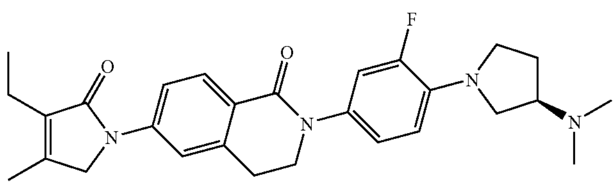 [SMILES: CCC1=C(C)CN(c2ccc3c(c2)CCN(c2ccc(N4CC[C@@H](N(C)C)C4)c(F)c2)C3=O)C1=O] | C28H33FN4O2 | 476,60 | 477 |
| 104 | 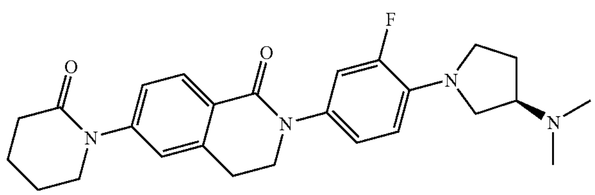 [SMILES: CN(C)[C@@H]1CCN(c2ccc(N3CCc4cc(N5CCCCC5=O)ccc4C3=O)cc2F)C1] | C26H31FN4O2 | 450,56 | 451 |
| 105 | 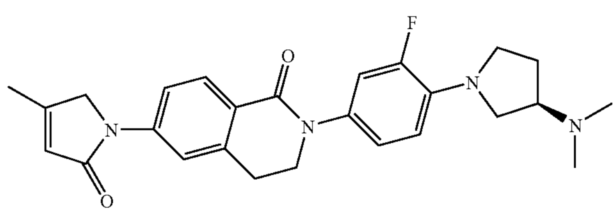 | C26H29FN4O2 | 448,55 | 449 |
| 106 | 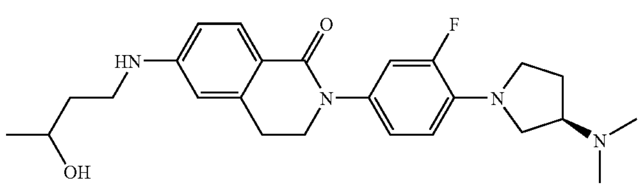 [SMILES: CC(O)CCNc1ccc2c(c1)CCN(c1ccc(N3CC[C@@H](N(C)C)C3)c(F)c1)C2=O] | C25H33FN4O2 | 440,57 | 441 |

TABLE 9-continued

| Ex. No. | Structure | Empirical formula | Molecular weight | ESI-MS [M + H]+ |
|---|---|---|---|---|
| 107 | 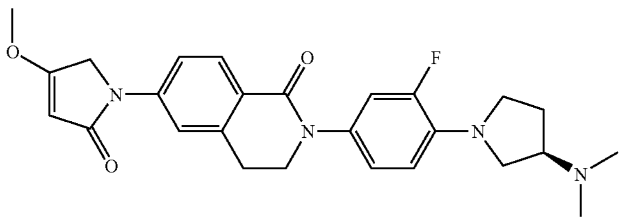 [SMILES: COC1=CC(=O)N(c2ccc3c(c2)CCN(c2ccc(N4CC[C@@H](N(C)C)C4)c(F)c2)C3=O)C1] | C26H29FN4O3 | 464, 54 | 465 |
| 108 | 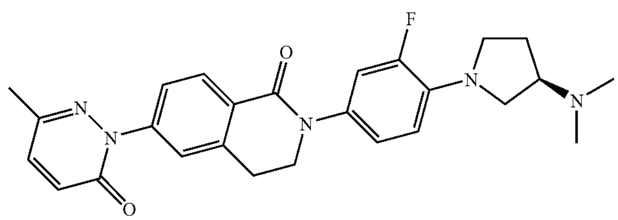 | C26H28FN5O2 | 461, 54 | 462 |
| 109 | 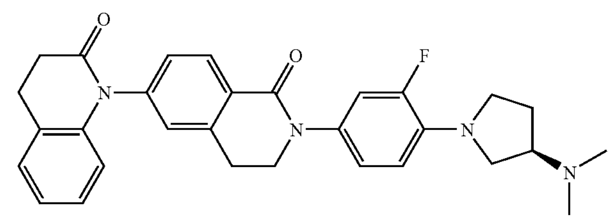 [SMILES: CN(C)[C@@H]1CCN(c2ccc(N3CCc4cc(N5C(=O)CCc6ccccc65)ccc4C3=O)cc2F)C1] | C30H31FN4O2 | 498, 61 | 499 |
| 110 | 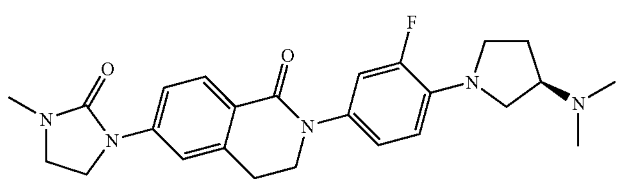 | C25H30FN5O2 | 451, 55 | 452 |
| 111 | 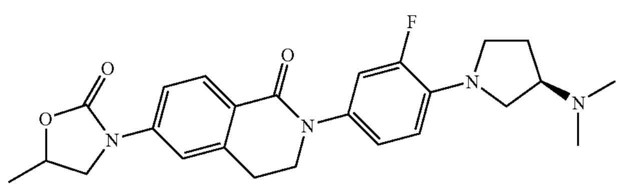 | C25H29FN4O3 | 452, 53 | 453 |
| 112 | 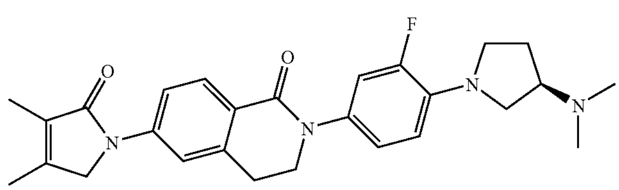 | C27H31FN4O2 | 462, 57 | 463 |
| 113 | 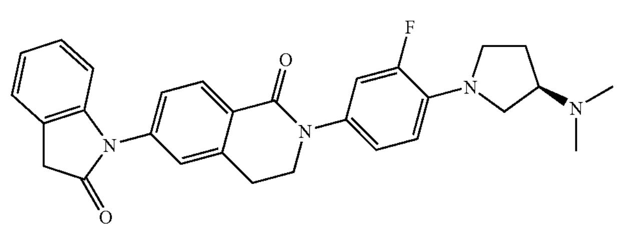 [SMILES: CN(C)[C@@H]1CCN(c2ccc(N3CCc4cc(N5C(=O)Cc6ccccc65)ccc4C3=O)cc2F)C1] | C29H29FN4O2 | 484, 58 | 485 |

Reaction of trifluoro-methanesulfonic acid 2-[4-((R)-3-dimethylamino-pyrrolidin-1-yl)-3-fluorophenyl]-1-oxo-1,2,3,4-tetrahydro-isoquinolin-6-yl ester with 1-ethyl-1,3-dihydro-imidazol-2-one yielded two products (Examples 97 and 100).

1-Ethyl-1,3-dihydro-imidazol-2-one was obtained in accordance with the instructions in the literature (O. Wong et al., Heterocycles 1987, 26(12), 3153-8).

1-Ethyl-imidazolidin-2-one

1-Ethyl-1,3-dihydro-imidazol-2-one was hydrogenated according to Method F. In this way the product was obtained with molecular weight 114.15 (C5H10N2O); MS (ESI): 115 (M+H+).

(S)-Hexahydro-pyrrolo[1,2-c]imidazol-3-one

A mixture of C—(S)-1-pyrrolidin-2-yl-methylamine (512 mg), 1,1'-carbonyldiimidazole (0.83 g) and dichloromethane (5 mL) was stirred for 18 hours and then concentrated. The residue was purified by preparative HPLC. In this way the product was obtained with molecular weight 126.16 (C6H10N2O); MS (ESI): 127 (M+H+).

5-Methyl-oxazolidin-2-one 1,1'-Carbonyldiimidazole (21.6 g) was added in portions to a mixture of 1-amino-2-propanol (10 g) and dichloromethane (100 mL). After 2 hours, the resultant precipitate was sucked off and taken up in THF. The THF solution was heated under reflux for 6 hours. The cooled reaction mixture was distributed between ethyl acetate and hydrochloric acid (1 N). The organic phase was dried over magnesium sulfate and concentrated. In this way the product was obtained with molecular weight 101.11 (C4H7NO2); MS (ESI): 102 (M+H+).

The products presented in Table 10 were obtained according to Method M by reaction of the corresponding triflate with the corresponding terminal alkyne.

| Ex. No. | Structure | Empirical formula | Molecular weight | ESI-MS [M + H]+ |
|---|---|---|---|---|
| 114 | 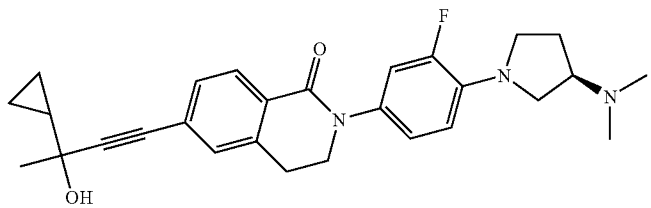 [SMILES: CN(C)[C@@H]1CCN(c2ccc(N3CCc4cc(C#CC(C)(O)C5CC5)ccc4C3=O)cc2F)C1] | C28H32FN3O2 | 461, 59 | 462 |
| 115 | 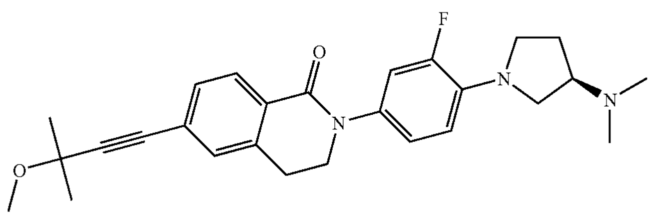 | C27H32FN3O2 | 449, 57 | 450 |
| 116 | 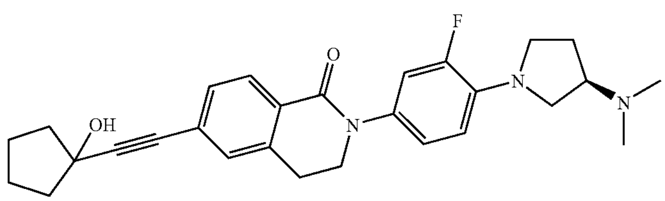 [SMILES: CN(C)[C@@H]1CCN(c2ccc(N3CCc4cc(C#CC5(O)CCCC5)ccc4C3=O)cc2F)C1] | C28H32FN3O2 | 461, 59 | 462 |
| 117 | 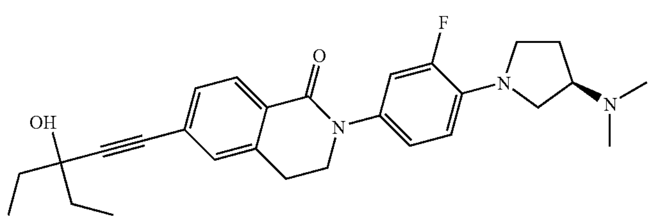 [SMILES: CCC(O)(C#Cc1ccc2c(c1)CCN(c1ccc(N3CC[C@@H](N(C)C)C3)c(F)c1)C2=O)CC] | C28H34FN3O2 | 463, 60 | 464 |
| 118 | 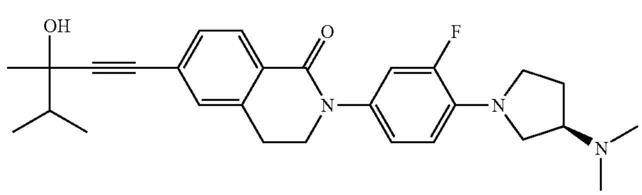 [SMILES: CC(C)C(C)(O)C#Cc1ccc2c(c1)CCN(c1ccc(N3CC[C@@H](N(C)C)C3)c(F)c1)C2=O] | C28H34FN3O2 | 463, 60 | 464 |

-continued

| Ex. No. | Structure | Empirical formula | Molecular weight | ESI-MS [M + H]+ |
|---|---|---|---|---|
| 119 | 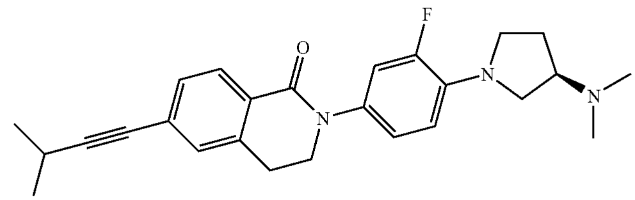 [SMILES: CC(C)C#Cc1ccc2c(c1)CCN(c1ccc(N3CC[C@@H](N(C)C)C3)c(F)c1)C2=O] | C26H30FN3O | 419, 55 | 420 |
| 120 | 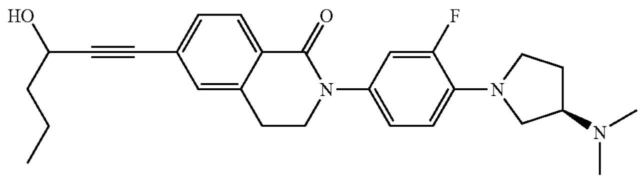 [SMILES: CCCC(O)C#Cc1ccc2c(c1)CCN(c1ccc(N3CC[C@@H](N(C)C)C3)c(F)c1)C2=O] | C27H32FN3O2 | 449, 57 | 450 |
| 121 | 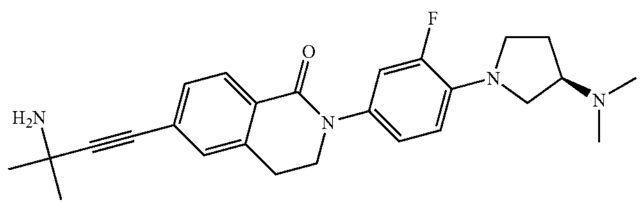 [SMILES: CN(C)[C@@H]1CCN(c2ccc(N3CCc4cc(C#CC(C)(C)N)ccc4C3=O)cc2F)C1] | C26H31FN4O | 434, 56 | 435 |
| 122 | 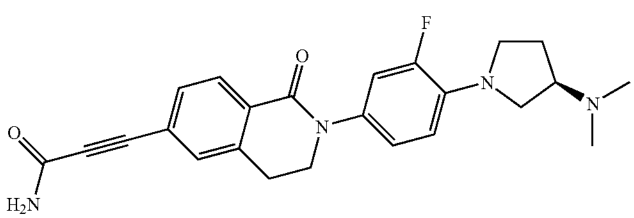 [SMILES: CN(C)[C@@H]1CCN(c2ccc(N3CCc4cc(C#CC(N)=O)ccc4C3=O)cc2F)C1] | C24H25FN4O2 | 420, 49 | 421 |
| 123 | 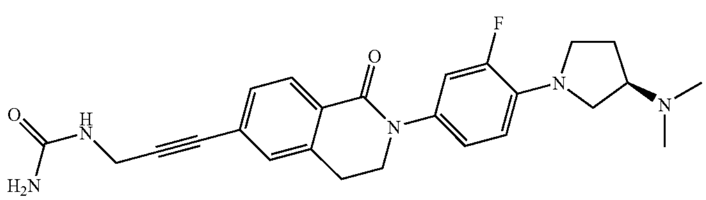 [SMILES: CN(C)[C@@H]1CCN(c2ccc(N3CCc4cc(C#CCNC(N)=O)ccc4C3=O)cc2F)C1] | C25H28FN5O2 | 449, 53 | 450 |
| 124 | 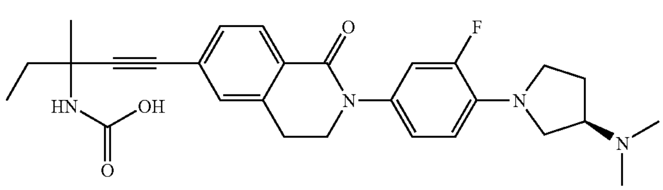 [SMILES: CCC(C)(C#Cc1ccc2c(c1)CCN(c1ccc(N3CC[C@@H](N(C)C)C3)c(F)c1)C2=O)NC(=O)O] | C28H33FN4O3 | 492, 60 | 493 |
| 125 | 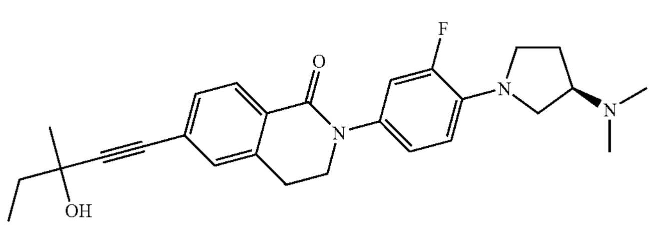 [SMILES: CCC(C)(O)C#Cc1ccc2c(c1)CCN(c1ccc(N3CC[C@@H](N(C)C)C3)c(F)c1)C2=O] | C27H32FN3O2 | 449, 57 | 450 |

| Ex. No. | Structure | Empirical formula | Molecular weight | ESI-MS [M + H]+ |
|---|---|---|---|---|
| 126 | 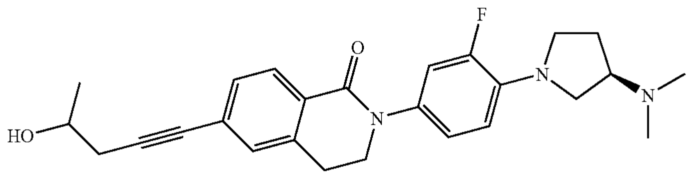 [SMILES: CC(O)CC#Cc1ccc2c(c1)CCN(c1ccc(N3CC[C@@H](N(C)C)C3)c(F)c1)C2=O] | C26H30FN3O2 | 435, 55 | 436 |
| 127 | 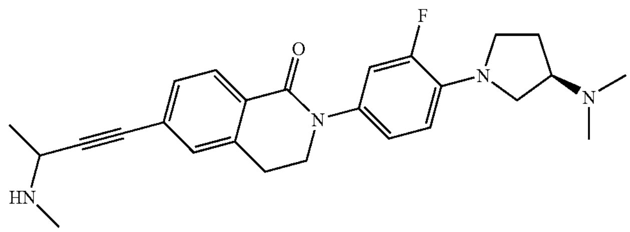 [SMILES: CNC(C)C#Cc1ccc2c(c1)CCN(c1ccc(N3CC[C@@H](N(C)C)C3)c(F)c1)C2=O] | C26H31FN4O | 434, 56 | 435 |
| 128 | 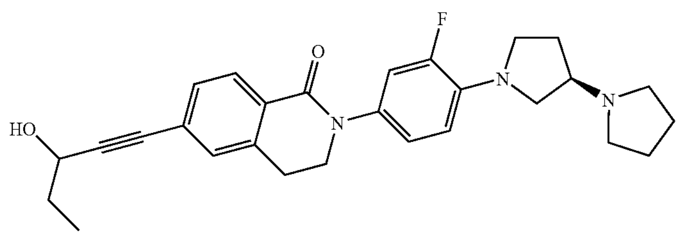 [SMILES: CCC(O)C#Cc1ccc2c(c1)CCN(c1ccc(N3CC[C@@H](N4CCCC4)C3)c(F)c1)C2=O] | C28H32FN3O2 | 461, 59 | 462 |
| 129 | 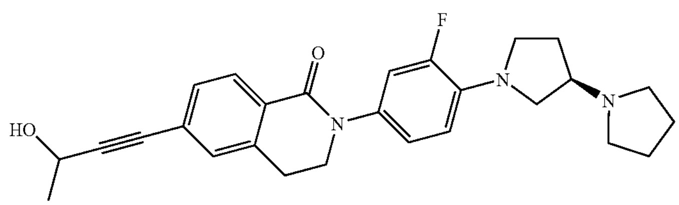 | C27H30FN3O2 | 447, 56 | 448 |
| 130 | 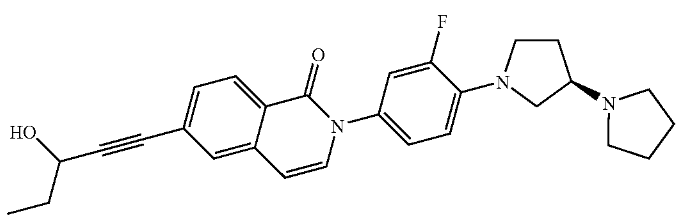 [SMILES: CCC(O)C#Cc1ccc2c(=O)n(-c3ccc(N4CC[C@@H](N5CCCC5)C4)c(F)c3)ccc2c1] | C28H30FN3O2 | 459, 57 | 460 |
| 131 | 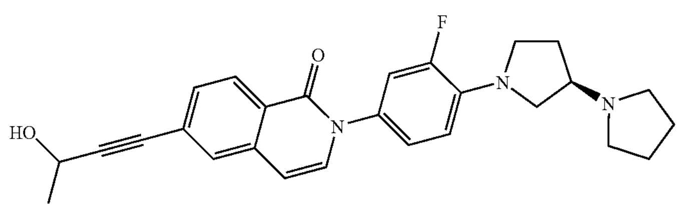 [SMILES: CC(O)C#Cc1ccc2c(=O)n(-c3ccc(N4CC[C@@H](N5CCCC5)C4)c(F)c3)ccc2c1] | C27H28FN3O2 | 445, 54 | 446 |
| 132 | 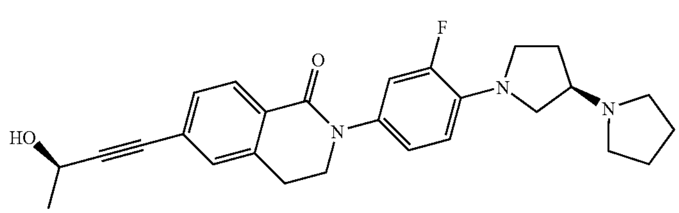 [SMILES: C[C@@H](O)C#Cc1ccc2c(c1)CCN(c1ccc(N3CC[C@@H](N4CCCC4)C3)c(F)c1)C2=O] | C27H30FN3O2 | 447, 56 | 448 |

-continued

| Ex. No. | Structure | Empirical formula | Molecular weight | ESI-MS [M + H]+ |
|---|---|---|---|---|
| 133 | 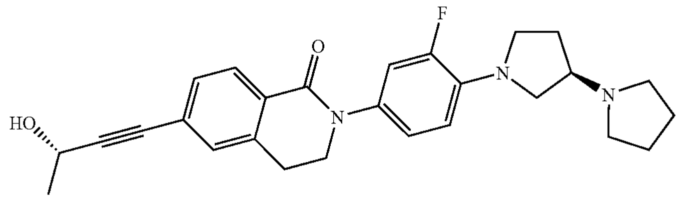 [SMILES: C[C@H](O)C#Cc1ccc2c(c1)CCN(c1ccc(N3CC[C@@H](N4CCCC4)C3)c(F)c1)C2=O] | C27H30FN3O2 | 447, 56 | 448 |
| 134 | 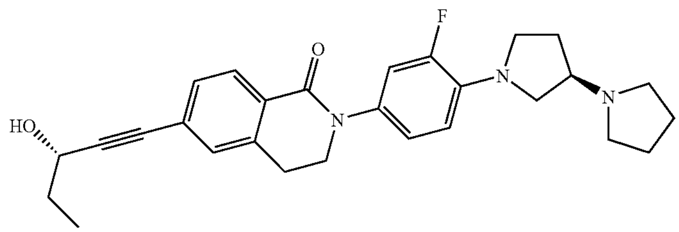 | C28H32FN3O2 | 461, 59 | 462 |
| 135 | 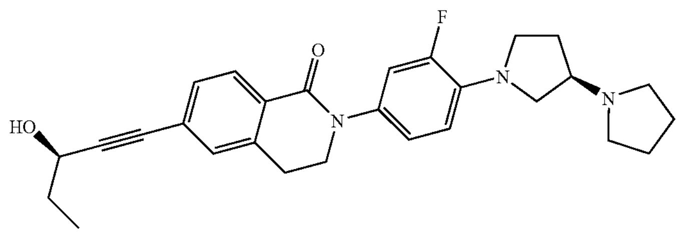 [SMILES: CC[C@@H](O)C#Cc1ccc2c(c1)CCN(c1ccc(N3CC[C@@H](N4CCCC4)C3)c(F)c1)C2=O] | C28H32FN3O2 | 461, 59 | 462 |
| 136 | 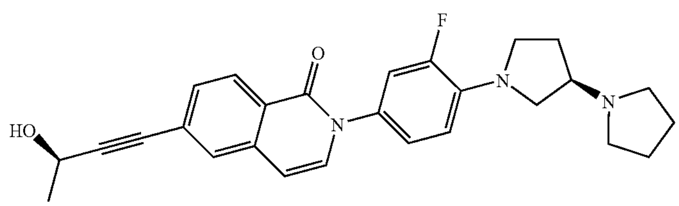 [SMILES: C[C@@H](O)C#Cc1ccc2c(=O)n(-c3ccc(N4CC[C@@H](N5CCCC5)C4)c(F)c3)ccc2c1] | C27H28FN3O2 | 445, 54 | 446 |
| 137 | 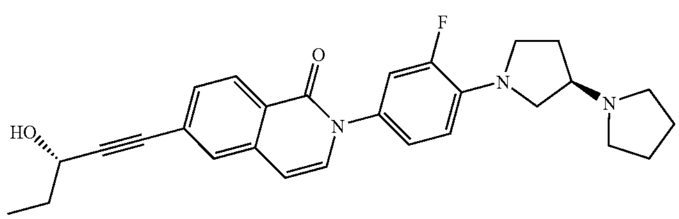 | C28H30FN3O2 | 459, 57 | 460 |
| 138 | 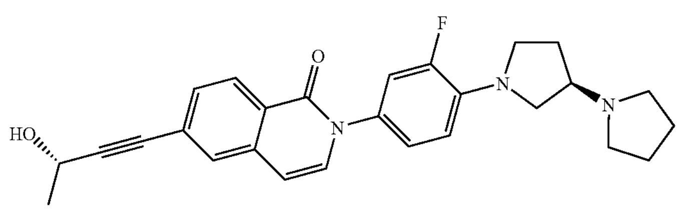 | C27H28FN3O2 | 445, 54 | 446 |
| 139 | 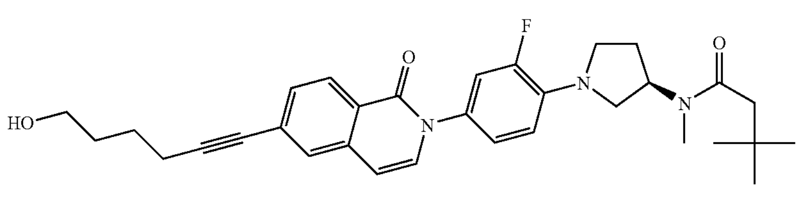 [SMILES: CN(C(=O)CC(C)(C)C)[C@@H]1CCN(c2ccc(-n3ccc4cc(C#CCCCCO)ccc4c3=O)cc2F)C1] | C31H36FN3O4 | 533, 65 | 534 |

| Ex. No. | Structure | Empirical formula | Molecular weight | ESI-MS [M + H]⁺ |
|---|---|---|---|---|
| 140 | 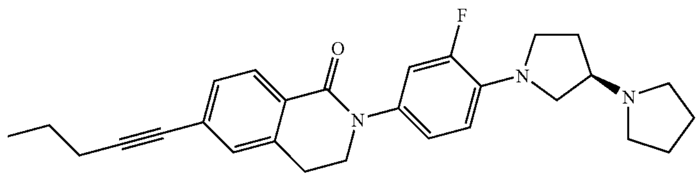 [SMILES: CCCC#Cc1ccc2c(c1)CCN(c1ccc(N3CC[C@@H](N4CCCC4)C3)c(F)c1)C2=O] | C28H30FN3O | 443, 57 | 444 |

Trifluoro-methanesulfonic acid 2-{4-[(R)-3-(tert-butoxy-carbonyl-methyl-amino)-pyrrolidin-1-yl]-3-fluorophenyl}-1-oxo-1,2-dihydro-isoquinolin-6-yl ester According to Method S, {(R)-1-[2-fluoro-4-(6-hydroxy-1-oxo-1H-isoquinolin-2-yl)-phenyl]-pyrrolidin-3-yl}-methyl-carbamic acid tert-butyl ester was reacted with trifluoromethanesulfonic acid anhydride. In this way the product was obtained with molecular weight 585.58 (C26H27N3O6); MS (ESI): 586 (M+H+).

The following triflates were obtained similarly from the corresponding phenols:

trifluoro-methanesulfonic acid 2-((R)-4-[1,3']bipyrrolidinyl-1'-yl-3-fluorophenyl)-1-oxo-1,2-dihydro-isoquinolin-6-yl ester;

trifluoro-methanesulfonic acid 2-((R)-4-[1,3']bipyrrolidinyl-1'-yl-3-fluorophenyl)-1-oxo-1,2,3,4-tetrahydro-isoquinolin-6-yl ester.

2-((R)-4-[1,3']Bipyrrolidinyl-1'-yl-3-fluorophenyl)-6-hydroxy-3,4-dihydro-2H-isoquinolin-1-one According to Method L, 2-((R)-4-[1,3']bipyrrolidinyl-1'-yl-3-fluorophenyl)-6-methoxy-3,4-dihydro-2H-isoquinolin-1-one was reacted with hydrogen bromide. In this way the product was obtained with molecular weight 395.48 (C23H26FN3O2); MS (ESI): 396 (M+H+).

2-((R)-4-[1,3']Bipyrrolidinyl-1'-yl-3-fluorophenyl)-6-hydroxy-2H-isoquinolin-1-one was obtained similarly from 2-((R)-4-[1,3']bipyrrolidinyl-1'-yl-3-fluorophenyl)-6-methoxy-2H-isoquinolin-1-one.

(S)-Pent-1-yn-3-ol

In accordance with instructions in the literature (T. Künstler et al., Tetrahedron: Asymmetry 1993, 4(7), 1645-50), racemic pent-1-yn-3-ol was reacted with N-tosyl-L-phenylalanine, the diastereomeric esters were separated by crystallization from ethanol/hexane, and the optically pure crystalline ester was saponified.

Example 141

2-[4-((R)-3-Dimethylamino-pyrrolidin-1-yl)-3-fluorophenyl]-6-(2-hydroxy-3-methyl-butoxy)-3,4-dihydro-2H-isoquinolin-1-one

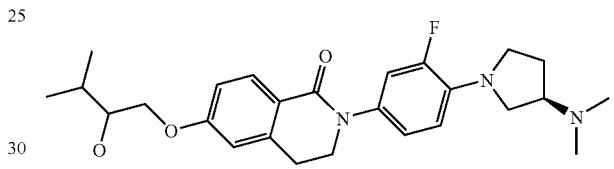

Method T

A mixture of 2-[4-((R)-3-dimethylamino-pyrrolidin-1-yl)-3-fluorophenyl]-6-hydroxy-3,4-dihydro-2H-isoquinolin-1-one (50 mg), 2-isopropyl-oxirane (12 mg), 2, 3, 4,6,7,8,9,10-octahydro-pyrimido[1,2-a]azepine (21 mg) and toluene (1 mL) was heated at 120° C. bath temperature. After 4 hours, the same amounts of epoxide and auxiliary base were added once again, heating for a further 8 hours at 120° C. The cooled reaction mixture was concentrated and purified by preparative HPLC. In this way the product was obtained with molecular weight 455.58 (C26H34FN3O3); MS (ESI): 456 (M+H+).

Alternatively cesium fluoride in DMF as solvent can also be used as auxiliary base.

The products presented in Table 11 were obtained according to Method T by reaction of the corresponding phenol with the corresponding epoxide.

| Ex. No. | Structure | Empirical formula | Molecular weight | ESI-MS [M + H]⁺ |
|---|---|---|---|---|
| 142 | 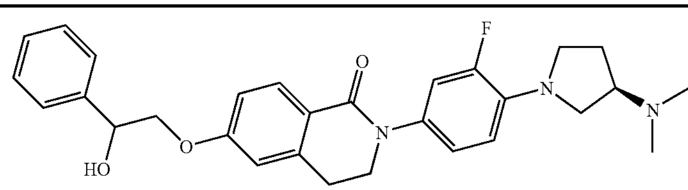 | C29H32FN3O3 | 489, 60 | 490 |
| 143 | 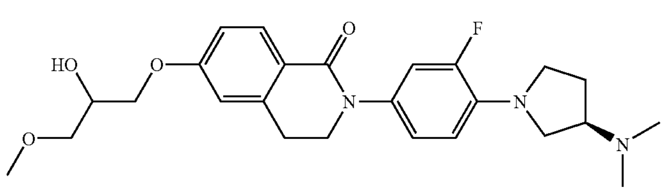 | C25H32FN3O4 | 457, 55 | 458 |

-continued

| Ex. No. | Structure | Empirical formula | Molecular weight | ESI-MS [M + H]+ |
|---|---|---|---|---|
| 144 | 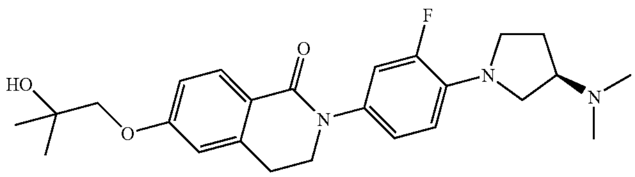 [SMILES: CN(C)[C@@H]1CCN(c2ccc(N3CCc4cc(OCC(C)(C)O)ccc4C3=O)cc2F)C1] | C25H32FN3O3 | 441,55 | 442 |
| 145 | 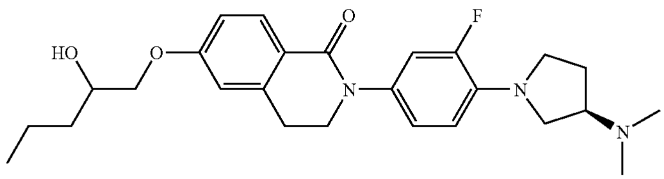 [SMILES: CCCC(O)COc1ccc2c(c1)CCN(c1ccc(N3CC[C@@H](N(C)C)C3)c(F)c1)C2=O] | C26H34FN3O3 | 455,58 | 456 |
| 146 | 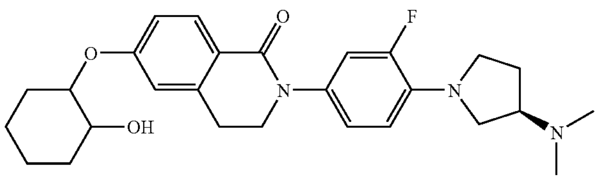 [SMILES: CN(C)[C@@H]1CCN(c2ccc(N3CCc4cc(OC5CCCCC5O)ccc4C3=O)cc2F)C1] | C27H34FN3O3 | 467,59 | 468 |
| 147 | 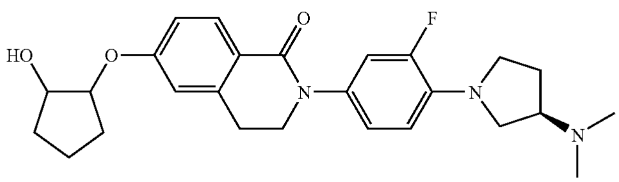 [SMILES: CN(C)[C@@H]1CCN(c2ccc(N3CCc4cc(OC5CCCC5O)ccc4C3=O)cc2F)C1] | C26H32FN3O3 | 453,56 | 454 |
| 148 | 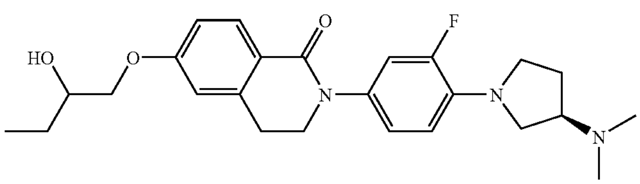 [SMILES: CCC(O)COc1ccc2c(c1)CCN(c1ccc(N3CC[C@@H](N(C)C)C3)c(F)c1)C2=O] | C25H32FN3O3 | 441,55 | 442 |
| 149 | 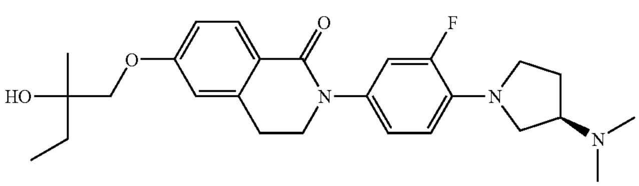 [SMILES: CCC(C)(O)COc1ccc2c(c1)CCN(c1ccc(N3CC[C@@H](N(C)C)C3)c(F)c1)C2=O] | C26H34FN3O3 | 455,58 | 456 |
| 150 | 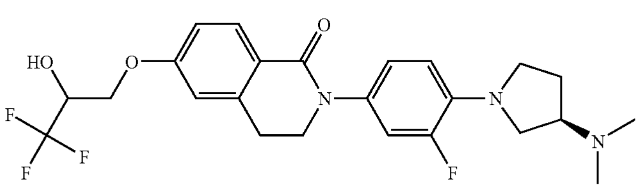 [SMILES: CN(C)[C@@H]1CCN(c2ccc(N3CCc4cc(OCC(O)C(F)(F)F)ccc4C3=O)cc2F)C1] | C24H27F4N3O3 | 481,50 | 482 |
| 151 | 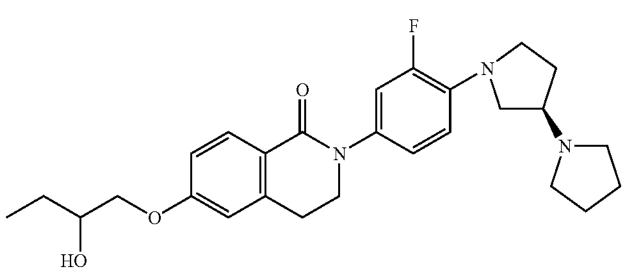 [SMILES: CCC(O)COc1ccc2c(c1)CCN(c1ccc(N3CC[C@@H](N4CCCC4)C3)c(F)c1)C2=O] | C27H34FN3O3 | 467,59 | 468 |

-continued

| Ex. No. | Structure | Empirical formula | Molecular weight | ESI-MS [M + H]+ |
|---|---|---|---|---|
| 152 | 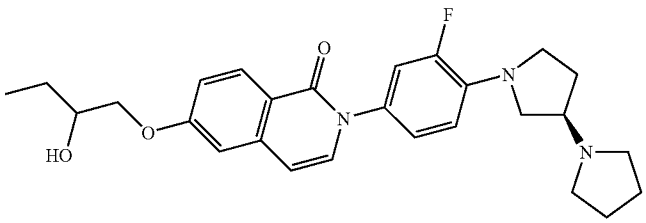 [SMILES: CCC(O)COc1ccc2c(=O)n(-c3ccc(N4CC[C@@H](N5CCCC5)C4)c(F)c3)ccc2c1] | C27H32FN3O3 | 465, 57 | 466 |
| 153 | 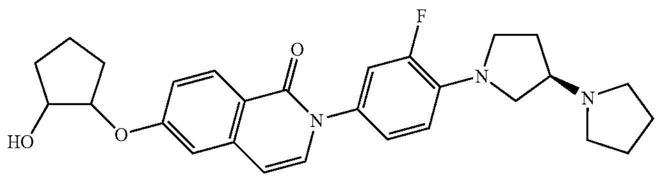 | C28H32FN3O3 | 477, 58 | 478 |
| 154 | 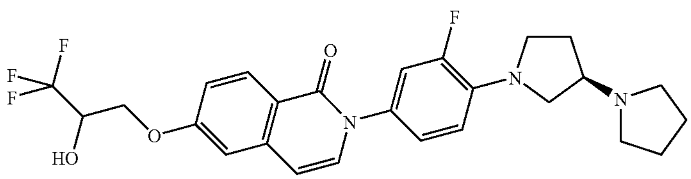 [SMILES: O=c1c2ccc(OCC(O)C(F)(F)F)cc2ccn1-c1ccc(N2CC[C@@H](N3CCCC3)C2)c(F)c1] | C26H27F4N3O3 | 505, 52 | 506 |
| 155 | 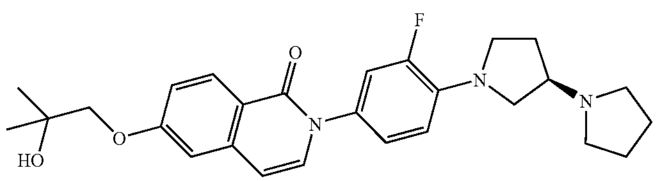 [SMILES: CC(C)(O)COc1ccc2c(=O)n(-c3ccc(N4CC[C@@H](N5CCCC5)C4)c(F)c3)ccc2c1] | C27H32FN3O3 | 465, 57 | 466 |
| 156 | 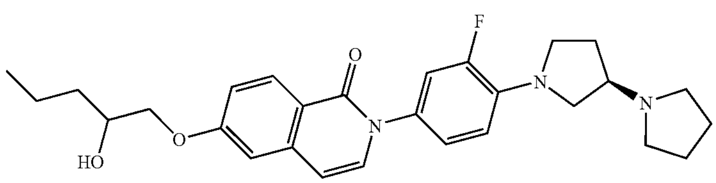 [SMILES: CCCC(O)COc1ccc2c(=O)n(-c3ccc(N4CC[C@@H](N5CCCC5)C4)c(F)c3)ccc2c1] | C28H34FN3O3 | 479, 60 | 480 |
| 157 | 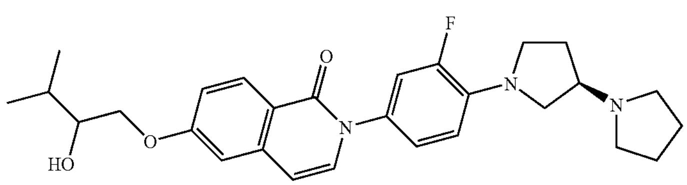 [SMILES: CC(C)C(O)COc1ccc2c(=O)n(-c3ccc(N4CC[C@@H](N5CCCC5)C4)c(F)c3)ccc2c1] | C28H34FN3O3 | 479, 60 | 480 |
| 158 | 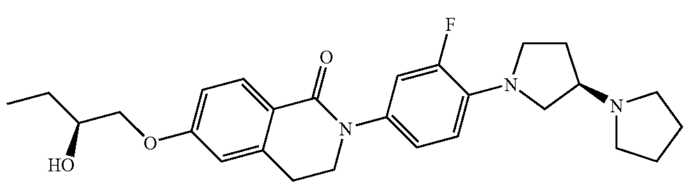 [SMILES: CC[C@H](O)COc1ccc2c(c1)CCN(c1ccc(N3CC[C@@H](N4CCCC4)C3)c(F)c1)C2=O] | C27H34FN3O3 | 467, 59 | 468 |
| 159 | 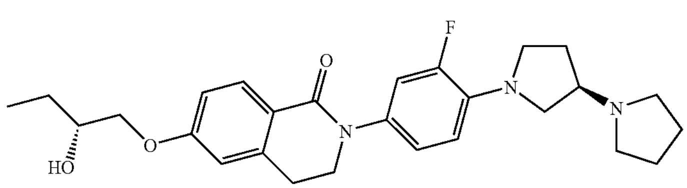 [SMILES: CC[C@@H](O)COc1ccc2c(c1)CCN(c1ccc(N3CC[C@@H](N4CCCC4)C3)c(F)c1)C2=O] | C27H34FN3O3 | 467, 59 | 468 |

-continued

| Ex. No. | Structure | Empirical formula | Molecular weight | ESI-MS [M + H]+ |
|---|---|---|---|---|
| 160 | 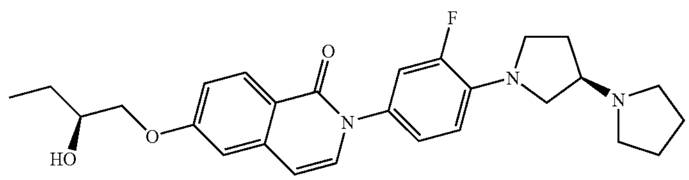 [SMILES: CC[C@H](O)COc1ccc2c(=O)n(-c3ccc(N4CC[C@@H](N5CCCC5)C4)c(F)c3)ccc2c1] | C27H32FN3O3 | 465, 57 | 466 |
| 161 | 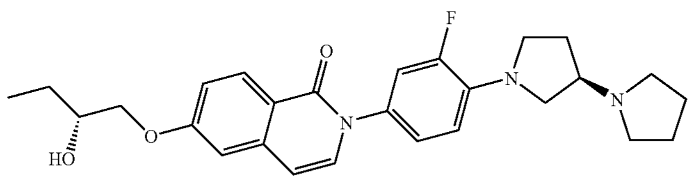 [SMILES: CC[C@@H](O)COc1ccc2c(=O)n(-c3ccc(N4CC[C@@H](N5CCCC5)C4)c(F)c3)ccc2c1] | C27H32FN3O3 | 465, 57 | 466 |
| 162 | 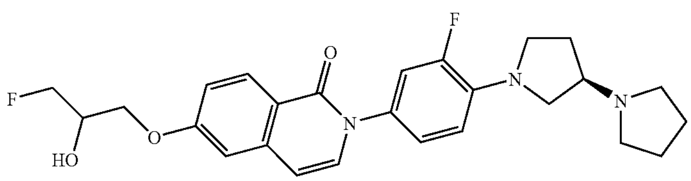 [SMILES: O=c1c2ccc(OCC(O)CF)cc2ccn1-c1ccc(N2CC[C@@H](N3CCCC3)C2)c(F)c1] | C26H29F2N3O3 | 469, 54 | 470 |
| 163 | 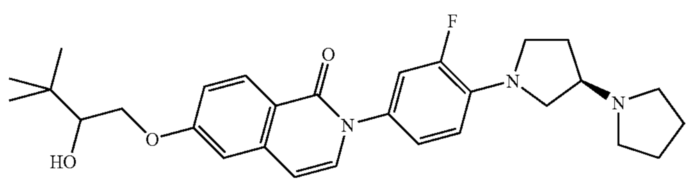 [SMILES: CC(C)(C)C(O)COc1ccc2c(=O)n(-c3ccc(N4CC[C@@H](N5CCCC5)C4)c(F)c3)ccc2c1] | C29H36FN3O3 | 493, 63 | 494 |
| 164 | 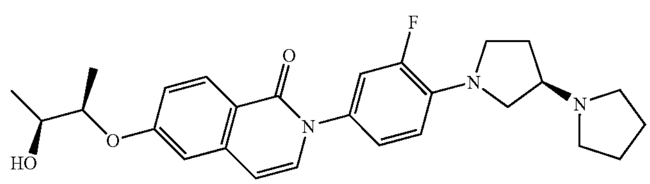 [SMILES: C[C@H](O)[C@@H](C)Oc1ccc2c(=O)n(-c3ccc(N4CC[C@@H](N5CCCC5)C4)c(F)c3)ccc2c1] | C27H32FN3O3 | 465, 57 | 466 |
| 165 | 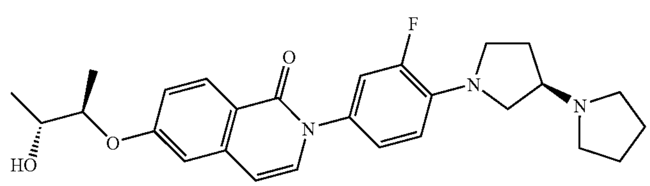 [SMILES: C[C@@H](O)[C@@H](C)Oc1ccc2c(=O)n(-c3ccc(N4CC[C@@H](N5CCCC5)C4)c(F)c3)ccc2c1] | C27H32FN3O3 | 465, 57 | 466 |
| 166 | 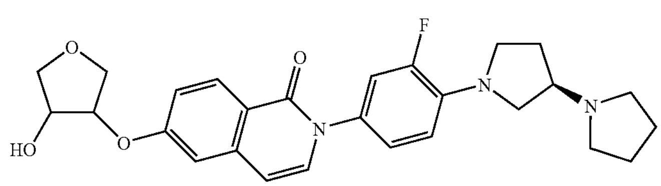 [SMILES: O=c1c2ccc(OC3COCC3O)cc2ccn1-c1ccc(N2CC[C@@H](N3CCCC3)C2)c(F)c1] | C27H30FN3O4 | 479, 56 | 480 |
| 167 | 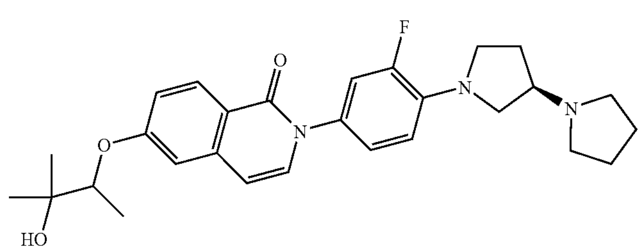 [SMILES: CC(Oc1ccc2c(=O)n(-c3ccc(N4CC[C@@H](N5CCCC5)C4)c(F)c3)ccc2c1)C(C)(C)O] | C28H34FN3O3 | 479, 60 | 480 |

-continued

| Ex. No. | Structure | Empirical formula | Molecular weight | ESI-MS [M + H]+ |
|---|---|---|---|---|
| 168 | 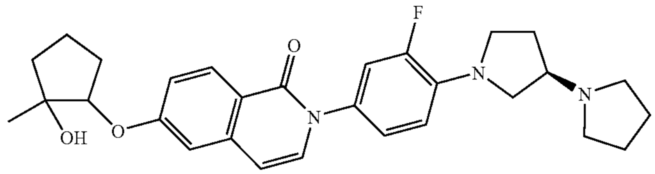 [SMILES: CC1(O)CCCC1Oc1ccc2c(=O)n(-c3ccc(N4CC[C@@H](N5CCCC5)C4)c(F)c3)ccc2c1] | C29H34FN3O3 | 491, 61 | 492 |
| 169 | 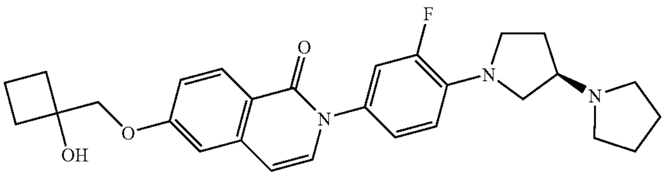 [SMILES: O=c1c2ccc(OCC3(O)CCC3)cc2ccn1-c1ccc(N2CC[C@@H](N3CCCC3)C2)c(F)c1] | C28H32FN3O3 | 477, 58 | 478 |
| 170 | 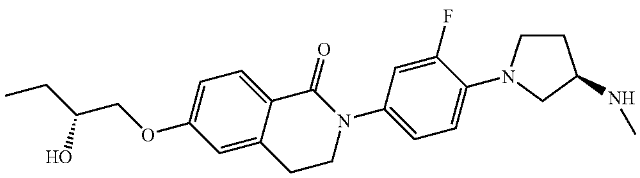 [SMILES: CC[C@@H](O)COc1ccc2c(c1)CCN(c1ccc(N3CC[C@@H](NC)C3)c(F)c1)C2=O] | C24H30FN3O3 | 427, 52 | 428 |
| 171 | 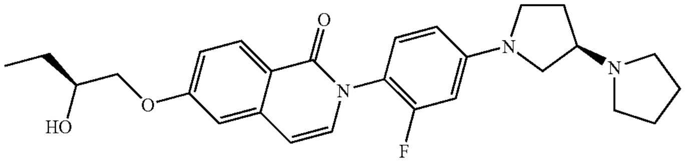 [SMILES: CC[C@H](O)COc1ccc2c(=O)n(-c3ccc(N4CC[C@@H](N5CCCC5)C4)cc3F)ccc2c1] | C27H32FN3O3 | 465, 57 | 466 |
| 172 | 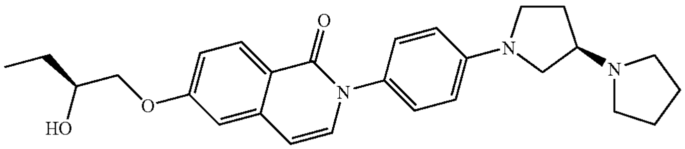 [SMILES: CC[C@H](O)COc1ccc2c(=O)n(-c3ccc(N4CC[C@@H](N5CCCC5)C4)cc3)ccc2c1] | C27H33N3O3 | 447, 58 | 448 |
| 173 | 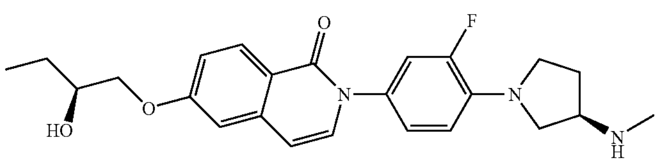 [SMILES: CC[C@H](O)COc1ccc2c(=O)n(-c3ccc(N4CC[C@@H](NC)C4)c(F)c3)ccc2c1] | C24H28FN3O3 | 425, 51 | 426 |
| 174 | 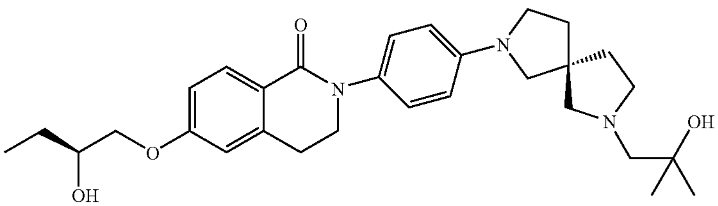 [SMILES: CC[C@H](O)COc1ccc2c(c1)CCN(c1ccc(N3CC[C@]4(CCN(CC(C)(C)O)C4)C3)cc1)C2=O] | C30H41N3O4 | 507, 68 | 508 |
| 175 | 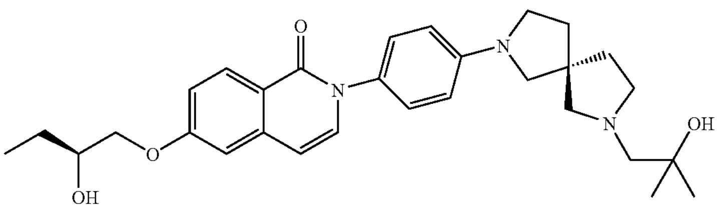 [SMILES: CC[C@H](O)COc1ccc2c(=O)n(-c3ccc(N4CC[C@]5(CCN(CC(C)(C)O)C5)C4)cc3)ccc2c1] | C30H39N3O4 | 505, 66 | 506 |

| Ex. No. | Structure | Empirical formula | Molecular weight | ESI-MS [M + H]+ |
|---|---|---|---|---|
| 176 | 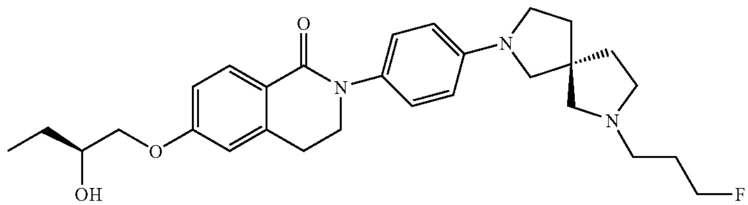 [SMILES: CC[C@H](O)COc1ccc2c(c1)CCN(c1ccc(N3CC[C@]4(CCN(CCCF)C4)C3)cc1)C2=O] | C29H38FN3O3 | 495, 64 | 496 |
| 177 | 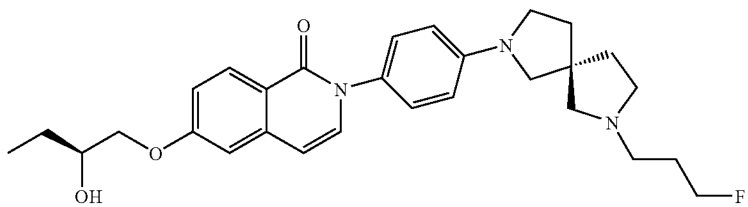 [SMILES: CC[C@H](O)COc1ccc2c(=O)n(-c3ccc(N4CC[C@]5(CCN(CCCF)C5)C4)cc3)ccc2c1] | C29H36FN3O3 | 493, 63 | 494 |

For preparation of Examples 170 and 173, the corresponding Boc-protected aminophenols ({(R)-1-[2-fluoro-4-(6-hydroxy-1-oxo-3,4-dihydro-1H-isoquinolin-2-yl)-phenyl]-pyrrolidin-3-yl}-methyl-carbamic acid tert-butyl ester or respectively {(R)-1-[2-fluoro-4-(6-hydroxy-1-oxo-1H-isoquinolin-2-yl)-phenyl]-pyrrolidin-3-yl}-methyl-carbamic acid tert-butyl ester) were used in the reaction and finally the carbamate was cleaved from the intermediate alkylation product by treatment with hydrogen chloride (5 N in 2-propanol).

1-Oxa-Spiro[2.3]Hexane

A mixture of methylene-cyclobutane (5.0 g) and dichloromethane (20 mL) was cooled on an ice bath and meta-chloroperbenzoic acid (12.7 g) was added in portions. At the end of addition, it was stirred for a further 3 hours at room temperature and the resultant precipitate was filtered off. The solvent was removed by careful distillation and the residue was reacted further directly.

2-((R)-4-[1,3']Bipyrrolidinyl-1'-yl-phenyl)-6-hydroxy-2H-isoquinolin-1-one

According to Method L, 2-((R)-4-[1,3']bipyrrolidinyl-1'-yl-phenyl)-6-methoxy-2H-isoquinolin-1-one was treated with hydrogen bromide. In this way the product was obtained with molecular weight 375.47 (C23H25N3O2); MS (ESI): 376 (M+H+).

6-Hydroxy-2-{4-[(S)-7-(2-hydroxy-2-methyl-propyl)-2,7-diaza-spiro[4.4]non-2-yl]-phenyl}-3,4-dihydro-2H-isoquinolin-1-one Method U
A mixture of 2-[(S)-4-(2,7-diaza-spiro[4.4]non-2-yl)-phenyl]-6-hydroxy-3,4-dihydro-2H-isoquinolin-1-one (0.50 g), isobutylene oxide (0.10 g), lithium bromide (0.12 g) and NMP (1 mL) was heated at 65° C. for 5 hours. The cooled reaction mixture was distributed between ethyl acetate and water. The organic phase was dried over magnesium sulfate and concentrated. In this way the product was obtained with molecular weight 435.57 (C26H33N3O3); MS (ESI): 436 (M+H+).

2-[(S)-4-(2,7-Diaza-spiro[4.4]non-2-yl)-phenyl]-6-hydroxy-3,4-dihydro-2H-isoquinolin-1-one According to Method L, (S)-7-[4-(6-methoxy-1-oxo-3,4-dihydro-1H-isoquinolin-2-yl)-phenyl]-2,7-diaza-spiro[4.4]nonane-2-carboxylic acid tert-butyl ester was treated with hydrogen bromide. In this way the product was obtained with molecular weight 363.46 (C22H25N3O2); MS (ESI): 364 (M+H+).

(S)-7-[4-(6-Methoxy-1-oxo-3,4-dihydro-1H-isoquinolin-2-yl)-phenyl]-2,7-diaza-spiro[4.4]nonane-2-carboxylic acid tert-butyl ester According to Method A, 2-(2-chloroethyl)-4-methoxy-benzoyl chloride was reacted with (S)-7-(4-amino-phenyl)-2,7-diaza-spiro[4.4]nonane-2-carboxylic acid tert-butyl ester. In this way the product was obtained with molecular weight 477.61 (C28H35N3O4); MS (ESI): 478 (M+H+).

(S)-7-(4-amino-phenyl)-2,7-diaza-spiro[4.4]nonane-2-carboxylic acid tert-butyl ester (S)-7-(4-nitro-phenyl)-2,7-diaza-spiro[4.4]nonane-2-carboxylic acid tert-butyl ester was hydrogenated according to Method F. In this way the product was obtained with molecular weight 317.43 (C18H27N3O2); MS (ESI): 318 (M+H+).

(S)-7-(4-Nitro-phenyl)-2,7-diaza-spiro[4.4]nonane-2-carboxylic acid tert-butyl ester Method V
A solution of sodium hydrogencarbonate (8.83 g) in water (200 mL) was added to a stirred mixture of (S)-2-(4-nitro-phenyl)-2,7-diaza-spiro[4.4]nonane (13.0 g) and 1,4-dioxan (100 mL) and then Boc2O (11.5 g) was added. After 12 hours, ethyl acetate was added to the reaction mixture and the phases were separated. The organic phase was washed with water, dried over magnesium sulfate and concentrated. In this way the product was obtained with molecular weight 347.42 (C18H25N3O4); MS (ESI): 348 (M+H+).

(S)-2-(4-Nitro-phenyl)-2,7-diaza-spiro[4.4]nonane

According to Method E, 1-fluoro-4-nitro-benzene was reacted with (S)-2,7-diaza-spiro[4.4]nonane. In this way the product was obtained with molecular weight 247.30 (C13H17N3O2); MS (ESI): 248 (M+H+).

(S)-2,7-Diaza-spiro[4.4]nonane

Method W (S)-2,7-Diaza-spiro[4.4]nonane-3,8-dione (20.0 g) was added in portions to a mixture of lithium aluminum hydride (17.2 g) and THF (300 mL). At the end of addition, it was boiled under reflux for 12 hours. As reaction was incomplete, more lithium aluminum hydride (8.6 g) was added, boiling under reflux for a further 12 hours. The operation was repeated with further lithium aluminum hydride (4.3 g). The mixture was cooled to −10° C. and water (10 mL), concentrated sodium hydroxide solution (10 mL) and water again (10 mL) were carefully added dropwise. Solid components were sucked off and
washed with dichloromethane. The filtrate was concentrated. In this way the product was obtained with molecular weight 126.20 (C7H14N2); MS (ESI): 127 (M+H+).

(S)-2,7-Diaza-spiro[4.4]nonane-3,8-dione

Racemic 2,7-diaza-spiro[4.4]nonane-3,8-dione (C. G. Overberger et al., J. Org. Chem. 1981, 46, 2757-64 and T. P. Culbertson et al., J. Med. Chem. 1990, 33, 2270-75) was separated into the enantiomers by chiral-phase chromatography (Daicel Chiralpak AS20; eluent ethanol/methanol 1:1). The enantiomer eluting later showed a positive specific rotation. Therefore, after comparing with the literature (M. Kajtar et al., Collect. Czech. Chem. Commun. 1982, 47, 936-49) this was assigned the (R)-configuration. The enantiomer eluting first was therefore (S)-2,7-diaza-spiro[4.4]nonane-3,8-dione.

6-Hydroxy-2-{4-[(S)-7-(2-hydroxy-2-methyl-propyl)-2,7-diaza-spiro[4.4]non-2-yl]-phenyl}-2H-isoquinolin-1-one According to Method U, 2-[(S)-4-(2,7-diaza-spiro[4.4] non-2-yl)-phenyl]-6-hydroxy-2H-isoquinolin-1-one was reacted with 2,2-dimethyl-oxirane. In this way the product was obtained with molecular weight 433.56 (C26H31N3O3); MS (ESI): 434 (M+H+).

2-[(S)-4-(2,7-Diaza-spiro[4.4]non-2-yl)-phenyl]-6-hydroxy-2H-isoquinolin-1-one According to Method L, (S)-7-[4-(6-methoxy-1-oxo-1H-isoquinolin-2-yl)-phenyl]-2,7-diaza-spiro[4.4]nonane-2-carboxylic acid tert-butyl ester was treated with hydrogen bromide. In this way the product was obtained with molecular weight 361.45 (C22H23N3O2); MS (ESI): 362 (M+H+).

(S)-7-[4-(6-Methoxy-1-oxo-1H-isoquinolin-2-yl)-phenyl]-2,7-diaza-spiro[4.4]nonane-2-carboxylic acid tert-butyl ester According to Method Q, (S)-7-[4-(4-methoxy-2-methyl-benzoylamino)-phenyl]-2,7-diaza-spiro[4.4]nonane-2-carboxylic acid tert-butyl ester was reacted with N-formylmorpholine. In this way the product was obtained with molecular weight 475.59 (C28H33N3O4); MS (ESI): 476 (M+H+).

(S)-7-[4-(4-Methoxy-2-methyl-benzoylamino)-phenyl]-2,7-diaza-spiro[4.4]nonane-2-carboxylic acid tert-butyl ester According to Method P, (S)-7-(4-amino-phenyl)-2,7-diaza-spiro[4.4]nonane-2-carboxylic acid tert-butyl ester was reacted with 4-methoxy-2-methyl-benzoic acid. In this way the product was obtained with molecular weight 465.60 (C27H35N3O4); MS (ESI): 466 (M+H+).

2-{4-[(S)-7-(3-Fluoro-propyl)-2,7-diaza-spiro[4.4] non-2-yl]-phenyl}-6-hydroxy-3,4-dihydro-2H-isoquinolin-1-one Method X A mixture of 2-[(S)-4-(2,7-diaza-spiro[4.4]non-2-yl)-phenyl]-6-hydroxy-3,4-dihydro-2H-isoquinolin-1-one (0.20 g), 1-bromo-3-fluoro-propane (76 mg), sodium hydrogencarbonate (10 mg) and NMP (5 mL) was heated at 50° C. for 15 hours. The reaction mixture was distributed between ethyl acetate and water. The organic phase was dried over magnesium sulfate and concentrated. The raw product was purified by preparative HPLC. In this way the product was obtained with molecular weight 423.54 (C25H30FN3O2); MS (ESI): 424 (M+H+).

2-{4-[(S)-7-(3-Fluoro-propyl)-2,7-diaza-spiro[4.4] non-2-yl]-phenyl}-6-hydroxy-2H-isoquinolin-1-one According to Method X, 2-[(S)-4-(2,7-diaza-spiro[4.4] non-2-yl)-phenyl]-6-hydroxy-2H-isoquinolin-1-one was reacted with 1-bromo-3-fluoro-propane. In this way the product was obtained with molecular weight 421.52 (C25H28FN3O2); MS (ESI): 422 (M+H+).

Example 178

6-Cyclopropylmethoxy-2-{3-fluoro-4-[7-(2-fluoroethyl)-2,7-diaza-spiro[4.4]non-2-yl]-phenyl}-2H-isoquinolin-1-one

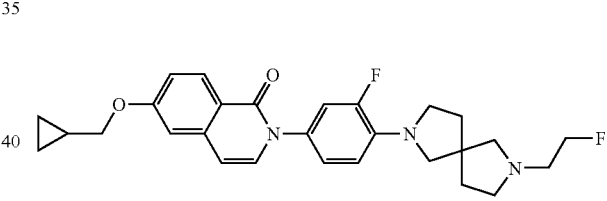

According to Method X, 6-cyclopropylmethoxy-2-[4-(2,7-diaza-spiro[4.4]non-2-yl)-3-fluorophenyl]-2H-isoquinolin-1-one was reacted with 1-bromo-2-fluoro-ethane. In this way the product was obtained with molecular weight 479.57 (C28H31F2N3O2); MS (ESI): 480 (M+H+).

6-Cyclopropylmethoxy-2-[4-(2,7-diaza-spiro[4.4] non-2-yl)-3-fluorophenyl]-2H-isoquinolin-1-one According to Method H, the carbamate was cleaved to 7-[4-(6-cyclopropylmethoxy-1-oxo-1H-isoquinolin-2-yl)-2-fluorophenyl]-2,7-diaza-spiro[4.4]nonane-2-carboxylic acid tert-butyl ester. In this way the product was obtained with molecular weight 433.53 (C26H28FN3O2); MS (ESI): 434 (M+H+).

7-[4-(6-Cyclopropylmethoxy-1-oxo-1H-isoquinolin-2-yl)-2-fluorophenyl]-2,7-diaza-spiro[4.4]nonane-2-carboxylic acid tert-butyl ester A mixture of 7-[2-fluoro-4-(6-hydroxy-1-oxo-1H-isoquinolin-2-yl)-phenyl]-2,7-diaza-spiro[4.4]nonane-2-carboxylic acid tert-butyl ester (250 mg), bromomethyl-cyclopropane (70 mg), cesium carbonate (170 mg) and NMP (5 mL) was heated for 4 hours at 60° C. The cooled reaction mixture was distributed between ethyl acetate and water. The organic phase was dried over magnesium sulfate and concentrated. The raw product was purified by preparative HPLC.

In this way the product was obtained with molecular weight 533.65 (C31H36FN3O4); MS (ESI): 534 (M+H+).

7-[2-Fluoro-4-(6-hydroxy-1-oxo-1H-isoquinolin-2-yl)-phenyl]-2,7-diaza-spiro[4.4]nonane-2-carboxylic acid tert-butyl ester According to Method E, 2,7-diaza-spiro[4.4]nonane-2-carboxylic acid tert-butyl ester was reacted with 1,2-difluoro-4-nitro-benzene. The nitro compound obtained was hydrogenated according to Method F. The aniline obtained was reacted with 4-methoxy-2-methyl-benzoic acid according to Method P. The amide obtained was reacted with N-formyl-morpholine according to Method Q. The isoquinolinone obtained was treated with hydrogen bromide according to Method L. Finally, the aminophenol obtained was reacted with Boc2O according to Method V. In this way the product was obtained with molecular weight 479.56 (C27H30FN3O4); MS (ESI): 480 (M+H+).

Example 179

2-{3-Fluoro-4-[7-(2-fluoroethyl)-2,7-diaza-spiro[4.4]non-2-yl]-phenyl}-6-(tetrahydrofuran-2-yl-methoxy)-2H-isoquinolin-1-one

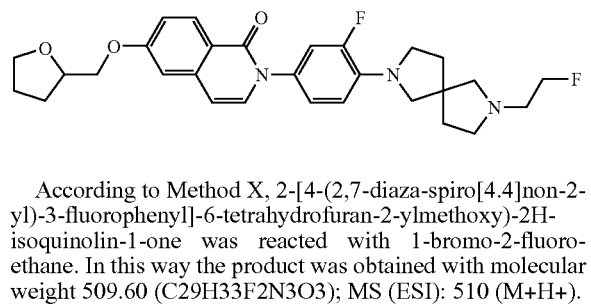

According to Method X, 2-[4-(2,7-diaza-spiro[4.4]non-2-yl)-3-fluorophenyl]-6-tetrahydrofuran-2-ylmethoxy)-2H-isoquinolin-1-one was reacted with 1-bromo-2-fluoro-ethane. In this way the product was obtained with molecular weight 509.60 (C29H33F2N3O3); MS (ESI): 510 (M+H+).

2-[4-(2,7-Diaza-spiro[4.4]non-2-yl)-3-fluorophenyl]-6-tetrahydrofuran-2-ylmethoxy)-2H-isoquinolin-1-one According to Method K, 7-[2-fluoro-4-(6-hydroxy-1-oxo-1H-isoquinolin-2-yl)-phenyl]-2,7-diaza-spiro[4.4]nonane-2-carboxylic acid tert-butyl ester was reacted with 2-bromomethyl-tetrahydrofuran and then the carbamate was cleaved with hydrogen chloride according to Method H. In this way the product was obtained with molecular weight 463.56 (C27H30FN3O3); MS (ESI): 464 (M+H+).

Example 180

6-Cyclopropylmethoxy-2-{3-fluoro-4-[7-(2-hydroxy-2-methyl-propyl)-2,7-diaza-spiro[4.4]non-2-yl]-phenyl}-2H-isoquinolin-1-one

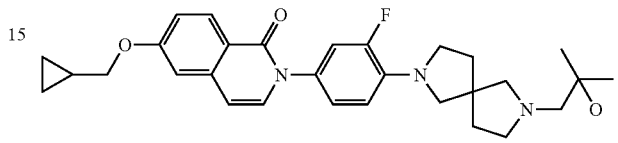

According to Method U, 6-cyclopropylmethoxy-2-[4-(2,7-diaza-spiro[4.4]non-2-yl)-3-fluorophenyl]-2H-isoquinolin-1-one was reacted with 2,2-dimethyl-oxirane. In this way the product was obtained with molecular weight 505.64 (C30H36FN3O3); MS (ESI): 506 (M+H+).

Example 181

2-{3-Fluoro-4-[7-(2-hydroxy-2-methyl-propyl)-2,7-diaza-spiro[4.4]non-2-yl]-phenyl}-6-(tetrahydrofuran-2-ylmethoxy)-2H-isoquinolin-1-one

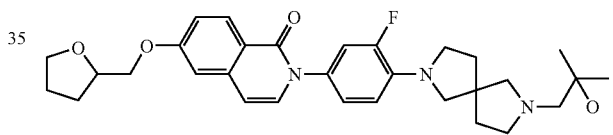

According to Method U, 2-[4-(2,7-diaza-spiro[4.4]non-2-yl)-3-fluorophenyl]-6-tetrahydrofuran-2-ylmethoxy)-2H-isoquinolin-1-one was reacted with 2,2-dimethyl-oxirane. In this way the product was obtained with molecular weight 535.66 (C31H38FN3O4); MS (ESI): 536 (M+H+).

Products that were obtained by reaction of the corresponding phenols according to Method K with the corresponding alkylating agents (bromide, mesylate) are presented in Table 12.

TABLE 12

| Ex. No. | Structure | Empirical formula | Molecular weight | ESI-MS [M + H]+ |
|---|---|---|---|---|
| 182 | 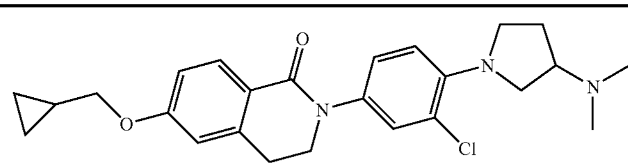 | C25H30ClN3O2 | 439, 99 | 440 |
| 183 | 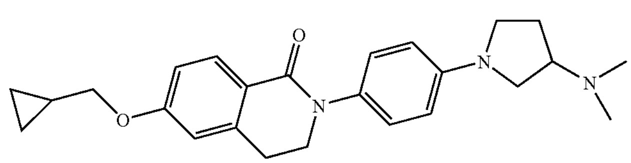 [SMILES: CN(C)C1CCN(c2ccc(N3CCc4cc(OCC5CC5)ccc4C3=O)cc2)C1] | C25H31N3O2 | 405, 55 | 406 |

TABLE 12-continued

| Ex. No. | Structure | Empirical formula | Molecular weight | ESI-MS [M + H]+ |
|---|---|---|---|---|
| 184 | 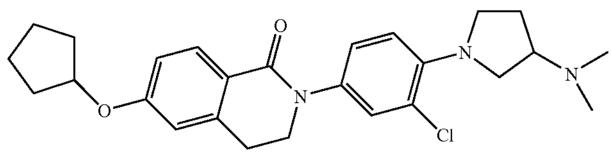 [SMILES: CN(C)C1CCN(c2ccc(N3CCc4cc(OC5CCCC5)ccc4C3=O)cc2Cl)C1] | C26H32ClN3O2 | 454,02 | 454 |
| 185 | 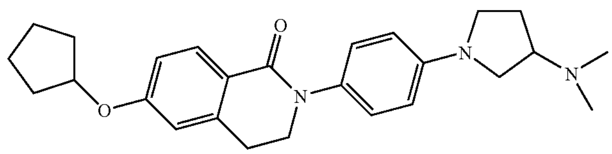 [SMILES: CN(C)C1CCN(c2ccc(N3CCc4cc(OC5CCCC5)ccc4C3=O)cc2)C1] | C26H33N3O2 | 419,57 | 420 |
| 186 | 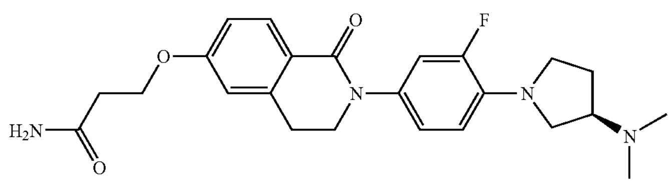 [SMILES: CN(C)[C@@H]1CCN(c2ccc(N3CCc4cc(OCCC(N)=O)ccc4C3=O)cc2F)C1] | C24H29FN4O3 | 440,52 | 441 |
| 187 | 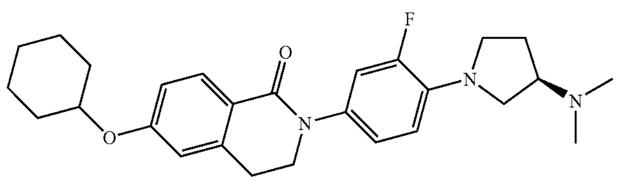 [SMILES: CN(C)[C@@H]1CCN(c2ccc(N3CCc4cc(OC5CCCCC5)ccc4C3=O)cc2F)C1] | C27H34FN3O2 | 451,59 | 452 |
| 188 | 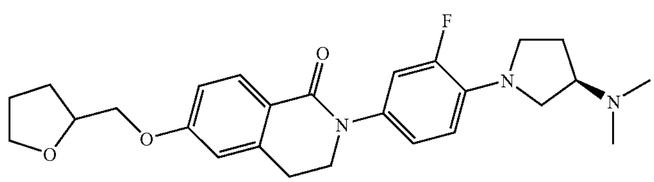 [SMILES: CN(C)[C@@H]1CCN(c2ccc(N3CCc4cc(OCC5CCCO5)ccc4C3=O)cc2F)C1] | C26H32FN3O3 | 453,56 | 454 |
| 189 | 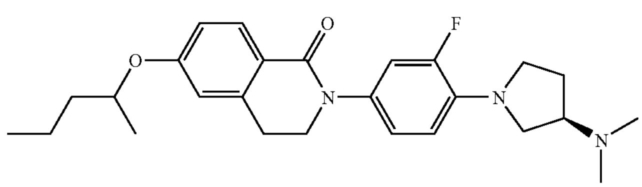 [SMILES: CCCC(C)Oc1ccc2c(c1)CCN(c1ccc(N3CC[C@@H](N(C)C)C3)c(F)c1)C2=O] | C26H34FN3O2 | 439,58 | 440 |
| 190 | 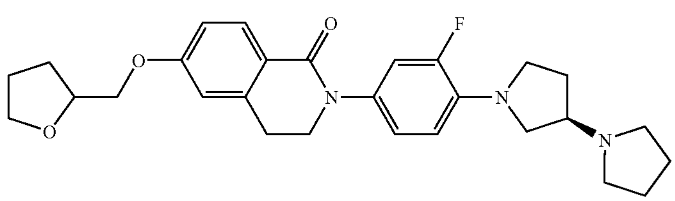 [SMILES: O=C1c2ccc(OCC3CCCO3)cc2CCN1c1ccc(N2CC[C@@H](N3CCCC3)C2)c(F)c1] | C28H34FN3O3 | 479,60 | 480 |
| 191 | 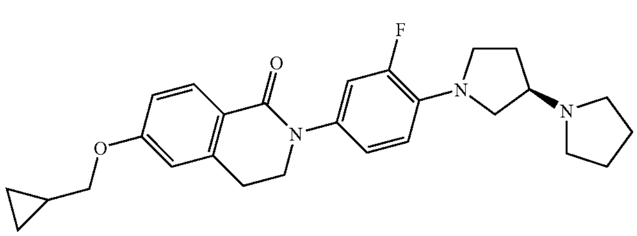 [SMILES: O=C1c2ccc(OCC3CC3)cc2CCN1c1ccc(N2CC[C@@H](N3CCCC3)C2)c(F)c1] | C27H32FN3O2 | 449,57 | 450 |

TABLE 12-continued

| Ex. No. | Structure | Empirical formula | Molecular weight | ESI-MS [M + H]+ |
|---|---|---|---|---|
| 192 | 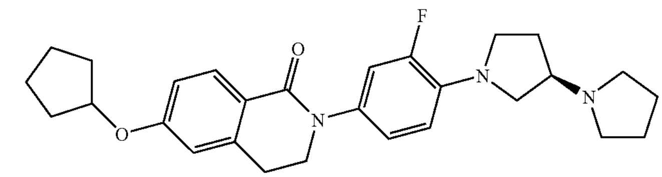 [SMILES: O=C1c2ccc(OC3CCCC3)cc2CCN1c1ccc(N2CC[C@@H](N3CCCC3)C2)c(F)c1] | C28H34FN3O2 | 463, 60 | 464 |
| 193 | 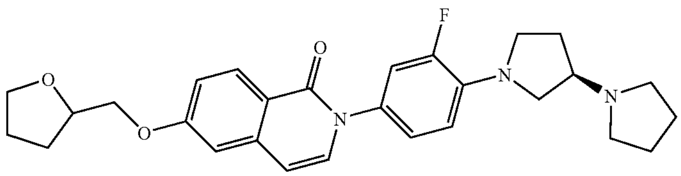 [SMILES: O=c1c2ccc(OCC3CCCO3)cc2ccn1-c1ccc(N2CC[C@@H](N3CCCC3)C2)c(F)c1] | C28H32FN3O3 | 477, 58 | 478 |
| 194 | 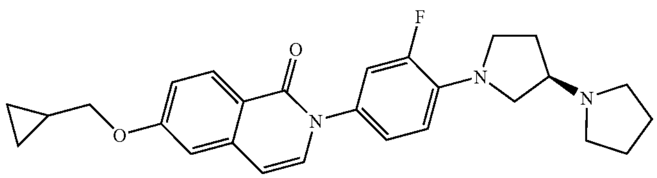 [SMILES: O=c1c2ccc(OCC3CC3)cc2ccn1-c1ccc(N2CC[C@@H](N3CCCC3)C2)c(F)c1] | C27H30FN3O2 | 447, 56 | 448 |
| 195 | 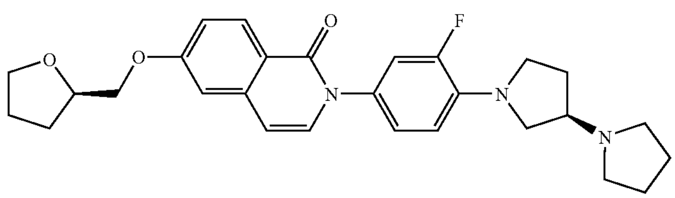 [SMILES: O=c1c2ccc(OC[C@H]3CCCO3)cc2ccn1-c1ccc(N2CC[C@@H](N3CCCC3)C2)c(F)c1] | C28H32FN3O3 | 477, 58 | 478 |
| 196 | 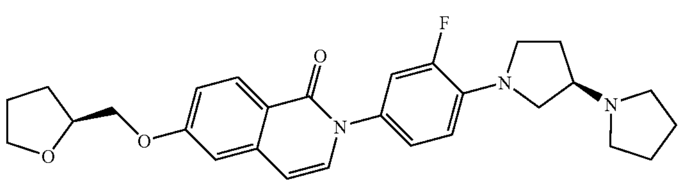 [SMILES: O=c1c2ccc(OC[C@@H]3CCCO3)cc2ccn1-c1ccc(N2CC[C@@H](N3CCCC3)C2)c(F)c1] | C28H32FN3O3 | 477, 58 | 478 |
| 197 | 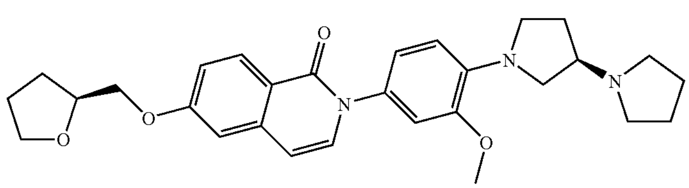 [SMILES: COc1cc(-n2ccc3cc(OC[C@@H]4CCCO4)ccc3c2=O)ccc1N1CC[C@@H](N2CCCC2)C1] | C29H35N3O4 | 489, 62 | 490 |
| 198 | 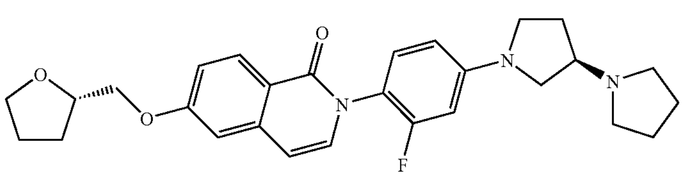 [SMILES: O=c1c2ccc(OC[C@@H]3CCCO3)cc2ccn1-c1ccc(N2CC[C@@H](N3CCCC3)C2)cc1F] | C28H32FN3O3 | 477, 58 | 478 |
| 199 | 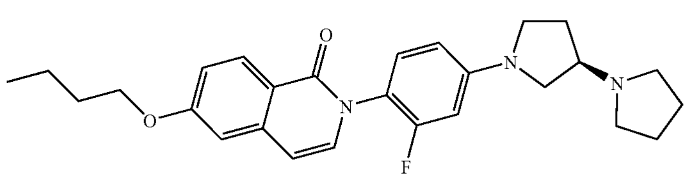 [SMILES: CCCCOc1ccc2c(=O)n(-c3ccc(N4CC[C@@H](N5CCCC5)C4)cc3F)ccc2c1] | C27H32FN3O2 | 449, 57 | 450 |

TABLE 12-continued

| Ex. No. | Structure | Empirical formula | Molecular weight | ESI-MS [M + H]+ |
|---|---|---|---|---|
| 200 | 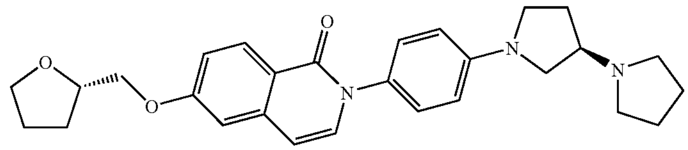 [SMILES: O=c1c2ccc(OC[C@@H]3CCCO3)cc2ccn1-c1ccc(N2CC[C@@H](N3CCCC3)C2)cc1] | C28H33N3O3 | 459, 59 | 460 |
| 201 | 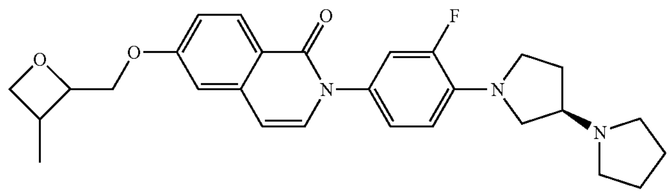 [SMILES: CC1COC1COc1ccc2c(=O)n(-c3ccc(N4CC[C@@H](N5CCCC5)C4)c(F)c3)ccc2c1] | C28H32FN3O3 | 477, 58 | 478 |
| 202 | 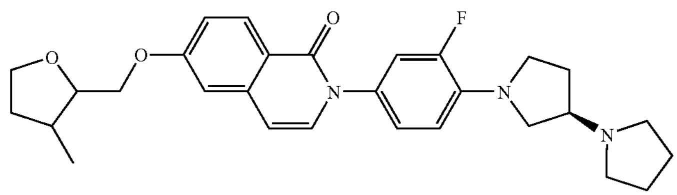 [SMILES: CC1CCOC1COc1ccc2c(=O)n(-c3ccc(N4CC[C@@H](N5CCCC5)C4)c(F)c3)ccc2c1] | C29H34FN3O3 | 491, 61 | 492 |
| 203 | 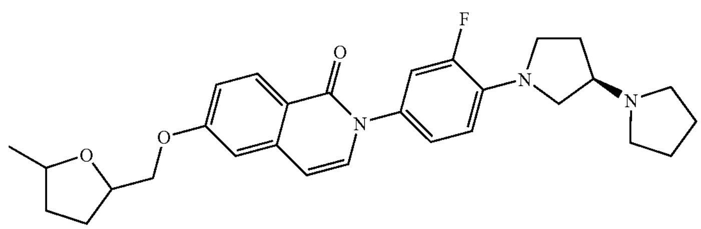 [SMILES: CC1CCC(COc2ccc3c(=O)n(-c4ccc(N5CC[C@@H](N6CCCC6)C5)c(F)c4)ccc3c2)O1] | C29H34FN3O3 | 491, 61 | 492 |
| 204 | 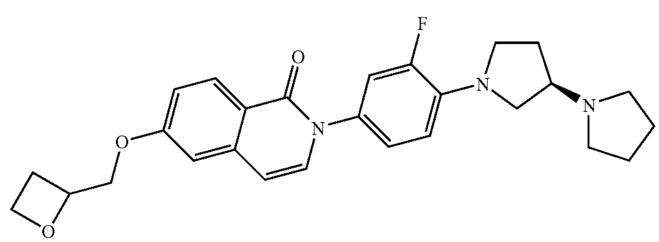 [SMILES: O=c1c2ccc(OCC3CCO3)cc2ccn1-c1ccc(N2CC[C@@H](N3CCCC3)C2)c(F)c1] | C27H30FN3O3 | 463, 56 | 464 |
| 205 | 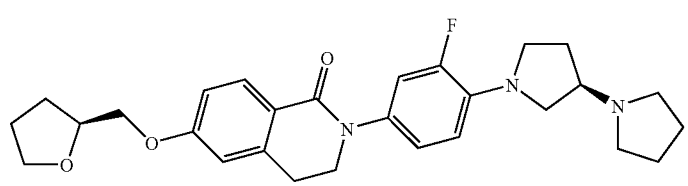 [SMILES: O=C1c2ccc(OC[C@@H]3CCCO3)cc2CCN1c1ccc(N2CC[C@@H](N3CCCC3)C2)c(F)c1] | C28H34FN3O3 | 479, 60 | 480 |
| 206 | 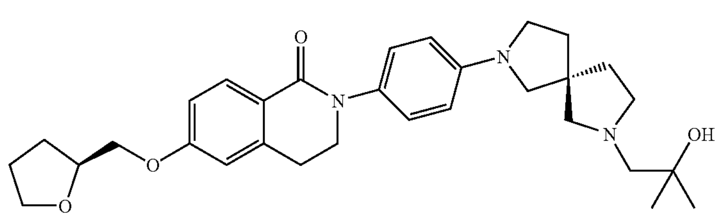 [SMILES: CC(C)(O)CN1CC[C@]2(CCN(c3ccc(-n4ccc5cc(OC[C@@H]6CCCO6)ccc5c4=O)cc3)C2)C1] | C31H41N3O4 | 519, 69 | 520 |

TABLE 12-continued

| Ex. No. | Structure | Empirical formula | Molecular weight | ESI-MS [M + H]+ |
|---|---|---|---|---|
| 207 | 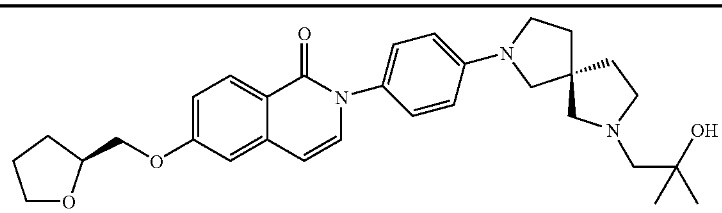 | C31H39N3O4 | 517, 67 | 518 |
| 208 | 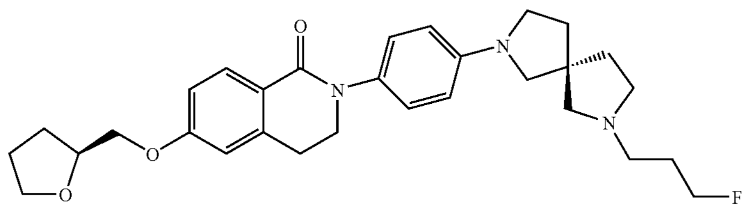 [SMILES: O=C1c2ccc(OC[C@@H]3CCCO3)cc2CCN1c1ccc(N2CC[C@]3(CCN(CCCF)C3)C2)cc1] | C30H38FN3O3 | 507, 65 | 508 |
| 209 | 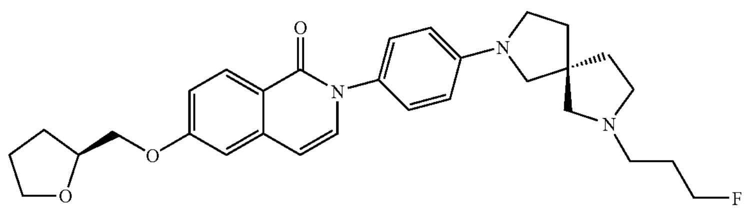 [SMILES: O=c1c2ccc(OC[C@@H]3CCCO3)cc2ccn1-c1ccc(N2CC[C@]3(CCN(CCCF)C3)C2)cc1] | C30H36FN3O3 | 505, 64 | 506 |
| 210 | 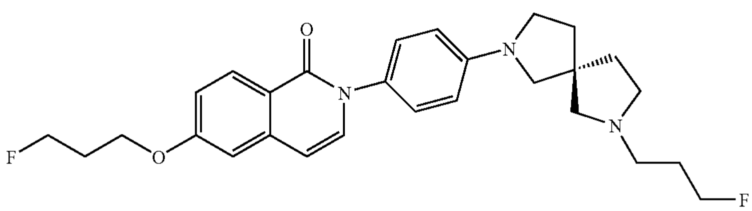 [SMILES: O=c1c2ccc(OCCCF)cc2ccn1-c1ccc(N2CC[C@]3(CCN(CCCF)C3)C2)cc1] | C28H33F2N3O2 | 481, 59 | 482 |

2-[3-Chloro-4-(3-dimethylamino-pyrrolidin-1-yl)-phenyl]-6-hydroxy-3,4-dihydro-2H-isoquinolin-1-one According to Method L, 2-[3-chloro-4-(3-dimethylamino-pyrrolidin-1-yl)-phenyl]-6-methoxy-3,4-dihydro-2H-isoquinolin-1-one was treated with hydrogen bromide. In this way the product was obtained with molecular weight 385.90 (C21H24ClN3O2); MS (ESI): 386 (M+H+).

2-[4-(3-Dimethylamino-pyrrolidin-1-yl)-phenyl]-6-hydroxy-3,4-dihydro-2H-isoquinolin-1-one According to Method A, [1-(4-amino-phenyl)-pyrrolidin-3-yl]-dimethylamine was reacted with 2-(2-chloroethyl)-4-methoxy-benzoyl chloride. The dihydroisoquinolinone thus obtained was treated with hydrogen bromide according to Method L. In this way the product was obtained with molecular weight 351.45 (C21H25N3O2); MS (ESI): 352 (M+H+).

2-((R)-4-[1,3']Bipyrrolidinyl-1'-yl-3-methoxy-phenyl)-6-hydroxy-2H-isoquinolin-1-one Under the conditions of Method F, 6-benzyloxy-2-((R)-4-[1,3']bipyrrolidinyl-1'-yl-3-methoxy-phenyl)-2H-isoquinolin-1-one was hydrogenated, with hydrogenolysis of the benzyl group. In this way the product was obtained with molecular weight 405.50 (C24H27N3O3); MS (ESI): 406 (M+H+).

6-Benzyloxy-2-((R)-4-[1,3']bipyrrolidinyl-1'-yl-3-methoxy-phenyl)-2H-isoquinolin-1-one According to Method Q, 4-benzyloxy-N—((R)-4-[1,3']bipyrrolidinyl-1'-yl-3-methoxy-phenyl)-2-methyl-benzamide was reacted with N-formylmorpholine. In this way the product was obtained with molecular weight 495.63 (C31H33N3O3); MS (ESI): 496 (M+H+).

4-Benzyloxy-N—((R)-4-[1,3']bipyrrolidinyl-1'-yl-3-methoxy-phenyl)-2-methyl-benzamide According to Method P, 4-benzyloxy-2-methyl-benzoic acid was reacted with (R)-4-[1,3']bipyrrolidinyl-1'-yl-3-methoxy-phenylamine. In this way the product was obtained with molecular weight 485.63 (C30H35N3O3); MS (ESI): 486 (M+H+).

(R)-4-[1,3']Bipyrrolidinyl-1'-yl-3-methoxy-phenylamine

According to Method E, 1-fluoro-2-methoxy-4-nitro-benzene was reacted with (R)-[1,3']bipyrrolidinyl. The nitro compound obtained was hydrogenated according to Method F. In this way the product was obtained with molecular weight 261.37 (C15H23N3O); MS (ESI): 262 (M+H+).

2-Iodomethyl-3-methyl-tetrahydrofuran

According to instructions in the literature (R. D. Evans et al., Synthesis 1988, 862-8), 3-methyl-pent-4-en-1-ol was reacted with bis(collidine)iodine hexafluorophosphate.

The following iodides were obtained similarly from the corresponding unsaturated alcohols:
2-iodomethyl-3-methyl-oxetane;
2-iodomethyl-oxetane;
2-iodomethyl-5-methyl-tetrahydrofuran.

Example 211

2-{3-Fluoro-4-[3-(4-hydroxy-piperidin-1-yl)-pyrrolidin-1-yl]-phenyl}-6-[(S)-1-(tetrahydrofuran-2-yl)methoxy]-3,4-dihydro-2H-isoquinolin-1-one

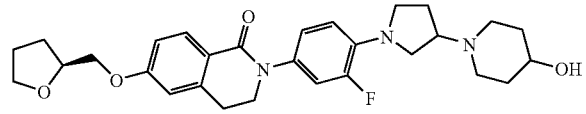 [SMILES: O=C1c2ccc(OC[C@@H]3CCCO3)cc2CCN1c1ccc(N2CCC(N3CCC(O)CC3)C2)c(F)c1]

According to Method J1, 2-[3-fluoro-4-(3-oxo-pyrrolidin-1-yl)-phenyl]-6-[(S)-1-(tetrahydrofuran-2-yl)methoxy]-3,4-dihydro-2H-isoquinolin-1-one was reacted with piperidin-4-ol. In this way the product was obtained with molecular weight 509.63 (C29H36FN3O4); MS (ESI): 510 (M+H+).

Example 212

2-[4-((R)-3-Dimethylamino-pyrrolidin-1-yl)-3-fluorophenyl]-6-(3-methoxy-butoxy)-3,4-dihydro-2H-isoquinolin-1-one

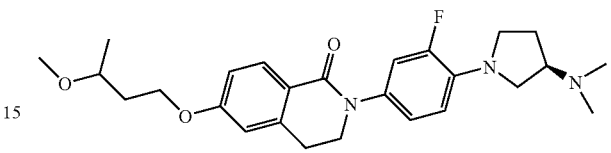

Method Y

A mixture of triphenylphosphine (polymer; 156 mg), 2-[4-((R)-3-dimethylamino-pyrrolidin-1-yl)-3-fluorophenyl]-6-hydroxy-3,4-dihydro-2H-isoquinolin-1-one (0.10 g) and THF (7 mL) was stirred for 15 minutes. Then di-tert-butyl-azodicarboxylate (0.10 g) in THF (1 mL) was added, stirring for a further 10 minutes. Then 3-methoxy-butan-1-ol (35 mg) was added and it was stirred for 12 hours. It was sucked off of the polymer and the filtrate was concentrated. The residue was purified by preparative HPLC. In this way the product was obtained with molecular weight 455.58 (C26H34FN3O3); MS (ESI): 456 (M+H+).

The products that were obtained according to Method Y by reaction of the corresponding phenols with the corresponding alcohols are presented in Table 13.

TABLE 13

| Ex. No. | Structure | Empirical formula | Molecular weight | ESI-MS [M + H]+ |
|---|---|---|---|---|
| 213 | 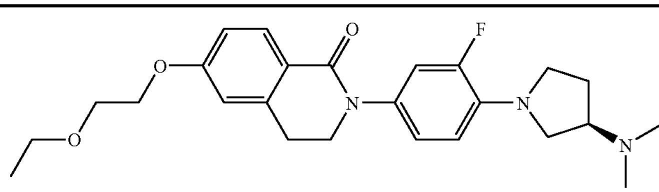 | C25H32FN3O3 | 441, 55 | 442 |
| 214 | 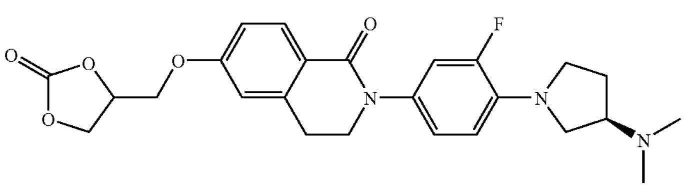 [SMILES: CN(C)[C@@H]1CCN(c2ccc(N3CCc4cc(OCC5COC(=O)O5)ccc4C3=O)cc2F)C1] | C25H28FN3O5 | 469, 52 | 470 |
| 215 | 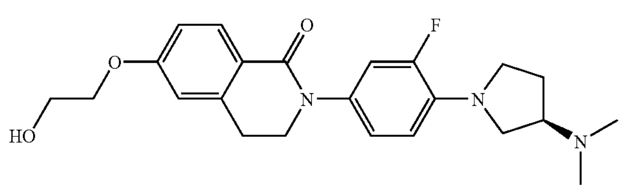 [SMILES: CN(C)[C@@H]1CCN(c2ccc(N3CCc4cc(OCCO)ccc4C3=O)cc2F)C1] | C23H28FN3O3 | 413, 50 | 414 |
| 216 | 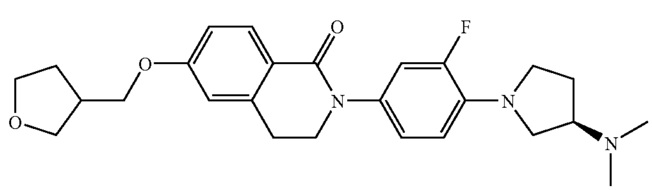 [SMILES: CN(C)[C@@H]1CCN(c2ccc(N3CCc4cc(OCC5CCOC5)ccc4C3=O)cc2F)C1] | C26H32FN3O3 | 453, 56 | 454 |

TABLE 13-continued

| Ex. No. | Structure | Empirical formula | Molecular weight | ESI-MS [M + H]+ |
|---|---|---|---|---|
| 217 | 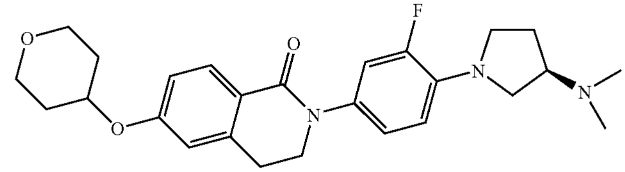 [SMILES: CN(C)[C@@H]1CCN(c2ccc(N3CCc4cc(OC5CCOCC5)ccc4C3=O)cc2F)C1] | C26H32FN3O3 | 453, 56 | 454 |
| 218 | 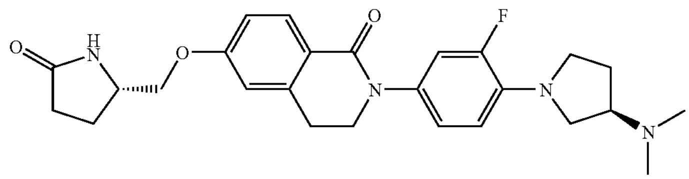 [SMILES: CN(C)[C@@H]1CCN(c2ccc(N3CCc4cc(OC[C@@H]5CCC(=O)N5)ccc4C3=O)cc2F)C1] | C26H31FN4O3 | 466, 56 | 467 |
| 219 | 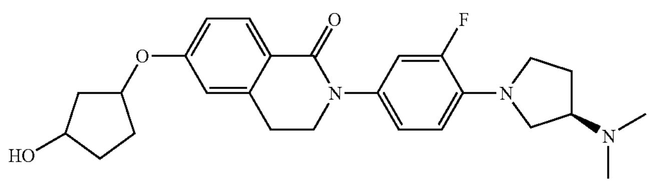 [SMILES: CN(C)[C@@H]1CCN(c2ccc(N3CCc4cc(OC5CCC(O)C5)ccc4C3=O)cc2F)C1] | C26H32FN3O3 | 453, 56 | 454 |
| 220 | 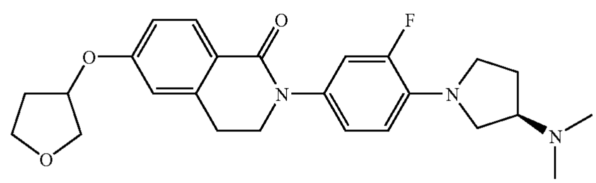 [SMILES: CN(C)[C@@H]1CCN(c2ccc(N3CCc4cc(OC5CCOC5)ccc4C3=O)cc2F)C1] | C25H30FN3O3 | 439, 54 | 440 |
| 221 | 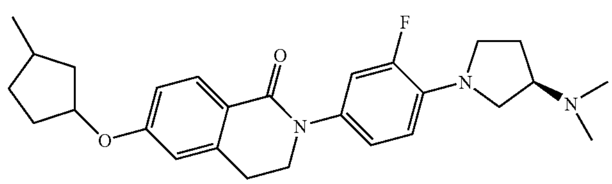 [SMILES: CC1CCC(Oc2ccc3c(c2)CCN(c2ccc(N4CC[C@@H](N(C)C)C4)c(F)c2)C3=O)C1] | C27H34FN3O2 | 451, 59 | 452 |
| 222 | 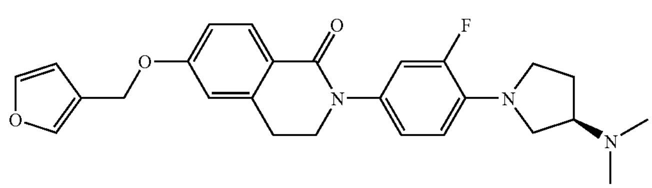 [SMILES: CN(C)[C@@H]1CCN(c2ccc(N3CCc4cc(OCc5ccoc5)ccc4C3=O)cc2F)C1] | C26H28FN3O3 | 449, 53 | 450 |
| 223 | 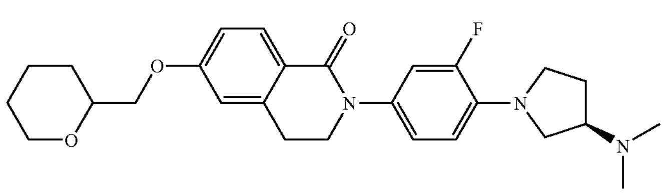 [SMILES: CN(C)[C@@H]1CCN(c2ccc(N3CCc4cc(OCC5CCCCO5)ccc4C3=O)cc2F)C1] | C27H34FN3O3 | 467, 59 | 468 |
| 224 | 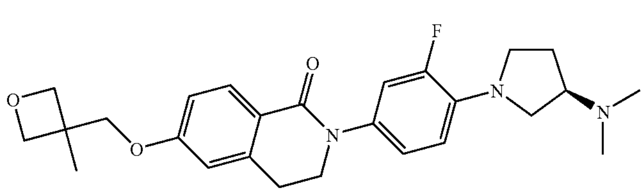 [SMILES: CN(C)[C@@H]1CCN(c2ccc(N3CCc4cc(OCC5(C)COC5)ccc4C3=O)cc2F)C1] | C26H32FN3O3 | 453, 56 | 454 |

TABLE 13-continued

| Ex. No. | Structure | Empirical formula | Molecular weight | ESI-MS [M + H]+ |
|---|---|---|---|---|
| 225 | 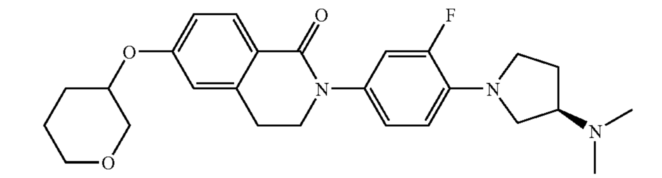 [SMILES: CN(C)[C@@H]1CCN(c2ccc(N3CCc4cc(OC5CCCOC5)ccc4C3=O)cc2F)C1] | C26H32FN3O3 | 453, 56 | 454 |
| 226 | 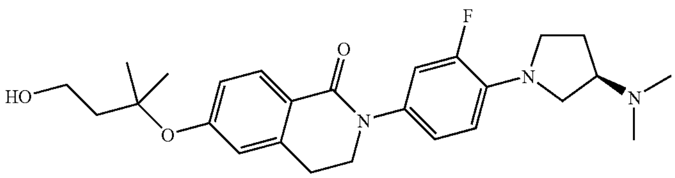 [SMILES: CN(C)[C@@H]1CCN(c2ccc(N3CCc4cc(OC(C)(C)CCO)ccc4C3=O)cc2F)C1] | C26H34FN3O3 | 455, 58 | 456 |
| 227 | 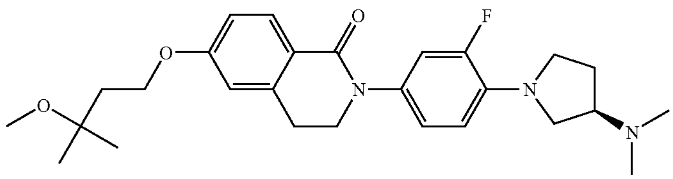 | C27H36FN3O3 | 469, 61 | 470 |
| 228 | 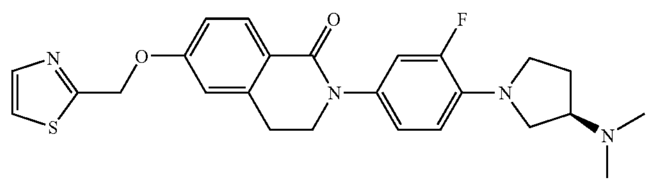 [SMILES: CN(C)[C@@H]1CCN(c2ccc(N3CCc4cc(OCc5nccs5)ccc4C3=O)cc2F)C1] | C25H27FN4O2S | 466, 58 | 467 |
| 229 | 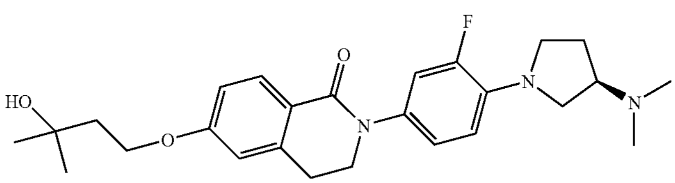 [SMILES: CN(C)[C@@H]1CCN(c2ccc(N3CCc4cc(OCCC(C)(C)O)ccc4C3=O)cc2F)C1] | C26H34FN3O3 | 455, 58 | 456 |

Example 230

2-[4-((R)-3-Dimethylamino-pyrrolidin-1-yl)-3-fluorophenyl]-6-(3-hydroxy-pentyl)-3,4-dihydro-2H-isoquinolin-1-one

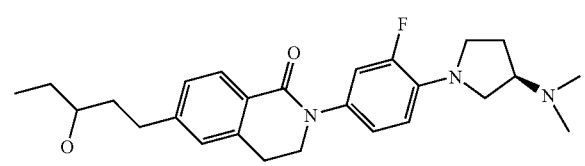

Method Z

A mixture of 2-[4-((R)-3-dimethylamino-pyrrolidin-1-yl)-3-fluorophenyl]-6-(3-hydroxy-pent-1-ynyl)-3,4-dihydro-2H-isoquinolin-1-one (20 mg), palladium (10% on charcoal; 5 mg) and methanol was stirred vigorously for 5 hours under a hydrogen atmosphere (balloon flask). It was sucked off of the catalyst and the filtrate was concentrated. The residue was purified by preparative HPLC. In this way the product was obtained with molecular weight 439.58 (C26H34FN3O2); MS (ESI): 440 (M+H+).

With shorter reaction times the only partially hydrogenated product can be obtained as main product:

2-[4-((R)-3-dimethylamino-pyrrolidin-1-yl)-3-fluorophenyl]-6-(3-hydroxy-pent-1-enyl)-3,4-dihydro-2H-isoquinolin-1-one

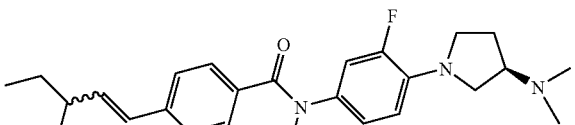

Molecular weight 437.56 (C26H32FN3O2); MS (ESI): 438 (M+H+).

Example 231

2-((R)-4-[1,3']Bipyrrolidinyl-1'-yl-3-fluorophenyl)-6-((R)-3-hydroxy-butyl)-2H-isoquinolin-1-one

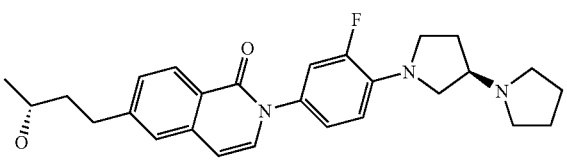 [SMILES: C[C@@H](O)CCc1ccc2c(=O)n(-c3ccc(N4CC[C@@H](N5CCCC5)C4)c(F)c3)ccc2c1]

2-((R)-4-[1,3']Bipyrrolidinyl-1'-yl-3-fluorophenyl)-6-((R)-3-hydroxy-but-1-ynyl)-2H-isoquinolin-1-one was hydrogenated according to Method Z. In this way the product was obtained with molecular weight 449.57 (C27H32FN3O2); MS (ESI): 450 (M+H+).

Example 232

2-((R)-4-[1,3']Bipyrrolidinyl-1'-yl-3-fluorophenyl)-6-((S)-3-hydroxy-pentyl)-2H-isoquinolin-1-one

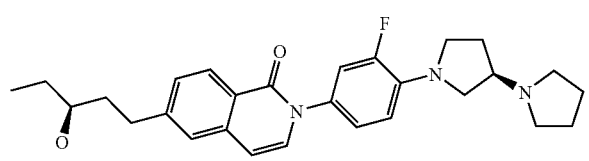 [SMILES: CC[C@H](O)CCc1ccc2c(=O)n(-c3ccc(N4CC[C@@H](N5CCCC5)C4)c(F)c3)ccc2c1]

2-((R)-4-[1,3']Bipyrrolidinyl-1'-yl-3-fluorophenyl)-6-((S)-3-hydroxy-pent-1-ynyl)-2H-isoquinolin-1-one was hydrogenated according to Method Z. In this way the product was obtained with molecular weight 463.60 (C28H34FN3O2); MS (ESI): 464 (M+H+).

Example 233

2-((R)-4-[1,3']Bipyrrolidinyl-1'-yl-3-fluorophenyl)-6-pentyl-2H-isoquinolin-1-one

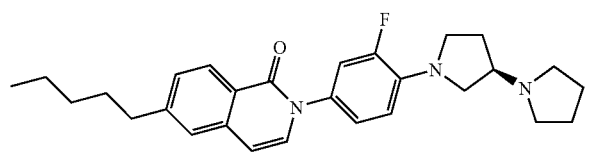 [SMILES: CCCCCc1ccc2c(=O)n(-c3ccc(N4CC[C@@H](N5CCCC5)C4)c(F)c3)ccc2c1]

2-((R)-4-[1,3']Bipyrrolidinyl-1'-yl-3-fluorophenyl)-6-pent-1-ynyl-2H-isoquinolin-1-one was hydrogenated according to Method Z. In this way the product was obtained with molecular weight 447.60 (C28H34FN3O); MS (ESI): 448 (M+H+).

Example 234

2-[3-fluoro-4-((R)-3-methylamino-pyrrolidin-1-yl)-phenyl]-6-(2-hydroxy-propoxy)-3,4-dihydro-2H-isoquinolin-1-one

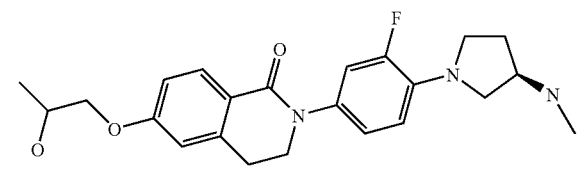 [SMILES: CN[C@@H]1CCN(c2ccc(N3CCc4cc(OCC(C)O)ccc4C3=O)cc2F)C1]

According to Method K, {(R)-1-[2-fluoro-4-(6-hydroxy-1-oxo-3,4-dihydro-1H-isoquinolin-2-yl)-phenyl]-pyrrolidin-3-yl}-methyl-carbamic acid tert-butyl ester was reacted with bromoacetone. The ketone obtained (500 mg) was dissolved in ethanol (10 mL) and sodium borohydride (37 mg) was added. After 1 hour, the reaction mixture was hydrolyzed with water and extracted with ethyl acetate. The organic phase was dried over magnesium sulfate and concentrated. The alcohol obtained (((R)-1-{2-fluoro-4-[6-(2-hydroxy-propoxy)-1-oxo-3,4-dihydro-1H-isoquinolin-2-yl]-phenyl}-pyrrolidin-3-yl)-methyl-carbamic acid tert-butyl ester) was treated with hydrogen chloride according to Method V. In this way the product was obtained with molecular weight 413.50 (C23H28FN3O3); MS (ESI): 414 (M+H+).

Example 235

2-[3-Fluoro-4-((R)-3-methylamino-pyrrolidin-1-yl)-phenyl]-6-(2-methoxy-propoxy)-3,4-dihydro-2H-isoquinolin-1-one

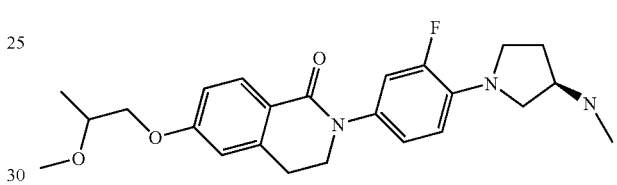

Method AA

Sodium hydride (55% in oil, 20 mg) was added to a mixture of ((R)-1-{2-fluoro-4-[6-(2-hydroxy-propoxy)-1-oxo-3,4-dihydro-1H-isoquinolin-2-yl]-phenyl}-pyrrolidin-3-yl)-methyl-carbamic acid tert-butyl ester (0.20 g) and NMP (5 mL). When gas ceased to be evolved, methyl iodide (55 mg) was added. After 1 hour the reaction mixture was distributed between water and ethyl acetate. The organic phase was dried over magnesium sulfate and concentrated.

The ether thus obtained was treated with hydrogen chloride according to Method V. In this way the product was obtained with molecular weight 427.52 (C24H30FN3O3); MS (ESI): 428 (M+H+).

Example 236

2-((R)-4-[1,3']Bipyrrolidinyl-1'-yl-3-fluorophenyl)-6-(2-methoxy-butoxy)-2H-isoquinolin-1-one

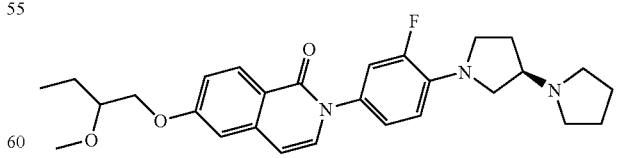

According to Method AA, 2-((R)-4-[1,3']bipyrrolidinyl-1'-yl-3-fluorophenyl)-6-(2-hydroxy-butoxy)-2H-isoquinolin-1-one was reacted with methyl iodide. In this way the product was obtained with molecular weight 479.60 (C28H34FN3O3); MS (ESI): 480 (M+H+).

Example 237

2-((R)-4-[1,3']Bipyrrolidinyl-1'-yl-3-fluorophenyl)-6-(pyridin-2-yloxy)-2H-isoquinolin-1-one

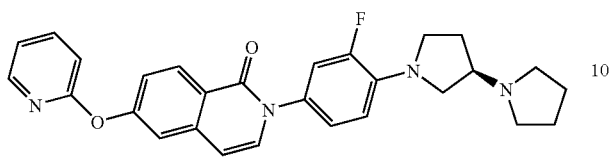

Method AB

A mixture of 2-((R)-4-[1,3']bipyrrolidinyl-1'-yl-3-fluorophenyl)-6-hydroxy-2H-isoquinolin-1-one (100 mg), 2-chloropyridine (58 mg), potassium tert.-butoxide (57 mg) and NMP (1 mL) was heated for 30 minutes at 180° C. by microwaving. The cooled raw mixture was purified by preparative HPLC. In this way the product was obtained with molecular weight 470.55 (C28H27FN4O2); MS (ESI): 471 (M+H+).

Example 238

2-((R)-4-[1,3']Bipyrrolidinyl-1'-yl-3-fluorophenyl)-6-(thiazol-2-yloxy)-2H-isoquinolin-1-one

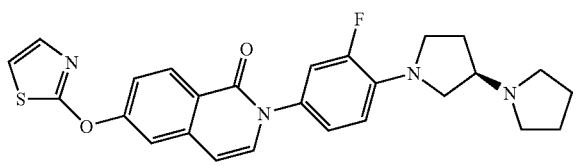 [SMILES: O=c1c2ccc(Oc3nccs3)cc2ccn1-c1ccc(N2CC[C@@H](N3CCCC3)C2)c(F)c1]

According to Method AB, 2-((R)-4-[1,3']bipyrrolidinyl-1'-yl-3-fluorophenyl)-6-hydroxy-2H-isoquinolin-1-one was reacted with 2-bromothiazole. In this way the product was obtained with molecular weight 476.58 (C26H25FN4O2S); MS (ESI): 477 (M+H+).

Example 239

2-{2-[3-Fluoro-4-((R)-3-methylamino-pyrrolidin-1-yl)-phenyl]-1-oxo-1,2-dihydro-isoquinolin-6-yloxy}-pentanoic acid ethyl ester

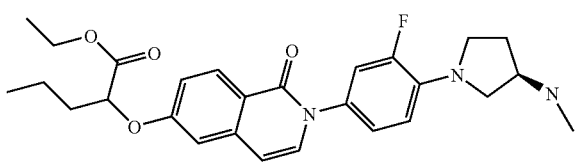 [SMILES: CCCC(Oc1ccc2c(=O)n(-c3ccc(N4CC[C@@H](NC)C4)c(F)c3)ccc2c1)C(=O)OCC]

According to Method K, {(R)-1-[2-fluoro-4-(6-hydroxy-1-oxo-1H-isoquinolin-2-yl)-phenyl]-pyrrolidin-3-yl}-methyl-carbamic acid tert-butyl ester was reacted with 2-bromopentanoic acid ethyl ester and then the carbamate in the 2-(2-{4-[(R)-3-(tert-butoxycarbonyl-methyl-amino)-pyrrolidin-1-yl]-3-fluorophenyl}-1-oxo-1,2-dihydro-isoquinolin-6-yloxy)-pentanoic acid ethyl ester obtained was cleaved by treatment with hydrogen chloride according to Method H. In this way the product was obtained with molecular weight 481.57 (C27H32FN3O4); MS (ESI): 482 (M+H+).

Example 240

2-[3-Fluoro-4-((R)-3-methylamino-pyrrolidin-1-yl)-phenyl]-6-(1-hydroxymethyl-butoxy)-2H-isoquinolin-1-one

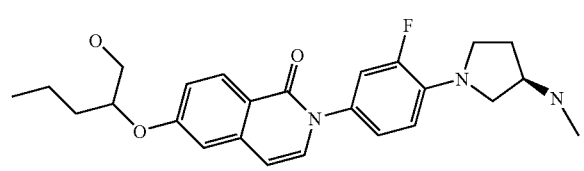 [SMILES: CCCC(CO)Oc1ccc2c(=O)n(-c3ccc(N4CC[C@@H](NC)C4)c(F)c3)ccc2c1]

Lithium borohydride (22 mg) was added to a mixture of 2-(2-{4-[(R)-3-(tert-butoxycarbonyl-methyl-amino)-pyrrolidin-1-yl]-3-fluorophenyl}-1-oxo-1,2-dihydro-isoquinolin-6-yloxy)-pentanoic acid ethyl ester (300 mg) and THF (5 mL). After 12 hours, methanol (1 mL) was added and the mixture was distributed between water and ethyl acetate. The organic phase was dried over magnesium sulfate and concentrated. The residue was purified by chromatography on silica gel. The carbamate in the alcohol thus obtained was cleaved by treatment with hydrogen chloride according to Method H. In this way the product was obtained with molecular weight 439.53 (C25H30FN3O3); MS (ESI): 440 (M+H+).

Example 241

6-Butoxy-2-[4-((R)-3-dimethylamino-pyrrolidin-1-yl)-phenyl]-3,4-dihydro-2H-isoquinolin-1-one

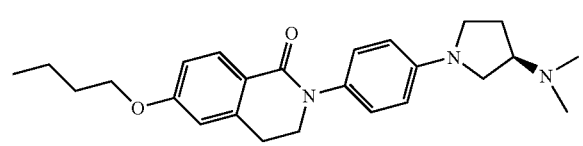 [SMILES: CCCCOc1ccc2c(c1)CCN(c1ccc(N3CC[C@@H](N(C)C)C3)cc1)C2=O]

According to Method R, 2-(4-bromophenyl)-6-butoxy-3,4-dihydro-2H-isoquinolin-1-one was reacted with dimethyl-(R)-pyrrolidin-3-yl-amine. In this way the product was obtained with molecular weight 407.56 (C25H33N3O2); MS (ESI): 408 (M+H+).

2-(4-Bromo-phenyl)-6-butoxy-3,4-dihydro-2H-isoquinolin-1-one

According to Method A, 4-bromo-phenylamine was reacted with 4-butoxy-2-(2-chloroethyl)-benzoyl chloride. In this way the product was obtained with molecular weight 374.28 (C19H20BrNO2); MS (ESI): 374 (M+H+).

Example 242

2-(4-[1,3']Bipyrrolidinyl-1'-yl-phenyl)-6-butoxy-3,4-dihydro-2H-isoquinolin-1-one

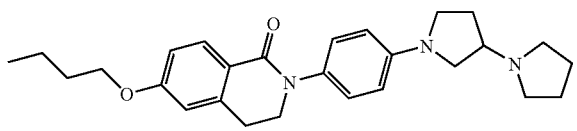 [SMILES: CCCCOc1ccc2c(c1)CCN(c1ccc(N3CCC(N4CCCC4)C3)cc1)C2=O]

According to Method J, 6-butoxy-2-[4-(3-oxo-pyrrolidin-1-yl)-phenyl]-3,4-dihydro-2H-isoquinolin-1-one was reacted with pyrrolidine. In this way the product was obtained with molecular weight 433.60 (C27H35N3O2); MS (ESI): 434 (M+H+).

Example 243

2-((R)-4-[1,3']Bipyrrolidinyl-1'-yl-3-fluorophenyl)-6-((3R*,4R*)-4-hydroxy-tetrahydro-pyran-3-yloxy)-2H-isoquinolin-1-one

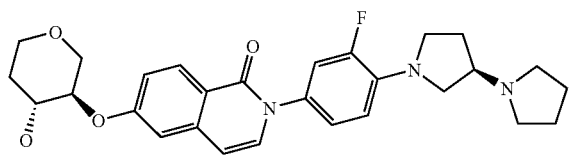 [SMILES: O=c1c2ccc(O[C@@H]3COCC[C@H]3O)cc2ccn1-c1ccc(N2CC[C@@H](N3CCCC3)C2)c(F)c1]

According to Method T, 2-((R)-4-[1,3']bipyrrolidinyl-1'-yl-3-fluorophenyl)-6-hydroxy-2H-isoquinolin-1-one, with cesium fluoride as auxiliary base, was reacted with 3,7-dioxa-bicyclo[4.1.0]heptane. In this way the product was obtained with molecular weight 493.58 (C28H32FN3O4); MS (ESI): 494 (M+H+).

3,7-Dioxa-bicyclo[4.1.0]heptane

In accordance with instructions in the literature, firstly tetrahydro-pyran-4-ol was converted with mesyl chloride to the corresponding mesylate and was then reacted by treatment with DBU to 3,6-dihydro-2H-pyran (M. J. Suto et al., J. Med. Chem. 1991, 34, 2484-88). Epoxidation with MCPBA gave 3,7-dioxa-bicyclo[4.1.0]heptane (G. Berti et al., Tetrahedron 1974, 30, 4013-20).

Example 244

2-((R)-4-[1,3']Bipyrrolidinyl-1'-yl-3-fluorophenyl)-6-((Z)-pent-1-enyl)-2H-isoquinolin-1-one

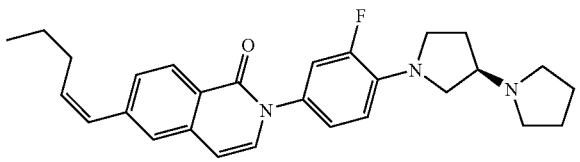 [SMILES: CCC/C=C\c1ccc2c(=O)n(-c3ccc(N4CC[C@@H](N5CCCC5)C4)c(F)c3)ccc2c1]

A mixture of 2-((R)-4-[1,3']bipyrrolidinyl-1'-yl-3-fluorophenyl)-6-pent-1-ynyl-2H-isoquinolin-1-one (2.7 g), quinoline (0.4 g), pyridine (50 mL) and palladium (5% on barium carbonate; 100 mg) was stirred vigorously for 2 hours under a hydrogen atmosphere (balloon flask). It was sucked off of the catalyst and the filtrate was concentrated. The residue was purified by chromatography on silica gel. In this way the product was obtained with molecular weight 445.59 (C28H32FN3O); MS (ESI): 446 (M+H+).

Example 245

2-((R)-4-[1,3']Bipyrrolidinyl-1'-yl-3-fluorophenyl)-6-((1R*,2S*)-1,2-dihydroxy-pentyl)-2H-isoquinolin-1-one

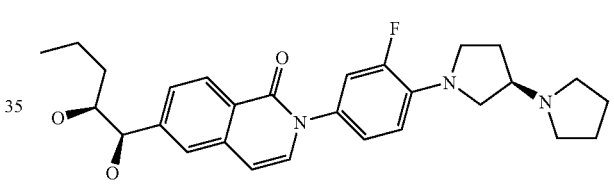

Firstly, osmium tetroxide (solution in tert.-butanol, 0.1 equiv.) was added to a mixture of 2-((R)-4-[1,3']bipyrrolidinyl-1'-yl-3-fluorophenyl)-6-((Z)-pent-1-enyl)-2H-isoquinolin-1-one (0.10 g) and THF (10 mL), and then a solution of N-methyl-morpholine-N-oxide (89 mg) in water (1 mL) was added. After 48 hours the reaction mixture was concentrated and the residue was purified by preparative HPLC. In this way the product was obtained with molecular weight 479.60 (C28H34FN3O3); MS (ESI): 480 (M+H+).

The products that were obtained by reaction of 2-((R)-4-[1,3']bipyrrolidinyl-1'-yl-3-fluorophenyl)-6-hydroxy-2H-isoquinolin-1-one with the corresponding alcohols are presented in Table 14.

TABLE 14

| Ex. No. | Structure | Empirical formula | Molecular weight | ESI-MS [M + H]+ |
|---|---|---|---|---|
| 246 | 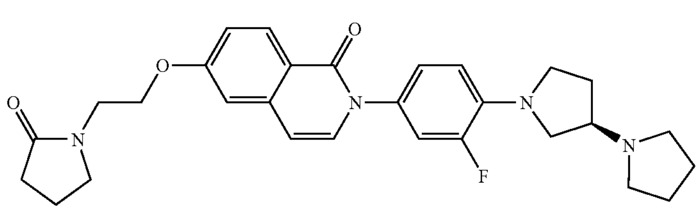 [SMILES: O=C1CCCN1CCOc1ccc2c(=O)n(-c3ccc(N4CC[C@@H](N5CCCC5)C4)c(F)c3)ccc2c1] | C29H33FN4O3 | 504, 61 | 505 |

TABLE 14-continued

| Ex. No. | Structure | Empirical formula | Molecular weight | ESI-MS [M + H]+ |
|---|---|---|---|---|
| 247 | 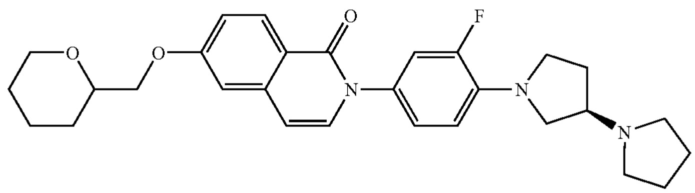 [SMILES: O=c1c2ccc(OCC3CCCCO3)cc2ccn1-c1ccc(N2CC[C@@H](N3CCCC3)C2)c(F)c1] | C29H34FN3O3 | 491, 61 | 492 |
| 248 | 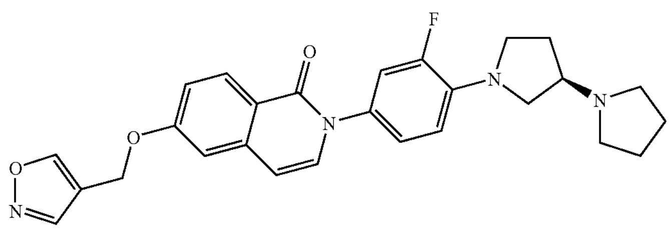 [SMILES: O=c1c2ccc(OCc3cnoc3)cc2ccn1-c1ccc(N2CC[C@@H](N3CCCC3)C2)c(F)c1] | C27H27FN4O3 | 474, 54 | 475 |
| 249 | 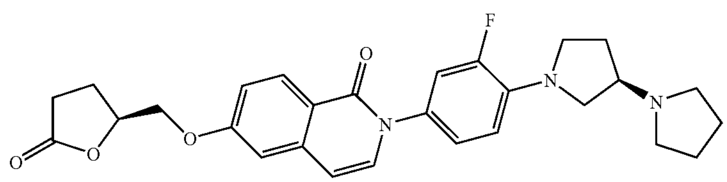 [SMILES: O=C1CC[C@@H](COc2ccc3c(=O)n(-c4ccc(N5CC[C@@H](N6CCCC6)C5)c(F)c4)ccc3c2)O1] | C28H30FN3O4 | 491, 57 | 492 |
| 250 | 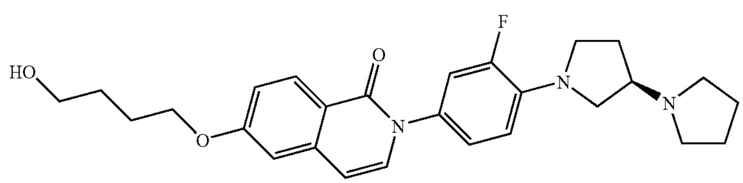 [SMILES: O=c1c2ccc(OCCCCO)cc2ccn1-c1ccc(N2CC[C@@H](N3CCCC3)C2)c(F)c1] | C27H32FN3O3 | 465, 57 | 466 |
| 251 | 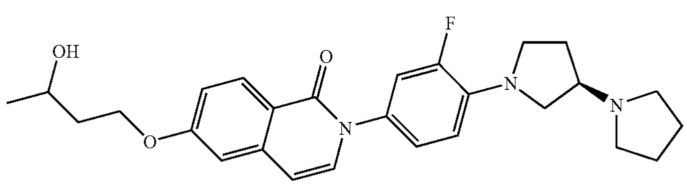 [SMILES: CC(O)CCOc1ccc2c(=O)n(-c3ccc(N4CC[C@@H](N5CCCC5)C4)c(F)c3)ccc2c1] | C27H32FN3O3 | 465, 57 | 466 |
| 252 | 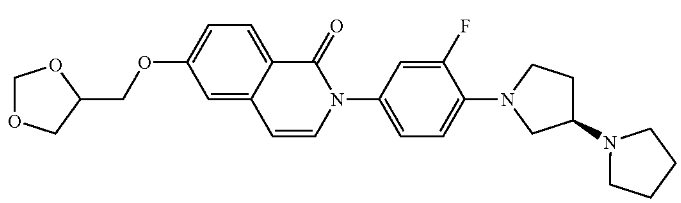 [SMILES: O=c1c2ccc(OCC3COCO3)cc2ccn1-c1ccc(N2CC[C@@H](N3CCCC3)C2)c(F)c1] | C27H30FN3O4 | 479, 56 | 480 |

Example 253

2-{3-Fluoro-4-[3-(3-fluoro-propylamino)-pyrrolidin-1-yl]-phenyl}-6-[(S)-1-(tetrahydrofuran-2-yl)methoxy]-3,4-dihydro-2H-isoquinolin-1-one

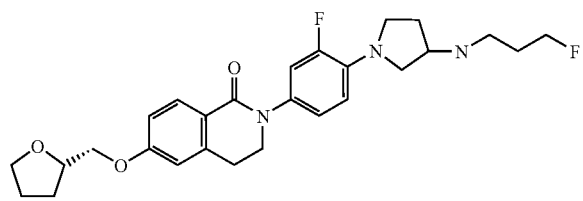

Method J1

Acetic acid (30.0 mg) and 1M solution of sodium cyanoborohydride in THF (1 M in THF; 0.5 mL) were added to a mixture of 2-[3-fluoro-4-(3-oxo-pyrrolidin-1-yl)-phenyl]-6-[(S)-1-(tetrahydrofuran-2-yl)methoxy]-3,4-dihydro-2H-isoquinolin-1-one (235.8 mg) and 3-fluoro-propylamine (38.6 mg) in methanol/methylene chloride (5 mL/3 mL). The reaction mixture was stirred for 8 h at room temperature. Then the solvent was removed in vacuum and the residue was taken up in ethyl acetate and water. The ethyl acetate phase was washed with water several times, then it was dried over sodium sulfate and the solvent was removed in vacuum. The raw product was purified by preparative HPLC. In this way the product was obtained with molecular weight 485.25 (C27H33F2N3O3); MS (ESI): 486 (M+H+).

2-[3-Fluoro-4-(3-oxo-pyrrolidin-1-yl)-phenyl]-6-[(S)-1-(tetrahydrofuran-2-yl)methoxy]-3,4-dihydro-2H-isoquinolin-1-one Method AD A mixture of 2-[4-(1,4-dioxa-7-aza-spiro[4.4]non-7-yl)-3-fluorophenyl]-6-[(S)-1-(tetrahydrofuran-2-yl)methoxy]-3,4-dihydro-2H-isoquinolin-1-one (8.4 g) and p-toluenesulfonic acid (3.4 g) in acetone/water (80 mL/40 mL) was heated for 12 h at 70° C. Then the acetone was removed in vacuum and the aqueous phase was neutralized with sodium hydrogencarbonate solution and then extracted several times with ethyl acetate. The organic phases were combined, dried over sodium sulfate and the solvent was removed in vacuum. In this way the product was obtained with molecular weight 424.47 (C24H25FN2O4); MS (ESI): 425 (M+H+).

2-[4-(1,4-Dioxa-7-aza-spiro[4.4]non-7-yl)-3-fluorophenyl]-6-[(S)-1-(tetrahydrofuran-2-yl)methoxy]-3,4-dihydro-2H-isoquinolin-1-one Method K1

A mixture of 2-[4-(1,4-dioxa-7-aza-spiro[4.4]non-7-yl)-3-fluorophenyl]-6-hydroxy-3,4-dihydro-2H-isoquinolin-1-one (6.9 g), (S)-2-methanesulfonylmethyl-tetrahydrofuran (3.9 g) and cesium carbonate (17.6 g) in DMF (81.6 mL) was heated overnight at 75° C. Then the reaction mixture was diluted with ethyl acetate and water. The organic phase was washed several times with water, dried over sodium sulfate and the solvent was removed in vacuum. In this way the product was obtained with molecular weight 468.53 (C26H29FN2O5); MS (ESI): 469 (M+H+).

2-[4-(1,4-Dioxa-7-aza-spiro[4.4]non-7-yl)-3-fluorophenyl]-6-hydroxy-3,4-dihydro-2H-isoquinolin-1-one Method AE Potassium carbonate (2.5 g) was added to a mixture of 2-[4-(1,4-dioxa-7-aza-spiro[4.4]non-7-yl)-3-fluorophenyl]-6-methoxy-3,4-dihydro-2H-isoquinolin-1-one (7.2 g) and thiophenol (2 g) in NMP (80.2 mL). Small portions of the reaction mixture were each heated for 20 min at 200° C. in a microwave. Then ethyl acetate and water were added to the mixture. The aqueous phase was extracted several times with ethyl acetate. The organic phases were combined, dried over sodium sulfate and the solvent was removed in vacuum. In this way the product was obtained with molecular weight 384.41 (C21H21FN2O4); MS (ESI): 385 (M+H+).

2-[4-(1,4-Dioxa-7-aza-spiro[4.4]non-7-yl)-3-fluorophenyl]-6-methoxy-3,4-dihydro-2H-isoquinolin-1-one Method AC A mixture of 2-(2-hydroxyethyl)-4-methoxy-benzoic acid (6.1 g) and thionyl chloride (22.5 mL) was heated for 4 h under reflux. Then the thionyl chloride together with added toluene was removed in vacuum. The residue was dissolved in THF (55.6 mL), and 4-(1,4-dioxa-7-aza-spiro[4.4]non-7-yl)-3-fluorophenylamine (7.4 g) was added. The reaction mixture was cooled to 0° C. and potassium-tert-butylate (7.0 g) was added. Then the reaction mixture was allowed to warm slowly to room temperature, being stirred at this temperature for 3 h. The solvent was removed in vacuum and the residue was taken up in ethyl acetate/water. The ethyl acetate phase was washed with 10% citric acid solution, dried over sodium sulfate and then the solvent was removed in vacuum. In this way the product was obtained with molecular weight 398.43 (C22H23FN2O4); MS (ESI): 399 (M+H+).

4-(1,4-Dioxa-7-aza-spiro[4.4]non-7-yl)-3-fluorophenylamine

According to Method F, 7-(2-fluoro-4-nitro-phenyl)-1,4-dioxa-7-aza-spiro[4.4]nonane was reduced using Pd/C. In this way the product was obtained with molecular weight 238.26 (C12H15FN2O2); MS (ESI): 239 (M+H+).

7-(2-Fluoro-4-nitro-phenyl)-1,4-dioxa-7-aza-spiro[4.4]nonane

Method E1

Potassium carbonate (6.9 g) was added to a mixture of 3,4-difluoronitrobenzene (8.0 g) and 1,4-dioxa-7-aza-spiro[4.4]nonane (12.9 g) in acetonitrile (34.6 mL) and the reaction mixture was heated for 2 h at 75° C. Ethyl acetate and water were added to the reaction mixture. The aqueous phase was extracted several times with ethyl acetate. The organic phases were combined, dried over sodium sulfate and the solvent was removed in vacuum. In this way the product was obtained with molecular weight 268.24 (C12H13FN2O4); MS (ESI): 269 (M+H+).

The compounds in Table 15 were synthesized similarly.

TABLE 15

| Ex. No. | Structure | Empirical formula | Molecular weight | ESI-MS [M + H]+ |
|---|---|---|---|---|
| 254 | 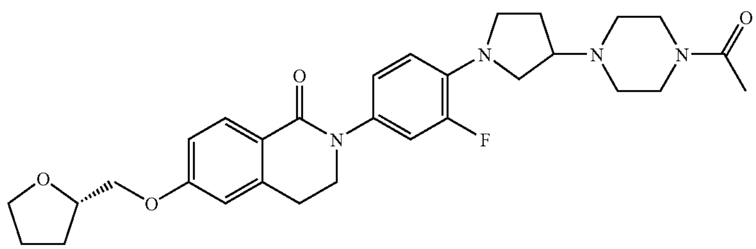 [SMILES: CC(=O)N1CCN(C2CCN(c3ccc(N4CCc5cc(OC[C@@H]6CCCO6)ccc5C4=O)cc3F)C2)CC1] | C30H37FN4O4 | 536.65 | 537 |
| 255 | 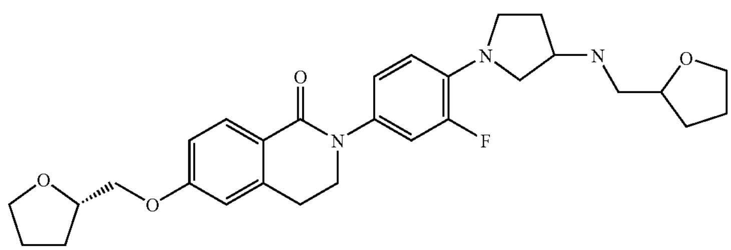 [SMILES: O=C1c2ccc(OC[C@@H]3CCCO3)cc2CCN1c1ccc(N2CCC(NCC3CCCO3)C2)c(F)c1] | C25H28FN3O2 | 509.63 | 510 |
| 256 | 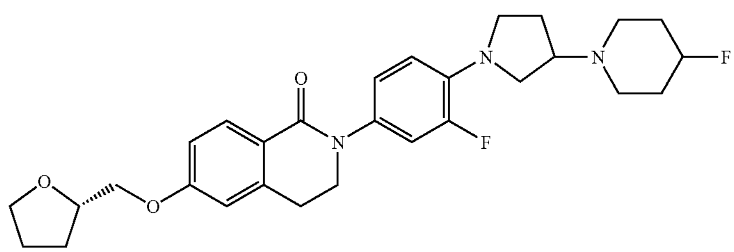 [SMILES: O=C1c2ccc(OC[C@@H]3CCCO3)cc2CCN1c1ccc(N2CCC(N3CCC(F)CC3)C2)c(F)c1] | C29H35F2N3O3 | 511.61 | 512 |
| 257 | 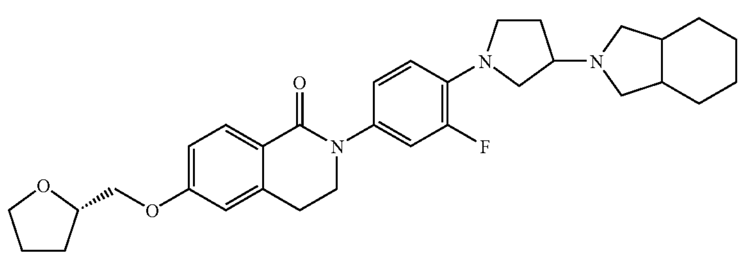 [SMILES: O=C1c2ccc(OC[C@@H]3CCCO3)cc2CCN1c1ccc(N2CCC(N3CC4CCCCC4C3)C2)c(F)c1] | C32H40FN3O3 | 533.69 | 534 |
| 258 | 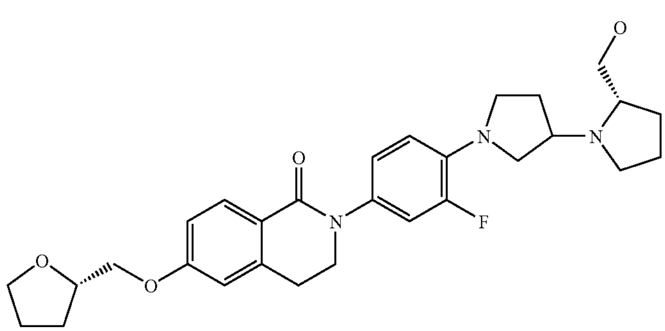 [SMILES: O=C1c2ccc(OC[C@@H]3CCCO3)cc2CCN1c1ccc(N2CCC(N3CCC[C@H]3CO)C2)c(F)c1] | C29H36FN3O4 | 509.62 | 510 |

TABLE 15-continued
| Ex. No. | Structure | Empirical formula | Molecular weight | ESI-MS [M + H]+ |
|---|---|---|---|---|
| 259 | 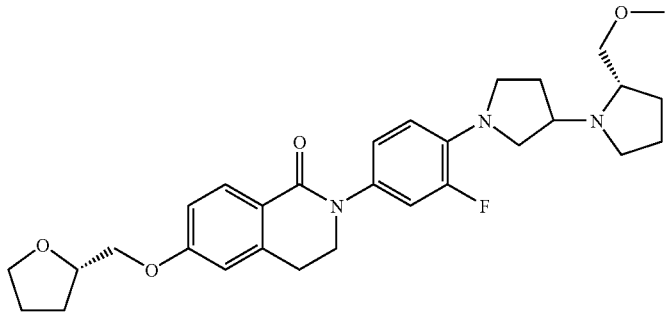 [SMILES: COC[C@@H]1CCCN1C1CCN(c2ccc(N3CCc4cc(OC[C@@H]5CCCO5)ccc4C3=O)cc2F)C1] | C30H38FN3O4 | 523.65 | 524 |
| 260 | 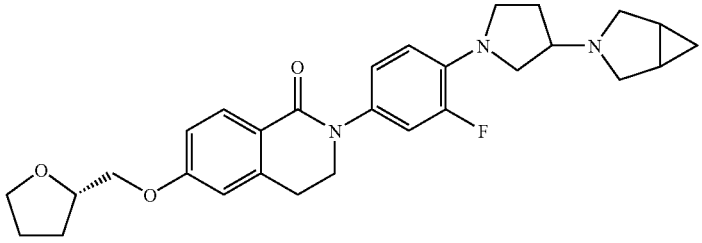 [SMILES: O=C1c2ccc(OC[C@@H]3CCCO3)cc2CCN1c1ccc(N2CCC(N3CC4CC4C3)C2)c(F)c1] | C29H34FN3O3 | 491.61 | 492 |
| 261 | 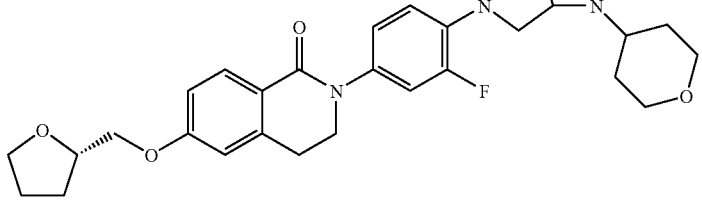 | C29H36FN3O4 | 509.62 | 510 |
| 262 | 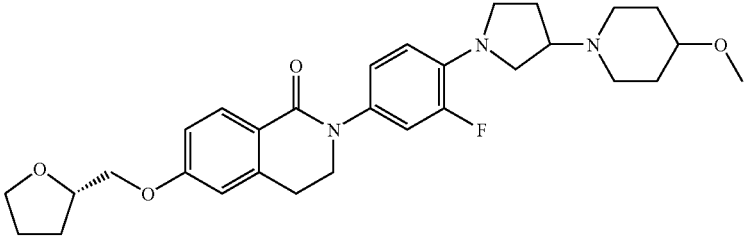 [SMILES: COC1CCN(C2CCN(c3ccc(N4CCc5cc(OC[C@@H]6CCCO6)ccc5C4=O)cc3F)C2)CC1] | C30H38FN3O4 | 523.65 | 524 |
| 263 | 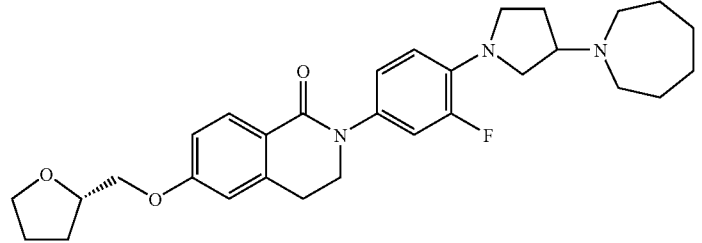 [SMILES: O=C1c2ccc(OC[C@@H]3CCCO3)cc2CCN1c1ccc(N2CCC(N3CCCCCC3)C2)c(F)c1] | C30H38FN3O3 | 507.65 | 508 |
| 264 | 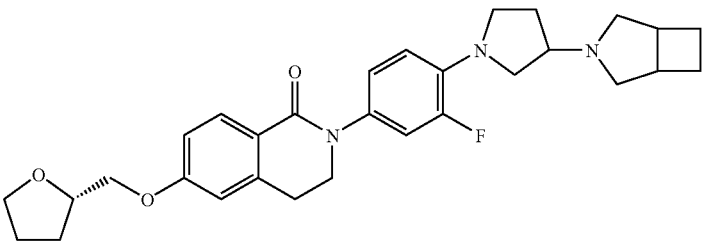 [SMILES: O=C1c2ccc(OC[C@@H]3CCCO3)cc2CCN1c1ccc(N2CCC(N3CC4CCC4C3)C2)c(F)c1] | C30H36FN3O3 | 505.64 | 506 |

TABLE 15-continued

| Ex. No. | Structure | Empirical formula | Molecular weight | ESI-MS [M + H]+ |
|---|---|---|---|---|
| 265 | 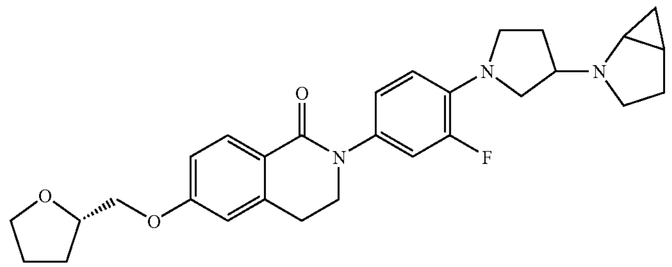 [SMILES: O=C1c2ccc(OC[C@@H]3CCCO3)cc2CCN1c1ccc(N2CCC(N3CCC4CC43)C2)c(F)c1] | C29H34FN3O3 | 491.61 | 492 |
| 266 | 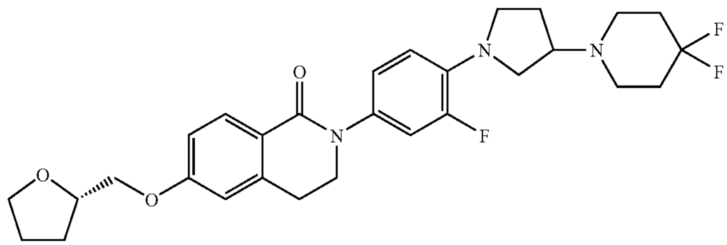 [SMILES: O=C1c2ccc(OC[C@@H]3CCCO3)cc2CCN1c1ccc(N2CCC(N3CCC(F)(F)CC3)C2)c(F)c1] | C29H34F3N3O3 | 529.61 | 530 |
| 267 | 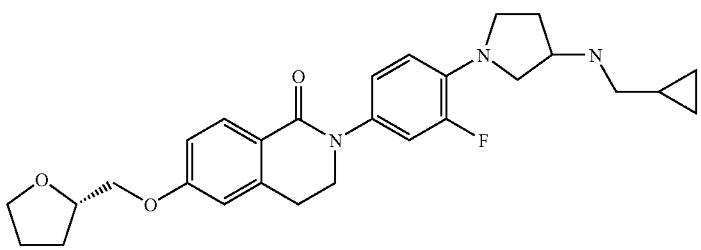 [SMILES: O=C1c2ccc(OC[C@@H]3CCCO3)cc2CCN1c1ccc(N2CCC(NCC3CC3)C2)c(F)c1] | C28H34FN3O3 | 479.60 | 480 |
| 268 | 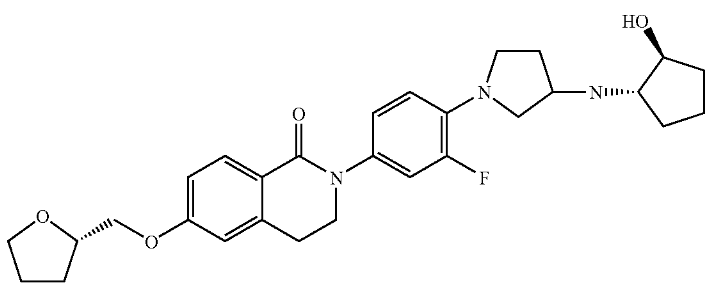 [SMILES: O=C1c2ccc(OC[C@@H]3CCCO3)cc2CCN1c1ccc(N2CCC(N[C@H]3CCC[C@@H]3O)C2)c(F)c1] | C29H36FN3O3 | 509.63 | 510 |
| 269 | 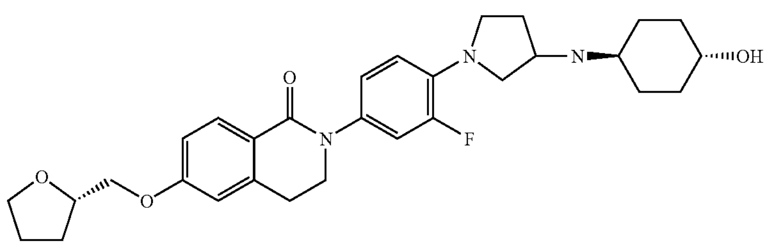 [SMILES: O=C1c2ccc(OC[C@@H]3CCCO3)cc2CCN1c1ccc(N2CCC(N[C@H]3CC[C@H](O)CC3)C2)c(F)c1] | C30H38FN3O4 | 523.65 | 524 |

3-Aza-bicyclo[3.1.0]hexane

Method AH

Pd/C (5%) (7.4 mg) was added to a solution of 3-benzyl-3-aza-bicyclo[3.1.0]hexane (240 mg) in methanol (20 mL). The solution was stirred for 6 h at room temperature under hydrogen atmosphere (normal pressure). The reaction mixture was filtered on Celite and the solvent was removed in vacuum. In this way the product was obtained with molecular weight 83.07 (C5H9N); MS (ESI): 84 (M+H+).

3-Benzyl-3-aza-bicyclo[3.1.0]hexane

A solution of iodine (2.27 g) in THF (27.9 mL) was added dropwise at 0° C. to a mixture of sodium borohydride (818 mg) in dry THF (45 mL) within 40 min. At this temperature, a solution of 3-benzyl-3-aza-bicyclo[3.1.0]hexane-2,4-dione (750 mg) in THF (11.1 mL) was then added dropwise. Then the reaction mixture was heated for 6 h under reflux. The mixture was cooled to 0° C., and 3N HCl was carefully added. Then the reaction solution was neutralized with 2N sodium hydroxide solution. The aqueous phase was extracted three times with ethyl acetate. The organic phases were combined, dried over sodium sulfate and the solvent was removed in vacuum. The raw product was purified by preparative HPLC. In this way the product was obtained with molecular weight 173.12 (C12H15N); MS (ESI): 174 (M+H+).

2-Aza-bicyclo[3.1.0]hexane

Method H1

A mixture of 2-aza-bicyclo[3.1.0]hexane-2-carboxylic acid tert-butyl ester (960 mg) and 4M HCl in dioxane (26 mL) was stirred for 15 min at room temperature. Then, after previously adding toluene, the solvent was removed in vacuum. The raw product obtained was purified chromatographically on silica gel (gradient: 90:10:1:1 to 70:30:5:5; methylene chloride:methanol:acetic acid:water). In this way the product was obtained with molecular weight 83.07 (C5H9N); MS (ESI): 84 (M+H+).

2-Aza-bicyclo[3.1.0]hexane-2-carboxylic acid tert-butyl ester

TMEDA (0.11 mL) was slowly added dropwise at −78° C. to a mixture of sec-butyllithium (1.4 M; 0.52 mL) and THF (1.8 mL). Then it was stirred for a further 30 min at −78° C. and then a solution of 4-chloro-piperidine-1-carboxylic acid tert-butyl ester (160 mg) in a little THF was slowly added dropwise. The reaction mixture was stirred for 2 h at −78° C., then it was allowed to return slowly to room temperature. Ethyl acetate and water were added to the reaction mixture and the aqueous phase was extracted several times with ethyl acetate. The organic phases were combined, dried over sodium sulfate and the solvent was removed in vacuum.

4-Chloro-piperidine-1-carboxylic acid tert-butyl ester

A mixture of 4-chloro-piperidine hydrochloride (156.1 mg), di-tert-butyl-bicarbonate (240 mg), triethylamine (0.1 mL) and catalytic amounts of DMAP in THF (2 mL) was heated for 6 h at 65° C. Then the reaction mixture was diluted with ethyl acetate and washed with 10% citric acid. The organic phase was dried over sodium sulfate and the solvent was removed in vacuum.

Example 270

2-{3-Methoxy-4-[4-(2-methoxy-1-methyl-ethyl)-[1,4]diazepan-1-yl]-phenyl}-6-[(R)-1-(tetrahydrofuran-2-yl)methoxy]-3,4-dihydro-2H-isoquinolin-1-one

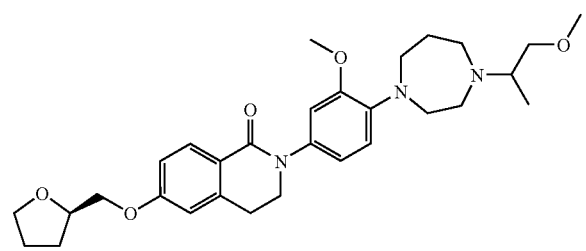 [SMILES: COCC(C)N1CCCN(c2ccc(N3CCc4cc(OC[C@H]5CCCO5)ccc4C3=O)cc2OC)CC1]

6-Hydroxy-2-{3-methoxy-4-[4-(2-methoxy-1-methyl-ethyl)-[1,4]diazepan-1-yl]-phenyl}-3,4-dihydro-2H-isoquinolin-1-one and (R)-2-methanesulfonylmethyl-tetrahydrofuran were reacted according to Method K1. In this way the product was obtained with molecular weight 523.68 (C30H41N3O5); MS (ESI): 524 (M+H+).

6-Hydroxy-2-{3-methoxy-4-[4-(2-methoxy-1-methyl-ethyl)-[1,4]diazepan-1-yl]-phenyl}-3,4-dihydro-2H-isoquinolin-1-one 2-(4-[1,4]Diazepan-1-yl-3-methoxy-phenyl)-6-hydroxy-3,4-dihydro-2H-isoquinolin-1-one and 1-methoxy-propan-2-one were reacted according to Method J1. In this way the product was obtained with molecular weight 439.56 (C25H33N3O4); MS (ESI): 440 (M+H+).

2-(4-[1,4]Diazepan-1-yl-3-methoxy-phenyl)-6-hydroxy-3,4-dihydro-2H-isoquinolin-1-one Method L1

A solution of 4-[2-methoxy-4-(6-methoxy-1-oxo-3,4-dihydro-1H-isoquinolin-2-yl)-phenyl]-[1,4]diazepane-1-carboxylic acid tert-butyl ester in 48% HBr (10 mL) was stirred for 48 h at 80° C. The mixture was neutralized with sodium hydroxide solution, extracted with dichloromethane, dried over magnesium sulfate and concentrated. In this way the product was obtained with molecular weight 367.45 (C21H25N3O3); MS (ESI): 368 (M+H+).

4-[2-Methoxy-4-(6-methoxy-1-oxo-3,4-dihydro-1H-isoquinolin-2-yl)-phenyl]-[1,4]diazepane-1-carboxylic acid tert-butyl ester 6-Methoxy-isochroman-1-one and 4-(4-amino-2-methoxyphenyl)-[1,4]diazepane-1-carboxylic acid tert-butyl ester were reacted according to Method AC. In this way the product was obtained with molecular weight 481.60 (C27H35N3O5); MS (ESI): 482 (M+H+).

4-(4-Amino-2-methoxyphenyl)-[1,4]diazepane-1-carboxylic acid tert-butyl ester According to methods E and F 1-Fluoro-2-methoxy-4-nitro-benzene was reacted with [1,4]Diazepane-1-carboxylic acid tert-butyl ester and then the obtained nitro compound was hydrogenated. In this way the product was obtained with molecular weight 321.42 (C17H27N3O3); MS (ESI): 322 (M+H+).

6-Methoxy-isochroman-1-one

A 1.6M solution of n-butyllithium in hexane (145.9 mL) was added dropwise at −78° C. to a solution of diisopropylamine (33.5 mL) in dry THF (190 mL). Then the reaction mixture was warmed to room temperature for 5 min, and then cooled again to −78° C., and a solution of 4-methoxy-2-methylbenzoic acid in dry THF (210 mL) was added dropwise. After stirring at this temperature for 10 min, paraformaldehyde (7 g) was added. Then the reaction mixture was allowed to return to room temperature and it was stirred at this temperature for 4 h. Water was added to the reaction mixture, then the THF was removed in vacuum and then the aqueous phase was extracted with diethyl ether. The aqueous phase was acidified with conc. HCl, the precipitate obtained was filtered off and washed with water several times. In this way the product was obtained with molecular weight 178.06 (C10H10O3); MS (ESI): 179 (M+H+).

The compounds in Table 16 were synthesized similarly:

TABLE 16

| Ex. No. | Structure | Empirical formula | Molecular weight | ESI-MS [M + H]+ |
|---|---|---|---|---|
| 271 | 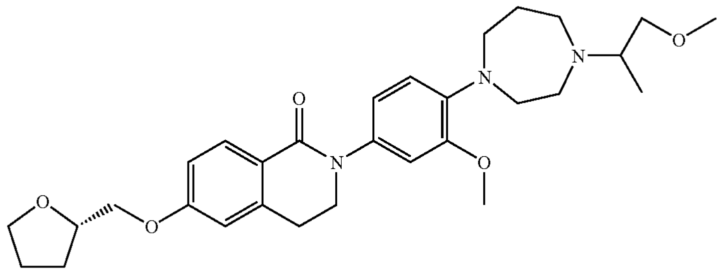 [SMILES: COCC(C)N1CCCN(c2ccc(N3CCc4cc(OC[C@@H]5CCCO5)ccc4C3=O)cc2OC)CC1] | C30H41N3O5 | 523.68 | 524 |
| 272 | 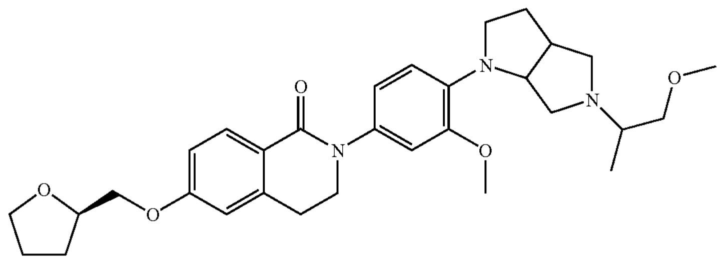 [SMILES: COCC(C)N1CC2CCN(c3ccc(N4CCc5cc(OC[C@H]6CCCO6)ccc5C4=O)cc3OC)C2C1] | C31H41N3O5 | 535.66 | 536 |
| 273 | 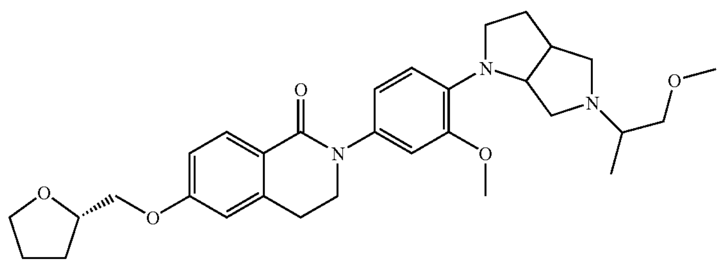 [SMILES: COCC(C)N1CC2CCN(c3ccc(N4CCc5cc(OC[C@@H]6CCCO6)ccc5C4=O)cc3OC)C2C1] | C31H41N3O5 | 535.66 | 536 |

Example 274

6-((S)-2-Hydroxy-butoxy)-2-{3-methoxy-4-[4-(2-methoxy-1-methyl-ethyl)-[1,4]diazepan-1-yl]-phenyl}-3,4-dihydro-2H-isoquinolin-1-one

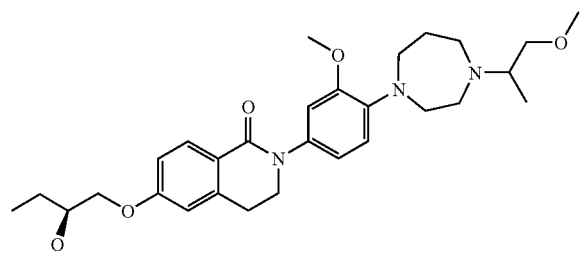 [SMILES: CC[C@H](O)COc1ccc2c(c1)CCN(c1ccc(N3CCCN(C(C)COC)CC3)c(OC)c1)C2=O]

Method T1

A mixture of 6-hydroxy-2-{3-methoxy-4-[4-(2-methoxy-1-methyl-ethyl)-[1,4]diazepan-1-yl]-phenyl}-3,4-dihydro-2H-isoquinolin-1-one (39 mg), (S)-(−)-1,2-epoxybutane (15 mg) and cesium fluoride (32 mg) in DMF (0.5 mL) was stirred at 130° C. for 4 h. After adding water it was extracted with dichloromethane, dried over magnesium sulfate and concentrated. The residue was purified by preparative HPLC. In this way the product was obtained with molecular weight 511.67 (C29H41N3O5); MS (ESI): 512 (M+H+).

The following compound was synthesized similarly:

| Ex. No. | Structure | Empirical formula | Molecular weight | ESI-MS [M + H]+ |
|---|---|---|---|---|
| 275 | 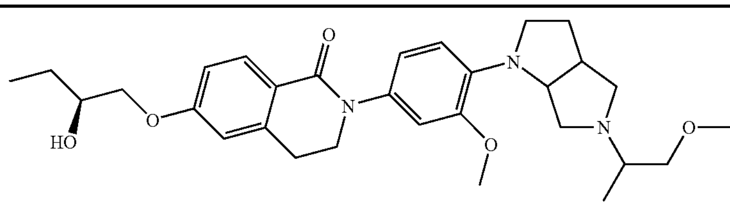 | C30H41N3O5 | 523.68 | 524 |

Example 276

2-{4-[4-(2-Hydroxy-2-methyl-propyl)-[1,4]diazepan-1-yl]-3-methoxy-phenyl}-6-[(R)-1-(tetrahydrofuran-2-yl)methoxy]-3,4-dihydro-2H-isoquinolin-1-one

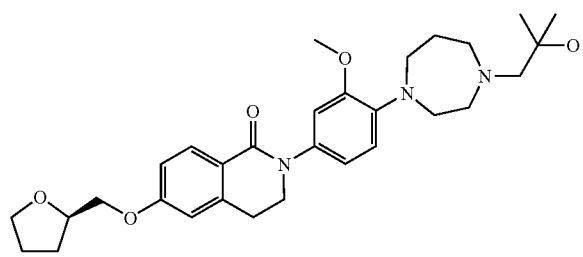 [SMILES: COc1cc(N2CCc3cc(OC[C@H]4CCCO4)ccc3C2=O)ccc1N1CCCN(CC(C)(C)O)CC1]

6-Hydroxy-2-{4-[4-(2-hydroxy-2-methyl-propyl)-[1,4]diazepan-1-yl]-3-methoxy-phenyl}-3,4-dihydro-2H-isoquinolin-1-one and (R)-2-methanesulfonylmethyl-tetrahydrofuran were reacted according to Method K1. In this way the product was obtained with molecular weight 523.68 (C30H41N3O5); MS (ESI): 524 (M+H+).

6-Hydroxy-2-{4-[4-(2-hydroxy-2-methyl-propyl)-[1,4]diazepan-1-yl]-3-methoxy-phenyl}-3,4-dihydro-2H-isoquinolin-1-one A solution of 2-(4-[1,4]diazepan-1-yl-3-methoxy-phenyl)-6-hydroxy-3,4-dihydro-2H-isoquinolin-1-one (193 mg) and isobutylene oxide (300 mg) in NMP (0.8 mL) was stirred at 65° C. for 16 h. The reaction mixture was purified by preparative HPLC. In this way the product was obtained with molecular weight 439.56 (C25H33N3O4); MS (ESI): 440 (M+H+).

The compounds in Table 17 were synthesized similarly:

TABLE 17

| Ex. No. | Structure | Empirical formula | Molecular weight | ESI-MS [M + H]+ |
|---|---|---|---|---|
| 277 | 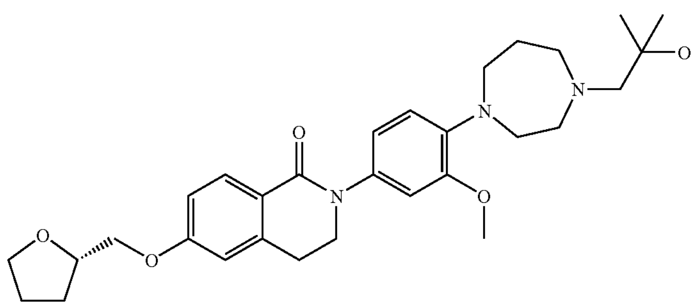 [SMILES: COc1cc(N2CCc3cc(OC[C@@H]4CCCO4)ccc3C2=O)ccc1N1CCCN(CC(C)(C)O)CC1] | C30H41N3O5 | 523.66 | 524 |
| 278 | 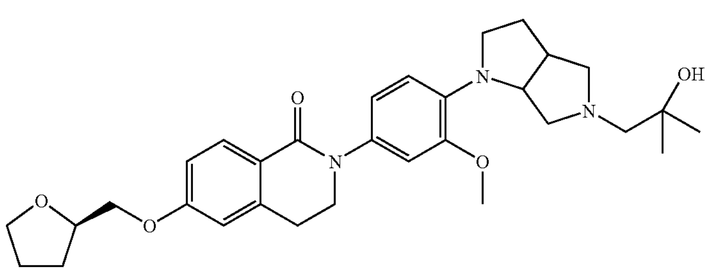 [SMILES: COc1cc(N2CCc3cc(OC[C@H]4CCCO4)ccc3C2=O)ccc1N1CCC2CN(CC(C)(C)O)CC21] | C31H41N3O5 | 535.69 | 536 |
| 279 | 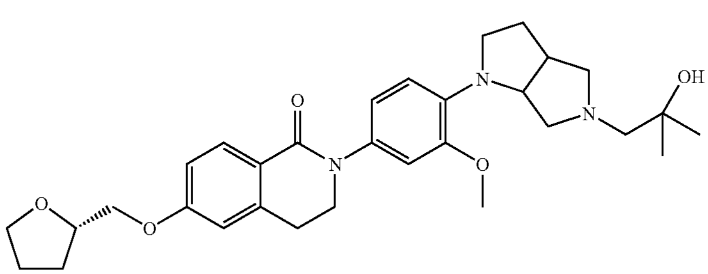 [SMILES: COc1cc(N2CCc3cc(OC[C@@H]4CCCO4)ccc3C2=O)ccc1N1CCC2CN(CC(C)(C)O)CC21] | C31H41N3O5 | 535.69 | 536 |

Example 280

6-((S)-2-Hydroxy-butoxy)-2-{4-[4-(2-hydroxy-2-methyl-propyl)-[1,4]diazepan-1-yl]-3-o methoxy-phenyl}-3,4-dihydro-2H-isoquinolin-1-one

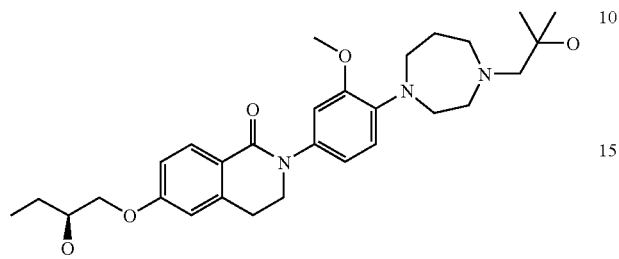

6-Hydroxy-2-{4-[4-(2-hydroxy-2-methyl-propyl)-[1,4]diazepan-1-yl]-3-methoxy-phenyl}-3,4-dihydro-2H-isoquinolin-1-one and (S)-(−)-1,2-epoxybutane were reacted according to Method T1. In this way the product was obtained with molecular weight 511.67 (C29H41N3O5); MS (ESI): 512 (M+H+).

The following compound was synthesized similarly:

| Ex. No. | Structure | Empirical formula | Molecular weight | ESI-MS [M + H]+ |
|---|---|---|---|---|
| 281 | 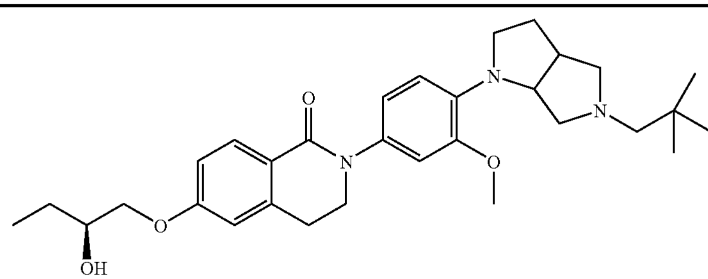 | C30H41N3O5 | 523.68 | 524 |

Example 282

2-[4-(4-Methyl-[1,4]diazepan-1-yl)-phenyl]-6-[(R)-1-(tetrahydrofuran-2-yl)methoxy]-3,4-dihydro-2H-isoquinolin-1-one

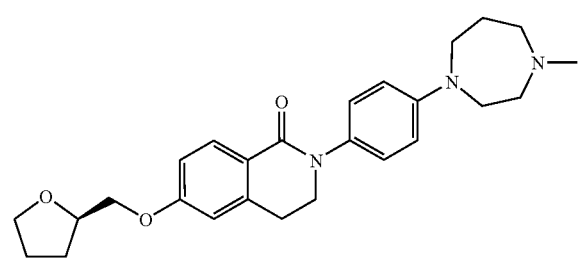 [SMILES: CN1CCCN(c2ccc(N3CCc4cc(OC[C@H]5CCCO5)ccc4C3=O)cc2)CC1]

6-Hydroxy-2-[4-(4-methyl-[1,4]diazepan-1-yl)-phenyl]-3,4-dihydro-2H-isoquinolin-1-one and (R)-2-methanesulfonylmethyl-tetrahydrofuran were reacted according to Method K1. In this way the product was obtained with molecular weight 435.57 (C26H33N3O3); MS (ESI): 436 (M+H+).

6-Hydroxy-2-[4-(4-methyl-[1,4]diazepan-1-yl)-phenyl]-3,4-dihydro-2H-isoquinolin-1-one 6-Methoxy-2-[4-(4-methyl-[1,4]diazepan-1-yl)-phenyl]-3,4-dihydro-2H-isoquinolin-1-one was reacted with 48% HBr according to Method L1. In this way the product was obtained with molecular weight 351.45 (C21H25N3O2); MS (ESI): 352 (M+H+).

6-Methoxy-2-[4-(4-methyl-[1,4]diazepan-1-yl)-phenyl]-3,4-dihydro-2H-isoquinolin-1-one 6-Methoxy-isochromen-1-one and 4-(4-methyl-[1,4]diazepan-1-yl)-phenylamine were reacted according to Method AC. In this way the product was obtained with molecular weight 365.48 (C22H27N3O2); MS (ESI): 366 (M+H+).

The compounds in Table 18 were synthesized similarly:

TABLE 18

| Ex. No. | Structure | Empirical formula | Molecular weight | ESI-MS [M + H]+ |
|---|---|---|---|---|
| 283 | 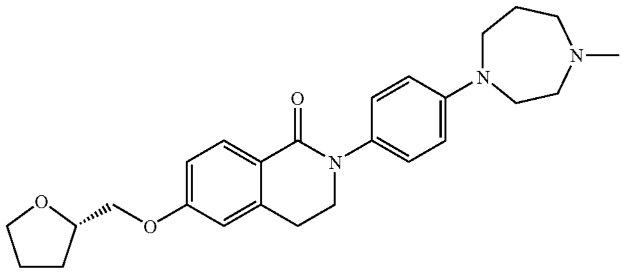 [SMILES: CN1CCCN(c2ccc(N3CCc4cc(OC[C@@H]5CCCO5)ccc4C3=O)cc2)CC1] | C26H33N3O3 | 435.57 | 436 |
| 284 | 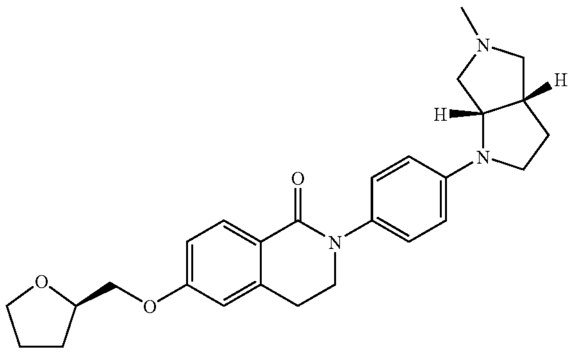 [SMILES: CN1C[C@@H]2CCN(c3ccc(N4CCc5cc(OC[C@H]6CCCO6)ccc5C4=O)cc3)[C@@H]2C1] | C27H33N3O3 | 447.58 | 448 |
| 285 | 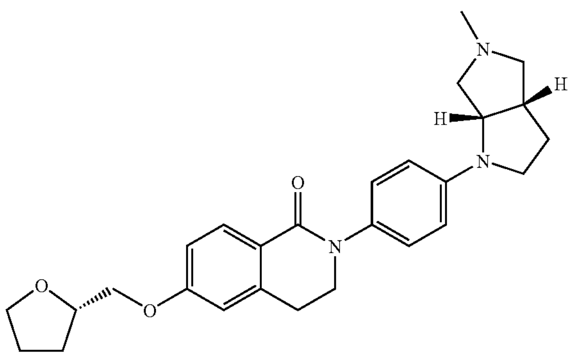 [SMILES: CN1C[C@@H]2CCN(c3ccc(N4CCc5cc(OC[C@@H]6CCCO6)ccc5C4=O)cc3)[C@@H]2C1] | C27H33N3O3 | 447.58 | 448 |

Example 286

6-((S)-2-Hydroxy-butoxy)-2-[4-(4-methyl-[1,4]diazepan-1-yl)-phenyl]-3,4-dihydro-2H-isoquinolin-1-one

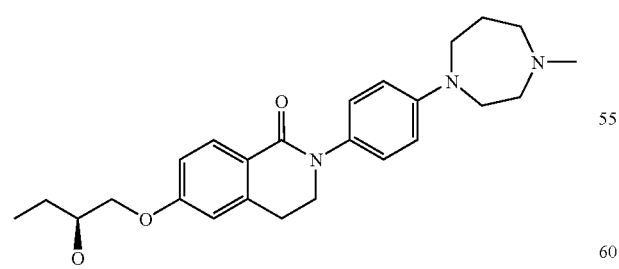

6-Hydroxy-2-[4-(4-methyl-[1,4]diazepan-1-yl)-phenyl]-3,4-dihydro-2H-isoquinolin-1-one and (S)-(−)-1,2-epoxybutane were reacted according to Method T1. In this way the product was obtained with molecular weight 423.56 (C25H33N3O3); MS (ESI): 424 (M+H+).

The following compound was synthesized similarly:

| Ex. No. | Structure | Empirical formula | Molecular weight | ESI-MS [M + H]+ |
|---|---|---|---|---|
| 287 | 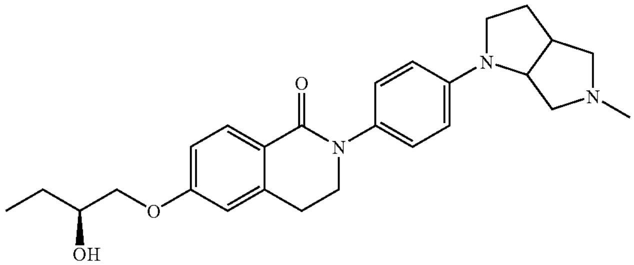 [SMILES: CC[C@H](O)COc1ccc2c(c1)CCN(c1ccc(N3CCC4CN(C)CC43)cc1)C2=O] | C27H35N3O4 | 435.57 | 436 |

Example 288

2-[4-(3-Azetidin-1-yl-pyrrolidin-1-yl)-3-fluorophenyl]-6-[(R)-1-(tetrahydrofuran-2-yl)methoxy]-2H-isoquinolin-1-one

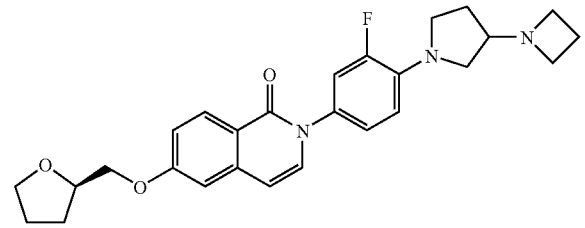 [SMILES: O=c1c2ccc(OC[C@H]3CCCO3)cc2ccn1-c1ccc(N2CCC(N3CCC3)C2)c(F)c1]

2-[3-Fluoro-4-(3-oxo-pyrrolidin-1-yl)-phenyl]-6-[(R)-1-(tetrahydrofuran-2-yl)methoxy]-2H-isoquinolin-1-one was reacted with azetidine according to Method J1. In this way the product was obtained with molecular weight 463.23 (C27H30FN3O3); MS (ESI): 464 (M+H+).

2-[3-Fluoro-4-(3-oxo-pyrrolidin-1-yl)-phenyl]-6-[(R)-1-(tetrahydrofuran-2-yl)methoxy]-2H-isoquinolin-1-one

2-[4-(1,4-Dioxa-7-aza-spiro[4.4]non-7-yl)-3-fluorophenyl]-6-[(R)-1-(tetrahydrofuran-2-yl)methoxy]-2H-isoquinolin-1-one was reacted according to Method AD. In this way the product was obtained with molecular weight 422.16 (C24H23FN2O4); MS (ESI): 423 (M+H+).

2-[4-(1,4-Dioxa-7-aza-spiro[4.4]non-7-yl)-3-fluorophenyl]-6-[(R)-1-(tetrahydrofuran-2-yl)methoxy]-2H-isoquinolin-1-one

2-[4-(1,4-Dioxa-7-aza-spiro[4.4]non-7-yl)-3-fluorophenyl]-6-hydroxy-2H-isoquinolin-1-one was reacted with (R)-methanesulfonic acid tetrahydrofuran-2-ylmethyl ester according to Method K1. In this way the product was obtained with molecular weight 466.19 (C26H27FN2O5); MS (ESI): 467 (M+H+).

2-[4-(1,4-Dioxa-7-aza-spiro[4.4]non-7-yl)-3-fluorophenyl]-6-hydroxy-2H-isoquinolin-1-one

2-[4-(1,4-Dioxa-7-aza-spiro[4.4]non-7-yl)-3-fluorophenyl]-6-methoxy-2H-isoquinolin-1-one was reacted according to Method AE. In this way the product was obtained with molecular weight 382.13 (C21H19FN2O4); MS (ESI): 383 (M+H+).

2-[4-(1,4-Dioxa-7-aza-spiro[4.4]non-7-yl)-3-fluorophenyl]-6-methoxy-2H-isoquinolin-1-one

Method AF

Dess-Martin periodinane (7 g) was added to a solution of N-[4-(1,4-dioxa-7-aza-spiro[4.4]non-7-yl)-3-fluorophenyl]-2-(2-hydroxyethyl)-4-methoxy-benzamide (4.6 g) in methylene chloride (279 mL). The reaction mixture was stirred for 2 h at room temperature, then further Dess-Martin periodinane (1.4 g) was added, stirring for a further 4 h at room temperature. Then 5% Na2S2O3 solution was added to the reaction solution and the organic phase was then washed with water. The methylene chloride phase was dried over sodium sulfate and the solvent was removed in vacuum. The raw product was purified by preparative HPLC. In this way the product was obtained with molecular weight 396.15 (C22H21FN2O4); MS (ESI): 397 (M+H+).

N-[4-(1,4-Dioxa-7-aza-spiro[4.4]non-7-yl)-3-fluorophenyl]-2-(2-hydroxyethyl)-4-methoxy-benzamide

Method AG

A 2M solution of trimethylaluminum in toluene (14.9 mL) was added dropwise at 0° C. to a solution of 4-(1,4-dioxa-7-aza-spiro[4.4]non-7-yl)-3-fluorophenylamine (5.3 g) in methylene chloride (100.8 mL). The reaction mixture was stirred for 15 min at 0° C. and then for 30 min at room temperature. Then a solution of 6-methoxy-isochroman-1-one (3.8 g) in methylene chloride (40 mL) was added dropwise. The reaction mixture was stirred overnight at room temperature. Then saturated Rochelle salt solution was carefully added and the mixture was stirred for 1 h at room temperature. The aqueous phase was extracted several times with methylene chloride. The organic phases were combined, dried over sodium sulfate and the solvent was removed in vacuum. In this way the product was obtained with molecular weight 416.17 (C22H25FN2O5); MS (ESI): 417 (M+H+).

The compounds in Table 19 were synthesized similarly:

TABLE 19

| Ex. No. | Structure | Empirical formula | Molecular weight | ESI-MS [M + H]+ |
|---|---|---|---|---|
| 289 | 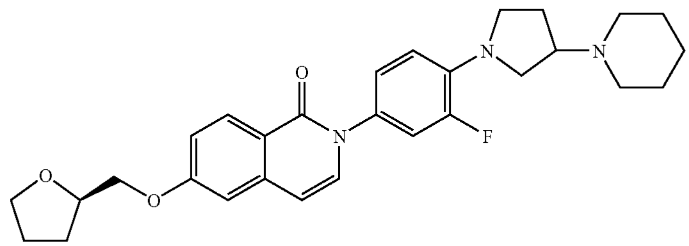 [SMILES: O=c1c2ccc(OC[C@H]3CCCO3)cc2ccn1-c1ccc(N2CCC(N3CCCCC3)C2)c(F)c1] | C29H34FN3O3 | 491.61 | 492 |
| 290 | 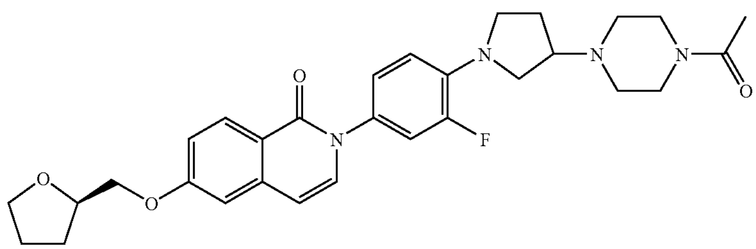 [SMILES: CC(=O)N1CCN(C2CCN(c3ccc(-n4ccc5cc(OC[C@H]6CCCO6)ccc5c4=O)cc3F)C2)CC1] | C30H35FN4O4 | 534.63 | 535 |
| 291 | 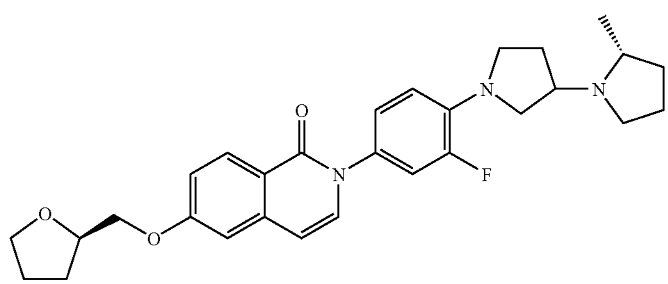 [SMILES: C[C@@H]1CCCN1C1CCN(c2ccc(-n3ccc4cc(OC[C@H]5CCCO5)ccc4c3=O)cc2F)C1] | C29H34FN3O3 | 491.61 | 492 |
| 292 | 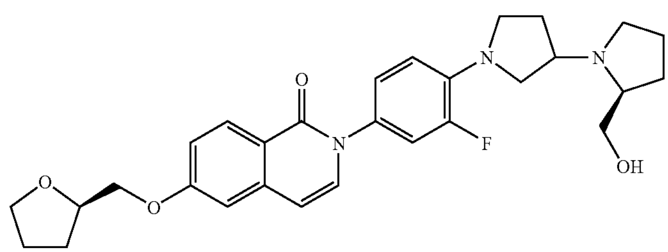 [SMILES: O=c1c2ccc(OC[C@H]3CCCO3)cc2ccn1-c1ccc(N2CCC(N3CCC[C@H]3CO)C2)c(F)c1] | C29H34FN3O4 | 507.61 | 508 |
| 293 | 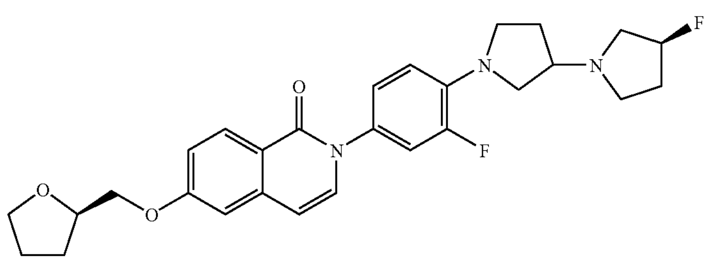 [SMILES: O=c1c2ccc(OC[C@H]3CCCO3)cc2ccn1-c1ccc(N2CCC(N3CC[C@H](F)C3)C2)c(F)c1] | C28H31F2N3O3 | 495.75 | 496 |
| 294 | 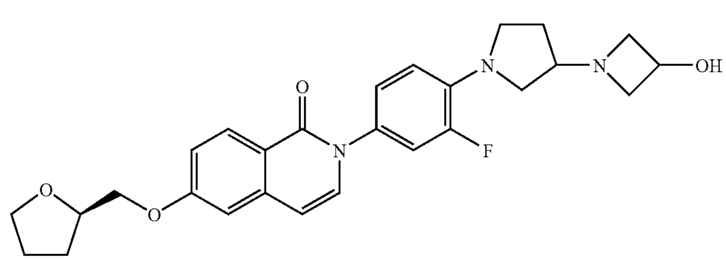 [SMILES: O=c1c2ccc(OC[C@H]3CCCO3)cc2ccn1-c1ccc(N2CCC(N3CC(O)C3)C2)c(F)c1] | C27H30FN3O4 | 479.55 | 480 |

TABLE 19-continued

| Ex. No. | Structure | Empirical formula | Molecular weight | ESI-MS [M + H]+ |
|---|---|---|---|---|
| 295 | 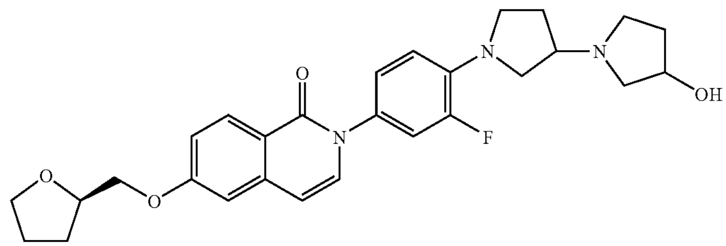 [SMILES: O=c1c2ccc(OC[C@H]3CCCO3)cc2ccn1-c1ccc(N2CCC(N3CCC(O)C3)C2)c(F)c1] | C28H32FN3O4 | 493.58 | 494 |
| 296 | 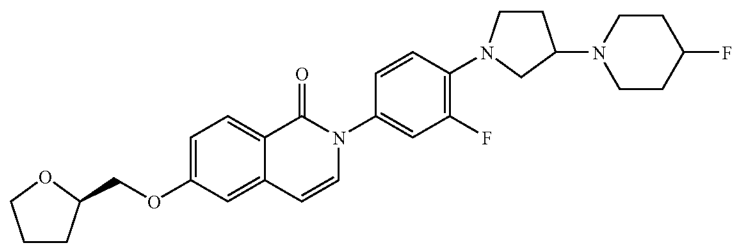 [SMILES: O=c1c2ccc(OC[C@H]3CCCO3)cc2ccn1-c1ccc(N2CCC(N3CCC(F)CC3)C2)c(F)c1] | C29H33F2N3O3 | 509.60 | 510 |
| 297 | 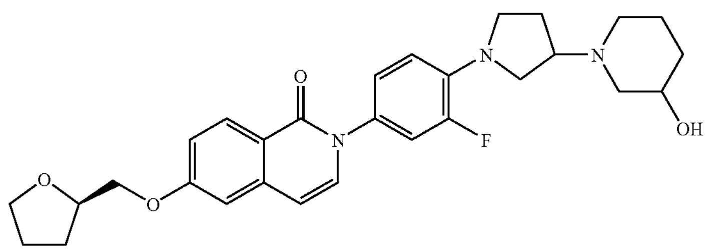 [SMILES: O=c1c2ccc(OC[C@H]3CCCO3)cc2ccn1-c1ccc(N2CCC(N3CCCC(O)C3)C2)c(F)c1] | C29H34FN3O4 | 507.61 | 508 |
| 298 | 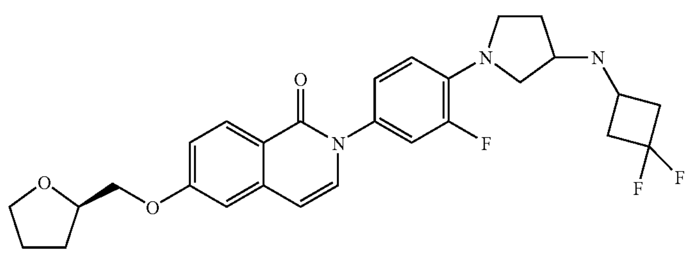 [SMILES: O=c1c2ccc(OC[C@H]3CCCO3)cc2ccn1-c1ccc(N2CCC(NC3CC(F)(F)C3)C2)c(F)c1] | C28H30F3N3O3 | 513.56 | 514 |
| 299 | 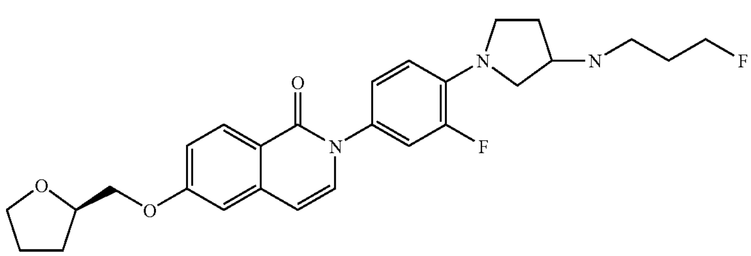 [SMILES: O=c1c2ccc(OC[C@H]3CCCO3)cc2ccn1-c1ccc(N2CCC(NCCCF)C2)c(F)c1] | C27H31F2N3O3 | 483.56 | 484 |
| 300 | 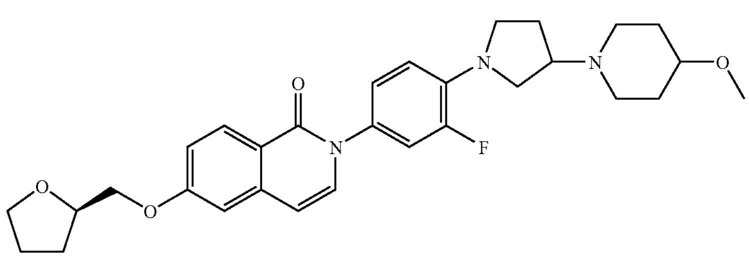 [SMILES: COC1CCN(C2CCN(c3ccc(-n4ccc5cc(OC[C@H]6CCCO6)ccc5c4=O)cc3F)C2)CC1] | C30H36FN3O4 | 521.63 | 522 |

TABLE 19-continued

| Ex. No. | Structure | Empirical formula | Molecular weight | ESI-MS [M + H]+ |
|---|---|---|---|---|
| 301 | 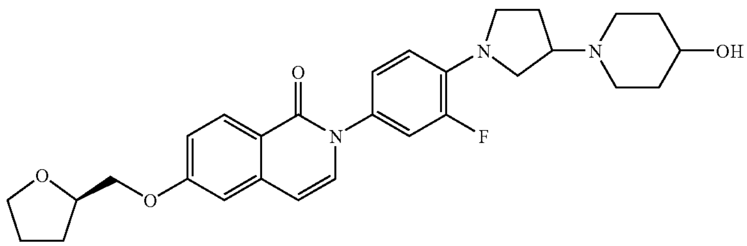 [SMILES: O=c1c2ccc(OC[C@H]3CCCO3)cc2ccn1-c1ccc(N2CCC(N3CCC(O)CC3)C2)c(F)c1] | C29H34FN3O4 | 507.61 | 508 |
| 302 | 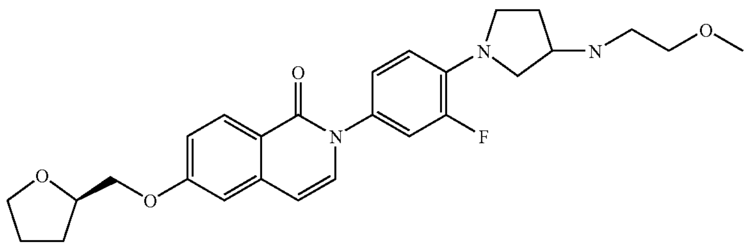 [SMILES: COCCNC1CCN(c2ccc(-n3ccc4cc(OC[C@H]5CCCO5)ccc4c3=O)cc2F)C1] | C27H32FN3O4 | 481.57 | 482 |
| 303 | 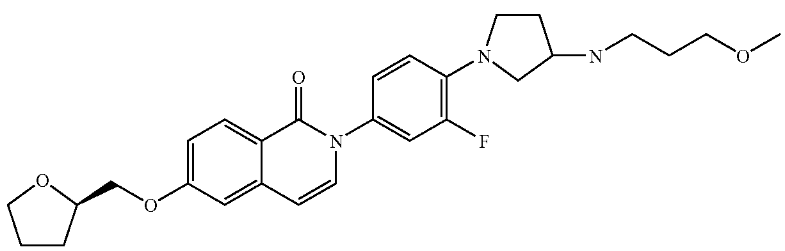 [SMILES: COCCCNC1CCN(c2ccc(-n3ccc4cc(OC[C@H]5CCCO5)ccc4c3=O)cc2F)C1] | C28H34FN3O4 | 495.59 | 496 |
| 304 | 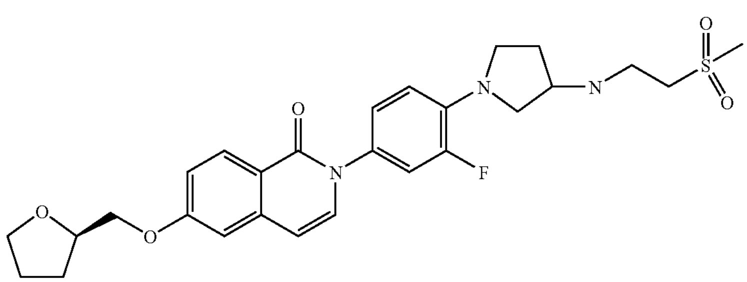 [SMILES: CS(=O)(=O)CCNC1CCN(c2ccc(-n3ccc4cc(OC[C@H]5CCCO5)ccc4c3=O)cc2F)C1] | C27H32FN3O5S | 592.63 | 593 |
| 305 | 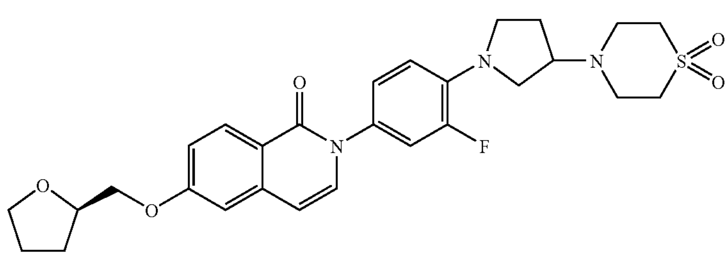 [SMILES: O=c1c2ccc(OC[C@H]3CCCO3)cc2ccn1-c1ccc(N2CCC(N3CCS(=O)(=O)CC3)C2)c(F)c1] | C28H32FN3O5S | 541.64 | 542 |
| 306 | 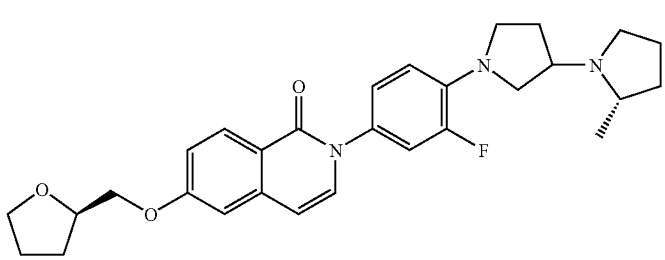 [SMILES: C[C@H]1CCCN1C1CCN(c2ccc(-n3ccc4cc(OC[C@H]5CCCO5)ccc4c3=O)cc2F)C1] | C29H34FN3O3 | 491.61 | 492 |

TABLE 19-continued
| Ex. No. | Structure | Empirical formula | Molecular weight | ESI-MS [M + H]+ |
|---|---|---|---|---|
| 307 | 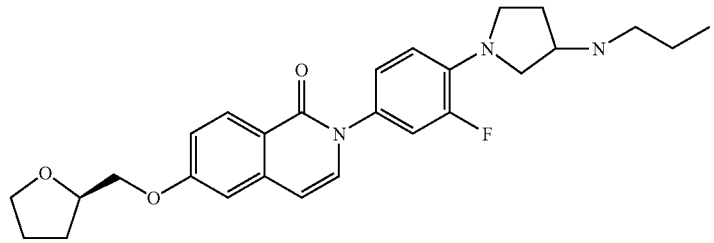 [SMILES: CCCNC1CCN(c2ccc(-n3ccc4cc(OC[C@H]5CCCO5)ccc4c3=O)cc2F)C1] | C27H32FN3O3 | 465.57 | 466 |
| 308 | 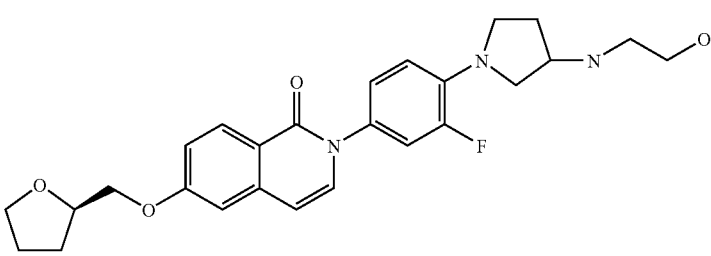 | C26H30FN3O4 | 467.54 | 468 |
| 309 | 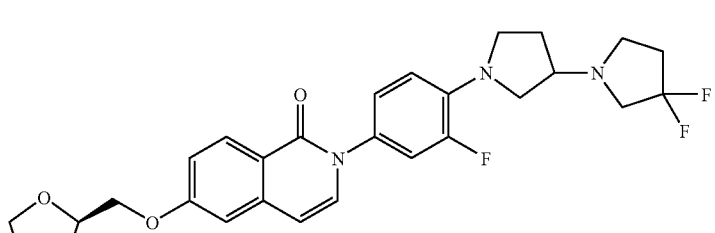 | C28H30F3N3O3 | 513.56 | 514 |
| 310 | 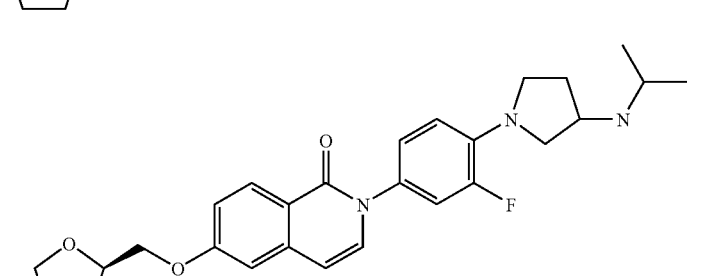 | C27H32FN3O3 | 465.57 | 466 |
| 311 | 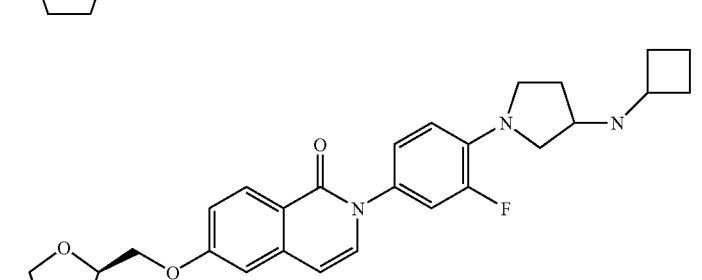 | C28H32FN3O3 | 477.58 | 478 |
| 312 | 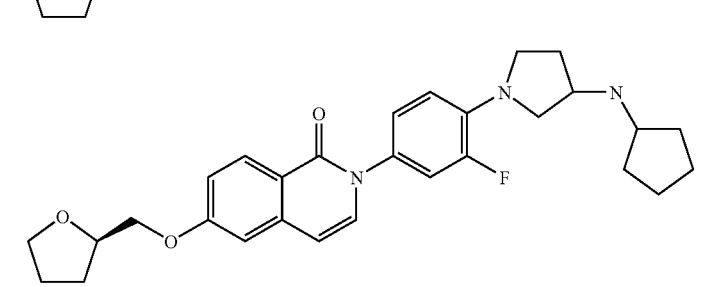 | C29H34FN3O3 | 491.61 | 492 |

TABLE 19-continued
| Ex. No. | Structure | Empirical formula | Molecular weight | ESI-MS [M + H]+ |
|---|---|---|---|---|
| 313 | 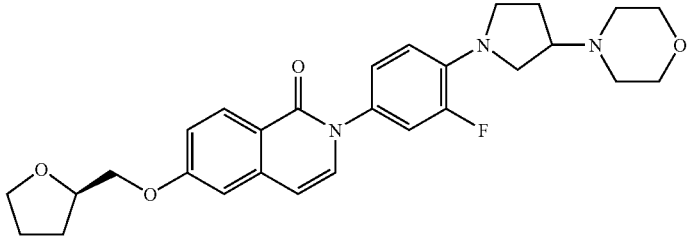 [SMILES: O=c1c2ccc(OC[C@H]3CCCO3)cc2ccn1-c1ccc(N2CCC(N3CCOCC3)C2)c(F)c1] | C28H32FN3O4 | 493.58 | 494 |
| 314 | 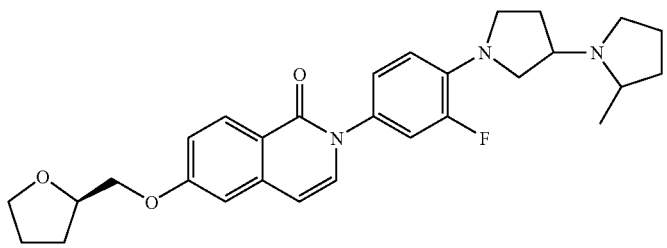 [SMILES: CC1CCCN1C1CCN(c2ccc(-n3ccc4cc(OC[C@H]5CCCO5)ccc4c3=O)cc2F)C1] | C29H34FN3O3 | 491.61 | 492 |
| 315 | 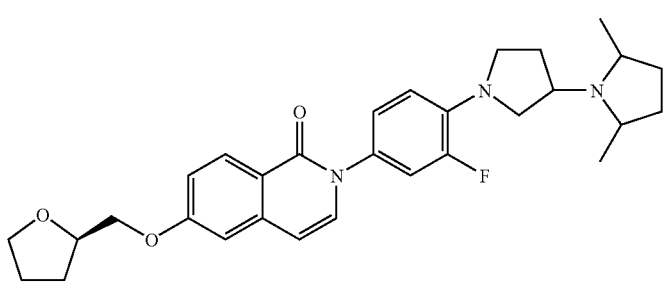 [SMILES: CC1CCC(C)N1C1CCN(c2ccc(-n3ccc4cc(OC[C@H]5CCCO5)ccc4c3=O)cc2F)C1] | C30H36FN3O3 | 505.64 | 506 |
| 316 | 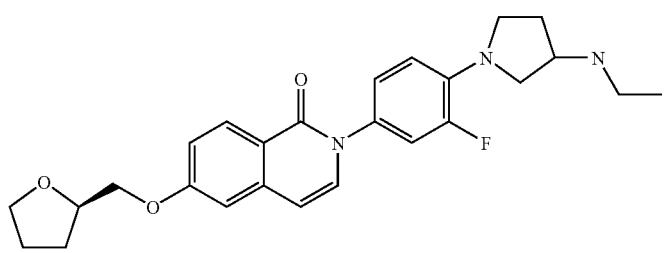 [SMILES: CCNC1CCN(c2ccc(-n3ccc4cc(OC[C@H]5CCCO5)ccc4c3=O)cc2F)C1] | C26H30FN3O3 | 451.54 | 452 |
| 317 | 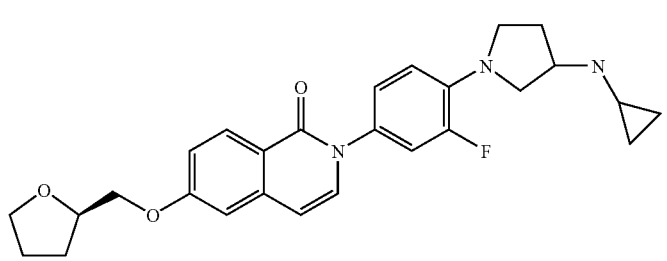 [SMILES: O=c1c2ccc(OC[C@H]3CCCO3)cc2ccn1-c1ccc(N2CCC(NC3CC3)C2)c(F)c1] | C27H30FN3O3 | 463.55 | 464 |
| 318 | 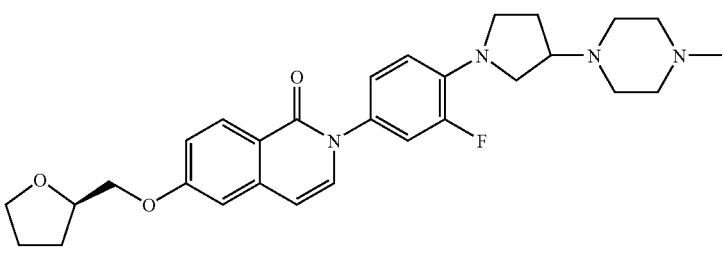 [SMILES: CN1CCN(C2CCN(c3ccc(-n4ccc5cc(OC[C@H]6CCCO6)ccc5c4=O)cc3F)C2)CC1] | C29H35FN4O3 | 506.62 | 507 |

TABLE 19-continued

| Ex. No. | Structure | Empirical formula | Molecular weight | ESI-MS [M + H]+ |
|---|---|---|---|---|
| 319 | 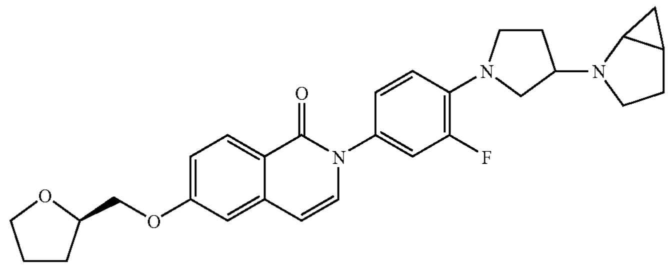 [SMILES: O=c1c2ccc(OC[C@H]3CCCO3)cc2ccn1-c1ccc(N2CCC(N3CCC4CC43)C2)c(F)c1] | C29H32FN3O3 | 489.59 | 490 |
| 320 | 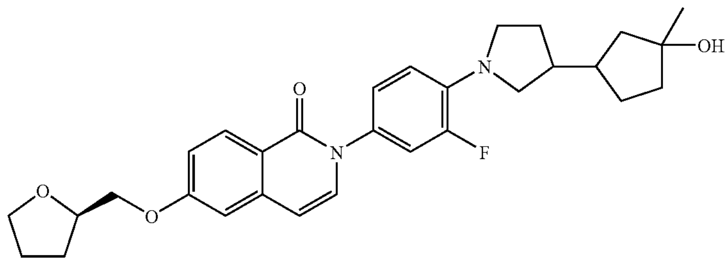 [SMILES: CC1(O)CCC(C2CCN(c3ccc(-n4ccc5cc(OC[C@H]6CCCO6)ccc5c4=O)cc3F)C2)C1] | C29H34FN3O4 | 507.61 | 508 |
| 321 | 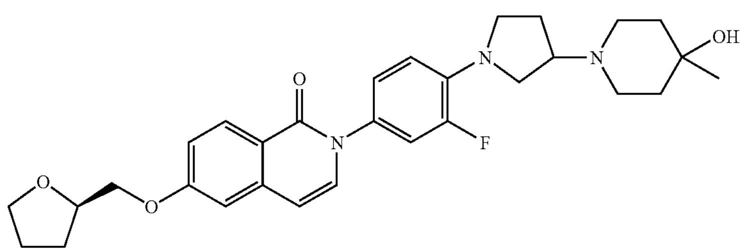 [SMILES: CC1(O)CCN(C2CCN(c3ccc(-n4ccc5cc(OC[C@H]6CCCO6)ccc5c4=O)cc3F)C2)CC1] | C30H36FN3O4 | 521.63 | 522 |

3-Methyl-pyrrolidin-3-ol

Method AI

A 1.6 M solution of methyllithium in diethyl ether (4.2 mL) was added dropwise at 0° C. to a solution of 1-benzyl-pyrrolidin-3-one (1 g) in THF (6.7 mL). The reaction mixture was allowed to return to room temperature and it was stirred for 2 h at this temperature. Then saturated ammonium chloride solution was added to the mixture and the aqueous phase was extracted three times with ethyl acetate. The organic phases were combined, dried over sodium sulfate and the solvent was removed in vacuum. The raw product was purified by preparative HPLC. 1-Benzyl-3-methyl-pyrrolidin-3-ol was hydrogenated in debenzylating conditions according to Method AH.

4-Methyl-piperidin-4-ol

1-Benzyl-piperidin-4-one was reacted with methyllithium according to Method AI and the 1-benzyl-4-methyl-piperidin-4-ol obtained was hydrogenated in debenzylating conditions according to Method AH. In this way the product was obtained with molecular weight 115.1 (C6H13NO); MS (ESI): 116 (M+H+).

Example 322

2-{3-Fluoro-4-[(R)-3-(2-hydroxy-2-methyl-propylamino)-pyrrolidin-1-yl]-phenyl}-6-[(R)-1-(tetrahydrofuran-2-yl)methoxy]-2H-isoquinolin-1-one

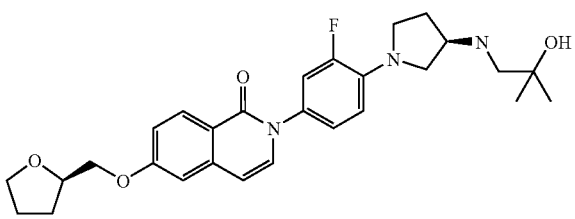 [SMILES: CC(C)(O)CN[C@@H]1CCN(c2ccc(-n3ccc4cc(OC[C@H]5CCCO5)ccc4c3=O)cc2F)C1]

Method AJ

A 2M solution of trimethylaluminum in toluene (0.213 mL) was added, at 0° C., to a mixture of 1-[(R)-1-(4-amino-2-fluorophenyl)-pyrrolidin-3-ylamino]-2-methyl-propan-2-ol (76 mg) and dichloromethane (2.1 mL), stirring for 15 min at 0° C. Then it was stirred for 30 min at room temperature and then a solution of 6-[(R)-1-(tetrahydrofuran-2-yl)methoxy]-

2-isochromen-1-one (70 mg) in methylene chloride (0.9 mL) was added. The reaction mixture was stirred for 3 h at room temperature, and as reaction was not complete, further trimethylaluminum solution (0.23 mL) was added. The reaction mixture was stirred overnight at room temperature. The mixture was cooled to 0° C. and saturated Rochelle salt solution was carefully added, and was stirred for 1 h at room temperature. Then the aqueous phase was extracted several times with methylene chloride. The organic phases were combined, dried over sodium sulfate and the solvent was removed in vacuum. The residue was dissolved in methanol and 4 M HCl solution in dioxane was added. This mixture was stirred for 1 h at room temperature and the solvent was removed in vacuum. The raw product was purified by preparative HPLC. In this way the product was obtained with molecular weight 495.25 (C28H34FN3O4); MS (ESI): 496 (M+H+).

1-[(R)-1-(4-Amino-2-fluorophenyl)-pyrrolidin-3-ylamino]-2-methyl-propan-2-ol

1-[(R)-1-(2-Fluoro-4-nitro-phenyl)-pyrrolidin-3-ylamino]-2-methyl-propan-2-ol was reduced according to Method F using Pd/C. In this way the product was obtained with molecular weight 267.17 (C14H22FN3O); MS (ESI): 268 (M+H+).

2-Methyl-1-[(R)-1-(2-methyl-4-nitro-phenyl)-pyrrolidin-3-ylamino]-propan-2-ol

LiBr (153.6 mg) and isobutylene oxide (85.1 mg) were added to a solution of (R)-1-(2-fluoro-4-nitro-phenyl)-pyrrolidin-3-ylamine (100 mg) in NMP (2 mL) and the reaction mixture was heated for 2 d at 80° C. Then ethyl acetate and water were added to the mixture. The aqueous phase was extracted several times with ethyl acetate. The organic phases were combined, dried over sodium sulfate and the solvent was removed in vacuum. The raw product was purified by preparative HPLC. In this way the product was obtained with molecular weight 297.15 (C14H20FN3O3); MS (ESI): 298 (M+H+).

(R)-1-(2-Fluoro-4-nitro-phenyl)-pyrrolidin-3-ylamine

[(R)-1-(2-Fluoro-4-nitro-phenyl)-pyrrolidin-3-yl]-carbamic acid tert-butyl ester was reacted according to Method H. In this way the product was obtained with molecular weight 225.09 (C10H12FN3O2); MS (ESI): 226 (M+H+).

6-[(R)-1-(Tetrahydrofuran-2-yl)methoxy]-2-isochromen-1-one

6-Hydroxy-2-isochromen-1-one was reacted with (R)-2-methanesulfonylmethyl-tetrahydrofuran according to Method K1. In this way the product was obtained with molecular weight 246.09 (C14H14O4); MS (ESI): 247 (M+H+).

6-Hydroxy-isochroman-1-one

Method L2

A 1M solution of boron tribromide in methylene chloride (101 mL) was added at 0° C. to a solution of 6-methoxy-isochromen-1-one (8.9 g) in methylene chloride (178 mL). Then the ice bath was removed and the reaction mixture was stirred overnight at room temperature. Then the mixture was cooled to 0° C., water was added and the aqueous phase was extracted several times with ethyl acetate. The organic phases were combined, dried over sodium sulfate and the solvent was removed in vacuum. In this way the product was obtained with molecular weight 162.03 (C9H6O3); MS (ESI): 163 (M+H+).

6-Methoxy-isochromen-1-one

A solution of 6-methoxy-isochroman-1-one (15.1 g), NBS (27 g) and benzoyl peroxide (500 mg) in tetrachloromethane (250 mL) was heated for 3 h under reflux, while irradiated with light. The mixture was filtered and the filtrate was concentrated. The residue was dissolved in triethylamine (100 mL) and stirred for 48 h at room temperature. The reaction mixture was distributed between water and ethyl acetate and was adjusted to pH 1 with concentrated hydrochloric acid. The organic phase was separated, dried over magnesium sulfate and concentrated. The residue was chromatographed on silica gel. In this way the product was obtained with molecular weight 176.17 (C10H8O3); MS (ESI): 177 (M+H+).

The compounds in Table 20 were synthesized similarly:

TABLE 20

| Ex. No. | Structure | Empirical formula | Molecular weight | ESI-MS [M + H]+ |
|---|---|---|---|---|
| 323 | 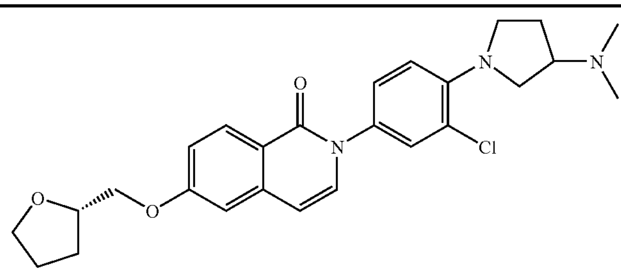 | C26H30ClN3O3 | 468.00 | 468 |
| 324 | 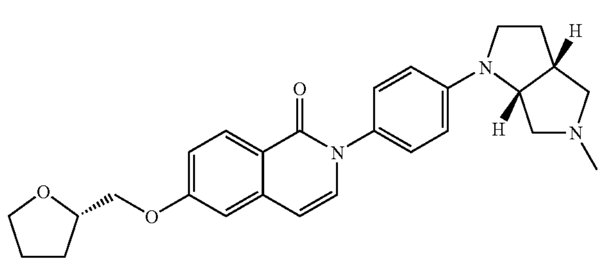 [SMILES: CN1C[C@H]2CCN(c3ccc(-n4ccc5cc(OC[C@@H]6CCCO6)ccc5c4=O)cc3)[C@H]2C1] | C27H31N3O3 | 445.57 | 446 |

TABLE 20-continued
| Ex. No. | Structure | Empirical formula | Molecular weight | ESI-MS [M + H]+ |
|---|---|---|---|---|
| 325 | 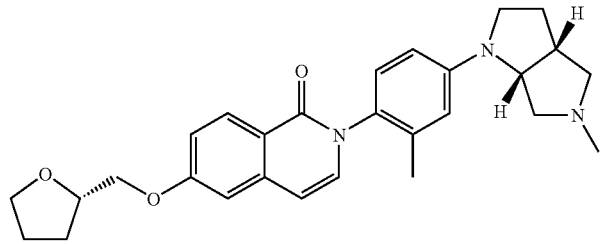 [SMILES: Cc1cc(N2CC[C@@H]3CN(C)C[C@@H]32)ccc1-n1ccc2cc(OC[C@@H]3CCCO3)ccc2c1=O] | C28H33N3O3 | 459.59 | 460 |
| 326 | 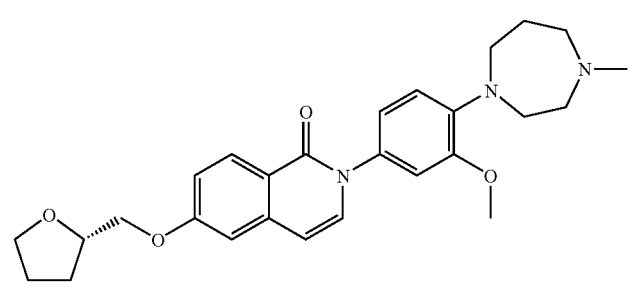 [SMILES: COc1cc(-n2ccc3cc(OC[C@@H]4CCCO4)ccc3c2=O)ccc1N1CCCN(C)CC1] | C27H33N3O4 | 463.58 | 464 |
| 327 | 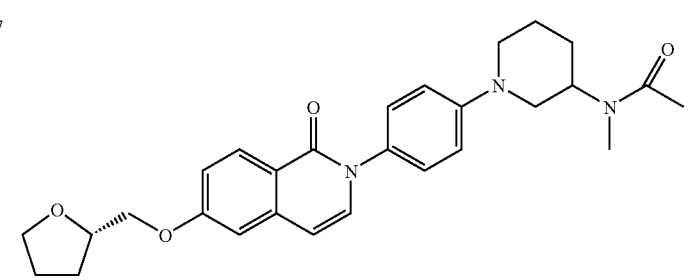 | C28H33N3O4 | 475.59 | 476 |
| 328 | 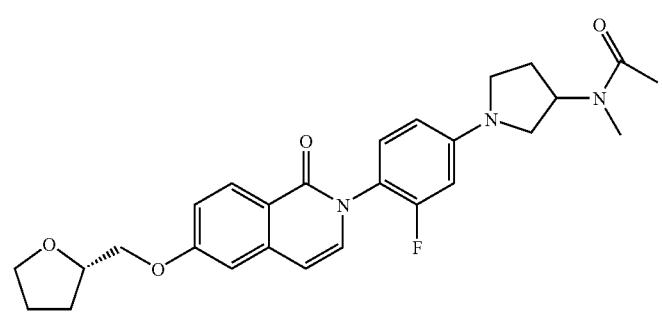 [SMILES: CC(=O)N(C)C1CCN(c2ccc(-n3ccc4cc(OC[C@@H]5CCCO5)ccc4c3=O)c(F)c2)C1] | C27H30FN3O4 | 479.56 | 480 |
| 329 | 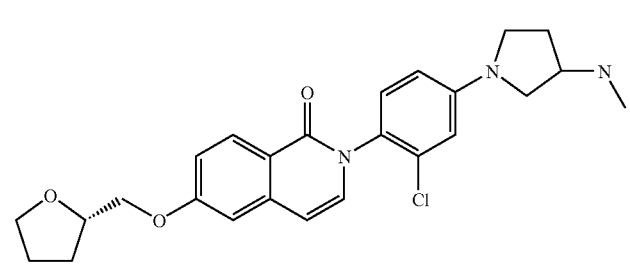 | C30H36ClN3O5 | 554.09 | 554 |

TABLE 20-continued
| Ex. No. | Structure | Empirical formula | Molecular weight | ESI-MS [M + H]+ |
|---|---|---|---|---|
| 330 | 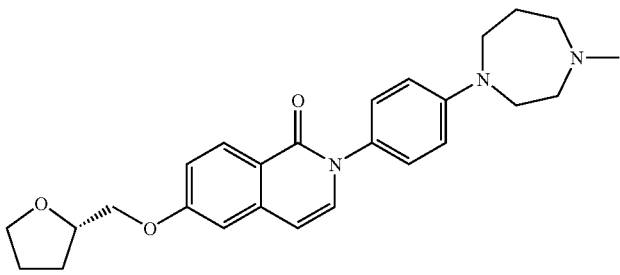 [SMILES: CN1CCCN(c2ccc(-n3ccc4cc(OC[C@@H]5CCCO5)ccc4c3=O)cc2)CC1] | C26H31N3O3 | 433.56 | 434 |
| 331 | 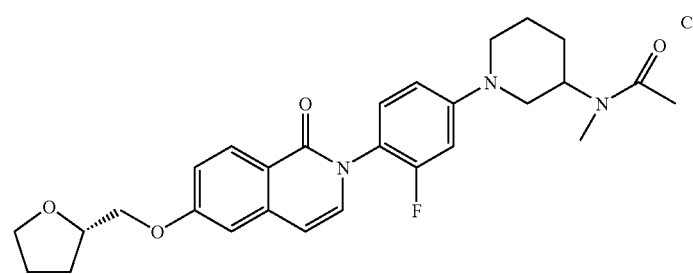 | C28H33FN3O4 | 493.58 | 494 |
| 332 | 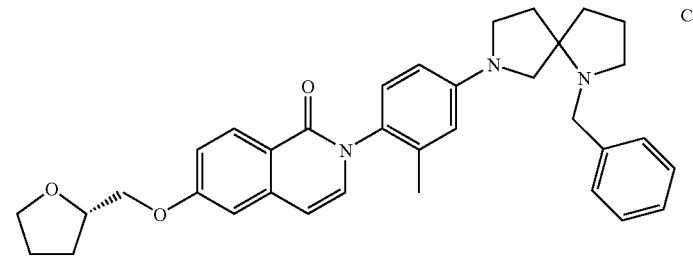 | C35H39N3O3 | 549.72 | 550 |
| 333 | 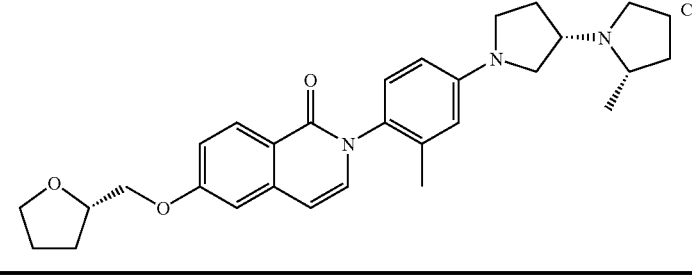 | C30H37N3O3 | 487.65 | 488 |

The anilines named below were prepared according to the methods E and F from the corresponding Fluoro-nitrobenzenes and amines:

2-Methyl-4-((3aR*,6aR*)-5-methyl-hexahydro-pyrrolo[3,4-b]pyrrol-1-yl)-phenylamine;

3-Methoxy-4-(4-methyl-[1,4]diazepan-1-yl)-phenylamine;
N-[1-(4-Amino-phenyl)-piperidin-3-yl]-N-methyl-acetamide;

N-[1-(4-Amino-3-fluoro-phenyl)-pyrrolidin-3-yl]-N-methyl-acetamide (2-Chloro-1,3-difluoro-4-nitro-benzene was employed as starting material);

[1-(4-Amino-3-chloro-phenyl)-pyrrolidin-3-yl]-methyl-carbamic acid tert-butyl ester;

N-[1-(4-Amino-3-fluoro-phenyl)-piperidin-3-yl]-N-methyl-acetamide (2-Chloro-1,3-difluoro-4-nitro-benzene was employed as starting material);

4-(1-Benzyl-1,7-diaza-spiro[4.4]non-7-yl)-2-methyl-phenylamine;

2-Methyl-4-((2S,3'S)-2-methyl-[1,3']bipyrrolidinyl-1'-yl)-phenylamine.

Example 334

6-((S)-2-Hydroxy-butoxy)-2-[3-methoxy-4-(4-methyl-[1,4]diazepan-1-yl)-phenyl]-2H-isoquinolin-1-one

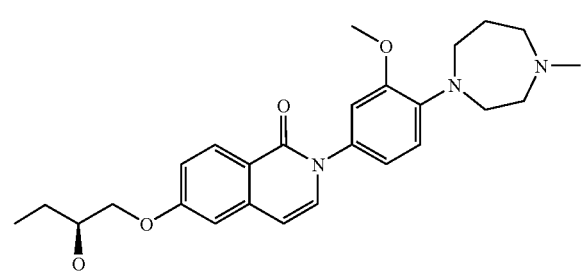 [SMILES: CC[C@H](O)COc1ccc2c(=O)n(-c3ccc(N4CCCN(C)CC4)c(OC)c3)ccc2c1]

6-((S)-2-Hydroxy-butoxy)-isochromen-1-one and 3-methoxy-4-(4-methyl-[1,4]diazepan-1-yl)-phenylamine were reacted according to Method AJ. In this way the product was obtained with molecular weight 451.57 (C22H33N3O4); MS (ESI): 452 (M+H+).

6-((S)-2-Hydroxy-butoxy)-isochromen-1-one

A mixture of 6-Hydroxy-isochromen-1-one (405 mg), (S)-(−)-1,2-epoxybutane (361 mg), cesium fluoride (1.1 g) and DMF (5 mL) was stirred for 4 h at 130° C. After adding water it was extracted with dichloromethane, dried over magnesium sulfate and concentrated. The residue was purified by preparative HPLC. In this way the product was obtained with molecular weight 234.25 (C13H14O4); MS (ESI): 235 (M+H+).

The following compound was synthesized similarly:

| Ex. No. | Structure | Empirical formula | Molecular weight | ESI-MS [M + H]+ |
|---|---|---|---|---|
| 335 | 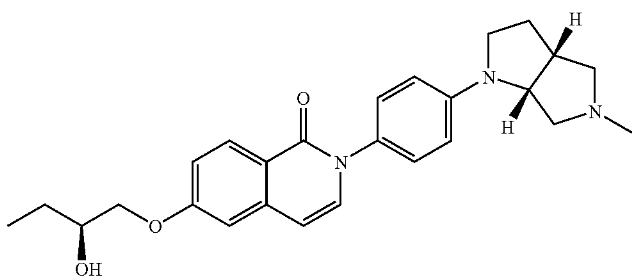 [SMILES: CC[C@H](O)COc1ccc2c(=O)n(-c3ccc(N4CC[C@@H]5CN(C)C[C@@H]54)cc3)ccc2c1] | C26H31N3O3 | 433.56 | 434 |

Example 336

2-[4-(3-Methylamino-piperidin-1-yl)-phenyl]-6-[(S)-1-(tetrahydrofuran-2-yl)methoxy]-2H-isoquinolin-1-one

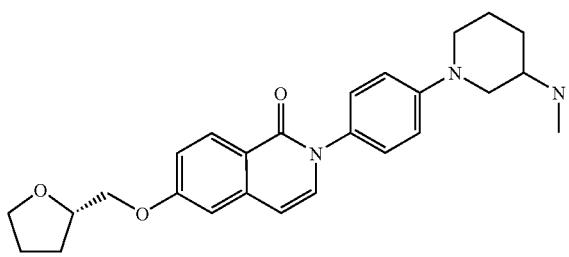 [SMILES: CNC1CCCN(c2ccc(-n3ccc4cc(OC[C@@H]5CCCO5)ccc4c3=O)cc2)C1]

A solution of N-methyl-N-[1-(4-{1-oxo-6-[(S)-1-(tetrahydrofuran-2-yl)methoxy]-1H-isoquinolin-2-yl}-phenyl)-piperidin-3-yl]-acetamide (552 mg) was stirred in 20% sulfuric acid (with methanol as solubilizing agent) for 16 h at 90° C. The mixture was neutralized with 2N NaOH, extracted with dichloromethane, dried over magnesium sulfate and concentrated. The residue was purified by preparative HPLC. In this way the product was obtained with molecular weight 433.56 (C26H31N3O3); MS (ESI): 434 (M+H+).

The following compound was synthesized similarly:

| Ex. No. | Structure | Empirical formula | Molecular weight | ESI-MS [M + H]+ |
|---|---|---|---|---|
| 337 | 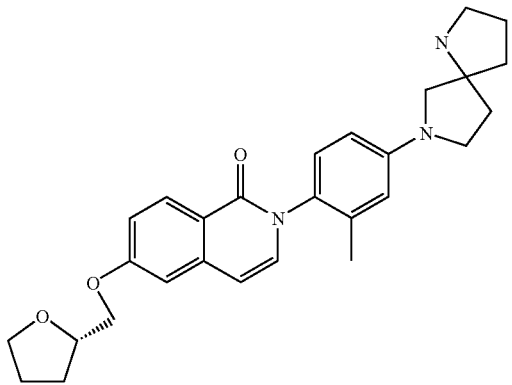 [SMILES: Cc1cc(N2CCC3(CCCN3)C2)ccc1-n1ccc2cc(OC[C@@H]3CCCO3)ccc2c1=O] | C25H28FN3O3 | 437.52 | 438 |

Example 338

2-[4-(1,7-Diaza-spiro[4.4]non-7-yl)-2-methyl-phenyl]-6-[(S)-1-(tetrahydrofuran-2-yl)methoxy]-3,4-dihydro-2H-isoquinolin-1-one

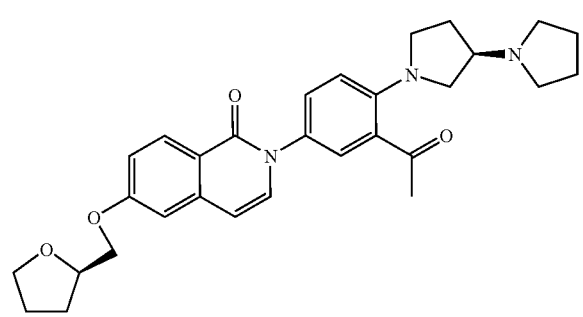 [SMILES: CC(=O)c1cc(-n2ccc3cc(OC[C@H]4CCCO4)ccc3c2=O)ccc1N1CC[C@@H](N2CCCC2)C1]

Method AH1

Palladium hydroxide on charcoal (20%; 14 mg) was added to a solution of 2-[4-(1-benzyl-1,7-diaza-spiro[4.4]non-7-yl)-2-methyl-phenyl]-6-[(S)-1-(tetrahydrofuran-2-yl)methoxy]-3,4-dihydro-2H-isoquinolin-1-one (105 mg) in ethanol (5 mL) and the mixture was hydrogenated in a hydrogen atmosphere for 16 h. The mixture was filtered and the filtrate was concentrated. The residue was purified by preparative HPLC. In this way the product was obtained with molecular weight 459.59 (C28H33N3O3); MS (ESI): 460 (M+H+).

Example 339

2-((R)-3-Acetyl-4-[1,3']bipyrrolidinyl-1'-yl-phenyl)-6-[(R)-1-(tetrahydrofuran-2-yl)methoxy]-2H-isoquinolin-1-one 6-[(R)-1-(Tetrahydrofuran-2-yl)methoxy]-isochromen-1-one and 1-((R)-5-amino-2-[1,3']bipyrrolidinyl-1'-yl-phenyl)-ethanone were reacted according to Method AJ. In this way the product was obtained with molecular weight 501.63 (C30H35N3O4); MS (ESI): 502 (M+H+).

1-((R)-5-Amino-2-[1,3']bipyrrolidinyl-1'-yl-phenyl)-ethanone

A solution of methyl magnesium bromide (1.4 M in THF, 1 mL) was added at room temperature to a solution of 5-amino-2-(R)-[1,3']bipyrrolidinyl-1'-yl-N-methoxy-N-methylbenzamide (100 mg) in THF (1 mL) and the mixture was stirred for 8 h at room temperature. After acidifying the reaction solution with 1N HCl it was washed with ethyl acetate and the aqueous phase was made basic with NaOH. The mixture was extracted with ethyl acetate, dried over magnesium sulfate and concentrated. In this way the product was obtained with molecular weight 237.38 (C16H23N3O); MS (ESI): 238 (M+H+).

5-Amino-2-(R)-[1,3']bipyrrolidinyl-1'-yl-N-methoxy-N-methyl-benzamide 2-(R)-[1,3']Bipyrrolidinyl-1'-yl-N-methoxy-N-methyl-5-nitro-benzamide was reduced with Pd/C according to Method F. In this way the product was obtained with molecular weight 318.42 (C17H26N4O2); MS (ESI): 319 (M+H+).

2-(R)-[1,3']Bipyrrolidinyl-1'-yl-N-methoxy-N-methyl-5-nitro-benzamide

2-Fluoro-N-methoxy-N-methyl-5-nitro-benzamide and (R)-[1,3']bipyrrolidinyl were reacted according to Method E1. In this way the product was obtained with molecular weight 348.41 (C17H24N4O4); MS (ESI): 349 (M+H+).

2-Fluoro-N-methoxy-N-methyl-5-nitro-benzamide

A mixture of 2-fluoro-5-nitro-benzoic acid (5 g) in thionyl chloride (6 mL) was heated under reflux for 2 h. The excess thionyl chloride was removed in vacuum and the residue was dissolved in dichloromethane (50 mL). N,O-Dimethylhydroxylamine (3.95 g) and triethylamine (8.2 g) were added successively at 0° C., stirring for 5 min. After adding water, the mixture was extracted with ether, washed with 1 N HCl, dried over magnesium sulfate and concentrated. In this way the product was obtained with molecular weight 228.18 (C9H9FN2O4); MS (ESI): 229 (M+H+).

Example 340

2-[4-(3-Amino-pyrrolidin-1-yl)-3-fluorophenyl]-6-[(R)-1-(tetrahydrofuran-2-yl)methoxy]-2H-isoquinolin-1-one

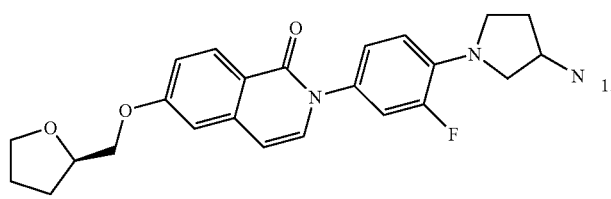

Method H2

A solution of [1-(2-fluoro-4-{1-oxo-6-[(R)-1-(tetrahydrofuran-2-yl)methoxy]-1H-isoquinolin-2-yl}-phenyl)-pyrrolidin-3-yl]-carbamic acid tert-butyl ester (26 mg) in dichloromethane/TFA 1:1 (2 mL) was stirred for 3 h at room temperature. The solvents were removed in vacuum. In this way the product was obtained with molecular weight 423.49 (C24H26FN3O3); MS (ESI): 424 (M+H+).

[1-(2-Fluoro-4-{1-oxo-6-[(R)-1-(tetrahydrofuran-2-yl)methoxy]-1H-isoquinolin-2-yl}-phenyl)-pyrrolidin-3-yl]-carbamic acid tert-butyl ester Method R1

A mixture of 2-(4-bromo-3-fluorophenyl)-6-[(R)-1-(tetrahydrofuran-2-yl)methoxy]-2H-isoquinolin-1-one (75 mg), palladium(II) acetate (3 mg), BINAP (14 mg), cesium carbonate (82 mg) and pyrrolidin-3-yl-carbamic acid tert-butyl ester (48 mg) in degassed toluene (2 mL) was stirred for 18 h at 100° C. The mixture was diluted with ethyl acetate, filtered and the filtrate was concentrated. The residue was purified by preparative HPLC. In this way the product was obtained with molecular weight 523.61 (C29H34FN3O5); MS (ESI): 524 (M+H+).

2-(4-Bromo-3-fluorophenyl)-6-[(R)-1-(tetrahydrofuran-2-yl)methoxy]-2H-isoquinolin-1-one 6-[(R)-1-(Tetrahydrofuran-2-yl)methoxy]-isochromen-1-one and 4-bromo-3-fluorophenylamine were reacted according to Method AJ. In this way the product was obtained with molecular weight 418.27 (C20H17BrFNO3); MS (ESI): 418 and 420 (M+H+).

The compounds in Table 21 were synthesized similarly:

TABLE 21

| Ex. No. | Structure | Empirical formula | Molecular weight | ESI-MS [M + H]+ |
|---|---|---|---|---|
| 341 | 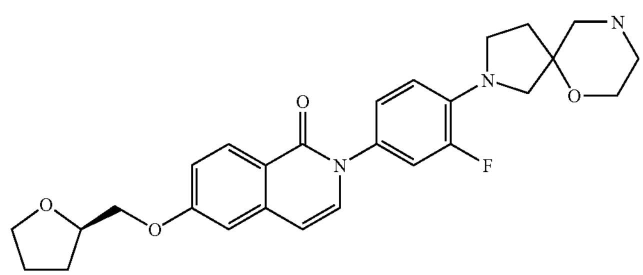 [SMILES: O=c1c2ccc(OC[C@H]3CCCO3)cc2ccn1-c1ccc(N2CCC3(CNCCO3)C2)c(F)c1] | C27H30FN3O4 | 479.56 | 480 |
| 342 | 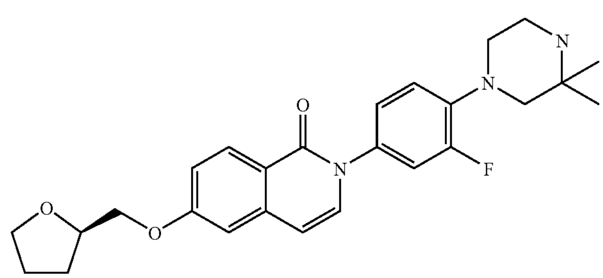 [SMILES: CC1(C)CN(c2ccc(-n3ccc4cc(OC[C@H]5CCCO5)ccc4c3=O)cc2F)CCN1] | C26H30FN3O3 | 451.55 | 452 |
| 343 | 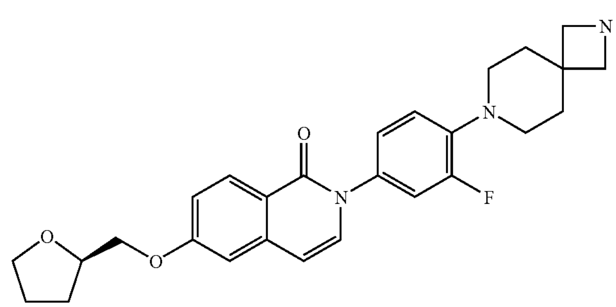 [SMILES: O=c1c2ccc(OC[C@H]3CCCO3)cc2ccn1-c1ccc(N2CCC3(CC2)CNC3)c(F)c1] | C27H30FN3O3 | 463.56 | 464 |

TABLE 21-continued

| Ex. No. | Structure | Empirical formula | Molecular weight | ESI-MS [M + H]+ |
|---|---|---|---|---|
| 344 | 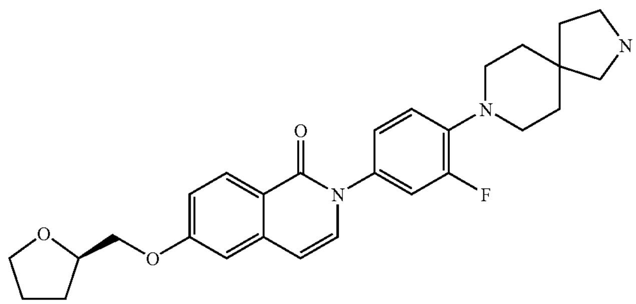 [SMILES: O=c1c2ccc(OC[C@H]3CCCO3)cc2ccn1-c1ccc(N2CCC3(CCNC3)CC2)c(F)c1] | C28H32FN3O3 | 477.58 | 478 |
| 345 | 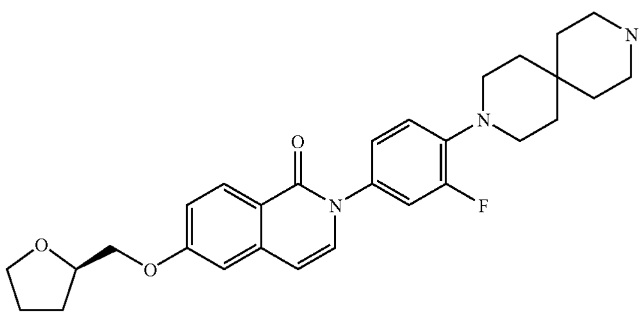 [SMILES: O=c1c2ccc(OC[C@H]3CCCO3)cc2ccn1-c1ccc(N2CCC3(CCNCC3)CC2)c(F)c1] | C29H34FN3O3 | 491.61 | 492 |
| 346 | 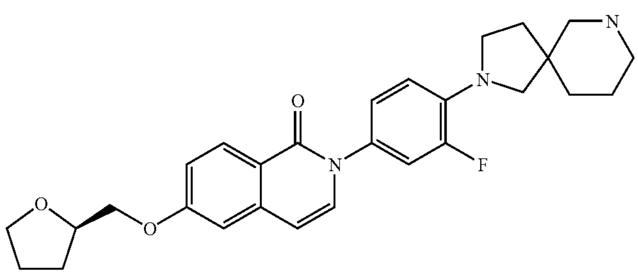 | C28H32FN3O3 | 477.58 | 478 |
| 347 | 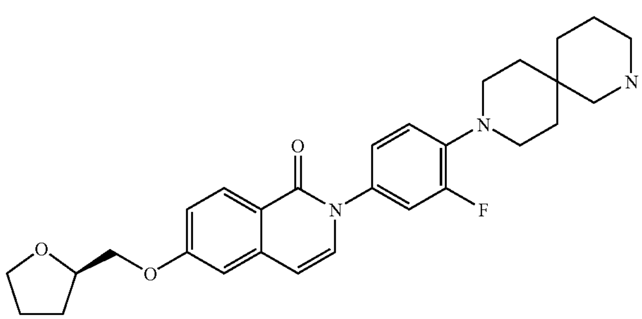 | C29H34FN3O3 | 491.61 | 492 |
| 348 | 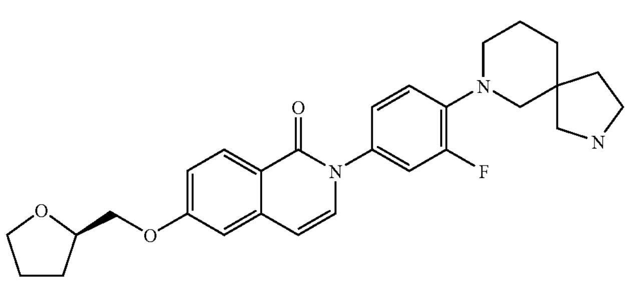 [SMILES: O=c1c2ccc(OC[C@H]3CCCO3)cc2ccn1-c1ccc(N2CCCC3(CCNC3)C2)c(F)c1] | C28H32FN3O3 | 477.58 | 478 |

TABLE 21-continued

| Ex. No. | Structure | Empirical formula | Molecular weight | ESI-MS [M + H]+ |
|---|---|---|---|---|
| 349 | 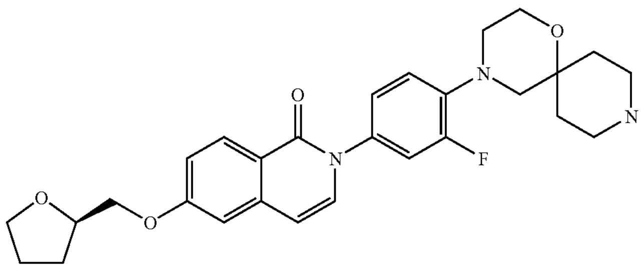 [SMILES: O=c1c2ccc(OC[C@H]3CCCO3)cc2ccn1-c1ccc(N2CCOC3(CCNCC3)C2)c(F)c1] | C28H32FN3O4 | 493.58 | 494 |
| 350 | 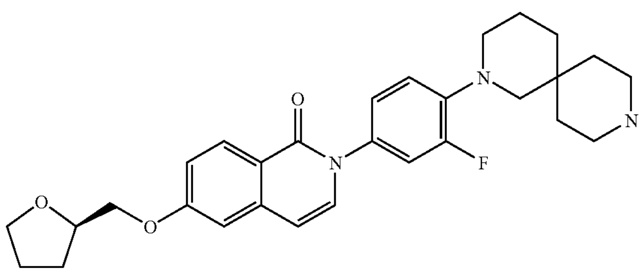 | C29H34FN3O3 | 491.61 | 492 |
| 351 | 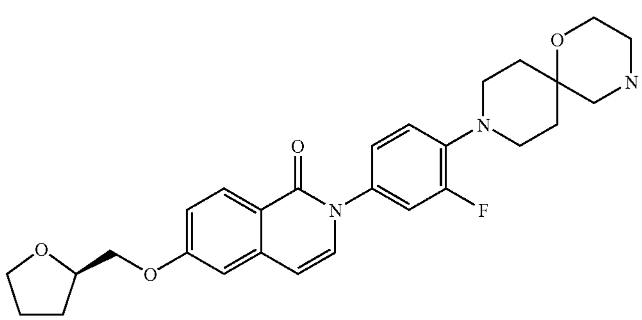 [SMILES: O=c1c2ccc(OC[C@H]3CCCO3)cc2ccn1-c1ccc(N2CCC3(CC2)CNCCO3)c(F)c1] | C28H32FN3O4 | 493.58 | 494 |
| 352 | 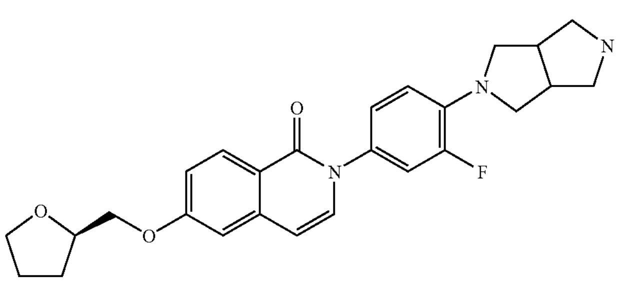 [SMILES: O=c1c2ccc(OC[C@H]3CCCO3)cc2ccn1-c1ccc(N2CC3CNCC3C2)c(F)c1] | C26H28FN3O3 | 449.53 | 450 |

Example 353

2-[4-((3R*,4R*)-3-Dimethylamino-4-methoxy-pyrrolidin-1-yl)-3-fluorophenyl]-6-[(R)-1-(tetrahydrofuran-2-yl)methoxy]-2H-isoquinolin-1-one

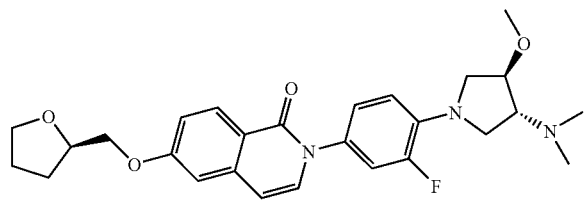 [SMILES: CO[C@@H]1CN(c2ccc(-n3ccc4cc(OC[C@H]5CCCO5)ccc4c3=O)cc2F)C[C@H]1N(C)C]

2-(4-Bromo-3-fluorophenyl)-6-[(R)-1-(tetrahydrofuran-2-yl)methoxy]-2H-isoquinolin-1-one and ((3R*,4R*)-4-methoxy-pyrrolidin-3yl)-dimethylamine were reacted according to Method R1. In this way the product was obtained with molecular weight 481.57 (C27H32FN3O4); MS (ESI): 482 (M+H+).

The compounds in Table 22 were synthesized similarly:

TABLE 22

| Ex. No. | Structure | Empirical formula | Molecular weight | ESI-MS [M + H]+ |
|---|---|---|---|---|
| 354 | 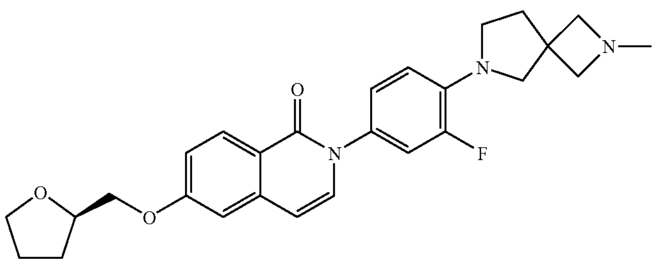 [SMILES: CN1CC2(CCN(c3ccc(-n4ccc5cc(OC[C@H]6CCCO6)ccc5c4=O)cc3F)C2)C1] | C27H30FN3O3 | 463.56 | 464 |
| 355 | 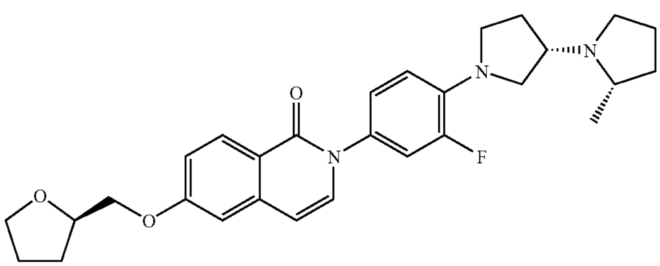 [SMILES: C[C@H]1CCCN1[C@H]1CCN(c2ccc(-n3ccc4cc(OC[C@H]5CCCO5)ccc4c3=O)cc2F)C1] | C29H34FN3O3 | 491.61 | 492 |

Example 356

2-[4-(3-Dimethylamino-3-methyl-pyrrolidin-1-yl)-3-fluorophenyl]-6-[(R)-1-(tetrahydrofuran-2-yl)methoxy]-2H-isoquinolin-1-one

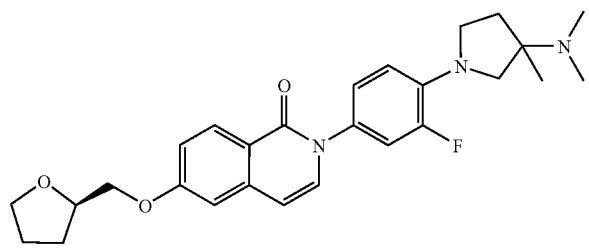 [SMILES: CN(C)C1(C)CCN(c2ccc(-n3ccc4cc(OC[C@H]5CCCO5)ccc4c3=O)cc2F)C1]

2-(4-Bromo-3-fluorophenyl)-6-[(R)-1-(tetrahydrofuran-2-yl)methoxy]-2H-isoquinolin-1-one and dimethyl-(3-methyl-pyrrolidin-3-yl)-amine were reacted according to Method R1. In this way the product was obtained with molecular weight 465.57 (C27H32FN3O3); MS (ESI): 466 (M+H+).

Dimethyl-(3-methyl-pyrrolidin-3-yl)-amine (1-Benzyl-3-methyl-pyrrolidin-3-yl)-dimethylamine was debenzylated according to Method AH1. In this way the product was obtained with molecular weight 128.22 (C7H16N2); MS (ESI): 129 (M+H+).

(1-Benzyl-3-methyl-pyrrolidin-3-yl)-dimethylamine

A solution of (1-benzyl-3-methyl-pyrrolidin-3-yl)-carbamic acid tert-butyl ester (682 mg) in aqueous formic acid/aqueous formaldehyde 1:2 (7 mL) was stirred at 90° C. for 4 h. The mixture was neutralized with sodium hydroxide solution, extracted with dichloromethane, dried over magnesium sulfate and concentrated. The residue was purified by preparative HPLC. In this way the product was obtained with molecular weight 218.34 (C14H22N2); MS (ESI): 219 (M+H+).

(1-Benzyl-3-methyl-pyrrolidin-3-yl)-carbamic acid tert-butyl ester

A solution of 1-benzyl-3-methyl-pyrrolidine-3-carboxylic acid (500 mg), triethylamine (231 mg) and diphenylphosphoryl azide (640 mg) in tert-butanol (15 mL) was stirred at 95° C. for 4 h. After adding water it was extracted with dichloromethane, dried over magnesium sulfate and concentrated. The residue was chromatographed on silica gel. In this way the product was obtained with molecular weight 290.41 (C17H26N2O2); MS (ESI): 291 (M+H+).

Example 357

2-[4-((S)-3-Dimethylamino-pyrrolidin-1-yl)-2-methyl-phenyl]-6-[(R)-1-(tetrahydrofuran-2-yl)methoxy]-2H-isoquinolin-1-one

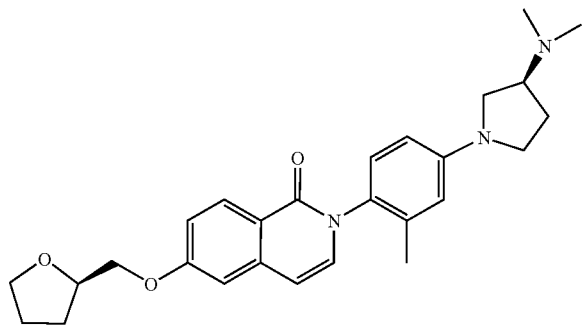 [SMILES: Cc1cc(N2CC[C@H](N(C)C)C2)ccc1-n1ccc2cc(OC[C@H]3CCCO3)ccc2c1=O]

Method AK

A solution of 3-hydroxy-6-[(R)-1-(tetrahydrofuran-2-yl)methoxy]-isochroman-1-one (50 mg) and [(S)-1-(4-amino-3-methyl-phenyl)-pyrrolidin-3-yl]-dimethylamine (62 mg) in NMP (1 mL) was heated at 200° C. for 15 min under microwave conditions. After adding water it was extracted with dichloromethane, dried over magnesium sulfate and concentrated. The residue was purified by preparative HPLC. In this way the product was obtained with molecular weight 447.58 (C27H33N3O3); MS (ESI): 448 (M+H+).

3-Hydroxy-6-[(R)-1-(tetrahydrofuran-2-yl)methoxy]-isochroman-1-one

A solution of periodic acid in water (0.5 M; 5.2 mL) was added at 0° C. to a solution of 2-hydroxy-5-[(R)-1-(tetrahydrofuran-2-yl)methoxy]-indan-1-one (581 mg) in water/THF 1:1 (12 mL) and the solution was stirred at 0° C. for 1 h. After adding water it was extracted with ether, dried over magnesium sulfate and concentrated. The residue was purified by preparative HPLC. In this way the product was obtained with molecular weight 264.28 (C14H16O5); MS (ESI): 265 (M+H+).

2-Hydroxy-5-[(R)-1-(tetrahydrofuran-2-yl)methoxy]-indan-1-one

A mixture of acetic acid 1-oxo-5-[(R)-1-(tetrahydrofuran-2-yl)methoxy]-indan-2-yl ester (1.02 g) and potassium carbonate (264 mg) in methanol (1 mL) was stirred at room temperature for 1 h. After adding water it was extracted with dichloromethane, dried over magnesium sulfate and concentrated. In this way the product was obtained with molecular weight 248.28 (C14H16O4); MS (ESI): 249 (M+H+).

Acetic acid 1-oxo-5-[(R)-1-(tetrahydrofuran-2-yl)methoxy]-indan-2-yl ester

A mixture of 5-[(R)-1-(tetrahydrofuran-2-yl)methoxy]-indan-1-one (1.25 g), acetic anhydride (3 mL), lead acetate (3.58 g) and acetic acid (3 mL) was stirred for 48 h at 100° C. After adding sodium carbonate solution it was extracted with ether, dried over magnesium sulfate and concentrated. The residue was chromatographed on silica gel. In this way the product was obtained with molecular weight 290.32 (C16H18O5); MS (ESI): 291 (M+H+).

5-[(R)-1-(Tetrahydrofuran-2-yl)methoxy]-indan-1-one

A solution of 5-hydroxyindanone (80 mg) and methanesulfonic acid (R)-1-(tetrahydrofuran-2-yl)methyl ester (107 mg) in DMF (1 mL) was stirred at 70° C. for 16 h. After adding water it was extracted with ether, dried over magnesium sulfate and concentrated. The residue was chromatographed on silica gel. In this way the product was obtained with molecular weight 232.28 (C14H16O3); MS (ESI): 233 (M+H+).

Example 358

2-Cyclopropylethynyl-6-[4-((R)-3-dimethylamino-pyrrolidin-1-yl)-phenyl]-5,6-dihydro-4H-thieno[2,3-c]pyridin-7-one

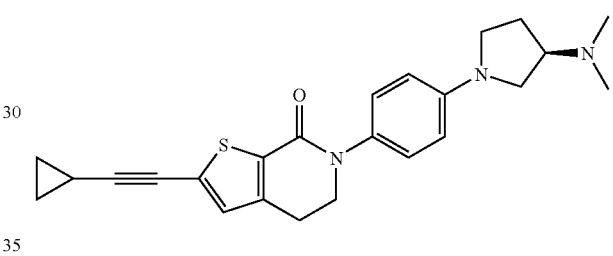

Method AL

A solution Ethynyl-cyclopropane (39.3 mg) and Morpholine (517.9 mg) in dioxane/water (0.69 mL/0.016 mL) was added to 2-Bromo-6-[4-((R)-3-dimethylamino-pyrrolidin-1-yl)-phenyl]-5,6-dihydro-4H-thieno[2,3-c]pyridin-7-one (50 mg), Bis(tri-tert.-butylphosphine) palladium (6.1 mg) and copper iodide (2.3 mg) which were provided in a heated argon flushed flask. The reaction mixture was stirred over night at room temperature. The solvent was removed and the residue taken into ethyl acetate and water. The aqueous phase was extracted three times with ethyl acetate. The combined organic phases were dried over sodium sulfate and concentrated. The crude product was purified by preparative HPLC. In this way the product was obtained with molecular weight 405.56 (C24H27N3OS); MS (ESI): 406 (M+H+).

2-Bromo-6-[4-((R)-3-dimethylamino-pyrrolidin-1-yl)-phenyl]-5,6-dihydro-4H-thieno[2,3-c]pyridin-7-one NaH (60% in oil; 175.4 mg) was added in small portions to a solution of 5-Bromo-3-(2-chloro-ethyl)-thiophene-2-carboxylic acid [4-((R)-3-dimethylamino-pyrrolidin-1-yl)-phenyl]-amide (612.2 mg) in THF (3.1 mL) at 0° C. The mixture was warmed to room temperature and stirred over night. Water and ethyl acetate was added to the mixture. The aqueous phase was extracted with ethyl acetate three times. The combined organic phases were dried over sodium sulfate and the solvent was removed in vacuum. In this way the product

5-Bromo-3-(2-chloro-ethyl)-thiophene-2-carboxylic acid [4-((R)-3-dimethylamino-pyrrolidin-1-yl)-phenyl]-amide To a mixture of [(R)-1-(4-Amino-phenyl)-pyrrolidin-3-yl]-dimethyl-amine (349 mg) and triethylamine (0.25 mL) in THF (4 mL) a solution of 5-Bromo-3-(2-chloro-ethyl)-thiophene-2-carbonyl chloride (489.6 mg) in THF (3 mL) added dropwise. The mixture was stirred for 2 h at room temperature. Then the solvent was removed in vacuum and then water and ethyl acetate were added to the residue. The aqueous phase was extracted with ethyl acetate three times. The combined organic phases were dried over sodium sulfate and the solvent was removed in vacuum. In this way the product was obtained with molecular weight 456.84 (C19H23BrClN3OS); MS (ESI): 456, 458 (M+H+).

5-Bromo-3-(2-chloro-ethyl)-thiophene-2-carbonyl chloride

A mixture of 2-Bromo-4,5-dihydro-thieno[2,3-c]pyran-7-one (400 mg), Lithium hydroxide (246.7 mg) in THF/water/methanol (1.7 mL/1.7 mL/0.2 mL) was stirred for 6 h at room temperature. Then the reaction mixture was acidified with 2 N HCl and the aqueous phase was extracted with ethyl acetate, dried over sodium sulfate and the solvent removed. The obtained crude product was heated to reflux with thionylchloride (6.2 mL) for 2 h. Toluene was added and the volatile components removed in vacuum. This step was repeated twice.

2-Bromo-4,5-dihydro-thieno[2,3-c]pyran-7-one

To a solution of 2-Trimethylsilanyl-4,5-dihydro-thieno[2,3-c]pyran-7-one (1.1 g) in DMF (23.4 mL) N-bromosuccinimide (2.6 g) was added in portions. The mixture was heated to 60° C. for 14 h. Then water and ethyl acetate were added to the mixture. The aqueous phase was extracted with ethyl acetate three times. The combined organic phases were dried over sodium sulfate and the solvent was removed in vacuum. In this way the product was obtained with molecular weight 233.08 (C7H5BrO2S); MS (ESI): 232, 234 (M+H+).

2-Trimethylsilanyl-4,5-dihydro-thieno[2,3-c]pyran-7-one

A mixture of 3-(2-Hydroxy-ethyl)-5-trimethylsilanyl-thiophene-2-carboxylic acid (4.1 g) and p-Toluenesulfonic acid (577.9 mg) in toluene (100 mL) was heated to 10° C. for 6 h. The solvent was removed in vacuum and the residue taken up in water and ethyl acetate. The aqueous phase was extracted with ethyl acetate three times. The combined organic phases were dried over sodium sulfate and the solvent was removed in vacuum. In this way the product was obtained with molecular weight 226.37 (C10H14O2SSi); MS (ESI): 227 (M+H+).

3-(2-Hydroxy-ethyl)-5-trimethylsilanyl-thiophene-2-carboxylic acid

Diisopropylamine (9.4 g) was added to a solution of n-Butyllithium (1.6 M in hexane, 43.7 mL) in THF (67 mL) at −78° C. The mixture was stirred for 10 min at 0° C. and then cooled to −78° C. and a solution of 3-Methyl-5-trimethylsilanyl-thiophene-2-carboxylic acid (5.0 g) in THF (40 mL) was added. The mixture was stirred at −78° C. for 30 min and then paraformaldehyde (3.2 g) was added. After warming to room temperature water and ethyl acetate were added. The aqueous phase was slightly acidified with HCl (10%) and then extracted three time with ethyl acetate. The combined organic phases were dried over sodium sulfate and the solvent was removed in vacuum. The raw product was purified by preparative HPLC. In this way the product was obtained with molecular weight 244.39 (C10H16O3SSi); MS (ESI): 245 (M+H+).

3-Methyl-5-trimethylsilanyl-thiophene-2-carboxylic acid

Diisopropylamine (3.1 g) was added to a solution of n-Butyllithium (1.6 M in hexane; 19.3 mL) in THF (69 mL) at −78° C. The mixture was stirred for 10 min at 0° C. and then cooled to −78° C. and a solution of 3-Methyl-thiophene-2-carboxylic acid (2.0 g) in THF (40 mL) was added. The mixture was stirred at −78° C. for 30 min and then Trimethylsilylchloride (1.5 g) was added. The mixture was stirred for 1 h at −78° C. After warming to room temperature water and ethyl acetate were added. The aqueous phase was neutralized with HCl (10%) and then extracted three time with ethyl acetate. The combined organic phases were dried over sodium sulfate and the solvent was removed in vacuum. The raw product was purified by preparative HPLC. In this way the product was obtained with molecular weight 214.36 (C9H14O2SSi); MS (ESI): 215 (M+H+).

The products that were prepared by method AL from 2-Bromo-6-[4-((R)-3-dimethylamino-pyrrolidin-1-yl)-phenyl]-5,6-dihydro-4H-thieno[2,3-c]pyridin-7-one and the corresponding alkynes are presented in table 23.

TABLE 23

| Ex. No. | Structure | Empirical formula | Molecular weight | ESI-MS [M + H]+ |
|---|---|---|---|---|
| 359 | 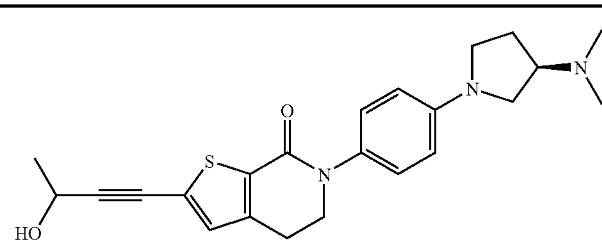 | C23H27N3O2S | 409.56 | 410 |

TABLE 23-continued

| Ex. No. | Structure | Empirical formula | Molecular weight | ESI-MS [M + H]+ |
|---|---|---|---|---|
| 360 | 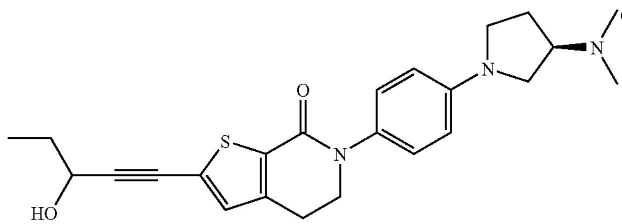 [SMILES: CCC(O)C#Cc1cc2c(s1)C(=O)N(c1ccc(N3CC[C@@H](N(C)C)C3)cc1)CC2] | C24H29N3O2S | 423.58 | 424 |
| 361 | 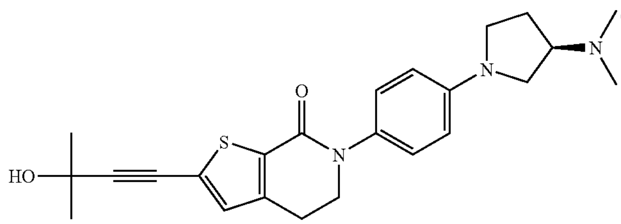 [SMILES: CN(C)[C@@H]1CCN(c2ccc(N3CCc4cc(C#CC(C)(C)O)sc4C3=O)cc2)C1] | C24H29N3O2S | 423.58 | 424 |
| 362 | 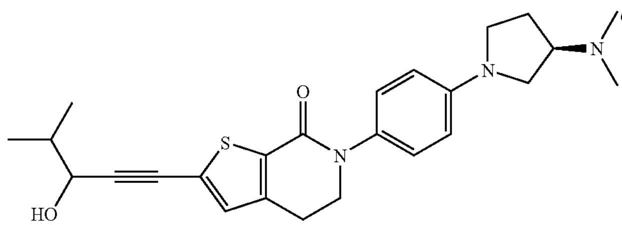 [SMILES: CC(C)C(O)C#Cc1cc2c(s1)C(=O)N(c1ccc(N3CC[C@@H](N(C)C)C3)cc1)CC2] | C25H31N3O2S | 437.61 | 438 |
| 363 | 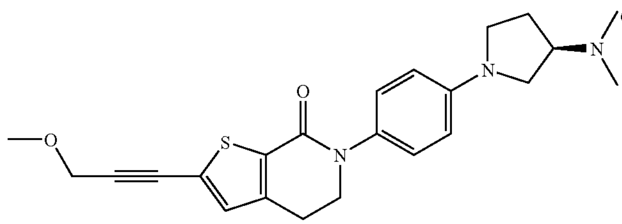 | C23H27N3O2S | 409.56 | 410 |

Example 364

2-{3-Fluoro-4-[(R)-3-(3-methoxy-propylamino)-pyrrolidin-1-yl]-phenyl}-6-[(S)-1-(tetrahydro-furan-2-yl)methoxy]-3,4-dihydro-2H-isoquinolin-1-one

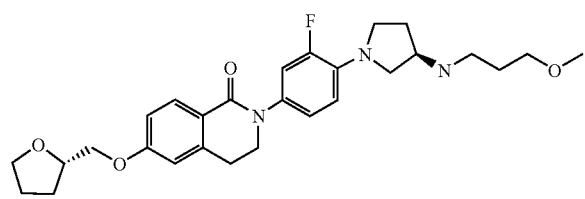 [SMILES: COCCCN[C@@H]1CCN(c2ccc(N3CCc4cc(OC[C@@H]5CCCO5)ccc4C3=O)cc2F)C1]

2-[4-((R)-3-Amino-pyrrolidin-1-yl)-3-fluoro-phenyl]-6-[(S)-1-(tetrahydro-furan-2-yl)methoxy]-3,4-dihydro-2H-isoquinolin-1-one was reacted with 1-Bromo-3-methoxypropane by method X. The product with the molecular weight of 497.62 (C28H36FN3O4) was obtained in this way; MS (ESI): 498 (M+H+).

2-[4-((R)-3-Amino-pyrrolidin-1-yl)-3-fluoro-phenyl]-6-[(S)-1-(tetrahydro-furan-2-yl)methoxy]-3,4-dihydro-2H-isoquinolin-1-one

[(R)-1-(2-Fluoro-4-{1-oxo-6-[(S)-1-(tetrahydro-furan-2-yl)methoxy]-3,4-dihydro-1H-isoquinolin-2-yl}-phenyl)-pyrrolidin-3-yl]-carbamic acid tert-butyl ester was deprotected by method H. The product with the molecular weight of 425.51 (C24H28FN3O3) was obtained in this way; MS (ESI): 426 (M+H+).

[(R)-1-(2-Fluoro-4-{1-oxo-6-[(S)-1-(tetrahydro-furan-2-yl)methoxy]-3,4-dihydro-1H-isoquinolin-2-yl}-phenyl)-pyrrolidin-3-yl]-carbamic acid tert-butyl ester

[(R)-1-(4-Amino-2-fluoro-phenyl)-pyrrolidin-3-yl]-carbamic acid tert-butyl ester was reacted with 6-[(S)-1-(Tetrahydro-furan-2-yl)methoxy]-isochroman-1-one by method AC. The product with the molecular weight of 525.63 (C29H36FN3O5) was obtained in this way; MS (ESI): 526 (M+H+).

[(R)-1-(4-Amino-2-fluoro-phenyl)-pyrrolidin-3-yl]-carbamic acid tert-butyl ester

[(R)-1-(2-Fluoro-4-nitro-phenyl)-pyrrolidin-3-yl]-carbamic acid tert-butyl ester was hydrogenated by method AH. The product with the molecular weight of 295.36 (C15H22FN3O2) was obtained in this way; MS (ESI): 296 (M+H+).

6-[(S)-1-(Tetrahydro-furan-2-yl)methoxy]-isochroman-1-one

6-Hydroxy-isochroman-1-one was reacted with Methanesulfonic acid (S)-1-(tetrahydro-furan-2-yl)methyl ester by method K1. The product with the molecular weight of 248.28 (C14H28FN3O3) was obtained in this way; MS (ESI): 249 (M+H+).

6-Hydroxy-isochroman-1-one

6-Methoxy-isochroman-1-one was deprotected by method L2. The product with the molecular weight of 164.16 (C9H8O3) was obtained in this way; MS (ESI): 165 (M+H+).

Example 365

2-{3-Fluoro-4-[(R)-3-(tetrahydro-pyran-4-ylamino)-pyrrolidin-1-yl]-phenyl}-6-[(S)-1-(tetrahydro-furan-2-yl)methoxy]-3,4-dihydro-2H-isoquinolin-1-one

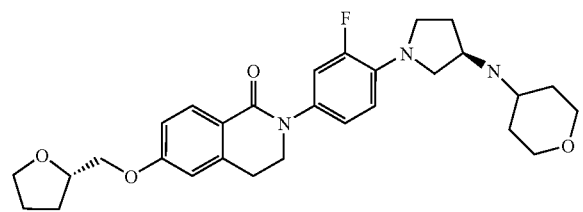 [SMILES: O=C1c2ccc(OC[C@@H]3CCCO3)cc2CCN1c1ccc(N2CC[C@@H](NC3CCOCC3)C2)c(F)c1]

2-[4-((R)-3-Amino-pyrrolidin-1-yl)-3-fluoro-phenyl]-6-[(S)-1-(tetrahydro-furan-2-yl)methoxy]-3,4-dihydro-2H-isoquinolin-1-one was reacted with Tedrahydro-pyran-4-one by method J1. The product with the molecular weight of 509.63 (C29H36FN3O4) was obtained in this way; MS (ESI): 510 (M+H+).

Example 366

2-{3-Fluoro-4-[(R)-3-(4-hydroxy-4-methyl-piperidin-1-yl)-pyrrolidin-1-yl]-phenyl}-6-[(S)-1-(tetrahydro-furan-2-yl)methoxy]-3,4-dihydro-2H-isoquinolin-1-one

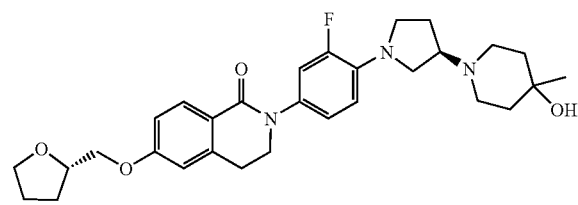 [SMILES: CC1(O)CCN([C@@H]2CCN(c3ccc(N4CCc5cc(OC[C@@H]6CCCO6)ccc5C4=O)cc3F)C2)CC1]

1-[(R)-1-(4-Amino-2-fluoro-phenyl)-pyrrolidin-3-yl]-4-methyl-piperidin-4-ol was reacted with 6-[(S)-1-(Tetrahydro-furan-2-yl)methoxy]-isochroman-1-one by method AC. The product with the molecular weight of 523.65 (C30H38FN3O4) was obtained in this way; MS (ESI): 524 (M+H+).

1-[(R)-1-(4-Amino-2-fluoro-phenyl)-pyrrolidin-3-yl]-4-methyl-piperidin-4-ol

1-[(R)-1-(2-Fluoro-4-nitro-phenyl)-pyrrolidin-3-yl]-4-methyl-piperidin-4-ol was reduced by method AH. The product with the molecular weight of 293.39 (C16H24FN3O) was obtained in this way; MS (ESI): 294 (M+H+).

1-[(R)-1-(2-Fluoro-4-nitro-phenyl)-pyrrolidin-3-yl]-4-methyl-piperidin-4-ol

4-Methyl-1-(R)-pyrrolidin-3-yl-piperidin-4-ol was reacted with 3,4-Dinitrofluorobenzene by method E1. The product with the molecular weight of 323.37 (C16H22FN3O3) was obtained in this way; MS (ESI): 324 (M+H+).

4-Methyl-1-(R)-pyrrolidin-3-yl-piperidin-4-ol (R)-3-(4-Hydroxy-4-methyl-piperidin-1-yl)-pyrrolidine-1-carboxylic acid tert-butyl ester was deprotected by method H. The product with the molecular weight of 184.28 (C10H20N2O) was obtained in this way; MS (ESI): 185 (M+H+).

(R)-3-(4-Hydroxy-4-methyl-piperidin-1-yl)-pyrrolidine-1-carboxylic acid tert-butyl ester To a mixture of 4-Methyl-piperidin-4-ol (2.2 g) and (S)-3-(Toluene-4-sulfonyloxy)-pyrrolidine-1-carboxylic acid tert-butyl ester (5.0 g) in acetonitrile (54 mL)/NMP (30 mL)/DMF (5 mL) was added potassium carbonate (9.2 g). The mixture was stirred at 80° C. for 12 h. Ethyl acetate and water was added. The aqueous phase was acidified, extracted with ethyl acetate. The collected organic phase were washed with water, dried over sodium sulfate and concentrated. The product with the molecular weight of 284.40 (C15H28N2O3) was obtained in this way; MS (ESI): 285 (M+H+).

(S)-3-(Toluene-4-sulfonyloxy)-pyrrolidine-1-carboxylic acid tert-butyl ester To a mixture of p-toluenesulfonyl chloride (10.0 g) in dry methylene chloride (40 mL) was added at 0° C. a solution of (S)-3-Hydroxy-pyrrolidine-1-carboxylic acid tert-butyl ester (2.8 g) in dry methylene chloride (15 mL). DMAP (1.1 g) and triethylamine (6.1 g) was added. The mixture was stirred at 0° C. for 3 h. The reaction mixture was then allowed to reach room temperature and stirred for 12 h. The mixture was acidified with 1 N HCl. The organic layer was washed two times with 1 N HCl, one time with saturated sodium hydrogen carbonate solution and one time with brine. The organic layers were dried over sodium sulfate and concentrated. The product with the molecular weight of 341.43 (C16H23NO5S) was obtained in this way; MS (ESI): 342 (M+H+).

Example 367

2-{4-[4-(3-Fluoro-propyl)-[1,4]diazepan-1-yl]-3-methoxy-phenyl}-6-[(S)-1-(tetrahydro-furan-2-yl)methoxy]-2H-isoquinolin-1-one

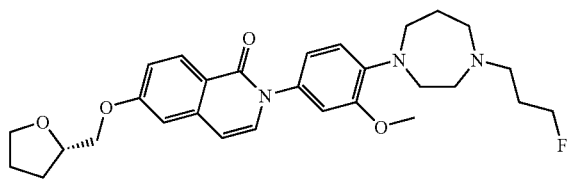 [SMILES: COc1cc(-n2ccc3cc(OC[C@@H]4CCCO4)ccc3c2=O)ccc1N1CCCN(CCCF)CC1]

To a solution of 2-(4-[1,4]Diazepan-1-yl-3-methoxy-phenyl)-6-[(S)-1-(tetrahydro-furan-2-yl)methoxy]-2H-isoquinolin-1-one (50 mg) and 1-Bromo-3-fluoro-propane (18 mg) in DMF (1 mL) was added cesium carbonate (54 mg) and the mixture was stirred overnight. The crude mixture was purified by preparative HPLC. The product with the molecular weight of 509.63 (C29H36FN3O4) was obtained in this way; MS (ESI): 510 (M+H+).

2-(4-[1,4]Diazepan-1-yl-3-methoxy-phenyl)-6-[(S)-1-(tetrahydro-furan-2-yl)methoxy]-2H-isoquinolin-1-one Reaction of 4-(2-Methoxy-4-{1-oxo-6-[(S)-1-(tetrahydro-furan-2-yl)methoxy]-1H-isoquinolin-2-yl}-phenyl)-[1,4]diazepane-1-carboxylic acid tert-butyl ester with trifluoroacetic acid by method H2 resulted in the desired product with the molecular weight of 449.55 (C26H31N3O4); MS (ESI): 450 (M+H+).

4-(2-Methoxy-4-{1-oxo-6-[(S)-1-(tetrahydro-furan-2-yl)methoxy]-1H-isoquinolin-2-yl}-phenyl)-[1,4]diazepane-1-carboxylic acid tert-butyl ester Reaction of 6-[(S)-1-(Tetrahydro-furan-2-yl)methoxy]-isochromen-1-one with 4-(4-Amino-2-methoxy-phenyl)-[1,4]diazepane-1-carboxylic acid tert-butyl ester by method AJ resulted in the desired product with the molecular weight of 549.67 (C31H39N3O6); MS (ESI): 550 (M+H+).

The compounds in table 24 were obtained analogously.

TABLE 24

| Ex. No. | Structure | Empirical formula | Molecular weight | ESI-MS [M + H]+ |
|---|---|---|---|---|
| 368 | 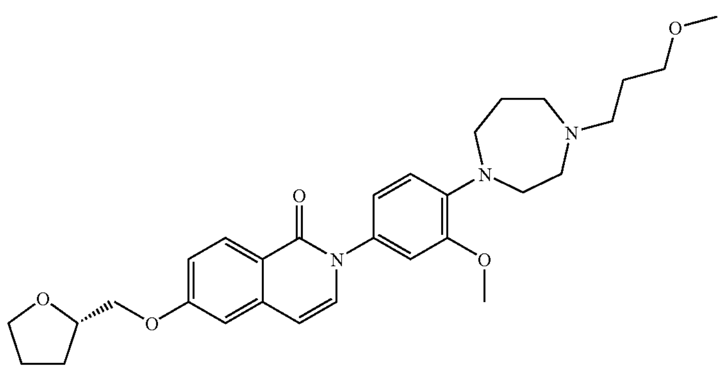 [SMILES: COCCCN1CCCN(c2ccc(-n3ccc4cc(OC[C@@H]5CCCO5)ccc4c3=O)cc2OC)CC1] | C30H39N3O5 | 521.66 | 522 |
| 369 | 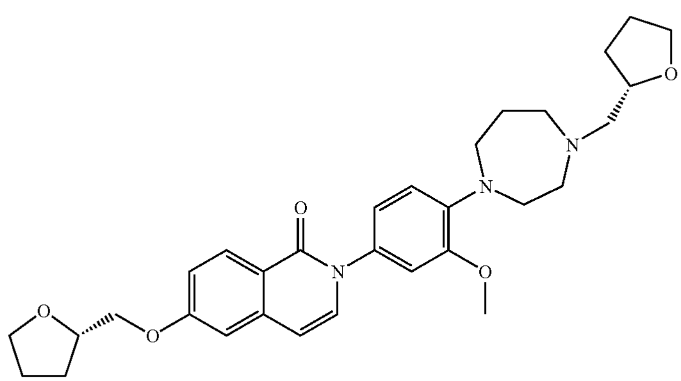 [SMILES: COc1cc(-n2ccc3cc(OC[C@@H]4CCCO4)ccc3c2=O)ccc1N1CCCN(C[C@@H]2CCCO2)CC1] | C31H39FN3O5 | 533.67 | 534 |

Example 370

4-(2-Methoxy-4-{1-oxo-6-[(S)-1-(tetrahydro-furan-2-yl)methoxy]-1H-isoquinolin-2-yl}-phenyl)-[1,4]diazepane-1-carboxylic acid 3-fluoro-propyl ester

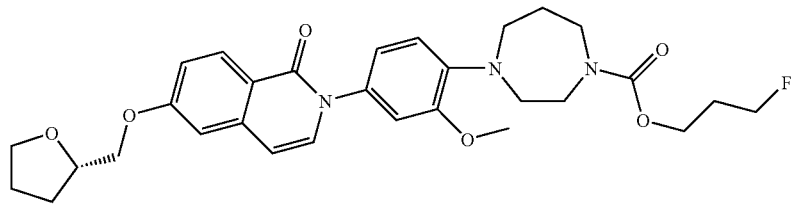 [SMILES: COc1cc(-n2ccc3cc(OC[C@@H]4CCCO4)ccc3c2=O)ccc1N1CCCN(C(=O)OCCCF)CC1]

To a solution of 2-(4-[1,4]Diazepan-1-yl-3-methoxy-phenyl)-6-[(S)-1-(tetrahydro-furan-2-yl)methoxy]-2H-isoquinolin-1-one (50 mg) and 1-Bromo-3-fluoro-propane (18 mg) in DMF (1 mL) was added cesium carbonate (54 mg) and the mixture was stirred overnight. The crude mixture was purified by preparative HPLC. The product with the molecular weight of 553.64 (C30H36FN3O6) was obtained in this way; MS (ESI): 554 (M+H+).

Example 371

2-{3-Methoxy-4-[4-(tetrahydro-pyran-4-yl)-[1,4]diazepan-1-yl]-phenyl}-6-[(S)-1-(tetrahydro-furan-2-yl)methoxy]-2H-isoquinolin-1-one

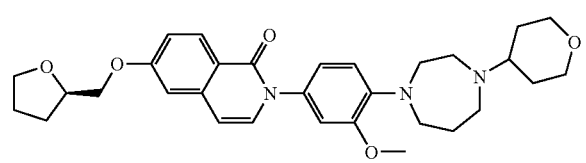 [SMILES: COc1cc(-n2ccc3cc(OC[C@H]4CCCO4)ccc3c2=O)ccc1N1CCCN(C2CCOCC2)CC1]

Reaction of 2-(4-[1,4]Diazepan-1-yl-3-methoxy-phenyl)-6-[(S)-1-(tetrahydro-furan-2-yl)methoxy]-2H-isoquinolin-1-one with Tetrahydro-pyran-4-one by method J resulted in the desired product with the molecular weight 533.67 (C31H39N3O5); MS (ESI): 534 (M+H+).

The following compound was obtained analogously.

Example 373

2-{4-[4-(2-Hydroxy-2-methyl-propyl)-[1,4]diazepan-1-yl]-3-methoxy-phenyl}-6-[(S)-1-(tetrahydro-furan-2-yl)methoxy]-2H-isoquinolin-1-one

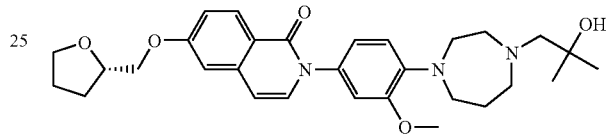

Reaction of 2-(4-[1,4]Diazepan-1-yl-3-methoxy-phenyl)-6-[(S)-1-(tetrahydro-furan-2-yl)methoxy]-2H-isoquinolin-1-one and 2,2-Dimethyl-oxirane by method U resulted in the desired product with the molecular weight 521.66 (C30H39N3O5); MS (ESI): 522 (M+H+).

Example 374

2-{3-Fluoro-4-[2-(2-methoxy-ethyl)-2,6-diaza-spiro[3.4]oct-6-yl]-phenyl}-6-[(S)-1-(tetrahydro-furan-2-yl)methoxy]-3,4-dihydro-2H-isoquinolin-1-one

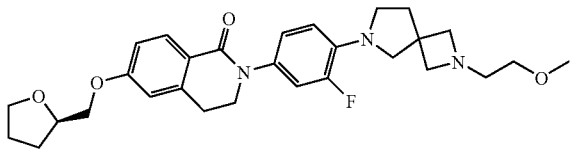 [SMILES: COCCN1CC2(CCN(c3ccc(N4CCc5cc(OC[C@H]6CCCO6)ccc5C4=O)cc3F)C2)C1]

| Ex. No. | Structure | Molecular formula | Molecular weight | ESI-MS [M + H]+ |
|---|---|---|---|---|
| 372 | 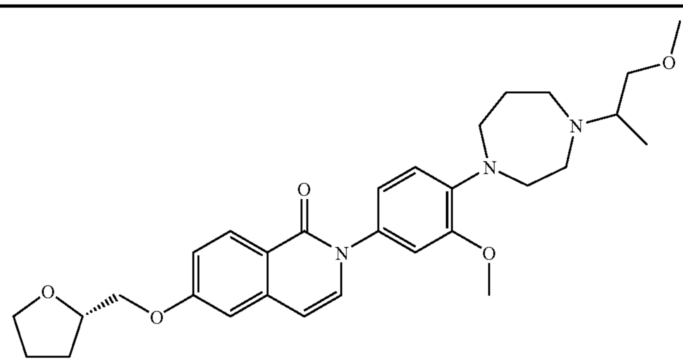 | C30H39N3O5 | 521.66 | 522 |

Reaction of 2-[4-(2,6-Diaza-spiro[3.4]oct-6-yl)-3-methoxy-phenyl]-6-[(S)-1-(tetrahydro-furan-2-yl)methoxy]-2H-isoquinolin-1-one with 1-Bromo-2-methoxy-ethane by method X resulted in the desired product with the molecular weight 509.63 (C29H36FN3O4); MS (ESI): 510 (M+H+).

2-[4-(2,6-Diaza-spiro[3.4]oct-6-yl)-3-methoxy-phenyl]-6-[(S)-1-(tetrahydro-furan-2-yl)methoxy]-2H-isoquinolin-1-one Reaction of 6-(2-Fluoro-4-{1-oxo-6-[(S)-1-(tetrahydro-furan-2-yl)methoxy]-3,4-dihydro-1H-isoquinolin-2-yl}-phenyl)-2,6-diaza-spiro[3.4]octane-2-carboxylic acid tert-butyl ester with trifluoroacetic acid by method H2 resulted in the desired product with the molecular weight 451, 55 (C26H30FN3O3); MS (ESI): 452 (M+H+).

6-(2-Fluoro-4-{1-oxo-6-[(S)-1-(tetrahydro-furan-2-yl)methoxy]-3,4-dihydro-1H-isoquinolin-2-yl}-phenyl)-2,6-diaza-spiro[3.4]octane-2-carboxylic acid tert-butyl ester Reaction of 6-[(S)-1-(Tetrahydro-furan-2-yl)methoxy]-isochroman-1-one with 6-(4-Amino-2-fluoro-phenyl)-2,6-diaza-spiro[3.4]octane-2-carboxylic acid tert-butyl ester by method AC resulted in the desired product with the molecular weight 551, 66 (C31H38FN3O5); MS (ESI): 552 (M+H+).

6-(4-Amino-2-fluoro-phenyl)-2,6-diaza-spiro[3.4]octane-2-carboxylic acid tert-butyl ester According to methods E and F, 1,2-Difluoro-4-nitro-benzene was reacted with 2,6-Diaza-spiro[3.4]octane-2-carboxylic acid tert-butyl ester and hydrogenated. The product with the molecular weight of 321, 40 (C17H24FN3O2) was obtained in this way; MS (ESI): 322 (M+H+).

2,6-Diaza-spiro[3.4]octane-2-carboxylic acid tert-butyl ester

The compound 6-Benzyl-2,6-diaza-spiro[3.4]octane (EP417631) was reacted with boc anhydride (method V) and then debenzylated by hydrogenolysis with palladium on carbon as catalyst (method AH).
The compounds in table 25 were obtained analogously.

Example 377

2-{3-Fluoro-4-[2-(2-methoxy-1-methyl-ethyl)-2,6-diaza-spiro[3.4]oct-6-yl]-phenyl}-6-[(S)-1-(tetrahydro-furan-2-yl)methoxy]-3,4-dihydro-2H-isoquinolin-1-one

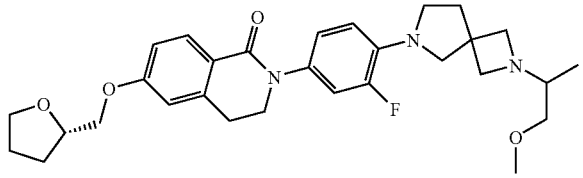

Reaction of 2-[4-(2,6-Diaza-spiro[3.4]oct-6-yl)-3-methoxy-phenyl]-6-[(S)-1-(tetrahydro-furan-2-yl)methoxy]-2H-isoquinolin-1-one with 1-Methoxy-propan-2-one by method J resulted in the desired product with the molecular weight 523.65 (C30H38FN3O4); MS (ESI): 524 (M+H+).

Example 378

2-{3-Fluoro-4-[2-(1-hydroxy-cyclobutylmethyl)-2,6-diaza-spiro[3.4]oct-6-yl]-phenyl}-6-[(S)-1-(tetrahydro-furan-2-yl)methoxy]-3,4-dihydro-2H-isoquinolin-1-one

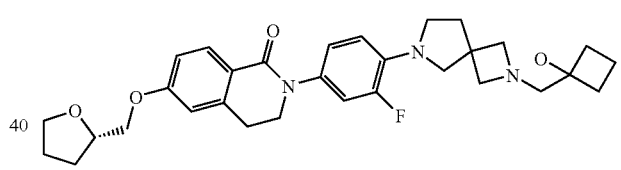

Reaction of 2-[4-(2,6-Diaza-spiro[3.4]oct-6-yl)-3-methoxy-phenyl]-6-[(S)-1-(tetrahydro-furan-2-yl)methoxy]-2H-isoquinolin-1-one with 1-Oxa-spiro[2.3]hexane by method U resulted in the desired product with the molecular weight 535.66 (C31H38FN3O4); MS (ESI): 536 (M+H+).

TABLE 25

| Ex. No. | Structure | Molecular Formula | Molecular weight | ESI-MS [M + H]+ |
|---|---|---|---|---|
| 375 | 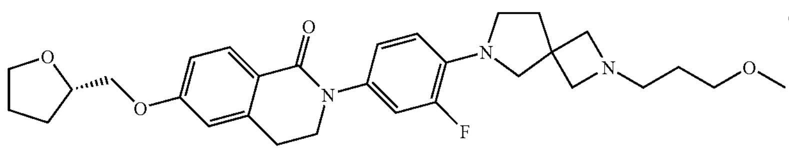 [SMILES: COCCCN1CC2(CCN(c3ccc(N4CCc5cc(OC[C@@H]6CCCO6)ccc5C4=O)cc3F)C2)C1] | C30H38FN3O4 | 523.65 | 524 |
| 376 | 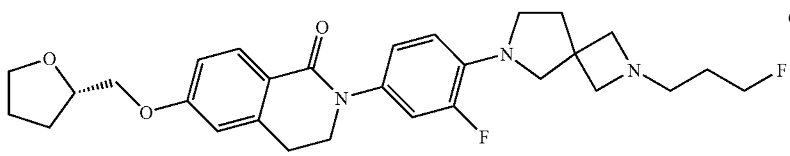 [SMILES: O=C1c2ccc(OC[C@@H]3CCCO3)cc2CCN1c1ccc(N2CCC3(CN(CCCF)C3)C2)c(F)c1] | C29H35F2N3O3 | 511.62 | 512 |

Example 379

2-((R)-4-[1,3']Bipyrrolidinyl-1'-yl-3-fluoro-phenyl)-6-((2R,3S)-3-hydroxy-tetrahydro-furan-2-yl-methoxy)-2H-isoquinolin-1-one

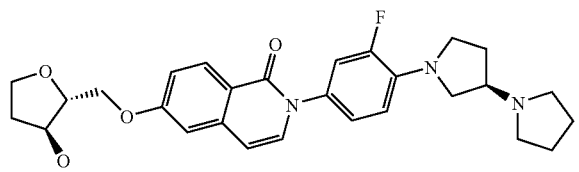 [SMILES: O=c1c2ccc(OC[C@H]3OCC[C@@H]3O)cc2ccn1-c1ccc(N2CC[C@@H](N3CCCC3)C2)c(F)c1]

2-((R)-4-[1,3']Bipyrrolidinyl-1'-yl-3-fluoro-phenyl)-6-hydroxy-2H-isoquinolin-1-one was reacted with (2R,3S)-2-Hydroxymethyl-tetrahydro-furan-3-ol by method Y. The product with the molecular weight of 493.58 (C28H32FN3O4) was obtained in this way; MS (ESI): 494 (M+H+).

Example 380

2-((R)-4-[1,3']Bipyrrolidinyl-1'-yl-3-fluoro-phenyl)-6-(3-hydroxy-1,3-dimethyl-butoxy)-2H-isoquinolin-1-one

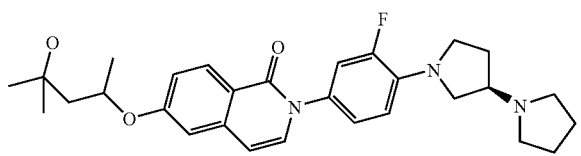 [SMILES: CC(CC(C)(C)O)Oc1ccc2c(=O)n(-c3ccc(N4CC[C@@H](N5CCCC5)C4)c(F)c3)ccc2c1]

2-((R)-4-[1,3']Bipyrrolidinyl-1'-yl-3-fluoro-phenyl)-6-hydroxy-2H-isoquinolin-1-one was reacted with 2-Methyl-pentane-2,4-diol by method Y. The product with the molecular weight of 493.63 (C29H36FN3O3) was obtained in this way; MS (ESI): 494 (M+H+).

Example 381

2-((R)-4-[1,3']Bipyrrolidinyl-1'-yl-3-fluoro-phenyl)-6-([1,3]dioxolan-2-ylmethoxy)-2H-isoquinolin-1-one

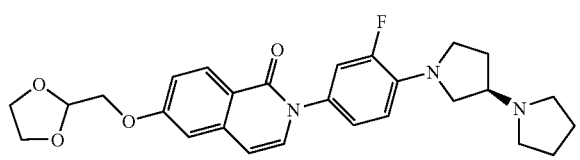 [SMILES: O=c1c2ccc(OCC3OCCO3)cc2ccn1-c1ccc(N2CC[C@@H](N3CCCC3)C2)c(F)c1]

2-((R)-4-[1,3']Bipyrrolidinyl-1'-yl-3-fluoro-phenyl)-6-hydroxy-2H-isoquinolin-1-one was reacted with 2-Bromomethyl-[1,3]dioxolane by method K. The product with the molecular weight of 479.56 (C27H30FN3O4) was obtained in this way; MS (ESI): 480 (M+H+).

Example 382

2-((R)-4-[1,3']Bipyrrolidinyl-1'-yl-3-fluoro-phenyl)-6-(tetrahydro-pyran-4-ylmethoxy)-2H-isoquinolin-1-one

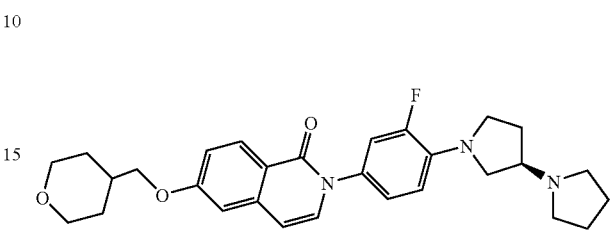

2-((R)-4-[1,3']Bipyrrolidinyl-1'-yl-3-fluoro-phenyl)-6-hydroxy-2H-isoquinolin-1-one was reacted with 4-Bromomethyl-tetrahydro-pyran by method K. The product with the molecular weight of 491.61 (C29H34FN3O3) was obtained in this way; MS (ESI): 492 (M+H+).

Table 26 summarizes results obtained with the above described calcium immobilization assay.

TABLE 26

| Bsp. No. | $IC_{50}/\mu M$ | Bsp. No. | $IC_{50}/\mu M$ | Bsp. No. | $IC_{50}/\mu M$ |
|---|---|---|---|---|---|
| 001 | 0.99 | 154 | 0.18 | 287 | 1.96 |
| 014 | 1.07 | 168 | 1.39 | 303 | 0.38 |
| 024 | 1.19 | 176 | 0.31 | 321 | 0.15 |
| 039 | 0.23 | 202 | 0.50 | 324 | 0.20 |
| 045 | 0.22 | 206 | 0.20 | 326 | 0.22 |
| 084 | 6.24 | 210 | 0.36 | 327 | 3.69 |
| 095 | 3.41 | 219 | 1.46 | 341 | 1.60 |
| 099 | 1.68 | 224 | 1.42 | 353 | 23.82 |
| 106 | 4.21 | 246 | 13.04 | 354 | 0.22 |
| 112 | 7.54 | 251 | 0.41 | 356 | 1.14 |
| 136 | 0.10 | 264 | 0.59 | 361 | 2.56 |

We claim:

1. A compound of formula (I)

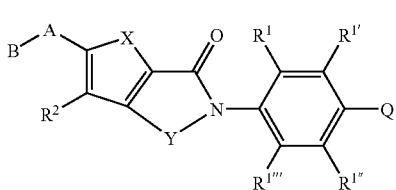

wherein:

R1, R1', R1" and R1'" are independently of one another H, F, Cl, Br, I, OH, $CF_3$, $NO_2$, CN, $OCF_3$, O—($C_1$-$C_6$)-alkyl, O—($C_1$-$C_4$)-alkoxy-($C_1$-$C_4$)-alkyl, S—($C_1$-$C_6$)-alkyl, ($C_1$-$C_6$)-alkyl, ($C_2$-$C_6$)-alkenyl, ($C_3$-$C_8$)-cycloalkyl, O—($C_3$-$C_8$)-cycloalkyl, ($C_3$-$C_8$)-cycloalkenyl, ($C_2$-$C_6$)-alkynyl, ($C_0$-$C_8$)-alkylene-aryl, O—($C_0$-$C_8$)-alkylene-aryl, S-aryl, N(R3)(R4), $SO_2$—$CH_3$, COOH, COO—($C_1$-$C_6$)-alkyl, CON(R5)(R6), N(R7)CO(R8), N(R9)$SO_2$(R10), CO(R11), or $(C(R12)(R13))_x$—O(R14);

R3, R4, R5, R6, R7 and R9 are
independently of one another H or $(C_1-C_8)$-alkyl,
or
R3 and R4, or R5 and R6
independently of one another taken together with the nitrogen atom to which they are bonded form a 5-6 membered ring which optionally contains one additional heteroatom selected from the group consisting of NH, N—$(C_1-C_6)$-alkyl, oxygen and sulfur;
R8, R10 and R11 are
independently of one another H, $(C_1-C_8)$-alkyl, or aryl;
R12 and R13 are
independently of one another H, or $(C_1-C_8)$-alkyl;
R14 is H, $(C_1-C_6)$-alkyl, or aryl;
x is 0, 1, 2, 3, 4, 5, or 6;
R2 is H;
Y is C(R27)(R27')C(R28)(R28') or C(R29)=C(R29');
R27, R27', R28, R28', R29 and R29' are H;
X is S, O, or C(R30)=C(R30');
R30 and R30' are H;
A is a bond or a linker having 1 to 8 members, where the members are selected from the group consisting of O, S, $SO_2$, N(R31), CO, C(R32)(R33), C(R34)=C(R34'), cyclopropylene, and C≡C, resulting in a chemically reasonable radical;
R31, R34 and R34' are
independently of one another H or $(C_1-C_8)$-alkyl;
R32 and R33 are
independently of one another H, $(C_1-C_6)$-alkyl, OH, or O—$(C_1-C_6)$-alkyl;
B is N(R35)(R36), hydroxy-$(C_1-C_4)$-alkyl, $(C_1-C_8)$-alkyl, $(C_1-C_4)$-alkoxy-$(C_1-C_4)$-alkyl, $(C_2-C_8)$-alkenyl, $(C_2-C_8)$-alkynyl, or a 3 to 10-membered mono-, bi-, tri- or spirocyclic nonaromatic ring which contains 0 to 4 heteroatoms selected from the group consisting of oxygen, nitrogen and sulfur, and the ring system is optionally substituted one or more times by F, Cl, Br, $CF_3$, $NO_2$, CN, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R37), CON(R38)(R39), hydroxy, COO(R40), N(R41)CO$(C_1-C_6)$-alkyl, N(R42)(R43), $SO_2CH_3$, $SCF_3$ or S—$(C_1-C_6)$-alkyl;
R35, R36, R37, R38, R39, R40, R41, R42 and R43 are
independently of one another H, or $(C_1-C_8)$-alkyl;
or
R38 and R39, or R42 and R43
independently of one another taken together with the nitrogen atom to which they are bonded form a 5-6 membered ring which optionally contains one additional heteroatom selected from the group consisting of NH, N—$(C_1-C_6)$-alkyl, oxygen and sulfur;
Q is mono-, bi-, tri- or spirocyclic saturated or partly unsaturated ring structure having one nitrogen atom and 0-3 additional heteroatoms selected from the group consisting of N, O and S, where the ring of the structure may be spiro-linked, fused or bridged, and where the ring system is optionally substituted one or more times by substituents selected from the group consisting of F, OH, $CF_3$, CN, $OCF_3$, oxo, O—$(C_1-C_8)$-alkyl, $(C_1-C_4)$-alkoxy-$(C_1-C_4)$-alkyl, $(C_1-C_6)$-alkyl, $(C_2-C_6)$-alkenyl, $(C_2-C_6)$-alkynyl, CO(R44), $(C(R45)(R46))_o$-R47, and $CO(C(R45)(R46))_p$-R48, where Q contains in total at least two N atoms;

or Q is selected from the group consisting of:

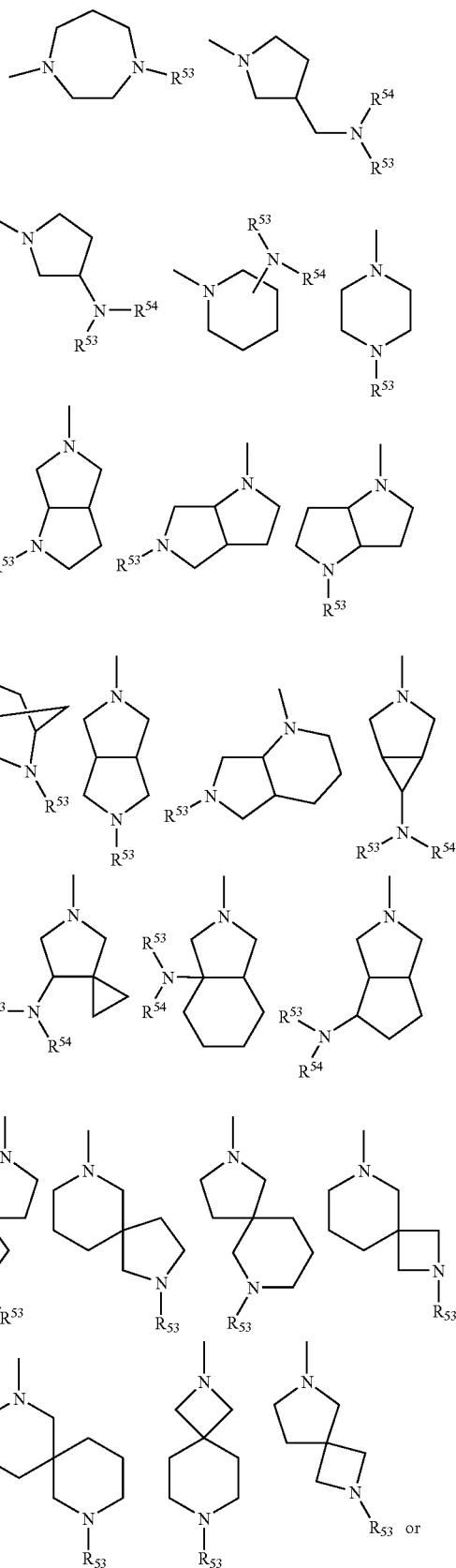

-continued

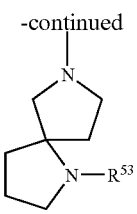

each of which is optionally substituted one or more times by F, OH, oxo, $(C_1\text{-}C_6)$-alkyl, O—$(C_1\text{-}C_6)$-alkyl, $(C_1\text{-}C_4)$-alkoxy-$(C_1\text{-}C_4)$-alkyl, or hydroxy-$(C_1\text{-}C_4)$-alkyl;

R44 is H or $(C_1\text{-}C_8)$-alkyl;

R45 and R46 are independently of one another H, $(C_1\text{-}C_8)$-alkyl, OH, $(C_3\text{-}C_8)$-cycloalkyl, or $(C_1\text{-}C_4)$-alkoxy-$(C_1\text{-}C_4)$-alkyl;

o and p are independently of one another 0, 1, 2, 3, 4, 5 or 6;

R47 and R48 are independently of one another OH, F, O—$(C_1\text{-}C_8)$-alkyl, CON(R49)(R50), N(R51)CO(R52), N(R53)(R54), $CO_2$(R55), $SO_2Me$, CN, or a 3-10 membered ring system having 0 to 3 heteroatoms selected from the group of N, O and S, which may be substituted by one or more of the following substituents: F, Cl, Br, $CF_3$, $(C_1\text{-}C_8)$-alkyl, O—$(C_1\text{-}C_8)$-alkyl, $(C_1\text{-}C_4)$-alkoxy-$(C_1\text{-}C_4)$-alkyl, CO(R56), oxo, or OH;

R49, R50, R51, R52, R55 and R56 are independently of one another H or $(C_1\text{-}C_8)$-alkyl, or R49 and R50 taken together with the nitrogen atom to which they are bonded form a 5-6 membered ring which optionally contains one additional heteroatom selected from the group consisting of NH, N—$(C_1\text{-}C_6)$-alkyl, oxygen and sulfur;

R53 and R54 are independently of one another H, $(C_1\text{-}C_8)$-alkyl, $(C_1\text{-}C_4)$-alkoxy-$(C_1\text{-}C_4)$-alkyl, $(C_3\text{-}C_8)$-alkenyl, $(C_3\text{-}C_8)$-alkynyl, CO(R57), (C(R58)(R59))$_q$-R60, CO(C(R61)(R62))$_r$-R63, or CO—O$(C_1\text{-}C_8)$-alkyl, or R53 and R54 taken together with the nitrogen atom to which they are bonded form a 4 to 10-membered mono-, bi- or spirocyclic ring which optionally contains 1 to 3 additional heteroatoms selected from the group consisting of N, O and S, and is optionally substituted one or more times by F, Cl, Br, $CF_3$, O—$(C_1\text{-}C_8)$-alkyl, $(C_1\text{-}C_6)$-alkyl, CO(R64), oxo, OH, $(C_1\text{-}C_4)$-alkoxy-$(C_1\text{-}C_4)$-alkyl, hydroxy-$(C_1\text{-}C_4)$-alkyl, CON(R65)(R66), N(R67)CO(R68), N(R69)(R70), $CO_2$(R71), or $SO_2$($C_1\text{-}C_6$)-alkyl;

R58 and R59 are independently of one another H, $(C_1\text{-}C_6)$-alkyl, or OH;

R57, R61, R62, R64, R65, R66, R67, R68, R69, R70 and R71 are independently of one another H or $(C_1\text{-}C_6)$-alkyl, or R69 and R70 taken together with the nitrogen atom to which they are bonded form a 5-6 membered ring which optionally contains one additional heteroatom selected from the group consisting of NH, N—$(C_1\text{-}C_6)$-alkyl, oxygen and sulfur;

q and r are independently of one another 0, 1, 2, 3, 4, 5 or 6;

R60 and R63 are independently of one another OH, F, O—$(C_1\text{-}C_6)$-alkyl, CN, COO(R78), N(R74)CO($C_1\text{-}C_6$)-alkyl, N(R76)(R77), CON(R72)(R73), $SO_2$($C_1\text{-}C_6$)-alkyl, or 3-12 membered mono-, bi- or spirocyclic ring which optionally contains one or more heteroatoms selected from the group consisting of N, O and S, and the 3-12 membered ring is optionally substituted by F, Cl, Br, OH, $CF_3$, $NO_2$, CN, $OCF_3$, oxo, $(C_1\text{-}C_4)$-alkoxy-$(C_1\text{-}C_4)$-alkyl, hydroxy-$(C_1\text{-}C_4)$-alkyl, S—$(C_1\text{-}C_6)$-alkyl, $(C_1\text{-}C_6)$-alkyl, $(C_2\text{-}C_6)$-alkenyl, $(C_3\text{-}C_8)$-cycloalkyl, O—$(C_3\text{-}C_8)$-cycloalkyl, $(C_3\text{-}C_8)$-cycloalkenyl, O—$(C_3\text{-}C_8)$-cycloalkenyl, $(C_2\text{-}C_6)$-alkynyl, N(R76)(R77), COO(R78), $SO_2$($C_1\text{-}C_6$)-alkyl or COOH; and R72, R73, R74, R76, R77 and R78 are independently of one another H or $(C_1\text{-}C_8)$-alkyl, or R72 and R73, or R76 and R77 independently of one another taken together with the nitrogen atom to which they are bonded form a 5-6 membered ring which optionally contains one additional heteroatom selected from the group consisting of NH, N—$(C_1\text{-}C_6)$-alkyl, oxygen and sulfur;

or a hydrate, solvate, or pharmaceutically acceptable salt thereof.

2. The compound according to claim 1, wherein:

B is N(R35)(R36), hydroxy-$(C_1\text{-}C_4)$-alkyl, $(C_1\text{-}C_8)$-alkyl, $(C_1\text{-}C_4)$-alkoxy-$(C_1\text{-}C_4)$-alkyl, $(C_2\text{-}C_8)$-alkenyl, $(C_2\text{-}C_8)$-alkynyl, or a 3 to 10-membered mono-, bi-, tri- or spirocyclic nonaromatic ring which contains 0 to 4 heteroatoms selected from the group consisting of oxygen, nitrogen and sulfur, where the ring system is optionally substituted one or more times by F, Cl, Br, $CF_3$, $NO_2$, CN, $(C_1\text{-}C_6)$-alkyl, O—$(C_1\text{-}C_8)$-alkyl, $(C_1\text{-}C_4)$-alkoxy-$(C_1\text{-}C_4)$-alkyl, hydroxy-$(C_1\text{-}C_4)$-alkyl, oxo, CO(R37), CON(R38)(R39), hydroxy, COO(R40), N(R41)CO($C_1\text{-}C_6$)-alkyl, N(R42)(R43) or $SO_2CH_3$.

3. The compound according to claim 1, wherein:

B is hydroxy-$(C_1\text{-}C_4)$-alkyl, $(C_1\text{-}C_8)$-alkyl, $(C_1\text{-}C_4)$-alkoxy-$(C_1\text{-}C_4)$-alkyl, or a 3 to 10-membered mono-, bi- or spirocyclic nonaromatic ring which contains 0 to 3 heteroatoms selected from the group consisting of oxygen, nitrogen and sulfur, where the ring system is optionally substituted by F, Cl, Br, $CF_3$, $NO_2$, CN, $(C_1\text{-}C_6)$-alkyl, O—$(C_1\text{-}C_8)$-alkyl, $(C_1\text{-}C_4)$-alkoxy-$(C_1\text{-}C_4)$-alkyl, hydroxy-$(C_1\text{-}C_4)$-alkyl, oxo, CO(R37), CON(R38)(R39), hydroxy, COO(R40), N(R41)CO($C_1\text{-}C_6$)-alkyl, N(R42)(R43) or $SO_2CH_3$.

4. The compound according to claim 1, wherein:

B is $(C_1\text{-}C_8)$-alkyl, hydroxy-$(C_1\text{-}C_4)$-alkyl, $(C_1\text{-}C_4)$-alkoxy-$(C_1\text{-}C_4)$-alkyl, or a 3 to 10-membered mono-, bi- or spirocyclic nonaromatic ring which contains 0 to 3 heteroatoms selected from the group consisting of oxygen, nitrogen and sulfur, where the ring system is optionally substituted by F, Cl, Br, $CF_3$, $(C_1\text{-}C_6)$-alkyl, O—$(C_1\text{-}C_8)$-alkyl, $(C_1\text{-}C_4)$-alkoxy-$(C_1\text{-}C_4)$-alkyl, hydroxy-$(C_1\text{-}C_4)$-alkyl, oxo, CO(R37), hydroxy, COO(R40), N(R41)CO($C_1\text{-}C_6$)-alkyl or $SO_2CH_3$.

5. The compound according to claim 1, wherein:

R53 is H, $(C_1\text{-}C_8)$-alkyl, (C(R58)(R59))$_q$-R60, $(C_1\text{-}C_4)$-alkoxy-$(C_1\text{-}C_4)$-alkyl, CO(C(R61)(R62))$_r$-R63, $(C_3\text{-}C_8)$-alkenyl, $(C_3\text{-}C_8)$-alkynyl, CO—$(C_1\text{-}C_6)$-alkyl, or CO—O$(C_1\text{-}C_8)$-alkyl, R54 is $(C_1\text{-}C_8)$-alkyl, (C(R58)(R59))$_q$-R60, $(C_1\text{-}C_4)$-alkoxy-$(C_1\text{-}C_4)$-alkyl, CO(C (R61)(R62))$_r$-R63, (C$_3$-C$_8$)-alkenyl, or (C$_3$-C$_8$)-alkynyl, or R53 and R54 taken together with the nitrogen atom to which they are bonded form a 4 to 10-membered mono-, bi- or spirocyclic ring which optionally contains 1 to 3 additional heteroatoms selected from the group consisting of N, O and S, and is optionally substituted one or more times by F, Cl, Br, CF$_3$, O—(C$_1$-C$_8$)-alkyl, (C$_1$-C$_6$)-alkyl, CO(R64), oxo, OH, (C$_1$-C$_4$)-alkoxy-(C$_1$-C$_4$)-alkyl, hydroxy-(C$_1$-C$_4$)-alkyl, CON(R65)(R66), N(R67)CO(R68), N(R69)(R70), CO$_2$(R71), or SO$_2$(C$_1$-C$_6$)-alkyl;

R45 is H or (C$_1$-C$_6$)-alkyl;

q and r are independently 0, 1, 2, 3 or 4; and

R60 and R63 are independently of one another OH, F, O—(C$_1$-C$_6$)-alkyl, N(R74)CO(C$_1$-C$_6$)-alkyl, SO$_2$(C$_1$-C$_6$)-alkyl, or 3-12 membered mono-, bi- or spirocyclic ring which optionally contains one or more heteroatoms selected from the group consisting of N, O and S, and the 3-12 membered ring is optionally substituted by F, Cl, Br, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, hydroxy-(C$_1$-C$_4$)-alkyl, (C$_1$-C$_6$)-alkyl, (C$_2$-C$_6$)-alkenyl, (C$_2$-C$_6$)-alkynyl, N(R76)(R77) or SO$_2$(C$_1$-C$_6$)-alkyl.

6. The compound according to claim 1, wherein:

R53, R54 are independently of one another (C$_1$-C$_8$)-alkyl, (C(R58)(R59))$_q$-R60, or (C$_1$-C$_4$)-alkoxy-(C$_1$-C$_4$)-alkyl, or R53 and R54 taken together with the nitrogen atom to which they are bonded form a 4 to 10-membered mono-, bi- or spirocyclic ring which optionally contains 1 to 2 additional heteroatoms selected from the group consisting of N, O and S, and is optionally substituted one or more times by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, CO(R64), oxo, OH, N(R67)CO(C$_1$-C$_6$)-alkyl or SO$_2$(C$_1$-C$_6$)-alkyl.

7. The compound according to claim 1, wherein:

R53 and R54 taken together with the nitrogen atom to which they are bonded form a 6 to 10-membered bi- or spirocyclic ring which optionally contains 1 to 2 additional heteroatoms selected from the group of N, O and S, and is optionally substituted one or more times by F, Cl, Br, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, CO(R64), oxo, OH, N(R67)CO(C$_1$-C$_6$)-alkyl, or SO$_2$(C$_1$-C$_6$)-alkyl;

or a hydrate, solvate, or pharmaceutically acceptable salt thereof.

8. The compound according to claim 1, wherein Q is

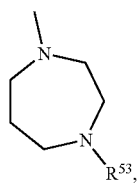

which is optionally substituted one or more times by F, OH, oxo, (C$_1$-C$_6$)-alkyl, O—(C$_1$-C$_6$)-alkyl, (C$_1$-C$_4$)-alkoxy-(C$_1$-C$_4$)-alkyl, or hydroxy-(C$_1$-C$_4$)-alkyl;

or a hydrate, solvate, or pharmaceutically acceptable salt thereof.

9. The compound according to claim 1, wherein Q is

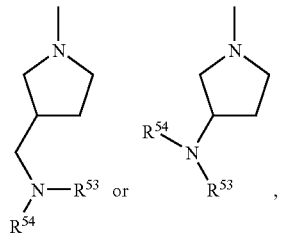

each of which is optionally substituted one or more times by F, OH, oxo, (C$_1$-C$_6$)-alkyl, O—(C$_1$-C$_6$)-alkyl, (C$_1$-C$_4$)-alkoxy-(C$_1$-C$_4$)-alkyl, or hydroxy-(C$_1$-C$_4$)-alkyl;

or a hydrate, solvate, or pharmaceutically acceptable salt thereof.

10. The compound according to claim 1, wherein Q is

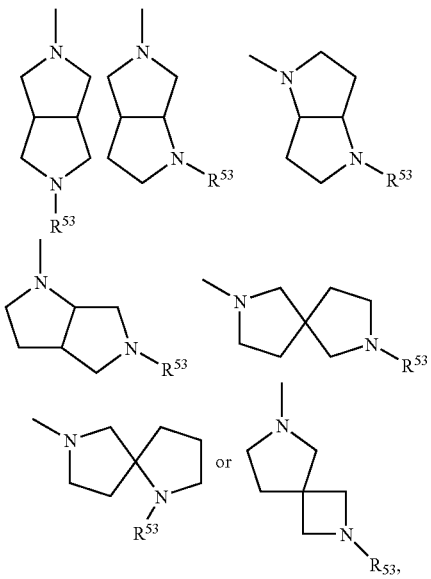

each of which is optionally substituted one or more times by F, OH, oxo, (C$_1$-C$_6$)-alkyl, O—(C$_1$-C$_6$)-alkyl, (C$_1$-C$_4$)-alkoxy-(C$_1$-C$_4$)-alkyl, or hydroxy-(C$_1$-C$_4$)-alkyl.

11. The compound according to claim 1, wherein Q is

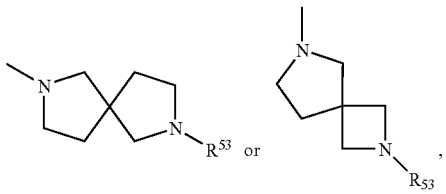

each of which is optionally substituted one or more times by F, OH, oxo, (C$_1$-C$_6$)-alkyl, O—(C$_1$-C$_6$)-alkyl, (C$_1$-C$_4$)-alkoxy-(C$_1$-C$_4$)-alkyl, hydroxy-(C$_1$-C$_4$)-alkyl.

12. The compound according to claim 1, wherein:

Y is C(R27)(R27')C(R28)(R28'); and

R27, R27', R28, and R28' are H.

13. The compound according to claim 1, wherein:
X is S or C(R30)=C(R30'), wherein R30 and R30' are H.

14. The compound according to claim 1, wherein:
X is C(R30)=C(R30'), wherein R30 and R30' are H.

15. The compound according to claim 1, wherein:
X is S or O;
or a hydrate, solvate, or pharmaceutically acceptable salt thereof.

16. The compound according to claim 1, wherein:
Y is C(R29)=C(R29'); and
R29 and R29' are H;
or a hydrate, solvate, or pharmaceutically acceptable salt thereof.

17. The compound according to claim 1, which is a compound of formula Ia:

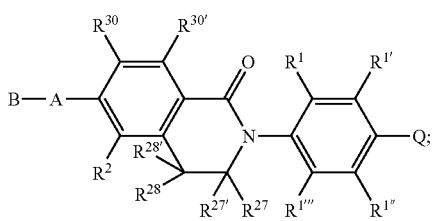

Ia or a hydrate, solvate, or pharmaceutically acceptable salt thereof.

18. The compound according to claim 1, wherein:
Y is C(R29)=C(R29'); and
X is C(R30)=C(R30');
or a hydrate, solvate, or pharmaceutically acceptable salt thereof.

19. The compound according to claim 1, wherein:
Y is C(R29)=C(R29');
X is C(R30)=C(R30');
Q is

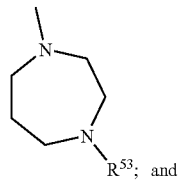
; and

R53 is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, or $(C(R58)(R59))_q$-R60;
or a hydrate, solvate, or pharmaceutically acceptable salt thereof.

20. The compound according to claim 1, wherein:
Y is C(R27)(R27')C(R28)(R28');
X is C(R30)=C(R30');
Q is

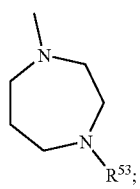

R53 is $(C_1-C_4)$-alkoxy-$(C_1-C_4)$-alkyl or $(C(R58)(R59))_q$-R60;

R58 and 59 are
independently of one another H or OH;
q and r are independently of one another 1, 2, 3 or 4; and
R60 and R63 are
independently of one another F, O—$(C_1-C_6)$-alkyl, N(R74)CO$(C_1-C_6)$-alkyl, SO$_2$$(C_1-C_6)$-alkyl, or 3-12 membered mono-, bi- or spirocyclic ring which contains 0 to 3 additional heteroatoms selected from the group consisting of O and S, and the 3-12 membered ring is optionally substituted by F, Cl, Br, OH, CF$_3$, NO$_2$, CN, OCF$_3$, oxo, O—$(C_1-C_6)$-alkyl, $(C_1-C_4)$-alkoxy-$(C_1-C_4)$-alkyl, hydroxy-$(C_1-C_4)$-alkyl, $(C_1-C_6)$-alkyl, $(C_2-C_6)$-alkenyl, $(C_2-C_6)$-alkynyl or SO$_2$$(C_1-C_6)$-alkyl;
or a hydrate, solvate, or pharmaceutically acceptable salt thereof.

21. The compound according to claim 1, wherein:
R1, R1', R1" and R1'" are independently of one another selected from H, F, Cl, methyl, O-methyl, and CO-methyl.

22. The compound according to claim 1, wherein:
A is a bond or a linker having 1 to 6 members, where the members are selected from the group consisting of O, N(R31), CO, C(R32)(R33), C(R34)=C(R34'), and C≡C, resulting in a chemically reasonable radical.

23. The compound according to claim 1, wherein:
A is selected from a bond, O, NH, CH(OH), CH$_2$, CO, C≡C, HC=CH, CH$_2$—O, CH(CH$_3$)—O, CO—CH(CH$_3$)—O, CO—NH, NH—CO, N(CH$_3$)—CO, COCH$_2$O, CH(OH)CH$_2$O, O—CO—NH, C(OH)(CH$_3$)—C≡C, and COCH$_2$CH$_2$O.

24. The compound according to claim 1, wherein:
B is hydroxy-$(C_1-C_4)$-alkyl, $(C_1-C_8)$-alkyl, $(C_1-C_4)$-alkoxy-$(C_1-C_4)$-alkyl, or a monocyclic ring selected from the group consisting of

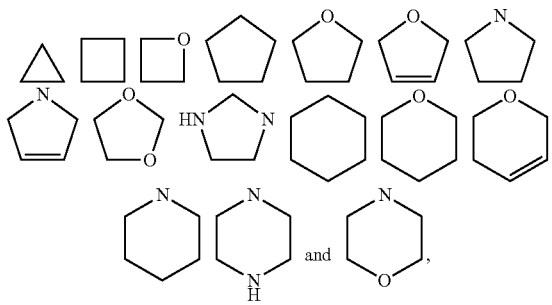

wherein the monocyclic ring is optionally substituted one or two times by F, CF$_3$, CN, methyl, ethyl, methoxy, oxo, hydroxy, or SO$_2$-methyl.

25. The compound according to claim 1, wherein B-A is

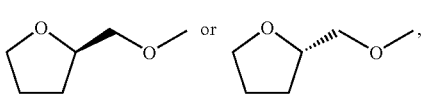

wherein the tetrahydrofuranyl ring is optionally substituted one time by methyl or OH.

26. The compound according to claim 1, wherein B-A is

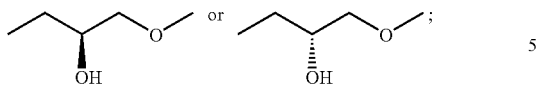

or a hydrate, solvate, or pharmaceutically acceptable salt thereof.

27. A pharmaceutical composition comprising the compound according to claim 1, or pharmaceutically acceptable salt thereof, in combination with at least one pharmaceutically acceptable carrier.

28. A pharmaceutical composition comprising the compound according to claim 1 or a pharmaceutically acceptable salt thereof, and at least one additional active ingredient that has a beneficial effect on a metabolic disturbance or a disorder associated therewith.

29. A pharmaceutical composition comprising the compound according to claim 1 or a pharmaceutically acceptable salt thereof, and at least one antidiabetic active ingredient.

30. A pharmaceutical composition comprising the compound according to claim 1 or a pharmaceutically acceptable salt thereof, and at least one lipid modulator.

31. A pharmaceutical composition comprising the compound according to claim 1 or a pharmaceutically acceptable salt thereof, and at least one antiobesity active ingredient.

* * * * *